US012721638B1

(12) United States Patent
Ginn

(10) Patent No.: US 12,721,638 B1
(45) Date of Patent: Sep. 1, 2026

(54) SYSTEMS, APPARATUS AND METHODS FOR STABILIZING SACROILIAC JOINTS

(71) Applicant: Tenon Medical, Inc., Los Gatos, CA (US)

(72) Inventor: Richard S Ginn, Powhatan, VA (US)

(73) Assignee: Tenon Medical, Inc., Los Gatos, CA (US)

( * ) Notice: Subject to any disclaimer, the term of this patent is extended or adjusted under 35 U.S.C. 154(b) by 0 days.

(21) Appl. No.: 19/098,165

(22) Filed: Apr. 2, 2025

(51) Int. Cl.
*A61B 17/17* (2006.01)
*A61B 17/70* (2006.01)

(52) U.S. Cl.
CPC ...... *A61B 17/1757* (2013.01); *A61B 17/7055* (2013.01)

(58) Field of Classification Search
CPC ....... A61B 17/7055; A61F 2002/30995; A61F 2002/30121; A61F 2002/30123; A61F 2002/30166; A61F 2002/3013
See application file for complete search history.

(56) References Cited

U.S. PATENT DOCUMENTS

| | | | | |
|---|---|---|---|---|
| 5,603,713 A * | 2/1997 | Aust | A61B 17/8061 | 606/279 |
| 6,629,998 B1 * | 10/2003 | Lin | A61F 2/447 | 623/17.11 |
| 8,585,742 B2 * | 11/2013 | Windolf | A61B 17/7028 | 606/257 |
| D951,455 S * | 5/2022 | Ginn | D24/155 | |
| 11,752,011 B2 * | 9/2023 | Stuart | A61F 2/447 | 623/17.11 |
| 11,872,141 B2 * | 1/2024 | Lee | A61B 17/8875 | |
| 11,938,031 B2 * | 3/2024 | Ginn | A61B 17/92 | |
| 2007/0156241 A1 * | 7/2007 | Reiley | A61B 17/56 | 623/17.11 |
| 2012/0083883 A1 * | 4/2012 | Ginn | A61B 17/1604 | 623/17.11 |
| 2016/0089138 A1 * | 3/2016 | Early | A61B 17/0642 | 606/75 |

(Continued)

*Primary Examiner* — Jacqueline T Johanas
(74) *Attorney, Agent, or Firm* — Francis Law Group

(57) ABSTRACT

Systems are described for conducting minimally invasive medical interventions utilizing instruments and assemblies thereof to stabilize and/or fixate a dysfunctional sacroiliac (SI) joint. The systems include a drill guide having a bone dislodging member adapted to create a pilot SI joint opening in the dysfunctional SI joint through an incision comprising a length no greater than 3.0 cm; portions of the pilot SI joint opening being disposed in the sacrum and ilium bone structures. The drill guide includes a tri-mode fixation system adapted to position and stabilize the drill guide during creation of the pilot SI joint opening in the dysfunctional SI joint and delivery of the SI joint prosthesis therein. The systems also include a prosthesis assembly that includes a prosthesis configured and adapted to be advanced into the pilot SI joint opening of the dysfunctional SI joint, whereby the prosthesis transfixes and, thereby, stabilizes the dysfunctional SI joint, and supplemental bone fixation means configured and adapted to be inserted into the prosthesis and expand when the prosthesis is advanced into the pilot SI joint opening of the dysfunctional SI joint and enhance fixation of the prosthesis therein.

1 Claim, 81 Drawing Sheets

(56) References Cited

U.S. PATENT DOCUMENTS

| | | | | |
|---|---|---|---|---|
| 2016/0192930 | A1* | 7/2016 | Finley | A61B 17/15<br>606/75 |
| 2017/0000537 | A1* | 1/2017 | Fallin | A61B 17/808 |
| 2019/0343640 | A1* | 11/2019 | Donner | A61F 2/447 |
| 2021/0169660 | A1* | 6/2021 | Reckling | A61B 17/1739 |
| 2021/0393408 | A1* | 12/2021 | Ginn | A61B 17/1757 |
| 2021/0393409 | A1* | 12/2021 | Ginn | A61B 17/92 |
| 2022/0273447 | A1* | 9/2022 | Ginn | A61B 5/055 |
| 2022/0273448 | A1* | 9/2022 | Ginn | A61B 5/0036 |
| 2022/0296378 | A1* | 9/2022 | Ginn | A61F 2/4601 |
| 2022/0304814 | A1* | 9/2022 | Ginn | A61F 2/30767 |
| 2023/0000631 | A1* | 1/2023 | Ginn | A61B 17/1664 |
| 2023/0000639 | A1* | 1/2023 | Stuart | A61B 17/1757 |
| 2023/0037755 | A1* | 2/2023 | Ginn | A61B 6/032 |
| 2023/0404762 | A1* | 12/2023 | Ginn | A61B 17/1664 |
| 2024/0261107 | A1* | 8/2024 | Ginn | A61B 17/7061 |
| 2024/0285410 | A1* | 8/2024 | Ginn | A61F 2/30988 |
| 2024/0390151 | A1* | 11/2024 | Ginn | A61B 17/7074 |

* cited by examiner

SYSTEMS, APPARATUS AND METHODS FOR STABILIZING SACROILIAC JOINTS

FIELD OF THE INVENTION

The present invention relates to systems, apparatus and methods for stabilizing diarthrodial synovial joints. More particularly, the present invention relates to systems, apparatus and methods for stabilizing dysfunctional sacroiliac (SI) joints.

BACKGROUND OF THE INVENTION

As is well known in the art, the sacroiliac (SI) joint 6 comprises a diarthrodial synovial joint, which, as illustrated in FIG. 1A, is defined by the interface between the articular surfaces of the sacrum 2 and the ilium 4. Thus, the SI joint 6 is defined by (and, hence, comprises) portions of the sacrum 2 and ilium 4.

As illustrated in FIG. 1B, the SI joint 6 generally comprises the shape of an inverted capital letter "L" (denoted "13"), where the long arm of the inverted "L" 15 (i.e., SI joint 6) is oriented along the posterior wall of the pelvis 11 (denoted "25" in FIG. 1A) and is also oriented relatively straight through its entire course.

The sacral floor (denoted "21" in FIG. 1C), which is defined by the region between the anterior sacral promontory 19*a* and the apex 19*b* of the sacrum 2, generally slopes downward and laterally at an approximately 30% grade relative to the cephalocaudal axis 27.

As illustrated in FIGS. 1B and 1C, the short arm of the inverted "L" (denoted "17") is generally oriented parallel to the transverse plane of the L5-S1 lumbosacral joint and limited superiorly by the sacral ala (denoted "23" in FIG. 1C).

The apex of the inverted "L" (denoted "29" in FIG. 1B) is positioned below the S2 segment region of the sacrum 2 (denoted "S2") proximate to the S3 segment region of the sacrum 2 (denoted "S3").

As illustrated in FIG. 1D, the SI joint 6 further comprises a SI joint dorsal recess or gap 7 that is disposed between the sacrum 2 and ilium 4 proximate the S2 segment region of the sacrum 2.

As is well known in the art, the SI joint further comprises articular cartilage, i.e., hyaline and fibrocartilage, and a strong, extensive ligamentous architecture, which stabilizes the SI joint.

Generally, the articular surfaces of the sacrum 2 and the ilium 4 that define the SI joint 6 comprise cortical bone 8, which is more compact, dense and hard relative to softer trabecular bone 10, which, as further illustrated in FIG. 1A, is disposed in the interior regions of the sacrum and ilium 2, 4.

The SI Joint is distinguished from other synovial joints by the atypical articulation of the different articular surfaces of the sacrum and ilium; the articular surface of the sacrum comprising hyaline cartilage and the articular surface of the ilium comprising substantially stronger fibrocartilage.

As is further well known in the art, the primary plane of motion of the SI joint is anterior-posterior along a transverse axis. The terms often employed to describe the relative motion of the sacrum and ilium are nutation, which refers to anterior-inferior movement of the sacrum while the coccyx (denoted "3" in FIGS. 1A and 1D) moves posteriorly relative to the ilium, and counternutation, which refers to posterior-superior movement of the sacrum while the coccyx moves anteriorly relative to the ilium.

In most healthy individuals, the SI joint range of motion in flexion-extension is approximately 3.0°, approximately 1.5° in axial rotation and approximately 0.8° in lateral bending.

As is well established, the SI joint performs several seminal biomechanical functions. The primary functions of the SI joint are to attenuate loads exerted on the upper body and to distribute the loads to the lower extremities. The SI joint also functions as a shock absorber for loads exerted on spine.

As is also well established, the noted loads and, hence, forces exerted on the SI joint can adversely affect the biomechanical functions of the SI joint, which can, and often will, result in SI joint dysfunction—an often-overlooked musculoskeletal pathology associated with lower back pain.

Indeed, SI joint dysfunction is estimated to be the primary cause of lower back pain in 15-30% of subjects afflicted with such pain. However, lower back pain associated with SI joint dysfunction is suspected to be far more common than most healthcare providers realize, since such pain is often associated with other skeletal and musculoskeletal dysfunctions.

SI joint dysfunction, and pain associated therewith, can be caused by various SI joint abnormalities and/or disorders, including traumatic fracture dislocation of the pelvis, degenerative arthritis, sacroiliitis, i.e., an inflammation or degenerative condition of the sacroiliac joint; osteitis condensans ilii, and other degenerative conditions of the SI joint structures.

In some instances, SI joint dysfunction, and pain associated therewith, is caused by a misaligned or dislodged surgical joint implant, such as a surgical pin or dowel, or screw, e.g., a sacral-alar iliac (S2AI) screw.

Various non-surgical methods, such as administration of pharmacological agents, e.g., the corticosteroid prednisone, and surgical methods and devices, i.e., prostheses, have been developed and employed to treat SI joint dysfunction.

The most common approach employed to treat SI joint dysfunctions (when non-surgical treatments fail to ameliorate pain associated therewith), at present, is SI joint stabilization, i.e., reinforcing or modulating articulation by and between the sacrum and ilium, via surgical intervention.

SI joint stabilization typically comprises surgical placement of a prosthesis proximate to or in a dysfunctional SI joint and is generally characterized by the direction of access to the dysfunctional SI joint, i.e., anterior, posterior or lateral trajectory.

Although several conventional SI joint stabilization surgical methods and associated bone prostheses have effectively ameliorated pain associated with SI joint dysfunction, there remains many disadvantages associated with the conventional methods and associated prostheses.

A major disadvantage associated with many conventional SI joint stabilization surgical methods is that the surgeon is required to make a substantial incision in and through the skin and tissues of a subject to access the dysfunctional SI joint. Often referred to as "open surgery" methods, these surgical methods have the attendant disadvantages of requiring general anesthesia and often involve increased operative time, pain, hospitalization, and recovery time due to the extensive soft tissue damage. There is also an increased probability of post-surgical complication associated with open surgery methods, such as nosocomial infection.

Minimally-invasive methods for SI joint stabilization have thus been developed to address the noted disadvantages associated with open surgery methods. Although conventional minimally-invasive SI joint stabilization methods, such as the methods disclosed in U.S. Pub. No. 2009/

0076551 to Petersen, have garnered some success in relieving pain associated with SI joint dysfunction and have effectively addressed many of the disadvantages associated with open surgery methods, there similarly remains many disadvantages associated with conventional minimally-invasive SI joint stabilization methods.

A major disadvantage associated with many conventional minimally-invasive SI joint stabilization methods is that such methods are difficult to perform and, hence, often require extensive, system-specific surgical training and experience. Despite the level of surgical training and experience that surgeons possess, when such conventional minimally-invasive SI joint stabilization methods are employed, there is still a substantial incidence of damage to the lumbosacral neurovascular structures proximate to the SI joint.

A further disadvantage associated with many conventional minimally-invasive SI joint stabilization methods and associated apparatus, i.e., prostheses, such as the methods and prostheses disclosed in U.S. Pub. No. 2009/0076551 to Petersen, is that pre-existing sacral abnormalities can lead to displacement of the implanted prostheses, which can, and often will result in damage to surrounding bone and soft tissue structures and, hence, post-procedure pain.

An additional disadvantage associated with many conventional minimally invasive SI joint stabilization methods is that they comprise anterior or lateral trajectories to the dysfunctional SI joint and, hence, muscles, e.g., gluteal aponeurotic fascia and gluteus medius, and ligaments are typically disrupted, and nerves and blood vessels are susceptible to damage during placement of a prosthesis in a dysfunctional SI joint.

Further, some conventional minimally-invasive SI joint stabilization methods are particularly prone to failure due to displacement of the prostheses in the dysfunctional SI joint and/or failure of the prostheses to effectively engage the SI joint structures, e.g., articular surfaces of the sacrum and/or ilium.

Various "improved" prostheses have thus been developed for use in minimally-invasive SI joint stabilization methods or procedures to effectively engage SI joint structures and maintain engagement thereto during SI joint function.

Although many of the "improved" prostheses, when deployed properly in a dysfunctional SI joint, can, and often will, effectively engage SI joint structures, there remains several disadvantages associated with the prostheses. Illustrative are the prostheses disclosed in U.S. Pat. No. 8,951,254 to Mayer, et al.

The prostheses disclosed in U.S. Pat. No. 8,951,254 comprise or are coated with a liquefiable synthetic polymer that is adapted to liquify upon administration of mechanical energy, e.g., high frequency vibration, when implanted and re-solidify thereafter to securely engage the SI joint structures, i.e., sacrum and ilium.

A major disadvantage associated with the prostheses disclosed in U.S. Pat. No. 8,951,254 is that the liquefiable synthetic polymers, when re-solidified in situ, are structurally inferior to the osseous or bone tissue of the sacrum and ilium. The fusion sites between the articular surfaces of the sacrum and ilium that define the SI joint are, thus, highly susceptible to structural fatigue and failure, which can, and often will, result in misalignment of the SI joint and ultimately increased pain for the subject.

A further disadvantage associated with the prostheses disclosed in U.S. Pat. No. 8,951,254 is that the synthetic liquefiable synthetic polymers are also substantially immunogenic and will induce an adverse immune response when the prostheses are implanted in a dysfunctional SI joint. As is well established, the adverse immune response can, and often will, prevent healing and osteogenic processes, e.g., remodeling of damaged osseous tissue and regeneration of new osseous tissue.

Additional disadvantages associated with the prostheses disclosed in U.S. Pat. No. 8,951,254 and many other prostheses designed for minimally-invasive SI joint stabilization are that the noted prostheses are difficult to accurately place in optimum positions in a dysfunctional SI joint and, in many instances, lack sufficient structural properties, such as rigidity and/or fatigue resistance, to effectively stabilize the dysfunctional SI joint.

It would thus be desirable to provide SI joint stabilization systems, apparatus and methods, which substantially reduce or eliminate the disadvantages associated with conventional SI joint stabilization systems, apparatus and methods.

It is therefore an object of the invention to provide improved SI joint stabilization systems, apparatus and methods, which substantially reduce or eliminate the disadvantages associated with conventional SI joint stabilization systems, apparatus and methods.

It is another object of the invention to provide improved minimally-invasive SI joint stabilization systems and apparatus, which can be readily employed to place prostheses in and, thereby, stabilize dysfunctional SI joints via a posterior trajectory.

It is another object of the invention to provide improved minimally-invasive SI joint stabilization systems, apparatus and methods, which can be readily employed to stabilize dysfunctional SI joints.

It is another object of the invention to provide improved minimally-invasive SI joint stabilization systems, apparatus and methods, which can readily be employed in minimally-invasive SI joint stabilization procedures to stabilize SI joint structures with misplaced or dislodged prior implants; particularly, surgical pins, dowels or screws.

It is another object of the invention to provide improved minimally-invasive SI joint stabilization systems, apparatus and methods, which can readily be employed in minimally-invasive SI joint stabilization procedures and provide supplemental stabilization of SI joint structures with prior implants, such as a surgical pin or screw.

It is another object of the invention to provide improved minimally-invasive SI joint stabilization systems, apparatus and methods, which can readily be employed in conjunction with surgical or orthopedic pins, dowels and screws to provide enhanced stabilization of SI joint structures.

It is another object of the invention to provide improved minimally-invasive SI joint stabilization systems and apparatus, which, when implanted in a dysfunctional SI joint, effectively ameliorate pain associated with the SI joint dysfunction.

It is another object of the invention to provide improved SI joint prostheses that can readily be employed in minimally-invasive SI joint stabilization methods and provide secure engagement to SI joint structures.

It is another object of the invention to provide improved SI joint prostheses that can readily be employed in minimally-invasive SI joint stabilization methods and possess optimal structural properties to effectively stabilize dysfunctional SI joints.

It is yet another object of the invention to provide improved SI joint prostheses that can readily be employed in minimally-invasive SI joint stabilization methods and facilitate remodeling of damaged osseous tissue and regeneration of new osseous tissue and osseous tissue structures.

SUMMARY OF THE INVENTION

The present invention is directed to apparatus, systems and methods for stabilizing dysfunctional SI joints.

In some embodiments, there is thus provided apparatus for stabilizing dysfunctional SI joints.

In some embodiments, the apparatus for stabilizing dysfunctional SI joints comprise a prosthesis assembly.

In one embodiment, a prosthesis assembly for stabilizing a dysfunctional SI joint comprises:

a prosthesis and supplemental bone fixation means, the prosthesis comprising a monolithic structure configured and adapted to be advanced into the dysfunctional SI joint in a posterior trajectory, whereby the prosthesis transfixes and, thereby, stabilizes the dysfunctional SI joint, the prosthesis comprising a first elongated section, a second elongated section, and a bridge section disposed between and connected to the first and second elongated sections, the first elongated section comprising a first open proximal end, a first open distal end, a first plurality of fenestrations, and a first internal lumen that extends from the first open proximal end to the first open distal end of the first elongated section, the second elongated section comprising a second open proximal end, a second open distal end, a second plurality of fenestrations, and a second internal lumen that extends from the second open proximal end to the second open distal end of the second elongated section, the supplemental bone fixation means comprising an expandable member or composition that is configured and adapted to be advanced into the first and second internal lumens of the prosthesis and expand when the prosthesis is advanced into the dysfunctional SI joint, wherein the expandable member or composition enhances fixation of the prosthesis to the dysfunctional SI joint.

In some embodiments, the supplemental bone fixation means comprises a bone stabilization pin configured and adapted to be advanced into and through the first and second internal lumens of the prosthesis, and into the dysfunctional SI joint.

In some embodiments, the bone stabilization pin comprises a plurality of tabs that are adapted to transition from a collapsed configuration to at least a first outwardly projecting configuration when the prosthesis is advanced into the dysfunctional SI joint and the bone stabilizing pin is advanced into the first and second internal lumens of the prosthesis, wherein, when the bone stabilizing pin is advanced into the first internal lumen of the prosthesis, at least a first tab of the plurality of tabs extends through and out of a first fenestration of the first plurality of fenestrations of the prosthesis and fixes the bone stabilizing pin to a first SI joint region in the dysfunctional SI joint and, thereby, enhances fixation of the prosthesis to the dysfunctional SI joint, and when the bone stabilizing pin is advanced into the second internal lumen of the prosthesis, at least a second tab of the plurality of tabs extends through and out of a second fenestration of the second plurality of fenestrations of the prosthesis and fixes the bone stabilizing pin to a second SI joint region in the dysfunctional SI joint and, thereby, enhances fixation of the prosthesis to the dysfunctional SI joint.

In some embodiments, the bone stabilization pin comprises an elongated pin member and an expandable end member adapted to engage the elongated pin member on a distal end, the expandable end member further adapted to transition from a collapsed configuration to an expanded configuration when the prosthesis is advanced into the dysfunctional SI joint, wherein, when the expandable end member is engaged to the bone stabilizing pin and the bone stabilizing pin is advanced into the first or second internal lumen of the prosthesis, wherein the expandable end member extends from the first or second internal lumen of the prosthesis, the expandable end member fixes the bone stabilizing pin to a third SI joint region in the dysfunctional SI joint and, thereby, enhances fixation of the prosthesis to the dysfunctional SI joint.

In some embodiments, the supplemental bone fixation means comprises a phase change osteogenic composition that is adapted to be disposed in the first and second internal lumens of the prosthesis in a fluidized state and transition to a solid state when the prosthesis is advanced into the dysfunctional SI joint, wherein, when the phase change osteogenic composition is disposed in the first internal lumen of the prosthesis, the phase change osteogenic composition flows through and out of at least a first fenestration of the first plurality of fenestrations of the prosthesis, transitions to a solid state and enhances fixation of the prosthesis to the dysfunctional SI joint, and, when the phase change osteogenic composition is disposed in the second internal lumen of the prosthesis, the phase change osteogenic composition flows through and out of at least a second fenestration of the second plurality of fenestrations of the prosthesis, transitions to a solid state and similarly enhances fixation of the prosthesis to the dysfunctional SI joint.

In some embodiments, there is thus also provided systems for stabilizing dysfunctional SI joints.

In one embodiment, a system for stabilizing a dysfunctional SI joint comprises:

a drill guide assembly and a prosthesis assembly, the prosthesis assembly comprising a prosthesis and supplemental bone fixation means, the drill guide assembly adapted to advance toward the dysfunctional SI joint in a posterior trajectory and create a pilot SI joint opening in the dysfunctional SI joint in the posterior trajectory, the prosthesis configured and adapted to be advanced into the pilot SI joint opening in the dysfunctional SI joint in the posterior trajectory, whereby the prosthesis transfixes and, thereby, stabilizes the dysfunctional SI joint, the prosthesis comprising a first elongated section, a second elongated section, and a bridge section disposed between and connected to the first and second elongated sections, the first elongated section comprising a first open proximal end, a first open distal end, a first plurality of fenestrations, and a first internal lumen that extends from the first open proximal end to the first open distal end of the first elongated section, the second elongated section comprising a second open proximal end, a second open distal end, a second plurality of fenestrations, and a second internal lumen that extends from the second open proximal end to the second open distal end of the second elongated section, the supplemental bone fixation means comprising an expandable member or composition that is configured and adapted to be advanced into the first and second internal lumens of the prosthesis and expand when the prosthesis is advanced into the dysfunctional SI joint, wherein the expandable member or composition enhances fixation of the prosthesis to the dysfunctional SI joint.

In some embodiments, the supplemental bone fixation means comprises a bone stabilization pin configured and adapted to be advanced into and through the first and second internal lumens of the prosthesis, and into the dysfunctional SI joint.

In some embodiments, the bone stabilization pin comprises a plurality of tabs that are adapted to transition from a collapsed configuration to at least a first outwardly projecting configuration when the prosthesis is advanced into the dysfunctional SI joint and the bone stabilizing pin is advanced into the first and second internal lumens of the prosthesis, wherein, when the bone stabilizing pin is advanced into the first internal lumen of the prosthesis, at least a first tab of the plurality of tabs extends through and out of a first fenestration of the first plurality of fenestrations of the prosthesis and fixes the bone stabilizing pin to a first SI joint region in the dysfunctional SI joint and, thereby, enhances fixation of the prosthesis to the dysfunctional SI joint, and when the bone stabilizing pin is advanced into the second internal lumen of the prosthesis, at least a second tab of the plurality of tabs extends through and out of a second fenestration of the second plurality of fenestrations of the prosthesis and fixes the bone stabilizing pin to a second SI joint region in the dysfunctional SI joint and, thereby, enhances fixation of the prosthesis to the dysfunctional SI joint.

In some embodiments, the bone stabilization pin comprises an elongated pin member and an expandable end member adapted to engage the elongated pin member on a distal end, the expandable end member further adapted to transition from a collapsed configuration to an expanded configuration when the prosthesis is advanced into the dysfunctional SI joint, wherein, when the expandable end member is engaged to the bone stabilizing pin and the bone stabilizing pin is advanced into the first or second internal lumen of the prosthesis, wherein the expandable end member extends from the first or second internal lumen of the prosthesis, the expandable end member fixes the bone stabilizing pin to a third SI joint region in the dysfunctional SI joint and, thereby, enhances fixation of the prosthesis to the dysfunctional SI joint.

In some embodiments, the supplemental bone fixation means comprises a phase change osteogenic composition that is adapted to be disposed in the first and second internal lumens of the prosthesis in a fluidized state and transition to a solid state when the prosthesis is advanced into the dysfunctional SI joint, wherein, when the phase change osteogenic composition is disposed in the first internal lumen of the prosthesis, the phase change osteogenic composition flows through and out of at least a first fenestration of the first plurality of fenestrations of the prosthesis, transitions to a solid state and enhances fixation of the prosthesis to the dysfunctional SI joint, and, when the phase change osteogenic composition is disposed in the second internal lumen of the prosthesis, the phase change osteogenic composition flows through and out of at least a second fenestration of the second plurality of fenestrations of the prosthesis, transitions to a solid state and similarly enhances fixation of the prosthesis to the dysfunctional SI joint.

In a preferred embodiment, the drill guide assembly comprises a guide pin, drill guide, drill guide insert and bone dislodging member,

- the guide pin configured and adapted to be advanced into a desired target position in the dysfunctional SI joint to guide the drill guide thereto,
- the drill guide comprising first and second drill guide fixation sub-systems,
- the first drill guide fixation sub-system comprising a plurality of first drill guide lumens configured and adapted to receive a plurality of K-wires therein, the plurality of K-wires configured and adapted to pierce and engage first and second bone structures of the dysfunctional SI joint,
- the second drill guide fixation sub-system comprising a K-wire pin member and a temporary fixation pin, the K-wire pin member and the temporary fixation pin adapted to pierce and engage the first and second bone structures of the dysfunctional SI joint,
- the drill guide further comprising a prosthesis internal access opening sized and configured to receive the drill guide insert and monolithic member therein,
- the drill guide insert comprising a second and third drill guide lumens, the second and third drill guide lumens adapted to receive the K-wire pin member, the temporary fixation pin, and the bone dislodging member therein,
- the bone dislodging member adapted to dislodge portions of bone in the dysfunctional SI joint to create the pilot SI joint opening in the dysfunctional SI joint.

In some embodiments, the system further comprises a prosthesis deployment assembly configured and adapted to engage the prosthesis and guide the prosthesis into and through the drill guide and into the dysfunctional SI joint.

In some embodiments, the system further comprises a bone harvester assembly adapted to extract and collect the dislodged portions of bone from the bone dislodging member during creation of the pilot SI joint in the dysfunctional SI joint.

In some embodiments, there is also provided methods for stabilizing dysfunctional SI joints.

In one embodiment, a method for stabilizing a dysfunctional SI joint comprises the following steps:

(i) providing a drill guide assembly adapted to advance toward the dysfunctional SI joint in a posterior trajectory and create a pilot SI joint opening in the dysfunctional SI joint in the posterior trajectory;

(ii) providing a prosthesis assembly comprising a prosthesis and supplemental bone fixation means, the prosthesis configured and adapted to be advanced into the pilot SI joint opening in the dysfunctional SI joint created by the drill guide assembly in the posterior trajectory, whereby the prosthesis stabilizes the dysfunctional SI joint,

- the prosthesis comprising a first elongated section, a second elongated section, and a bridge section disposed between and connected to the first and second elongated sections,
- the first elongated section comprising a first open proximal end, a first open distal end, a first plurality of fenestrations, and a first internal lumen that extends from the first open proximal end to the first open distal end of the first elongated section,
- the second elongated section comprising a second open proximal end, a second open distal end, a second plurality of fenestrations, and a second internal lumen that extends from the second open proximal end to the second open distal end of the second elongated section,
- the supplemental bone fixation means comprising a bone stabilization pin configured and adapted to be advanced into and thorough the first and second internal lumens of the prosthesis, and into the dysfunctional SI joint;

(iii) advancing the prosthesis into the pilot SI joint opening in the dysfunctional SI joint in the posterior trajectory; and (iv) advancing the bone stabilizing pin into the first or second internal lumen of the prosthesis, wherein the bone stabilizing pin expands and enhances fixation of the prosthesis to the dysfunctional SI joint.

In some embodiments, the bone stabilization pin comprises a plurality of tabs that are adapted to transition from a collapsed configuration to at least a first outwardly projecting configuration when the prosthesis is advanced into the dysfunctional SI joint and the bone stabilizing pin is advanced into the first and second internal lumens of the prosthesis, wherein, when the bone stabilizing pin is advanced into the first internal lumen of the prosthesis, at least a first tab of the plurality of tabs extends through and out of a first fenestration of the first plurality of fenestrations of the prosthesis and fixes the bone stabilizing pin to a first SI joint region in the dysfunctional SI joint and, thereby, enhances fixation of the prosthesis to the dysfunctional SI joint, and when the bone stabilizing pin is advanced into the second internal lumen of the prosthesis, at least a second tab of the plurality of tabs extends through and out of a second fenestration of the second plurality of fenestrations of the prosthesis and fixes the bone stabilizing pin to a second SI joint region in the dysfunctional SI joint and, thereby, enhances fixation of the prosthesis to the dysfunctional SI joint.

In some embodiments, the bone stabilization pin comprises an elongated pin member and an expandable end member adapted to engage the elongated pin member on a distal end, the expandable end member further adapted to transition from a collapsed configuration to an expanded configuration when the prosthesis is advanced into the dysfunctional SI joint, wherein, when the expandable end member is engaged to the bone stabilizing pin and the bone stabilizing pin is advanced into the first or second internal lumen of the prosthesis, wherein the expandable end member extends from the first or second internal lumen of the prosthesis, the expandable end member fixes the bone stabilizing pin to a third SI joint region in the dysfunctional SI joint and, thereby, enhances fixation of the prosthesis to the dysfunctional SI joint.

In another embodiment, a method for stabilizing a dysfunctional SI joint comprises the following steps:

(i) providing a drill guide assembly adapted to advance toward the dysfunctional SI joint in a posterior trajectory and create a pilot SI joint opening in the dysfunctional SI joint in the posterior trajectory;

(ii) providing a prosthesis assembly comprising a prosthesis and supplemental bone fixation means, the prosthesis configured and adapted to be advanced into the pilot SI joint opening in the dysfunctional SI joint created by the drill guide assembly in the posterior trajectory, whereby the prosthesis stabilizes the dysfunctional SI joint, the prosthesis comprising a first elongated section, a second elongated section, and a bridge section disposed between and connected to the first and second elongated sections, the first elongated section comprising a first open proximal end, a first open distal end, a first plurality of fenestrations, and a first internal lumen that extends from the first open proximal end to the first open distal end of the first elongated section, the second elongated section comprising a second open proximal end, a second open distal end, a second plurality of fenestrations, and a second internal lumen that extends from the second open proximal end to the second open distal end of the second elongated section, the supplemental bone fixation means comprising a phase change osteogenic composition that is adapted to be disposed in the first and second internal lumens of the prosthesis in a fluidized state and transition to a solid state when the prosthesis is advanced into the dysfunctional SI joint;

(iii) inserting the phase change osteogenic composition into the first or second internal lumen of the prosthesis; and (iv) advancing the prosthesis into the pilot SI joint opening in the dysfunctional SI joint in the posterior trajectory, wherein, when the phase change osteogenic composition is disposed in the first internal lumen of the prosthesis, the phase change osteogenic composition flows through and out of at least a first fenestration of the first plurality of fenestrations of the prosthesis, transitions to a solid state and enhances fixation of the prosthesis to the dysfunctional SI joint, and, when the phase change osteogenic composition is disposed in the second internal lumen of the prosthesis, the phase change osteogenic composition flows through and out of at least a second fenestration of the second plurality of fenestrations of the prosthesis, transitions to a solid state and similarly enhances fixation of the prosthesis to the dysfunctional SI joint.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 321 is a CT scan image showing a trajectory inlet view of the dysfunctional SI joint shown in FIG. 32B, showing a SI joint prosthesis properly positioned therein, in accordance with the invention.

DETAILED DESCRIPTION OF THE PREFERRED EMBODIMENT

Figure 1A:
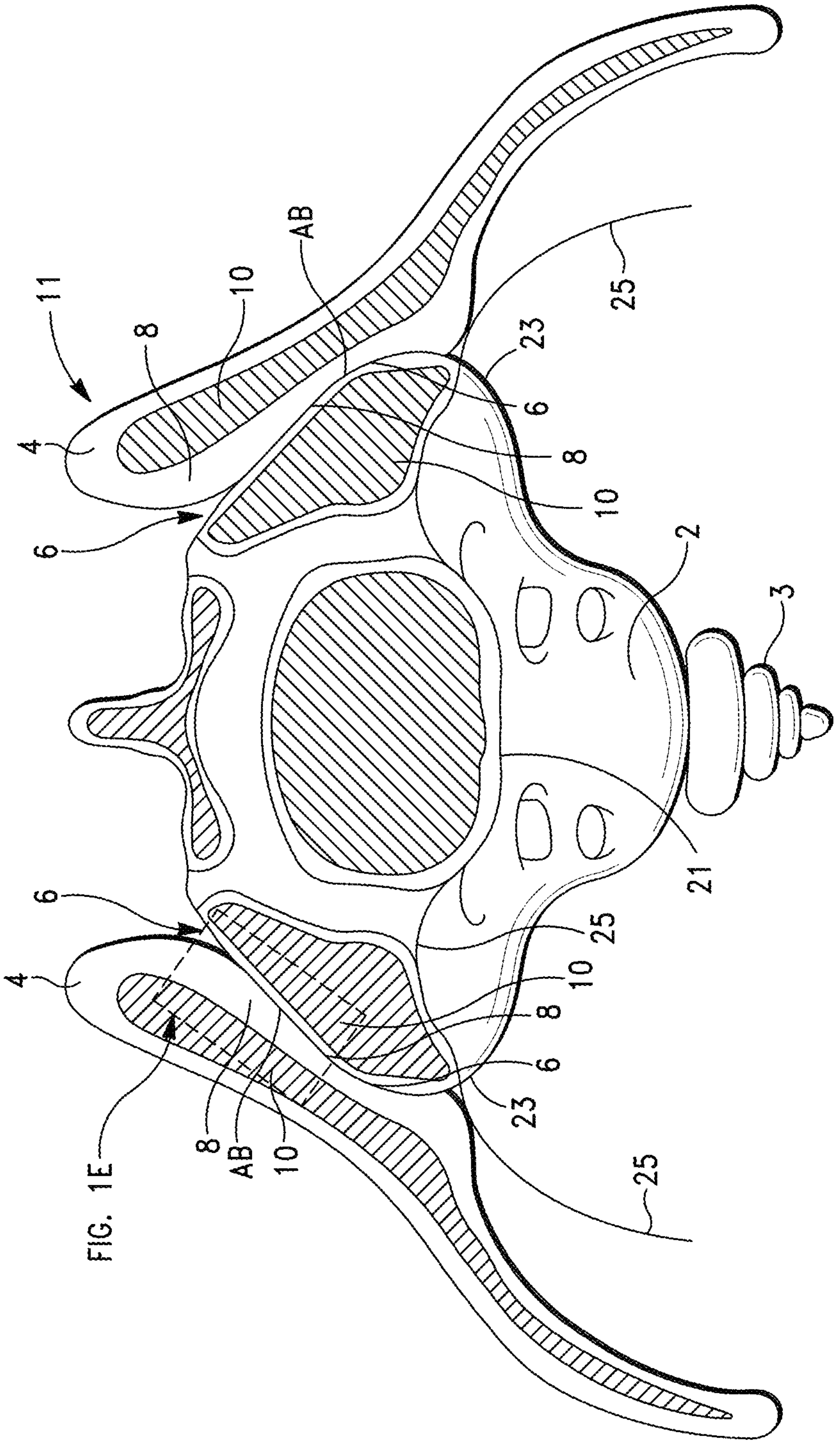
FIG. 1A is a schematic illustration of a human pelvic region from an anteroposterior (AP) perspective showing the SI joints thereof.

Before describing the present invention in detail, it is to be understood that this invention is not limited to particularly exemplified apparatus, systems, structures or methods as such may, of course, vary. Thus, although a number of apparatus, systems, structures and methods similar or equivalent to those described herein can be used in the practice of the present invention, the preferred apparatus, systems, structures and methods are described herein.

It is also to be understood that, although the present invention is described and illustrated in connection with SI joint stabilization, fixation and fusion procedures, the invention is not limited to such procedures. According to the invention, the apparatus, systems, structures and methods of the invention can also be employed to stabilize and/or fuse other articulating bone structures, including, without limitation, spinal vertebrae, tarsal bones and the like.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a," "an" and "the" include plural referents unless the content clearly dictates otherwise. Thus, for example, reference to "an incision" includes two or more incisions and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

Definitions

The terms "sacroiliac joint", "SI joint", "sacroiliac junction" and "SI junction" are used interchangeably herein, and mean and include any region proximate to articulating regions of the sacrum and ilium bone structures and, hence, a junction between and defined by sacrum and ilium bone structures.

The term "dysfunctional" as used in connection with a SI joint, means and includes a physiological abnormality, disorder or impairment of an SI joint, including, but limited to, traumatic fracture dislocation of the pelvis, degenerative arthritis, sacroiliitis, i.e., an inflammation or degenerative condition of the SI joint; osteitis condensans ilii, and other degenerative conditions of SI joint bone structures.

It is to be understood that the terms "SI joint" and "dysfunctional SI joint" are used interchangeably herein and are not to be construed as limiting in any manner unless expressly stated as such. Thus, although a SI joint stabilization, fixation and fusion procedure may, in some instances herein, be described in connection with a "SI joint", the term "SI joint" also means and includes a "dysfunctional SI joint" unless expressly stated otherwise.

The terms "articular surface" and "articulating surface" are used interchangeably herein in connection with bone structures; particularly, the sacrum and ilium bone structures of a SI joint, and mean and include a surface of a bone structure that forms an articulating junction (i.e., a synovial joint) with an adjacent bone structure, e.g., the articular surfaces of the sacrum and ilium bone structures.

The terms "fusion" and "arthrodesis" are used interchangeably herein in connection with bone structures, and mean and include partial or complete immobilization of adjacent bone structures; particularly, the sacrum and ilium bone structures of a SI joint; particularly, a dysfunctional SI joint.

The term "stabilization", as used herein, means and includes reinforcing, e.g., supporting, or modulating motion of adjacent articular bone structures; particularly, the sacrum and ilium bone structures of a SI joint. The term "stabilization", thus, in some instances, means and includes fusion and arthrodesis of adjacent bone structures.

The term "transfix", as used herein in connection with a SI joint, means and includes stabilization of the SI joint via advancement of a prosthesis of the invention into the SI joint and/or the position of the prosthesis after being advanced into a SI joint; particularly, a dysfunctional SI joint, wherein the prosthesis intersects (i.e., passes through) the axial and sagittal plans of the ilium and sacrum bone structures of the dysfunctional SI joint, whereby the SI joint is rendered motionless along its longitudinal axis.

The terms "prosthesis" and "SI joint prosthesis" are used interchangeably herein, and mean and include an apparatus or system configured and adapted to stabilize or modulate motion of articulating bone structures; particularly, the sacrum and ilium bone structures of a SI joint.

The term "biodegradable", as used herein, means the ability of a material; particularly, a polymer or adhesive, to breakdown and be absorbed within the physiological environment of a SI joint and/or a structure associated therewith, including sacrum and ilium bone structures, by one or more physical, chemical, or cellular processes.

Biodegradable polymers, according to the invention, thus include, without limitation, polylactide polymers (PLA), copolymers of lactic and glycolic acids, including poly (lactic-co-glycolic) acid (PLGA) and poly(¿-caprolactone-co-L-lactic) acid (PCL-LA); glycine/PLA co-polymers, polyethylene oxide (PEO)/PLA block copolymers, acetylated polyvinyl alcohol (PVA)/polycaprolactone copolymers, poly(glycerol sebacate) (PGS) and its derivatives, including poly(glycerol-co-sebacate acrylate) (PGSA); poly (polyol sebacate) (PPS), poly(xylitol sebacate) (PXS), poly (xylitol glutamate sebacate) (PXGS), hydroxybutyrate-hydroxyvalerate copolymers, polyesters such as, but not limited to, aspartic acid and different aliphatic diols; poly (alkylene tartrates) and their copolymers with polyurethanes, polyglutamates with various ester contents and with chemically or enzymatically degradable bonds, other biodegradable nonpeptidic polyamides, amino acid polymers, polyanhydride drug carriers such as, but not limited to, poly(sebacic acid) (PSA); aliphatic-aromatic homopolymers, and poly(anhydride-co-imides), poly(phosphoesters) by matrix or pendant delivery systems, poly(phosphazenes), poly(iminocarbonate), crosslinked poly(ortho ester), hydroxylated polyester-urethanes, or the like.

Biodegradable adhesives, according to the invention, thus include, without limitation, poly(glycerol-co-sebacate acrylate) (PGSA), poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol, and combinations thereof; fibrin-based compositions, collagen-based compositions, including collagen/poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and OctylSeal); poly(ethylene glycol) (PEG) based compositions, including FocalSeal®, Progel™ Duraseal™, DuraSeal™ Xact, Coseal® and ReSure Sealant; polysaccharide-based compositions, polypeptide-based compositions, and combinations thereof.

The term "osteogenic composition", as used herein, means and includes an agent or composition that induces or modulates an osteogenic physiological or biological process, or cellular activity, e.g., induces proliferation, and/or growth and/or remodeling and/or regeneration of bone or osseous tissue.

The term "osteogenic composition" thus means and includes, without limitation, the following osteogenic materials and compositions comprising same: demineralized bone matrix, autograft bone material, allograft bone material, xenograft bone material, polymethyl-methacrylate, calcium-based bone void filler material, including hydroxyapatite (HA), α-tricalcium phosphate (α-TCP), and tricalcium phosphate (TCP); and combinations or mixtures thereof.

The term "osteogenic composition" also means and includes, without limitation, the following polymer materials and compositions comprising same: poly(glycerol sebacate) (PGS), poly(glycerol-co-sebacate) acrylate (PGSA) and co-polymers, such as poly(glycerol sebacate)-co-poly (ethylene glycol) (PGS-PEG); and/or composites thereof, e.g., PGS-hydroxyapatite (HA) composites and PGS-poly (ε-caprolactone) (PGS-PCL) composites.

The term "osteogenic composition" also means and includes, without limitation, acellular extracellular matrix (ECM) derived from mammalian tissue sources.

The term "osteogenic composition" thus means and includes, without limitation, acellular ECM derived from bone or osseous tissue, small intestine submucosa (SIS), epithelium of mesodermal origin, i.e., mesothelial tissue, placental tissue, omentum tissue, and combinations thereof.

In some embodiments, the term "osteogenic composition" also means and includes, without limitation, the aforementioned biodegradable polymers, biodegradable adhesives, and compositions formed therewith.

The terms "biologically active agent" and "biologically active composition" are used interchangeably herein, and mean and include agent or composition that induces or modulates a physiological or biological process, or cellular activity, e.g., induces proliferation, and/or growth and/or regeneration of tissue, including osseous tissue.

The terms "biologically active agent" and "biologically active composition", as used herein, thus include agents and compositions that can be varied in kind or amount to provide a therapeutic level effective to mediate the formation or healing of osseous tissue, cartilage and connective tissue, e.g., tendons and ligaments. The term "biologically active composition", in some instances, thus means and includes an "osteogenic composition."

The terms "biologically active agent" and "biologically active composition" thus mean and include, without limitation, the following bone morphogenic proteins (BMPs) and compositions comprising same: BMP-1, BMP2a, BMP2b, BMP3, BMP4, BMP5, BMP6, BMP7 (also referred to as osteogenic protein 1 (OP-1)) and BMP8a.

The terms "biologically active agent" and "biologically active composition" also mean and include, without limitation, the following biological agents and compositions comprising same: platelet derived growth factor (PDGF), an insulin-like growth factor (IGF), including IGF-1 and IGF-2; basic fibroblast growth factor (bFGF) (also referred to as FGF2), transforming growth factor-β (TGF-β), including, TGF-β1 and TGF-β2; a growth hormone (GH), parathyroid hormone (PTH, including PTH1-34), transforming growth factor-α (TGF-α), granulocyte/macrophage colony stimulating factor (GM-CSF), epidermal growth factor (EGF), growth and differentiation factor-5 (GDF-5), vascular endothelial growth factor (VEGF), angiogenin, angiopoietin-1, del-1, follistatin, granulocyte colony-stimulating factor (G-CSF), hepatocyte growth factor/scatter factor (HGF/SF), interleukin-8 (IL-8), interleukin-10 (IL-10), leptin, midkine, placental growth factor, platelet-derived endothelial cell growth factor (PD-ECGF), platelet-derived growth factor-BB (PDGF-BB), pleiotrophin (PTN), progranulin, proliferin, a matrix metalloproteinase (MMP), angiopoietin 1 (ang1), angiopoietin 2 (ang2) and delta-like ligand 4 (DLL4).

The terms "biologically active agent" and "biologically active composition" also mean and include, without limitation, the following cells and compositions comprising same: bone marrow-derived progenitor cells, bone marrow stromal cells (BMSCs), osteoprogenitor cells, osteoblasts, osteocytes, osteoclasts, committed or partially committed cells from the osteogenic or chondrogenic lineage, hematopoietic stem cells, chondrocytes, chondrogenic progenitor cells (CPCs), mesenchymal stem cells (MSCs) and embryonic stem cells.

The terms "biologically active agent" and "biologically active composition" also mean and include an "extracellular vesicle (EV)", "exosome", "microsome" or "micro-vesicle", which are used interchangeably herein, and mean and include a biological structure formed from a hydrocarbon monolayer or bilayer configured to contain or encase a composition of matter.

The terms "extracellular vesicle (EV)", "exosome", "microsome" and "micro-vesicle" thus include, without limitation, a biological structure formed from a lipid layer configured to contain or encase biologically active agents and/or combinations thereof.

The terms "extracellular vesicle (EV)", "exosome", "microsome" and "micro-vesicle" also include, without limitation, EVs derived from the aforementioned cells and compositions comprising same, e.g., BMSC-derived EVs.

The terms "pharmacological agent" and "active agent" are used interchangeably herein, and mean and include an agent, drug, compound, composition or mixture thereof, including its formulation, which provides some therapeutic, often beneficial, effect. This includes any physiologically or pharmacologically active substance (or composition comprising same) that produces a localized or systemic effect or effects in animals, including warm blooded mammals.

The terms "pharmacological agent" and "active agent" thus mean and include, without limitation, the following osteoinductive agents and compositions comprising same: icaritin, tumor necrosis factor alpha (TNF-α) inhibitors, including etanercept and infliximab, disease-modifying anti-rheumatic drugs (DMARDs), including methotrexate and hydroxychloroquine, antibiotics, anti-viral agents, steroidal anti-inflammatoires, non-steroidal anti-inflammatoirenti-thrombotic agents, including anti-coagulants and anti-platelet agents, and vasodilating agents.

The terms "pharmacological agent" and "active agent" further mean and include, without limitation, the following bisphosphonate agents and compositions comprising same: risedronate (Actonel®), alendronate (Fosamax®), ibandronate (Boniva®), zoledronic acid (Reclast®), pamidronate (Aredia®) and etidronate (Didronel®).

The terms "pharmacological agent" and "active agent" further mean and include, without limitation, the following antibiotics and compositions comprising same: penicillin, carboxypenicillins, such as ticarcillin; tetracyclines, such as minocycline; gentamicin, vancomycin, ciprofloxacin, amikacin, aminoglycosides, cephalosporins, clindamycin, erythromycin, fluoroquinolones, macrolides, azolides, metronidazole, trimethoprim-sulfamethoxazole, polymyxin B, oxytetracycline, tobramycin, cefazolin and rifampin.

The terms "anti-inflammatory" and "anti-inflammatory agent" are also used interchangeably herein, and mean and include a "pharmacological agent", which, when a therapeutically effective amount is administered to a subject, prevents or treats bodily tissue inflammation, i.e., the protective tissue response to injury or destruction of tissues, which serves to destroy, dilute, or wall off both the injurious agent and the injured tissues.

Anti-inflammatory agents thus include, without limitation, dexamethasone, betamethasone, prednisone, prednisolone, methylprednisolone sodium succinate, methylprednisolone, cortisone, ketorolac, diclofenac and ibuprofen.

The terms "pharmacological agent" and "active agent" further mean and include, without limitation, the following metal-based antimicrobials and compositions comprising same: silver particles, copper particles, cobalt particles, nickel particles, zinc particles, zirconium particles, molybdenum particles, lead particles and mixtures thereof.

As indicated above, the term "pharmacological composition", as used herein, means and includes a composition comprising a "pharmacological agent" and "active agent".

The term "therapeutically effective", as used herein, means that the amount of the "pharmacological agent" and/or "pharmacological composition" and/or "biologically active agent" and/or "biologically active composition" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "one embodiment", "one aspect", and "an embodiment" and "an aspect", as used herein, mean that a particular feature, structure, or characteristic described in connection with the embodiment may be included in at least one embodiment and not that any particular embodiment is required to have a particular feature, structure or characteristic described herein unless set forth in the claim.

The phrase "in one embodiment" or similar phrases employed herein do not limit the inclusion of a particular element of the invention to a single embodiment. The element may thus be included in other, or all embodiments discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, a structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present invention is directed to apparatus, systems and methods for stabilizing dysfunctional SI joints.

In some embodiments of the invention, there are thus provided apparatus (referred to herein as "prostheses" and "SI joint prostheses") that can be readily employed in minimally-invasive procedures to stabilize dysfunctional SI joints.

In some embodiments of the invention, there are also provided apparatus (referred to herein as "prosthesis assemblies" and "SI joint prosthesis assemblies") that also can be readily employed in minimally-invasive procedures to stabilize dysfunctional SI joints.

Figure 11:
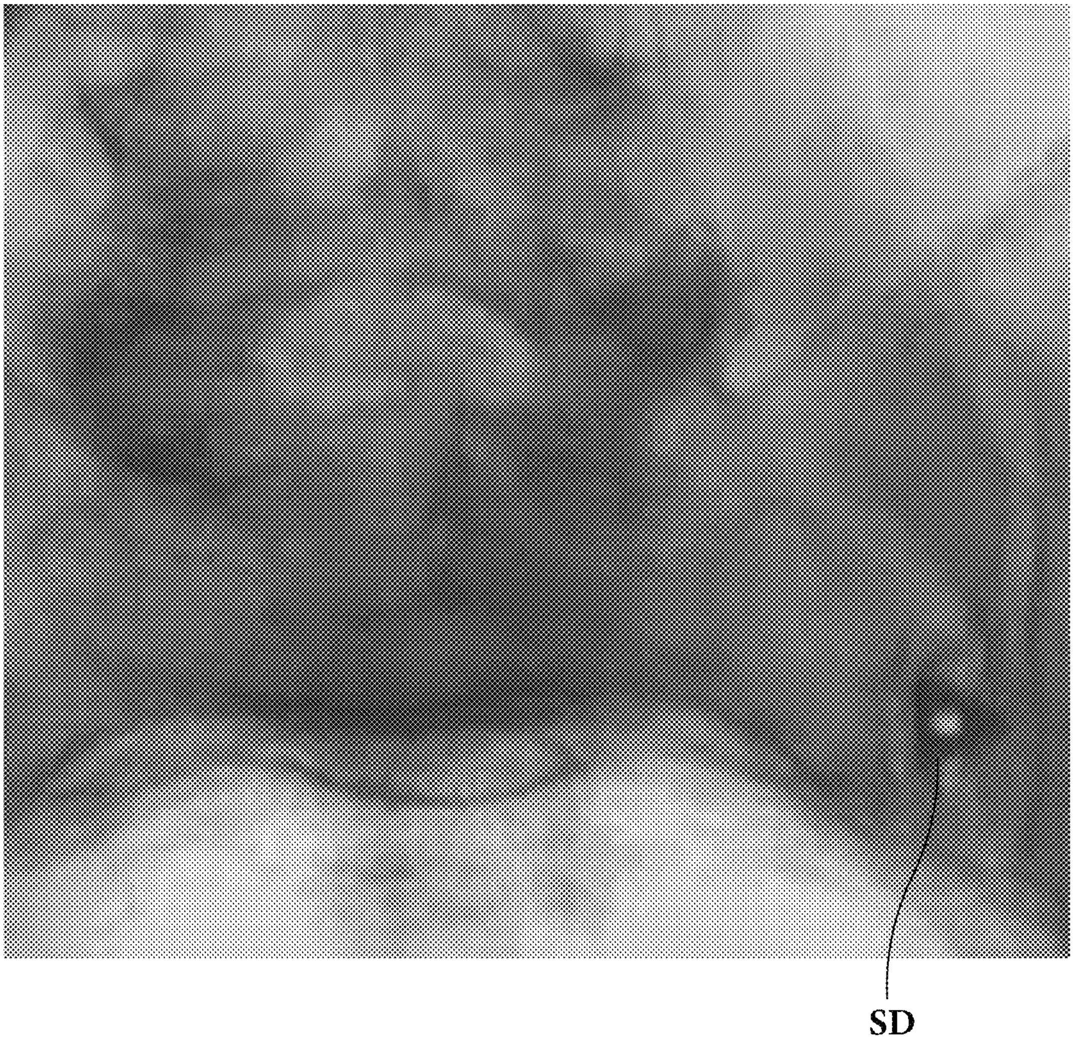
FIG. 11 is a CT scan of a SI joint from a posterior perspective with a surgical dowel implanted therein.
Figure 12:
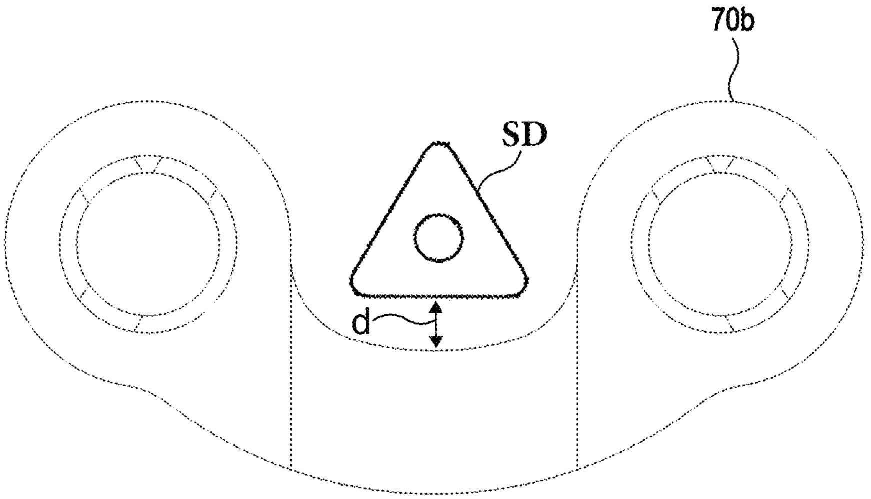
FIG. 12 is an illustration of the prosthesis shown in FIG. 3A with a surgical implant, i.e., surgical dowel, disposed between the elongated sections thereof, in accordance with the invention.

As discussed in detail herein, the SI joint prostheses and SI joint prosthesis assemblies can also be readily employed in minimally-invasive procedures to provide supplemental stabilization of SI joint structures with prior implants, such as a surgical dowel shown in FIGS. 11 and 12 (and denoted "SD").

According to the invention, the SI joint prostheses and SI joint prosthesis assemblies can also be readily employed in conjunction with surgical or orthopedic pins, dowels and screws to provide enhanced stabilization of SI joint structures.

As also discussed in detail herein, the SI joint prostheses, separately and as part of a SI joint prosthesis assembly, are specifically configured and adapted to be advanced into a dysfunctional SI joint in a posterior trajectory, whereby the SI joint prostheses transfix, and, thereby, stabilize the dysfunctional SI joint.

In some embodiments of the invention, there are thus also provided minimally-invasive systems for stabilizing dysfunctional SI joints. As indicated above, in a preferred embodiment, the minimally-invasive systems (also referred to herein as "minimally-invasive SI joint stabilization systems") can be readily employed in minimally-invasive methods or procedures to stabilize dysfunctional SI joints via a posterior trajectory.

As indicated above, SI joint stabilization (and, hence, treatment), including minimally-invasive SI joint stabilization, typically comprises surgical placement of a bone structure prosthesis proximate to or in a dysfunctional SI joint via anterior or lateral trajectories.

From the perspective of FIG. 1A, an anterior trajectory to the SI joint 6 shown in FIG. 1A (and, hence, a dysfunctional SI joint) would be substantially perpendicular to the page upon which FIG. 1A is printed.

Figure 1B:
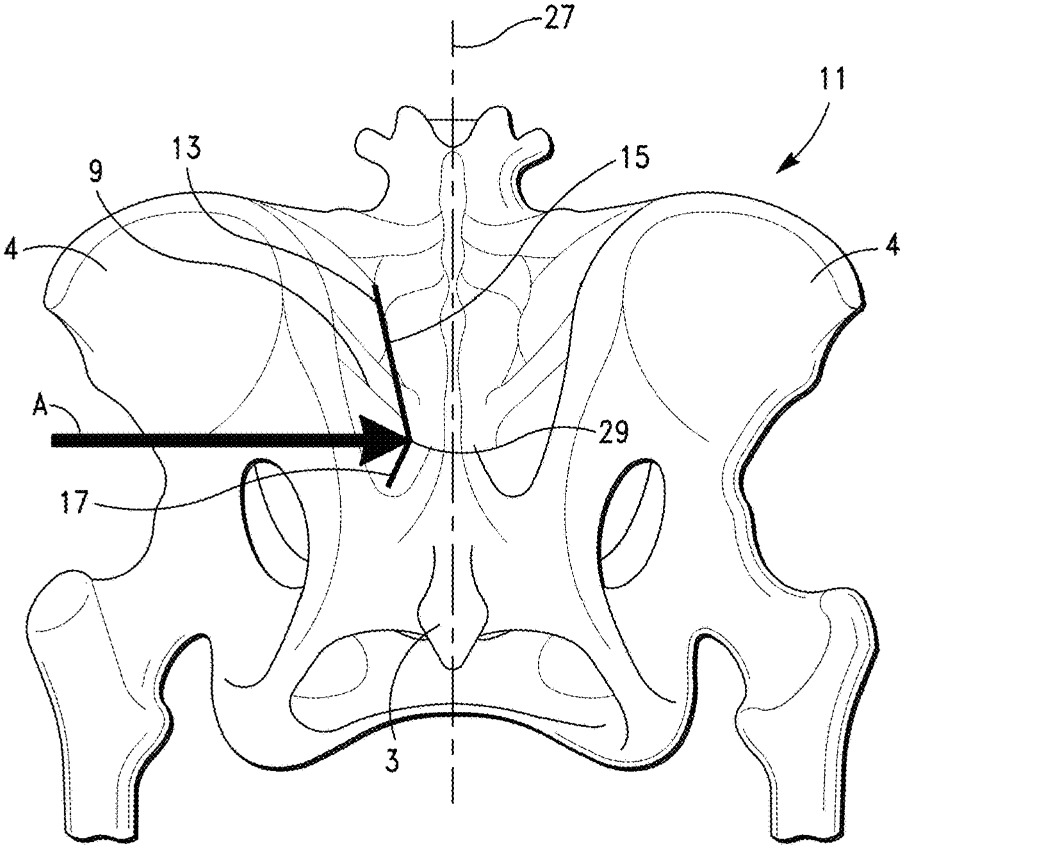
FIG. 1B is another schematic illustration of a human pelvic region from a posterior perspective showing the adjoining sacrum and ilium bone structures, and ligamentous structures thereof.

Referring to FIG. 1B, a lateral trajectory to the SI joint 6 is denoted by arrow "A."

Figure 1C:
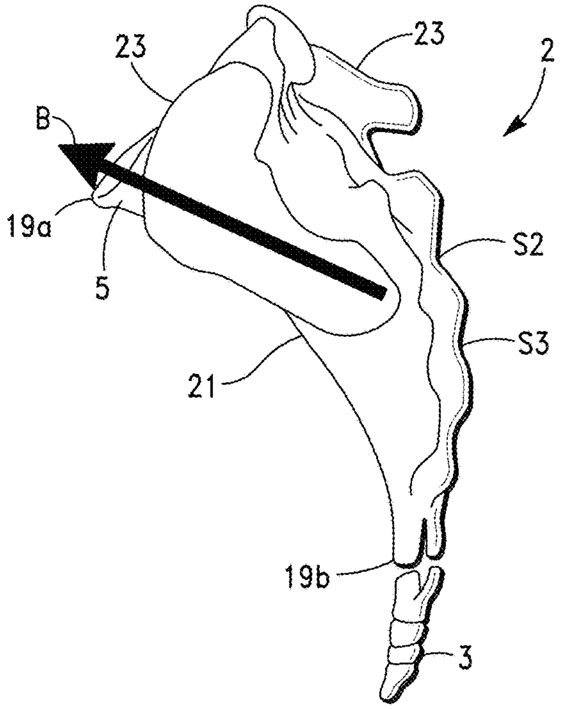
FIG. 1C is a schematic illustration of the sacrum and coccyx from a lateral perspective showing the sacral promontory and the articular surface of sacrum.
Figure 1D:
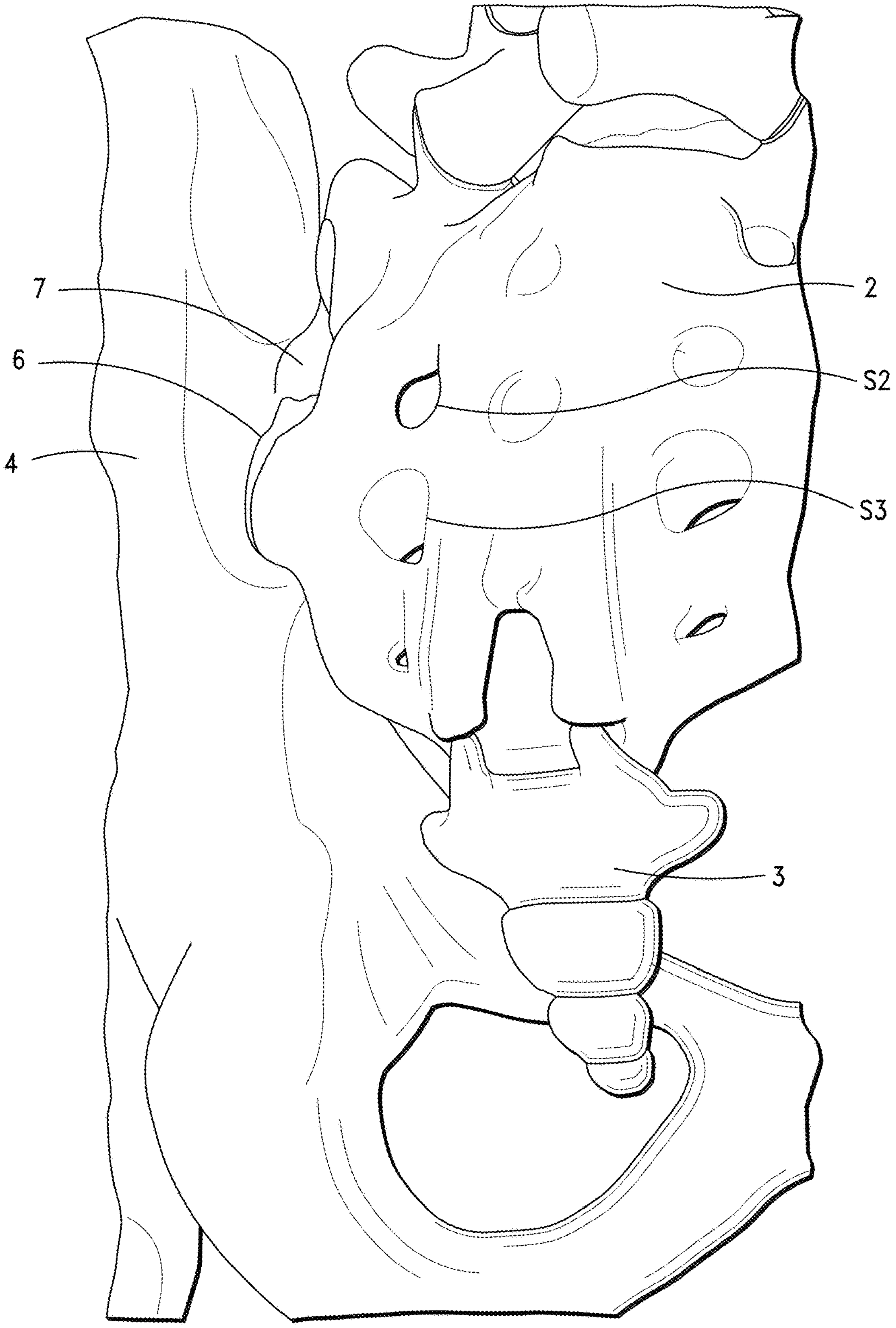
FIG. 1D is another schematic illustration of a human pelvic region from a posterior inferior perspective showing the adjoining sacrum and ilium bone structures of an SI joint, and an SI joint dorsal recess between the sacrum and ilium bone structures.
Figure 1E:
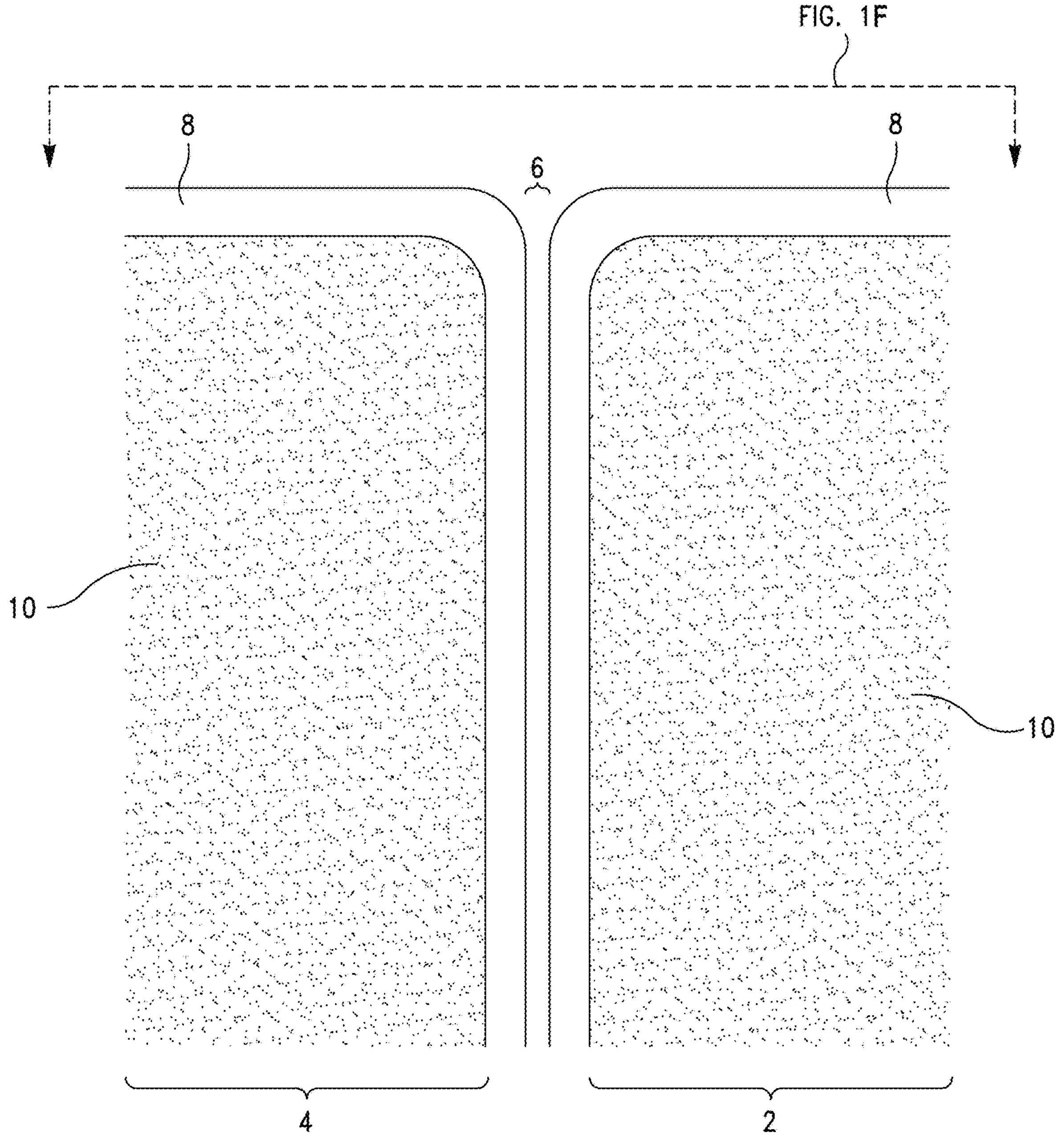
FIG. 1E is an illustration of a SI joint from a superior perspective showing the adjoining sacrum and ilium articular surfaces.

Referring now to FIG. 1E, there is shown an illustration of a portion of the leftmost SI joint 6 illustrated in FIG. 1A. For illustrative simplicity, a uniform layer of cortical bone 8 is shown adjacent a deeper layer of trabecular bone 10 on both of the depicted sacrum 2 and ilium 4 structures. However, in actuality, such layers are far less uniform, and homogeneous.

Figure 1F:
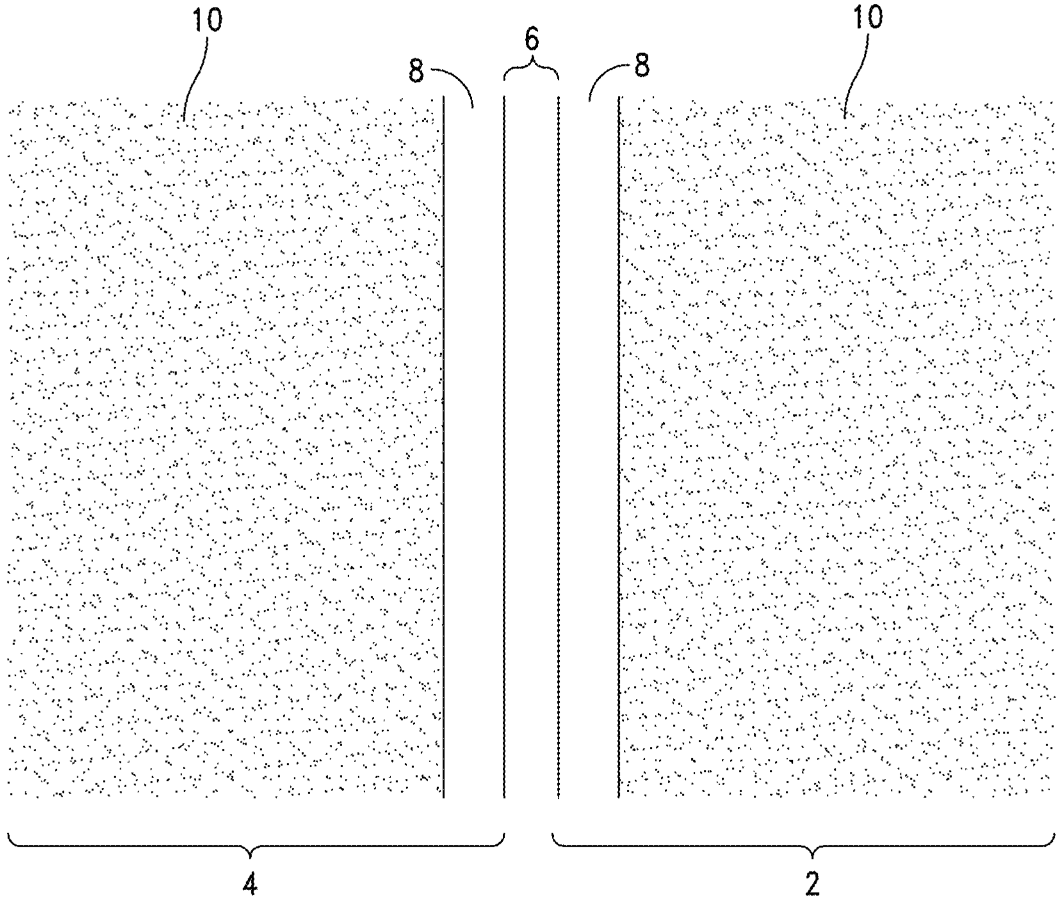
FIG. 1F is another illustration of a SI joint from a posterior perspective showing the adjoining sacrum and ilium articular surfaces.
Figure 1G:
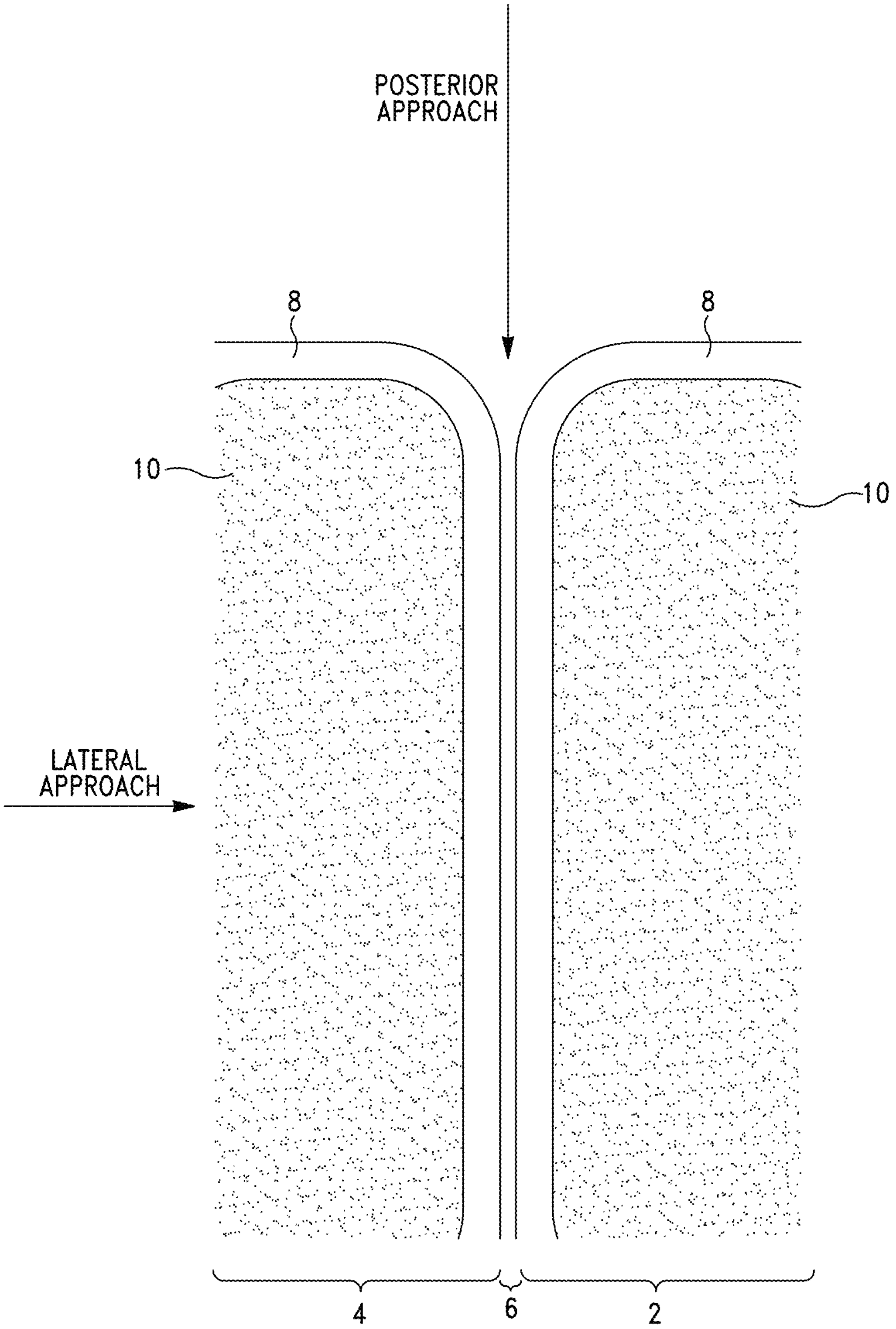
FIG. 1G is a further illustration of the SI joint shown in FIG. 1F showing lateral and posterior approaches to the SI joint, in accordance with the invention.

Referring now to FIG. 1F, there is shown a view of the same structure from a different posterior perspective. From the perspective of FIG. 1F, a posterior approach or trajectory to the SI joint 6 (and, hence, a dysfunctional SI joint) would be substantially perpendicular to the page upon which FIG. 1F is printed. Indeed, referring to FIG. 1G, a variation similar to that depicted in FIG. 1E is illustrated, showing an approximate approach vector for a lateral trajectory to the SI joint 6 versus a posterior trajectory, using the orientation paradigms introduced in FIGS. 1A and 1F-1G. Such paradigms are used to illustrate various embodiments of the subject invention in various figures that follow FIGS. 1A and 1F-1G.

As indicated above, a major disadvantage associated with many conventional anterior and lateral trajectories to a dysfunctional SI joint is that muscles and ligaments are typically disrupted and often damaged. Nerves and blood vessels are also susceptible to damage during such SI joint stabilization methods.

In contrast, a posterior trajectory; particularly, an inferior-posterior trajectory, such as illustrated in FIG. 1C and denoted by arrow "B", of SI joint prostheses of the invention to a dysfunctional SI joint is much less invasive. Indeed, less tissue and fewer muscles are disrupted, and nerves and large blood vessels are avoided. The SI joint prostheses, when advanced into a dysfunctional SI joint, are also transfixed to optimal regions of cortical bone proximate the dysfunctional SI joint and, thereby, provide superior arthrodesis of the dysfunctional SI joint.

As indicated above, in some embodiments, there are provided SI joint prostheses and SI joint prosthesis assemblies that that can be readily employed in minimally-invasive procedures to stabilize dysfunctional SI joints.

As also indicated above and discussed in detail below, in a preferred embodiment, the SI joint prosthesis assemblies comprise a SI joint prosthesis and supplemental bone fixation means, the SI joint prostheses, separately and as part of a SI joint prosthesis assembly, being configured and adapted to be advanced into a dysfunctional SI joint in a posterior trajectory, whereby the SI joint prostheses transfix, and, thereby, stabilize the dysfunctional SI joint.

As also indicated above and discussed in detail below, in some embodiments, there are also provided minimally-invasive systems for stabilizing dysfunctional SI joints. In a preferred embodiment of the invention, the SI joint stabilization systems of the invention generally comprise (i) a drill guide assembly configured and adapted to access the target dysfunctional SI joint in a posterior trajectory and create at least one pre-determined opening in the dysfunctional SI joint (referred to herein after as a "pilot SI joint opening"), and (ii) a SI joint prosthesis or a SI joint prosthesis assembly comprising a SI joint prosthesis, the SI joint prosthesis configured and adapted to be advanced into the pilot SI joint opening in a posterior trajectory, whereby the SI joint prosthesis stabilizes the dysfunctional SI joint when advanced therein.

In some embodiments of the invention, the SI joint stabilization systems further comprise a prosthesis deployment assembly configured and adapted to engage the SI joint prosthesis and advance the SI joint prosthesis into the dysfunctional SI joint.

The SI joint prostheses, SI joint prosthesis assemblies and drill guide assemblies, and a preferred prosthesis deployment assembly of the invention will now be described in detail.

Although the terms "SI joint prosthesis", "SI joint prostheses" and "SI joint assemblies" are used herein to describe apparatus, systems and methods to stabilize dysfunctional SI joints, the terms "SI joint prosthesis", "SI joint prostheses" and "SI joint assemblies", as used herein to describe apparatus, systems and methods to stabilize dysfunctional SI joints, are not meant to and, hence, should not be construed as apparatus and systems configured and adapted to solely stabilize dysfunctional SI joint. Indeed, according to the invention, the apparatus and systems described as "SI joint prosthesis", "SI joint prostheses" and "SI joint assemblies" can readily be employed to stabilize other orthopedic structures.

SI Joint Prostheses

Referring first to FIGS. 2A-2H, there is shown one embodiment of a SI joint prosthesis of the invention that is particularly suitable for advancement into pilot SI joint openings and, thereby, dysfunctional SI joints in a posterior trajectory.

Figure 2A:
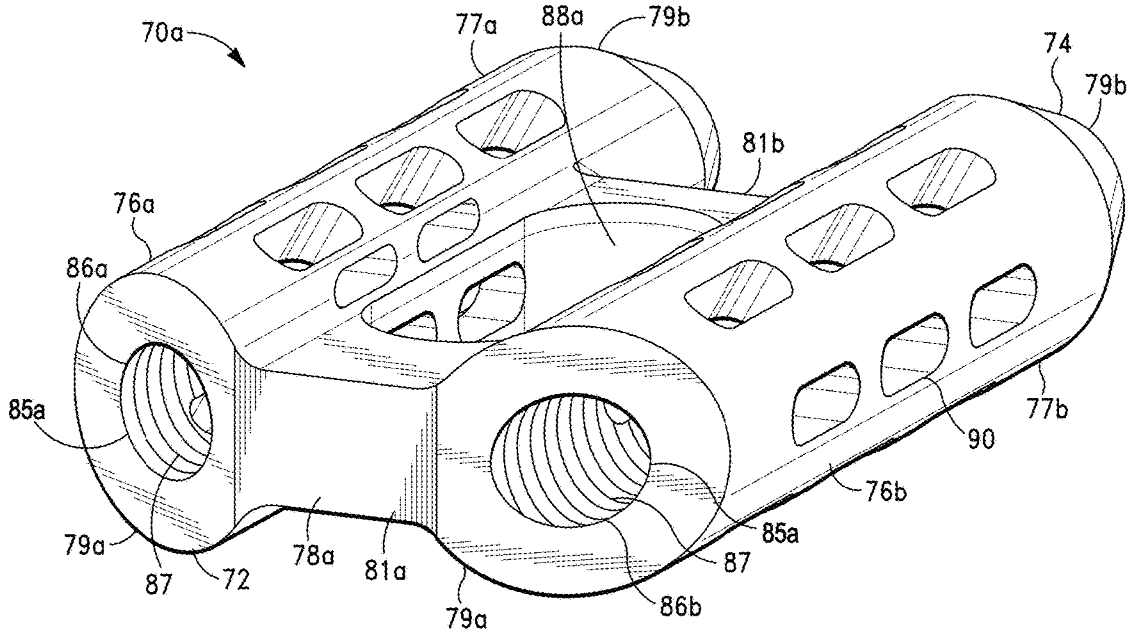
FIGS. 2A and 2B are perspective views of one embodiment of a SI joint prosthesis, in accordance with the invention.
Figure 2B:
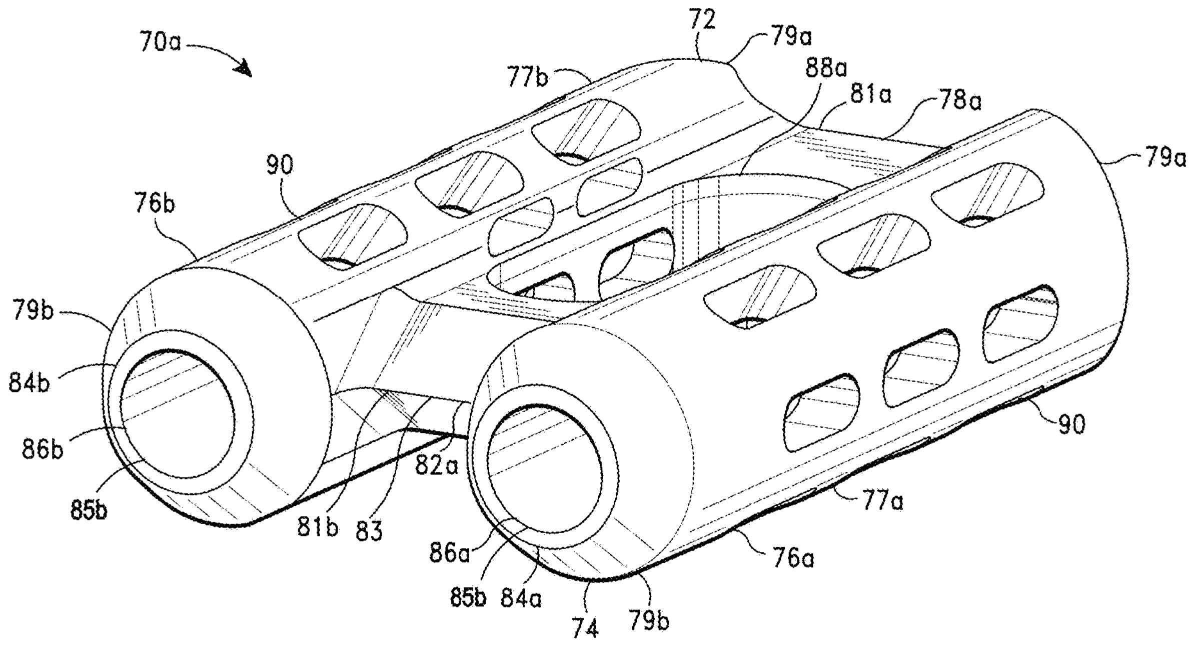

As illustrated in FIGS. 2A and 2B, the SI joint prosthesis (denoted "70*a*") comprises a biocompatible and, hence, monolithic structure comprising proximal and distal ends 72, 74, and first and second elongated partially cylindrical sections 76*a*, 76*b* connected to a bridge section 78*a*, whereby the SI joint prosthesis 70*a* comprises a continuous exterior surface comprising first and second partially cylindrical surface regions 77*a*, 77*b*.

As further illustrated in FIGS. 2A and 2B, the first and second partially cylindrical sections 76*a*, 76*b* comprise an open proximal end 79*a* and an open distal end 79*b*, and the bridge section 78*a* similarly comprises proximal and distal ends 81*a*, 81*b*.

Figure 2C:
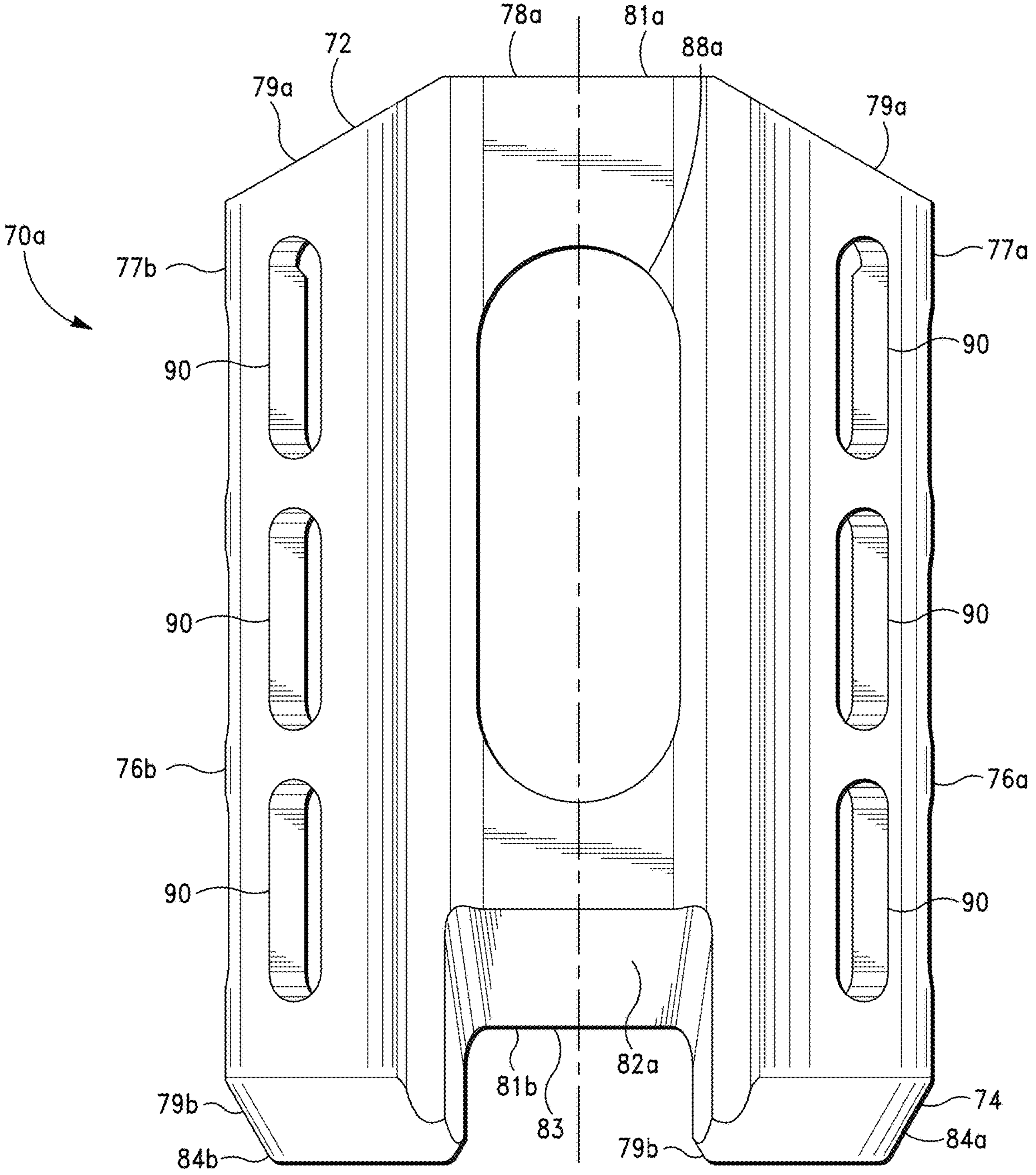
FIG. 2C is a top plan view of the SI joint prosthesis shown in FIGS. 2A and 2B, in accordance with the invention.

According to the invention, the partially cylindrical sections 76*a*, 76*b* can comprise equal lengths, as illustrated in FIG. 2C, and unequal lengths.

Figure 2D:
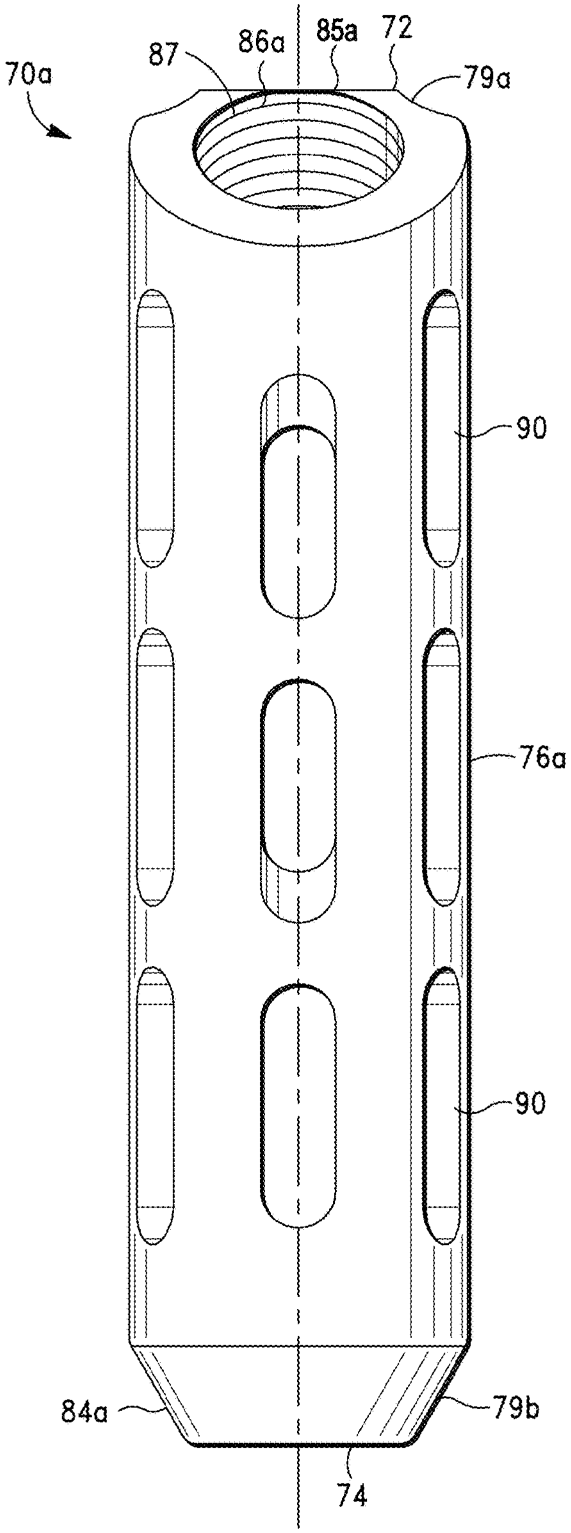
FIG. 2D is a right-side plan view of the SI joint prosthesis shown in FIGS. 2A and 2B, in accordance with the invention.
Figure 2E:
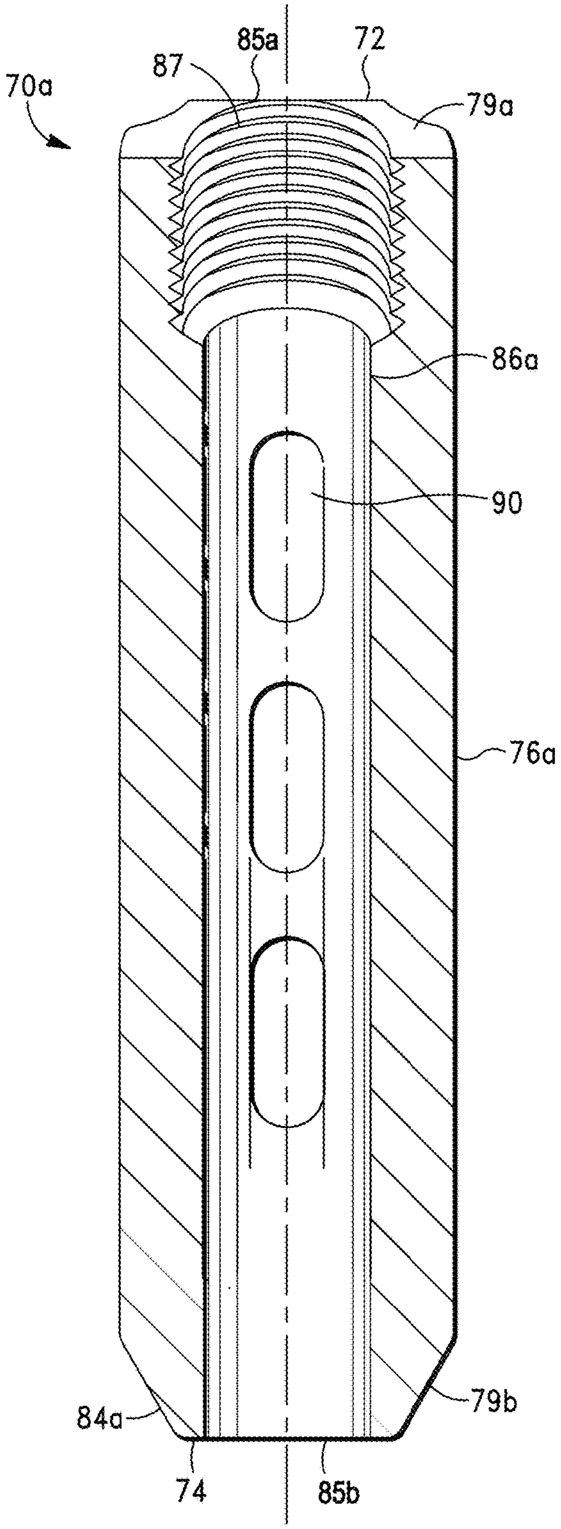
FIG. 2E is a right-side sectional plan view of the SI joint prosthesis shown in FIGS. 2A and 2B, in accordance with the invention.
Figure 2F:
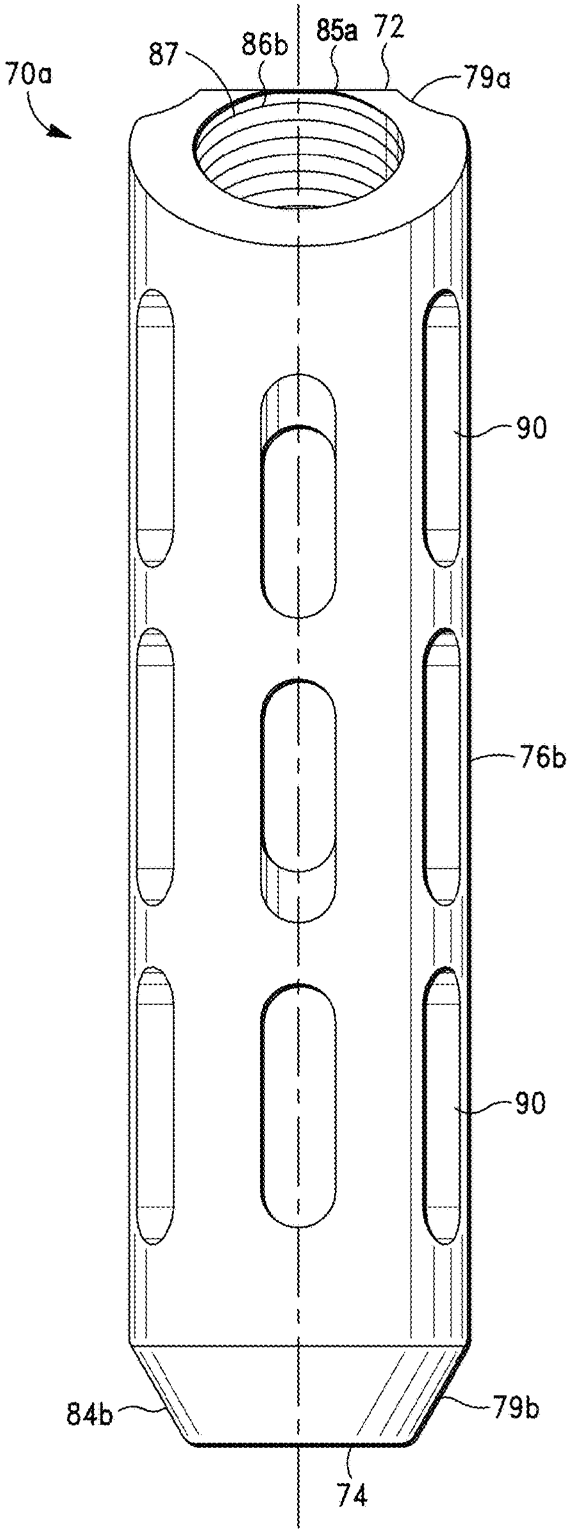
FIG. 2F is a left-side plan view of the SI joint prosthesis shown in FIGS. 2A and 2B, in accordance with the invention.
Figure 2G:
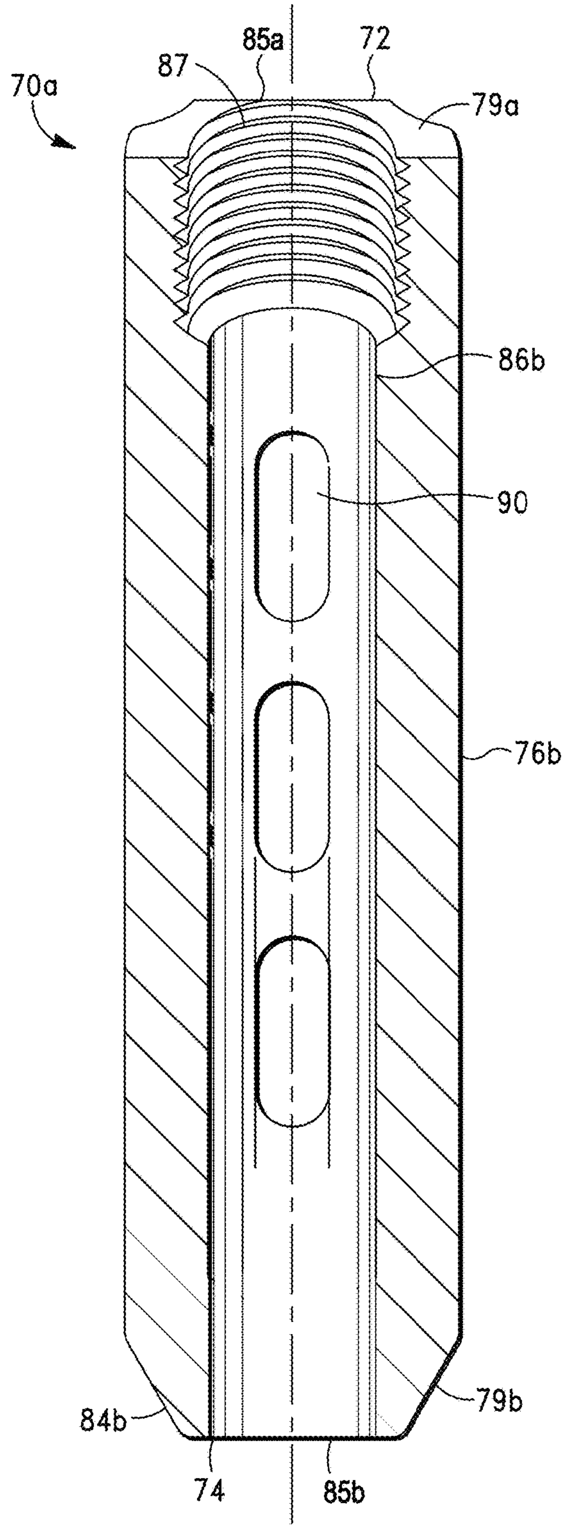
FIG. 2G is a left-side sectional plan view of the SI joint prosthesis shown in FIGS. 2A and 2B, in accordance with the invention.
Figure 2H:
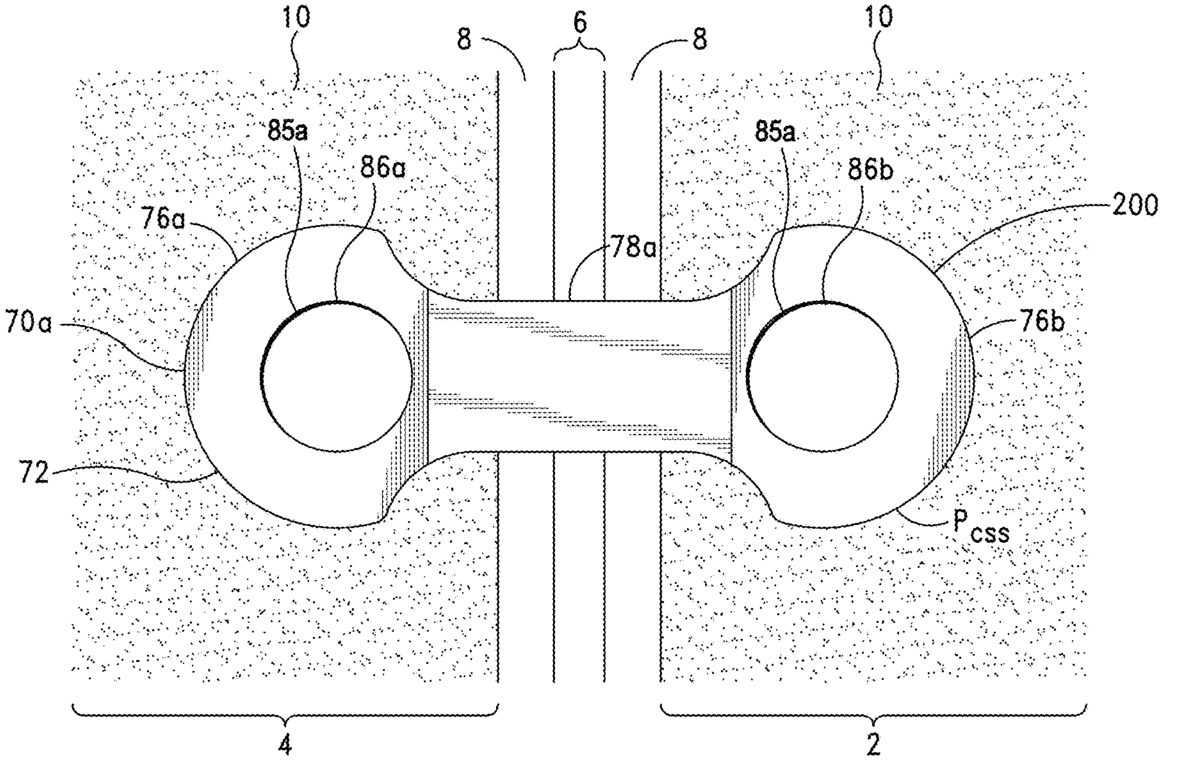
FIG. 2H is an illustration of the SI joint prosthesis shown in shown in FIGS. 2A and 2B disposed in a post-prosthesis insertion SI joint opening, in accordance with the invention.
Figure 27A:
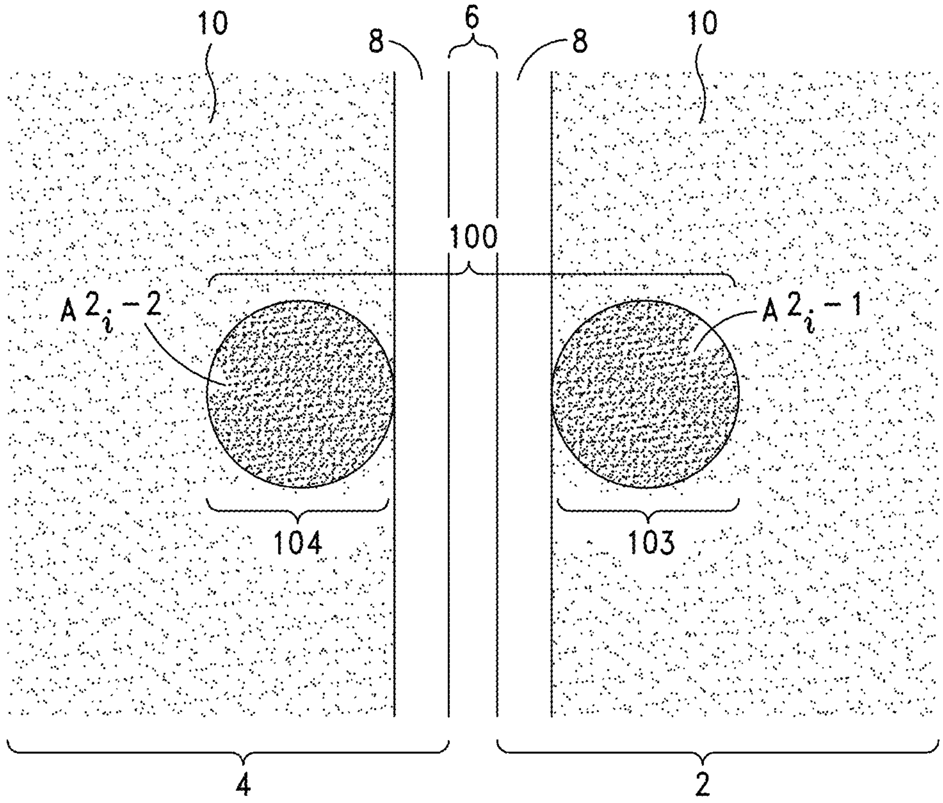
FIGS. 27A and 27B are illustrations of one embodiment of a pilot SI joint opening, in accordance with the invention.
Figure 27B:
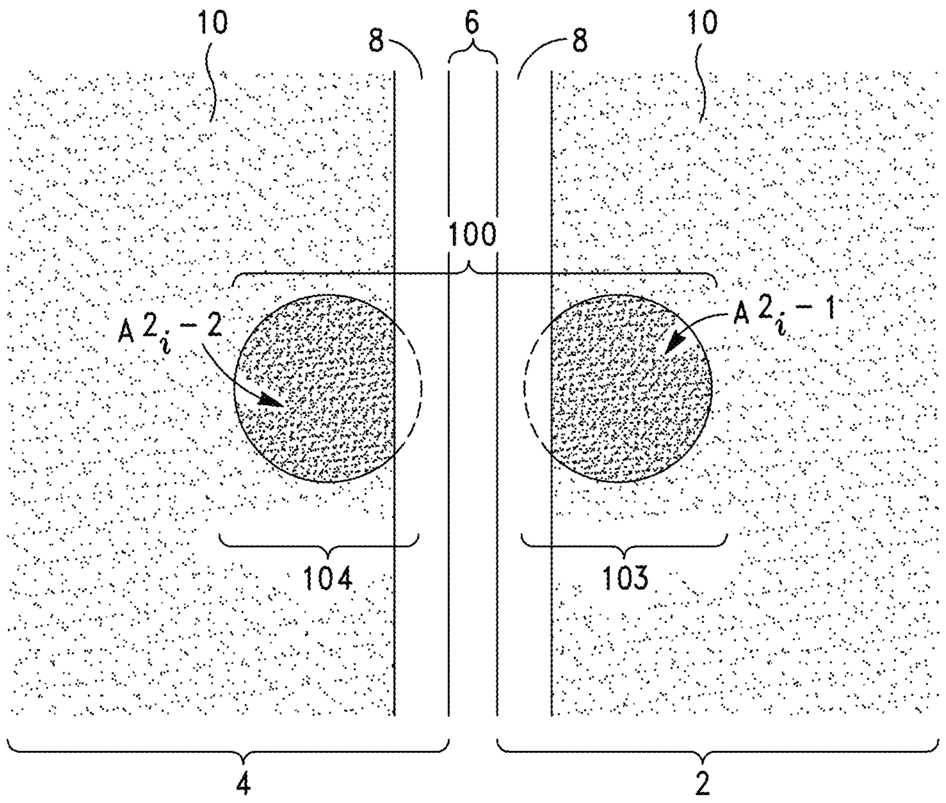

As illustrated in FIGS. 2H, 27A and 27B the first partially cylindrical surface region 77*a* preferably comprises a partially cylindrical surface region shape that conforms with at least a portion of the first lobe region (or ilium opening) 104 of a pilot SI joint opening 100 and/or the second lobe region (or sacrum opening) 103 of the pilot SI joint opening, created by a drill guide assembly of the invention, depending on the entry position of the SI Joint prosthesis 70*a* into the pilot SI joint opening 100.

The second partially cylindrical surface region 77*b* similarly preferably comprises a partially cylindrical surface region shape that conforms with at least a portion of the first lobe region (or ilium opening) 104 of the pilot SI joint opening 100 and/or the second lobe region (or sacrum opening) 103 of the pilot SI joint opening 100, again depending on the entry position of the SI Joint prosthesis 70*a* into the pilot SI joint opening 100.

Referring now to FIG. 2H, according to the invention, the continuous exterior surface of the SI Joint prosthesis 70*a* defines a prosthesis cross-sectional shape (denoted "Pcss") having a longitudinal axis LA1.

Figure 2I:
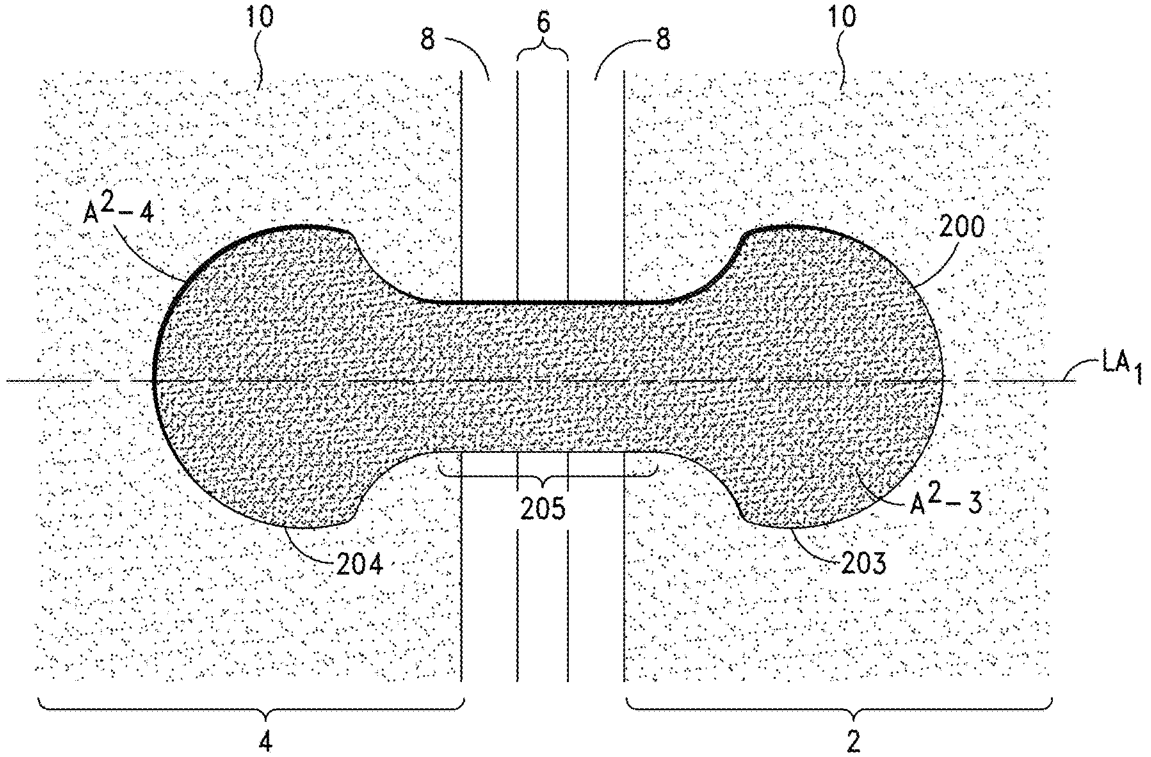
FIG. 2I is an illustration of the post-prosthesis insertion SI joint opening generated or induced when the prosthesis shown in FIGS. 2A and 2B is inserted in a pilot SI joint opening, in accordance with the invention.
Figure 21:
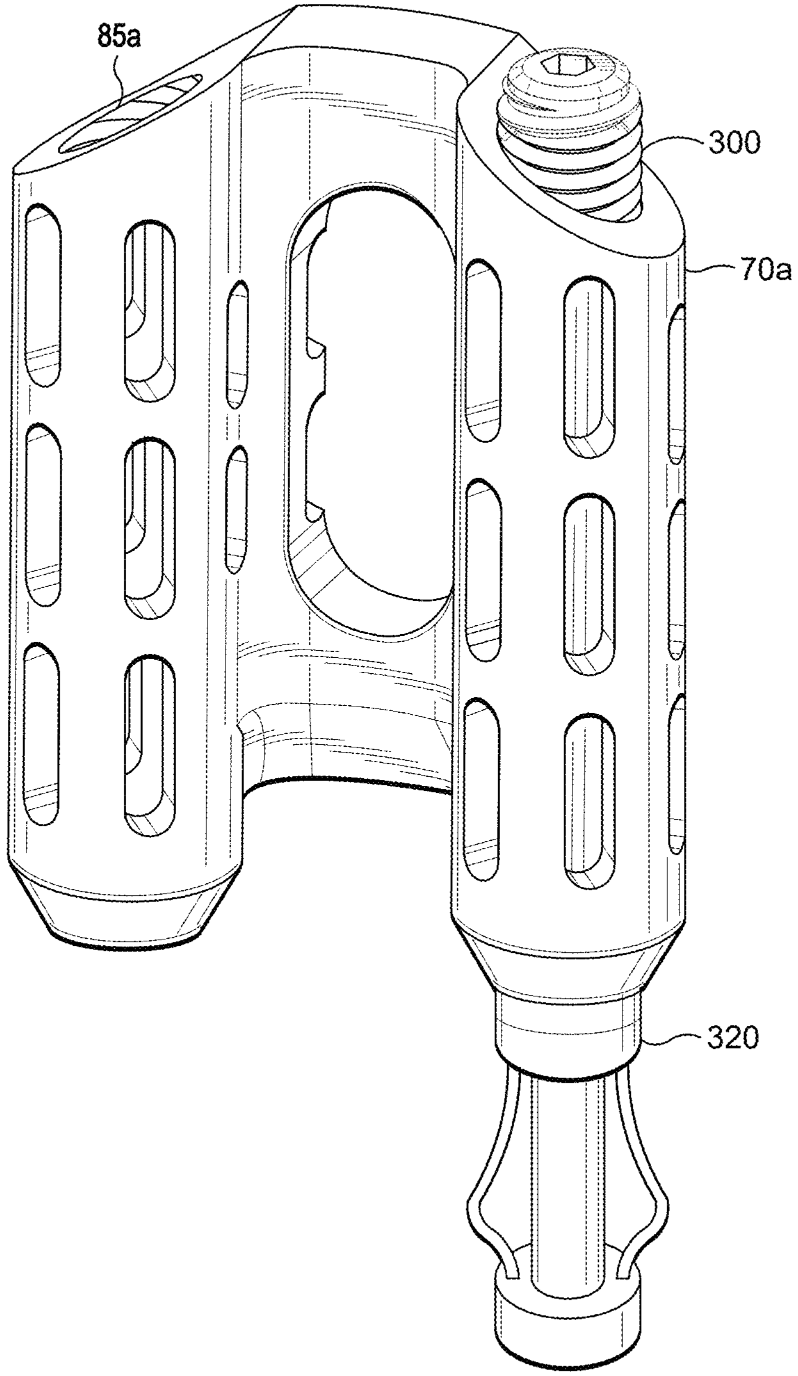
FIG. 21 is a perspective view of the expandable end member shown in FIG. 17A engaged to the bone stabilizing pin shown in FIG. 14A, which is operatively inserted in and through an internal lumen of the SI joint prosthesis shown in FIGS. 2A and 2B; in accordance with the invention.

In some embodiments of the invention, the length of the prosthesis cross-sectional shape Pccs along longitudinal axis LA1 is greater than the length of pilot SI joint opening 100, i.e., cross-sectional shape thereof, whereby, as illustrated in FIG. 21, when the SI joint prosthesis 70*a* is advanced into pilot SI joint opening 100 and, thereby, a dysfunctional SI joint, as shown in FIG. 2H, the pilot SI opening 100 transitions to a post-prosthesis insertion SI joint opening 200 comprising a larger cross-sectional length shape that corresponds to the length of the prosthesis cross-sectional shape Pccs, as shown in FIG. 2I.

As also illustrated in FIG. 2I, in a preferred embodiment, the cross-sectional area of the sacrum portion 203 of the post-prosthesis insertion SI joint opening 200 also comprises a cross-sectional area (denoted "A$^{2}$-3") that is greater than the cross-sectional area A$^{2}$;-1 of the sacrum opening 103 of the SI joint opening 100 illustrated in FIG. 27A, and the ilium opening 204 of the post-prosthesis insertion SI joint opening 200 comprises a cross-sectional area (denoted "A$^{2}$-4") that is greater than the cross-sectional area A$^{2}$;-2 of the ilium opening 104 of the SI joint opening 100 illustrated in FIG. 27A.

In a preferred embodiment, when SI joint prosthesis 70*a* is advanced into a dysfunctional SI joint, as described above, the prosthesis 70*a* transfixes and, thereby, stabilizes the dysfunctional SI joint.

As further illustrated in FIG. 21, the post-prosthesis insertion SI joint opening 200 also comprises a noncircular region (denoted "205"), which is achieved by virtue of the tapered bridge or osteotome 78*a* of the SI joint prosthesis 70*a* cutting into and through the articular cartilage and cortical bone 8, and the trabecular bone 10 proximate the SI joint 6.

Referring back to FIG. 2B, in a preferred embodiment, the distal ends 79*b* of the first and second elongated partially cylindrical sections 76*a*, 76*b* also comprise tapered regions 84*a*, 84*b*, which facilitate insertion of the SI joint prosthesis 70*a* into pilot SI joint openings created by a drill guide assembly of the invention, as discussed in detail below, and into dysfunctional SI joints.

As illustrated in FIGS. 2D and 2E, in a preferred embodiment, the first elongated partially cylindrical section 76*a* of the SI joint prosthesis 70*a* comprises an internal prosthesis lumen 86*a* that extends from the open proximal end 79*a* of the first elongated partially cylindrical section 76*a* to the open distal end 79*b* of the first elongated partially cylindrical section 76*a*. As further illustrated in FIGS. 2D and 2E, the internal prosthesis lumen 86*a* is in alignment with and, hence, comprises proximal and distal openings 85*a*, 85*b* of open proximal and distal ends 79*a*, 79*b* of the first elongated partially cylindrical section 76*a*.

As illustrated in FIGS. 2F and 2G, the second elongated partially cylindrical section 76*b* of the SI joint prosthesis 70*a* also comprises an internal prosthesis lumen 86*b* that extends from the open proximal end 79*a* of the second elongated partially cylindrical section 76*b* to the open distal end 79*b* of the second elongated partially cylindrical section 76*b*. As further illustrated in FIGS. 2F and 2G, the internal prosthesis lumen 86*b* is similarly in alignment with and, hence, comprises proximal and distal openings 85*a*, 85*b* of open proximal and distal ends 79*a*, 79*b* of the second elongated partially cylindrical section 76*b*.

In a preferred embodiment, the internal prosthesis lumens 86*a*, 86*b* are sized and configured to receive a bone stabilization pin of the invention; particularly, bone stabilization pins 300, 350 shown in FIGS. 21 and 24 and discussed below, and the prosthesis guide pin 606 and engagement rod 700 of the prosthesis deployment assemblies 600*a*, 600*b*, shown in FIGS. 30A and 31A, also discussed below.

Figure 30A:
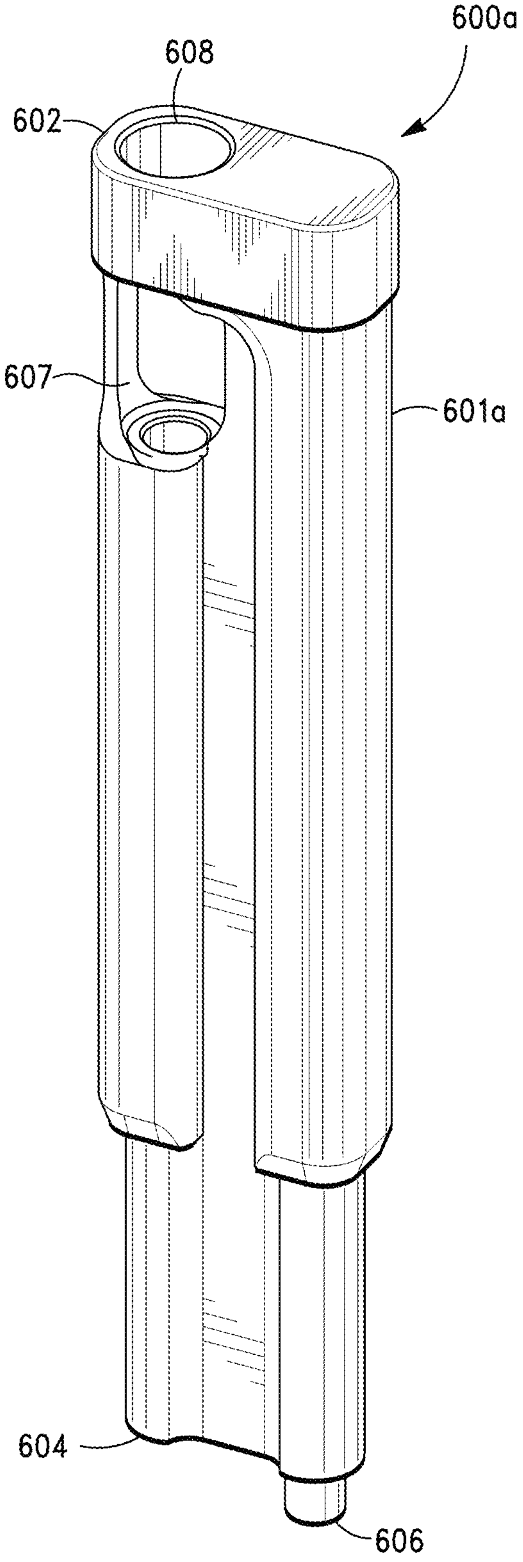
FIG. 30A is a perspective view of one embodiment of a prosthesis deployment assembly, in accordance with the invention.
Figure 30B:
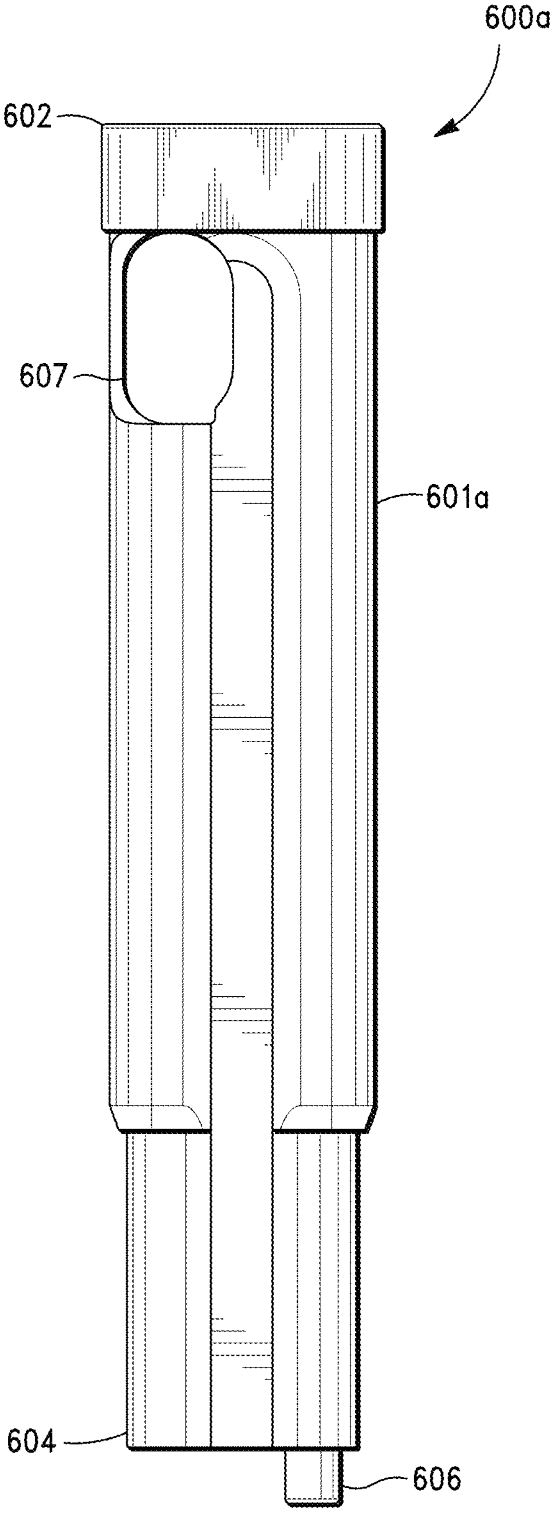
FIG. 30B is a front plan view of the prosthesis deployment assembly shown in FIG. 30A, in accordance with the invention.
Figure 30C:
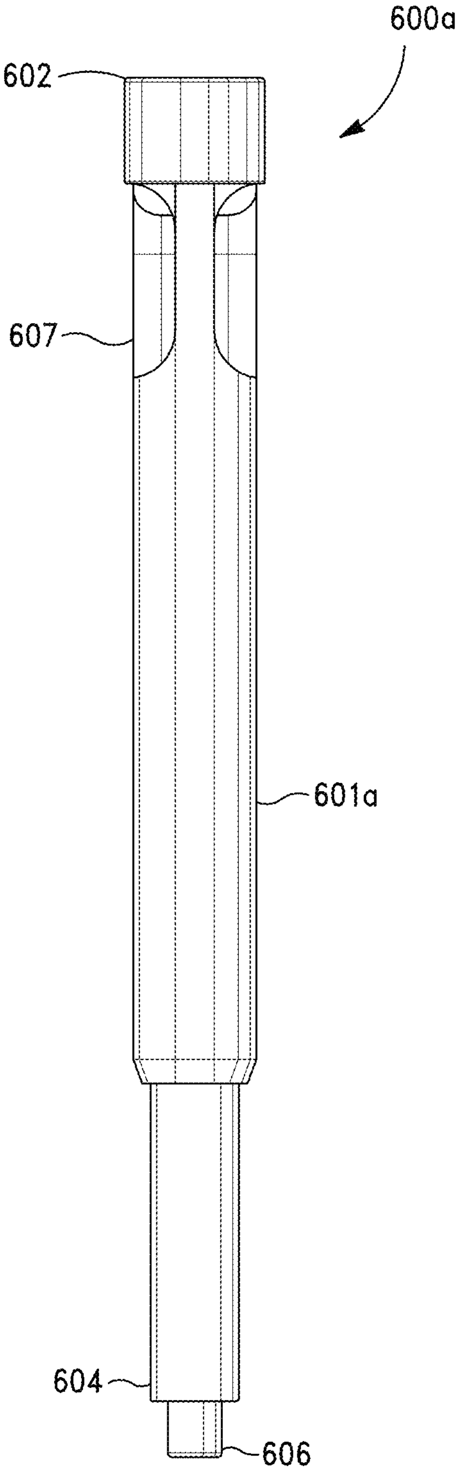
FIG. 30C is a left-side plan view of the prosthesis deployment assembly shown in FIG. 30A, in accordance with the invention.
Figure 30D:
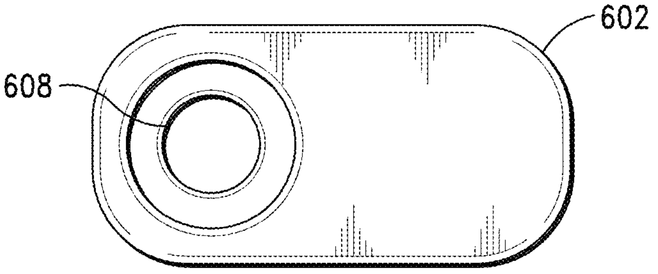
FIG. 30D is a top plan view of the prosthesis deployment assembly shown in FIG. 30A, in accordance with the invention.
Figure 30E:
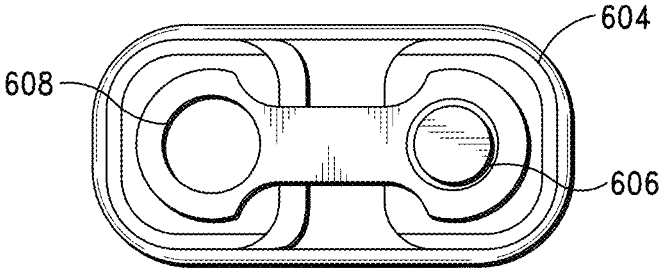
FIG. 30E is a bottom plan view of the prosthesis deployment assembly shown in FIG. 30A, in accordance with the invention.
Figure 30F:
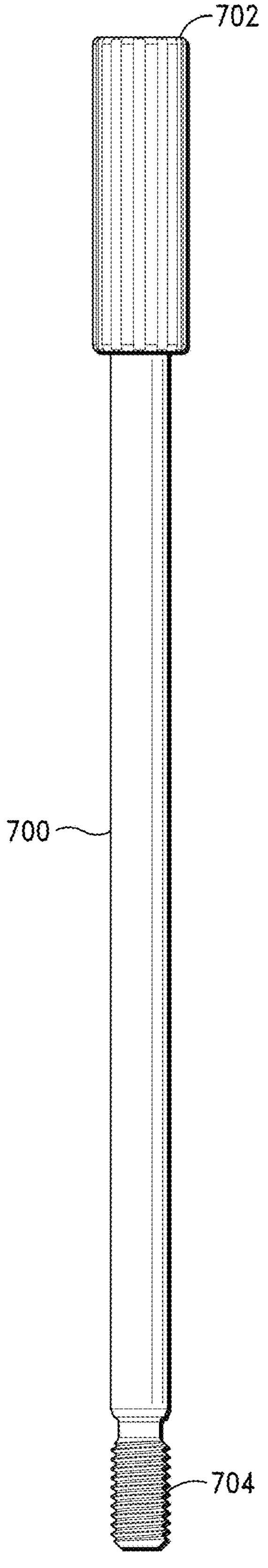
FIG. 30F is a front plan view of a prosthesis engagement rod of the prosthesis deployment assembly shown in FIG. 30A, in accordance with the invention.
Figure 30G:
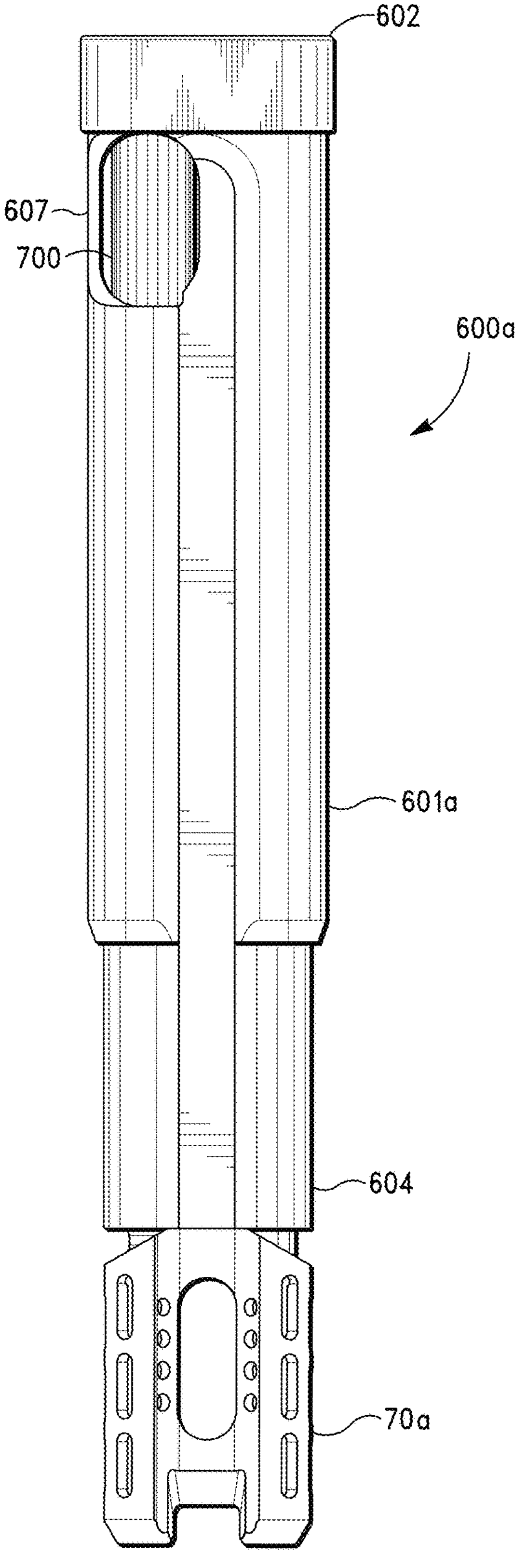
FIG. 30G is a perspective view of the prosthesis deployment assembly shown in FIG. 30A engaged to a SI joint prosthesis of the invention, in accordance with the invention.
Figure 31B:
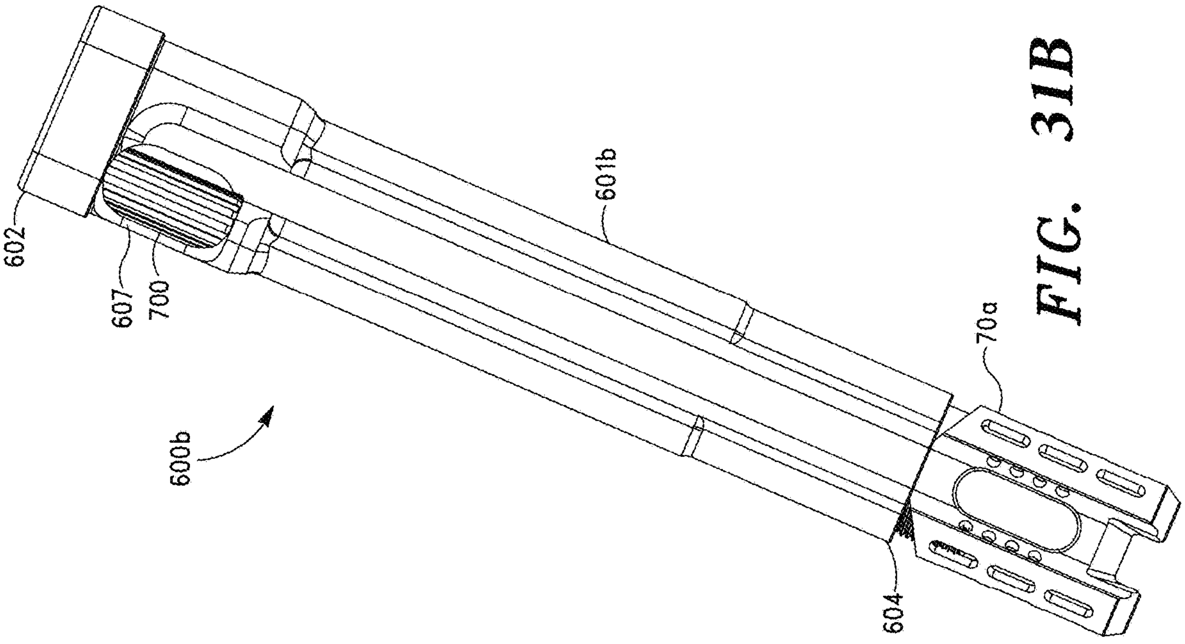
FIG. 31B is a perspective view of the prosthesis deployment assembly shown in FIG. 31A engaged to a prosthesis of the invention, in accordance with the invention.

As illustrated in FIGS. 2A and FIGS. 2D-2G, in a preferred embodiment, the internal prosthesis lumens 86*a*, 86*b* of the first and second elongated partially cylindrical sections 76*a*, 76*b* preferably comprise a threaded region 87 proximate the proximal end 79*a* that is sized and configured to receive and threadably engage the threaded distal ends 304, 354 of the bone stabilization pins 300, 350 (see FIGS. 21 and 24) and the threaded distal end 704 of the prosthesis engagement rod 700 of the prosthesis deployment assemblies 600*a*, 600*b*, discussed below (see FIGS. 30G and 31B).

In a preferred embodiment, the internal prosthesis lumens 86*a*, 86*b* are also configured to receive agents and compositions that further facilitate adhesion of the SI joint prosthesis 70*a* (and SI joint prostheses 70*b*, 70*c*, 70*d*, 70*e*, 70*f*, 70*g*, 70 *h* and 70*i*, discussed below), to the pilot SI openings created by a drill guide assembly of the invention and, thereby, sacrum and/or ilium, and bone material, including, without limitation, the aforementioned osteogenic agents, e.g., demineralized bone matrix, autograft bone material, allograft bone material and xenograft bone material, and compositions formed therewith, and pharmacological agents and compositions that facilitate osseous or bone tissue ingrowth into the SI joint prosthesis 70*a* (and SI joint prostheses 70*b*, 70*c*, 70*d*, 70*e*, 70*f*, 70*g*, 70 *h* and 70*i*) and healing of the SI joint bone structures, and the poly(glycerol sebacate) (PGS)-based compositions and phase change osteogenic agents, discussed in detail below.

As illustrated in FIGS. 2B and 2C, in a preferred embodiment, the distal end 81*b* of the bridge section 78*a* comprises a taper region 82*a* configured and adapted to disrupt, i.e., cut into and through, articular cartilage and cortical bone 8 (and, in some aspects, trabecular bone 10), and, hence, facilitate advancement of SI joint prosthesis 70*a* into a dysfunctional SI joint.

In some embodiments of the invention, the taper region 82*a* comprises two angled regions that intersect at a central point 83, i.e., pointed proximate the mid-region of the bridge section 78*a*, such as shown in FIG. 2B.

Referring back to FIGS. 2A-2C, in a preferred embodiment, the bridge section 78*a* comprises a central opening 88*a* and a plurality of fenestrations (or slots) 90 disposed in the first and second elongated partially cylindrical sections 76*a*, 76*b*, which preferably are in communication with the internal prosthesis lumens 86*a*, 86*b*.

In a preferred embodiment, the bone material, agents and compositions referenced above are adapted to extrude through the slots 90 of the SI joint prosthesis 70*a* (and SI joint prostheses 70*b*, 70*c*, 70*d*, 70*e*, 70*f*, 70*g*, 70 *h* and 70*i*), when the SI joint prosthesis 70*a* (and SI joint prostheses 70*b*, 70*c*, 70*d*, 70*e*, 70*f*, 70*g*, 70 *h* and 70*i*) is/are advanced into a pilot SI joint opening and, thereby, dysfunctional SI joint, to, as indicated above, (i) further facilitate fixation or adhesion of the SI joint prosthesis 70*a* (and SI joint prostheses 70*b*, 70*c*, 70*d*, 70*e*, 70*f*, 70*g*, 70 *h* and 70*i*) to the pilot SI openings created by a drill guide assembly of the invention and, thereby, dysfunctional SI joint, i.e., sacrum and/or ilium, and (ii) facilitate osseous or bone tissue ingrowth into the SI joint prosthesis 70*a* (and SI joint prostheses 70*b*, 70*c*, 70*d*, 70*e*, 70*f*, 70*g*, 70 *h* and 70*i*) and healing of the SI joint bone structures.

Figure 3A:
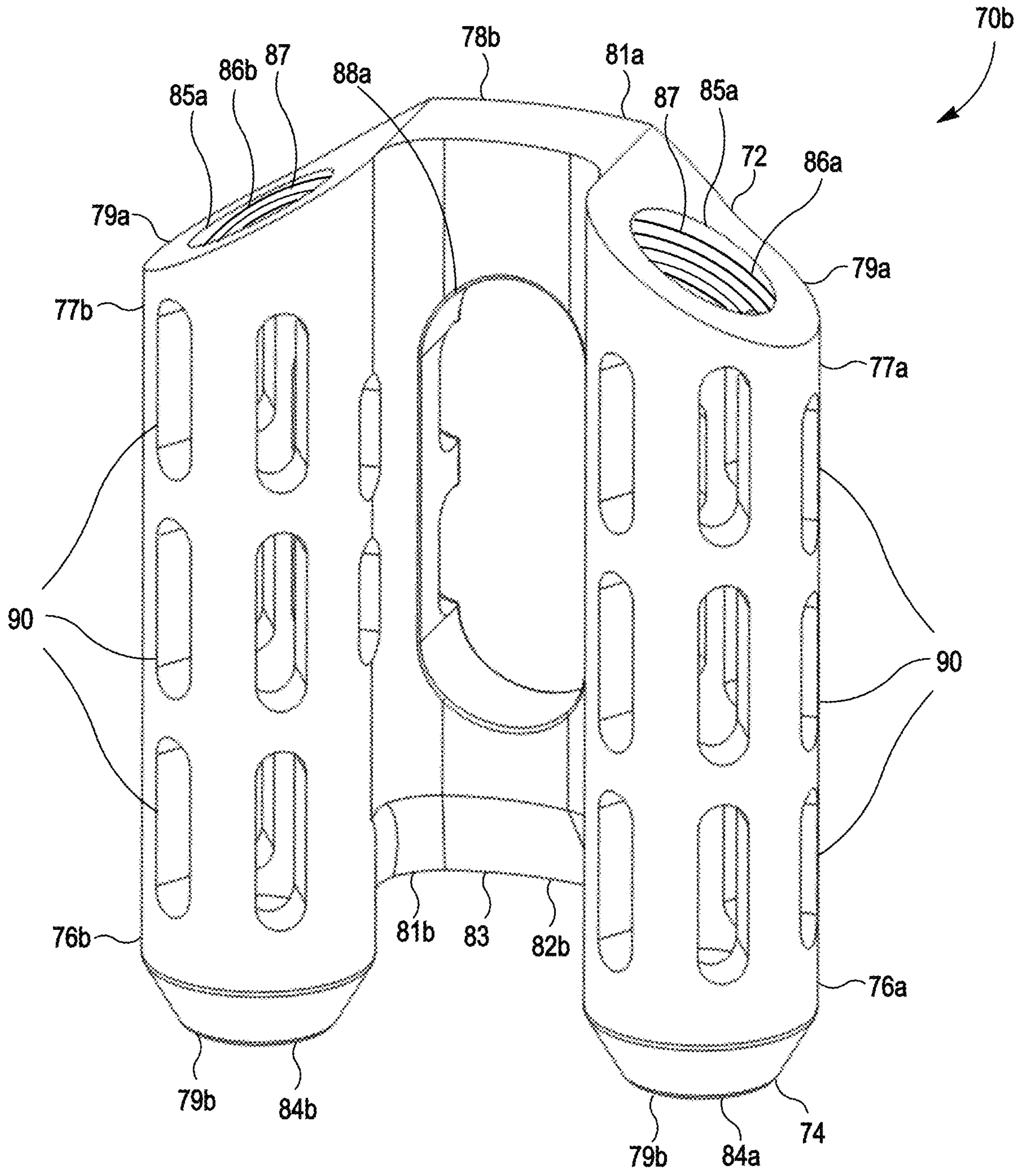
FIG. 3A is a top perspective view of another embodiment of a SI joint prosthesis having an offset, arched or radius-shaped bridge section, in accordance with the invention.
Figure 3B:
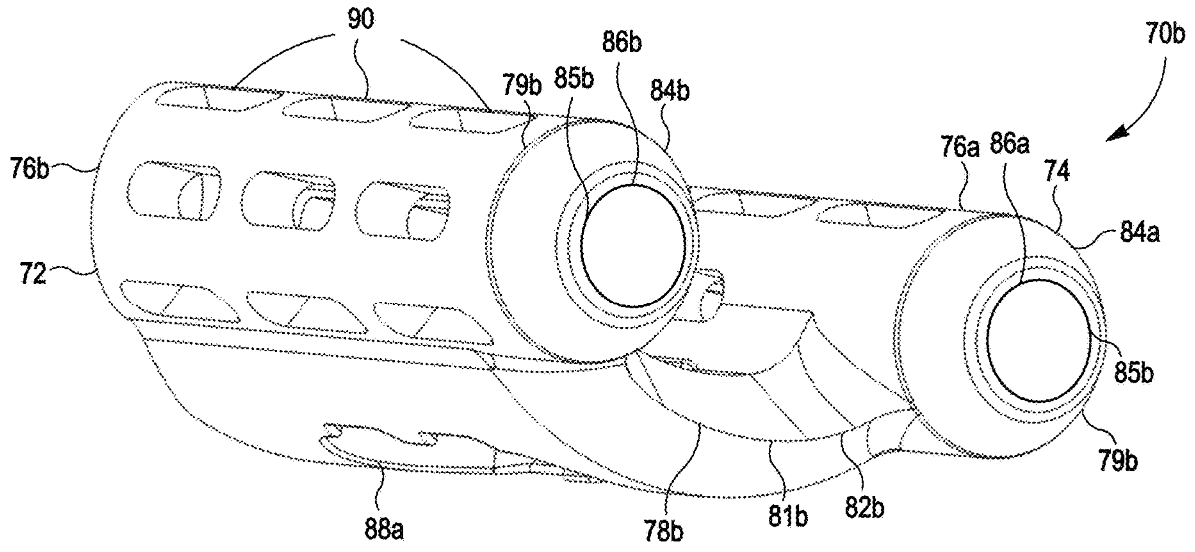
FIG. 3B is a front perspective view of the prosthesis shown in FIG. 3A, in accordance with the invention.
Figure 3C:
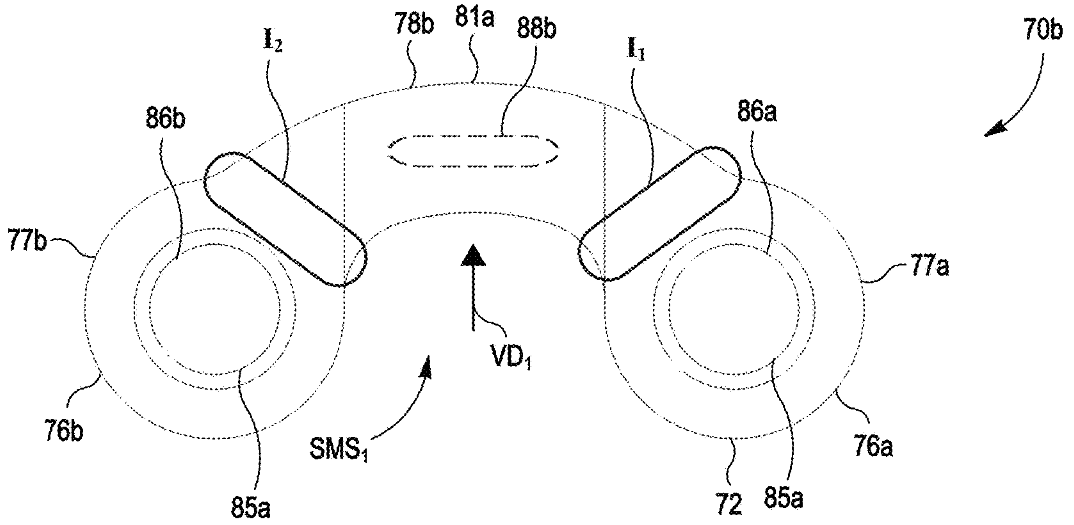
FIG. 3C is an end plan view of the prosthesis shown in FIG. 3A, in accordance with the invention.

Referring now to FIGS. 3A-3C, there is shown another embodiment of a SI joint prosthesis of the invention (denoted "70*b*"), which is similarly adapted to be advanced into a pilot SI joint opening created by a drill guide assembly of the invention and, thereby, into a dysfunctional SI joint in a posterior trajectory.

As illustrated in FIGS. 3A and 3B, the SI joint prosthesis 70*b* similarly comprises a monolithic structure comprising first and second elongated sections 76*a*, 76*b*, which comprise the same features of the first and second elongated sections 76*a*, 76*b* of SI joint prosthesis 70*a* described above.

In a preferred embodiment, when the SI joint prosthesis 70*b* is advanced into a dysfunctional SI joint in a posterior trajectory the prosthesis 70*b* similarly transfixes and, thereby, stabilizes the dysfunctional SI joint.

As illustrated in FIGS. 3B and 3C, the SI joint prosthesis 70*b* similarly comprises a bridge section or osteotome (in this embodiment, denoted "78*b*"), which, in this embodiment, comprises an off-set structure.

As further illustrated in FIGS. 3B and 3C, the offset bridge 78*b* is similarly disposed between the first and second elongated sections 76*a*, 76*b*, wherein the SI joint prosthesis 70*b* comprises a first interface of the bridge section 78*b* and the first elongated section 76*a* (denoted "I1") and a second interface of the bridge section 78*b* and the second elongated section 76*b* (denoted "I2").

As illustrated in FIG. 3A, in a preferred embodiment, the bridge section 78*b* does not extend beyond the proximal and distal ends 79*a*, 79*b* of the first and second elongated sections 76*a*, 76*b* in a longitudinal direction. However, in some embodiments of the invention, the distal end 81*b* of the bridge section 78*b* extends beyond the distal ends 79*b* of the first and second elongated sections 76*a*, 76*b*.

As further illustrated in FIGS. 3B and 3C, in a preferred embodiment, the bridge section 78*b* comprises an arched or radius structure that is offset in a vertical direction relative to the first and second elongated sections 76*a*, 76*b* (denoted by arrow "VD1"), whereby the bridge section 78*b* and the first and second elongated sections 76*a*, 76*b* define a prosthesis support member space between the first and second elongated sections 76*a*, 76*b* (denoted "SMS1") which is preferably sized to accommodate positioning of a surgical dowl or pin therein, such as illustrated in FIG. 12, wherein the dowl is denoted "SD."

In a preferred embodiment, the prosthesis support member space SMS1 comprises a size that is sufficient to receive and/or position a primary or supplemental joint support member or device, such as a surgical pin or screw (e.g., a sacral-alar iliac (S2AI) screw), in the prosthesis support member space SMS1 when the SI joint prosthesis 70*b* is advanced into and/or positioned in a dysfunctional SI joint, such as illustrated in FIG. 12.

In some embodiments, the offset of the bridge section 78*b* is further extended, such as illustrated in FIG. 3C, whereby the bridge section 78*b* extends beyond the first interface I1 of the bridge section 78*b* and the first elongated section 76*a* and a second interface I2 of the bridge section 78*b* and the second elongated section 76*b* to further facilitate the receipt and/or positioning of the primary or supplemental joint support member (or device) in the prosthesis support member space SMS1 when the SI joint prosthesis 70*b* is advanced into and/or positioned in a dysfunctional SI joint.

As illustrated in FIG. 3B, in a preferred embodiment, the distal end 81*b* of the bridge section 78*b*, i.e., offset radius structure, similarly comprises a taper region 82*b*, which is similarly configured and adapted to cut into and through at least articular cartilage and cortical bone, and, hence, facilitate advancement of SI joint prosthesis 70*b* into a dysfunctional SI joint.

As illustrated in FIG. 3A, in a preferred embodiment, the bridge section 78*b* similarly comprises central opening 88*a*.

As illustrated in FIG. 3C, according to the invention, the bridge section 78*b* can further comprise the bridge section opening 88*b* on the proximal end 81*a* (shown in phantom), which would similarly extend from the bridge section proximal end 81*a* to the central opening 88*a* and, hence, be in communication therewith.

According to the invention, the bridge section 78*b* can further comprise a plurality of slots 90, such as slots 90 in the first and second elongated sections 76*a*, 76*b*, with and without the central opening 88*a*.

Figure 4A:
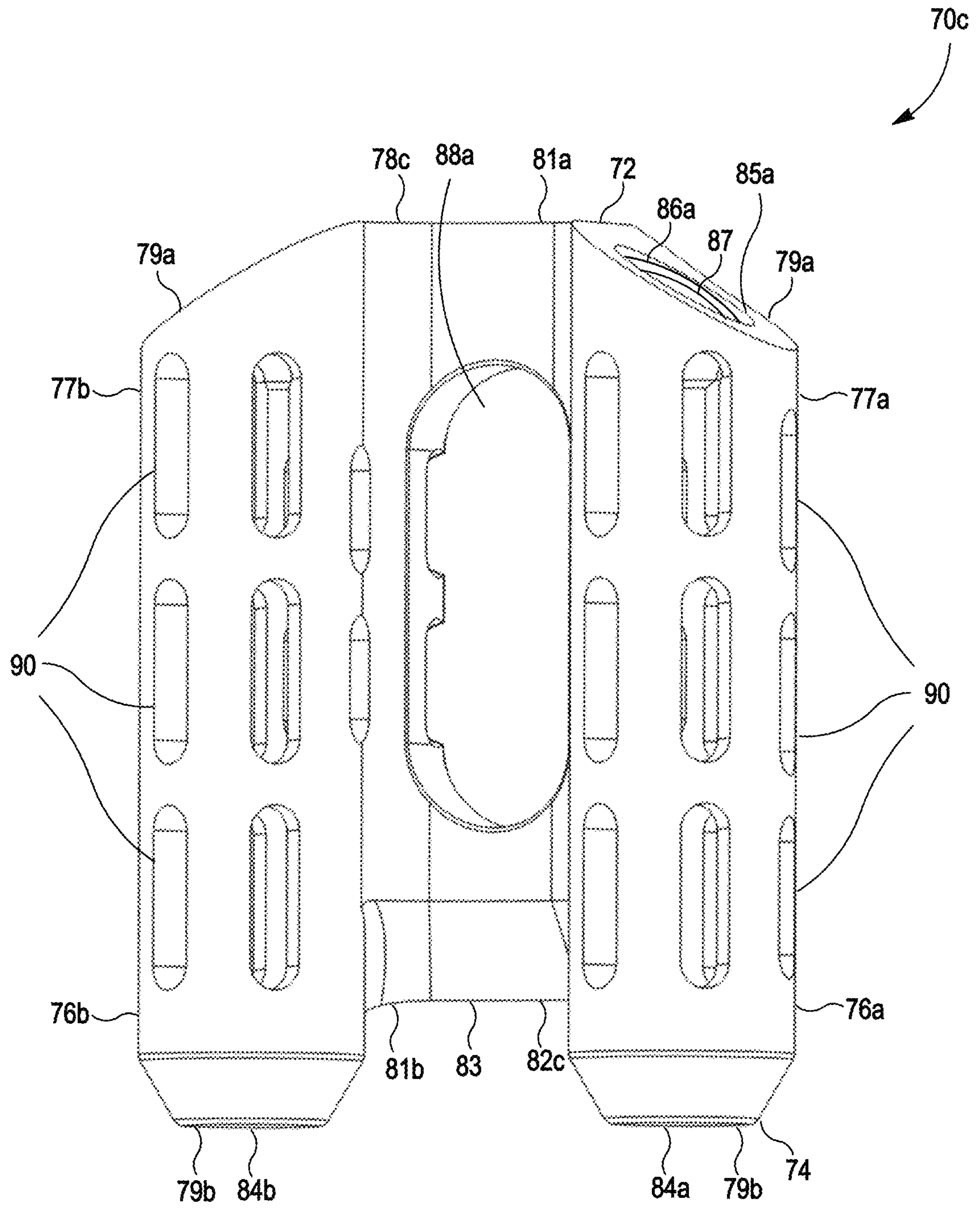
FIG. 4A is a top perspective view of another embodiment of a prosthesis having an offset, V-shaped bridge section, in accordance with the invention.
Figure 4B:
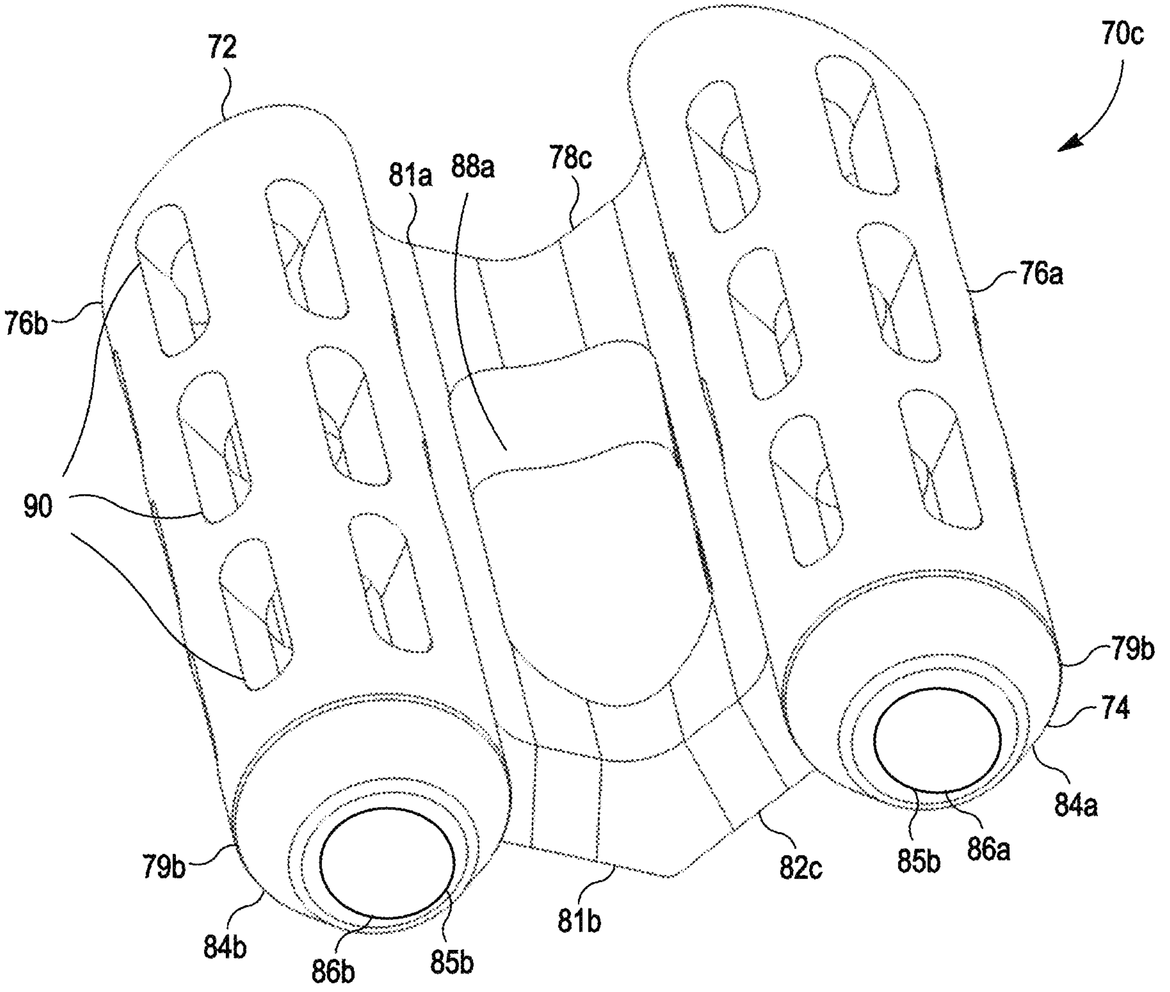
FIG. 4B is a front perspective view of the prosthesis shown in FIG. 4A, in accordance with the invention.
Figure 4C:
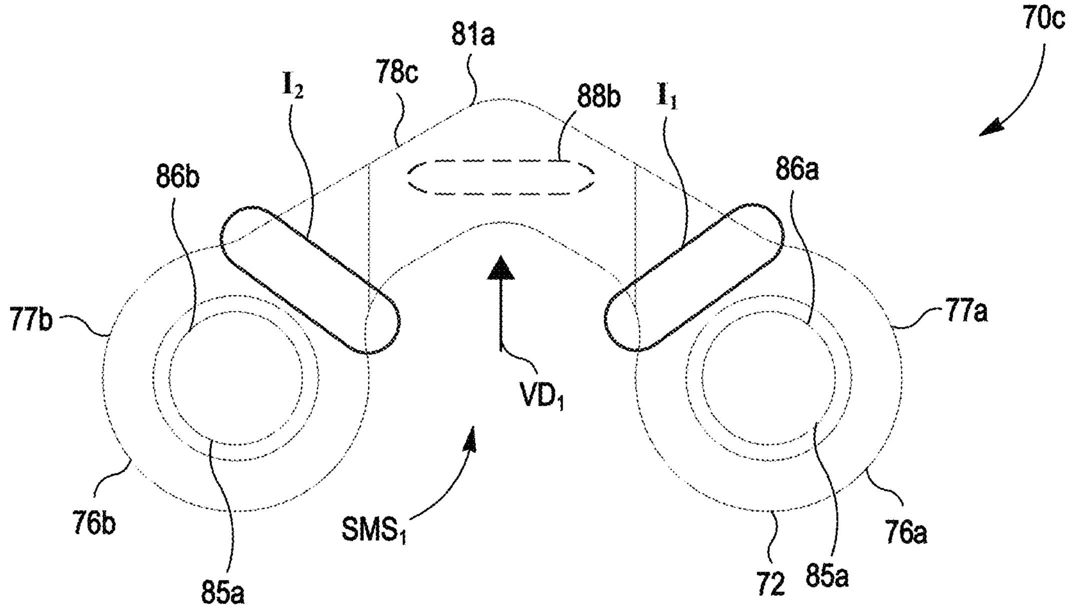
FIG. 4C is an end plan view of the prosthesis shown in FIG. 4A, in accordance with the invention.

Referring now to FIGS. 4A-4C, there is shown another embodiment of a SI joint prosthesis of the invention (denoted "70*c*"), which is similarly adapted to be advanced into a pilot SI joint opening created by a drill guide assembly of the invention and, thereby, into a dysfunctional SI joint in a posterior trajectory.

In a preferred embodiment, when the SI joint prosthesis 70*c* is advanced into a dysfunctional SI joint in a posterior trajectory, the prosthesis 70*c* similarly transfixes and, thereby, stabilizes the dysfunctional SI joint.

As illustrated in FIGS. 4A and 4B, the prosthesis 70*c* similarly comprises a monolithic structure comprising first and second elongated sections 76*a*, 76*b*, which similarly comprise the same features of the first and second elongated sections 76*a*, 76*b* of SI joint prosthesis 70*a* described above.

As illustrated in FIGS. 4B and 4C, the SI joint prosthesis 70*c* similarly comprises a bridge section or osteotome (in this embodiment, denoted "78*c*"), which similarly comprises an off-set structure.

As further illustrated in FIGS. 4B and 4C, the offset bridge 78*c* is similarly disposed between the first and second cylindrical sections 76*a*, 76*b*, whereby the SI joint prosthesis 70*c* similarly comprises a first interface of the bridge section 78*c* and the first elongated section 76*a* (denoted "I1") and a second interface of the bridge section 78*c* and the second elongated section 76*b* (denoted "I2").

As illustrated in FIG. 4A, in a preferred embodiment, the bridge section 78*c* similarly does not extend beyond the proximal and distal ends 79*a*, 79*b* of the first and second elongated sections 76*a*, 76*b*. However, in some embodiments of the invention, the distal end 81*b* of the bridge section 78*c* extends beyond the distal ends 79*b* of the first and second elongated sections 76*a*, 76*b*.

As further illustrated in FIGS. 4B and 4C, in a preferred embodiment, the bridge section 78*c* comprises a V-shaped structure that is similarly offset in a vertical direction relative to the first and second elongated sections 76*a*, 76*b* (again denoted by arrow "VD1"), whereby the bridge section 78*c* and the first and second elongated sections 76*a*, 76*b* similarly define a prosthesis support member space between the first and second elongated sections 76*a*, 76*b* (denoted "SMS1").

In a preferred embodiment, the prosthesis support member space SMS1 of SI joint prosthesis 70*c* similarly comprises a size that is sufficient to receive and/or position a primary or supplemental joint support member or device, such as a surgical pin or screw, in the prosthesis support member space SMS1 when the SI joint prosthesis 70*c* is advanced into and/or positioned in a dysfunctional SI joint.

In some embodiments, the offset of the bridge section 78*c* is similarly further extended, such as illustrated in FIG. 4C, whereby the bridge section 78*c* similarly extends beyond the first interface I1 of the bridge section 78*c* and the first elongated section 76*a* and a second interface I2 of the bridge section 78*c* and the second elongated section 76*b* to further facilitate the receipt and/or positioning of the primary or supplemental joint support member (or device) in the prosthesis support member space SMS1 when the SI joint prosthesis 70*c* is advanced into and/or positioned in a dysfunctional SI joint.

As illustrated in FIG. 4B, in a preferred embodiment, the distal end 81*b* of the bridge section 78*c*, i.e., V-shaped structure, similarly comprises a taper region 82*c* that is similarly configured to cut into and through at least articular cartilage and cortical bone and, hence, facilitate advancement of SI joint prosthesis 70*c* into a dysfunctional SI joint.

As illustrated in FIG. 4A, in a preferred embodiment, the bridge section 78*c* similarly comprises central opening 88*a*.

As illustrated in FIG. 4C, according to the invention, the bridge section 78*c* can similarly comprise the bridge section opening 88*b* on the proximal end 81*a* (shown in phantom), which would similarly extend from the bridge section proximal end 81*a* to the central opening 88*a* and, hence, be in communication therewith.

According to the invention, the bridge section 78*c* can similarly comprise a plurality of slots 90, such as slots 90 in the first and second elongated sections 76*a*, 76*b*, with and without the central opening 88*a*.

Figure 5A:
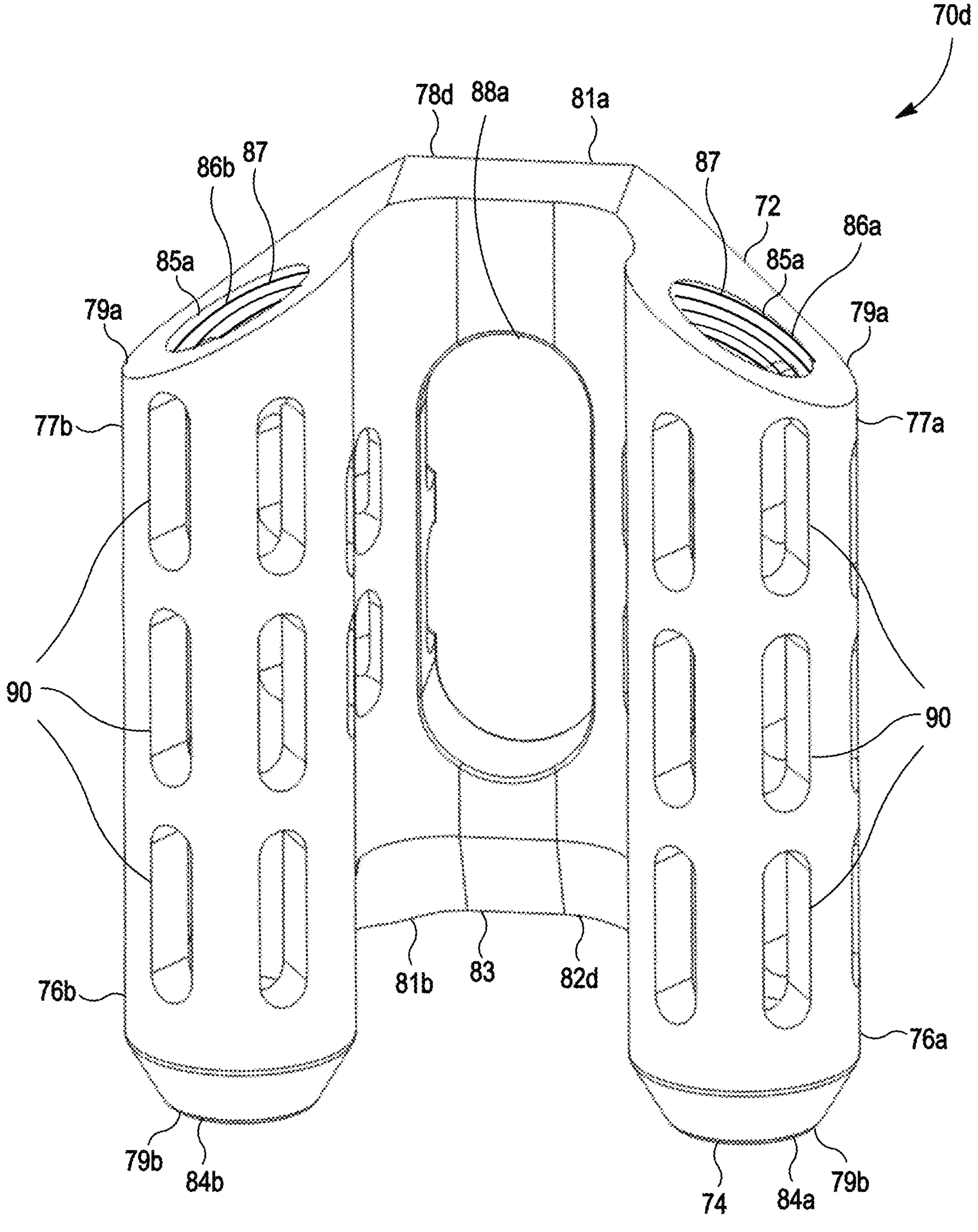
FIG. 5A is a top perspective view of another embodiment of a prosthesis having an offset, U-shaped bridge section, in accordance with the invention.
Figure 5B:
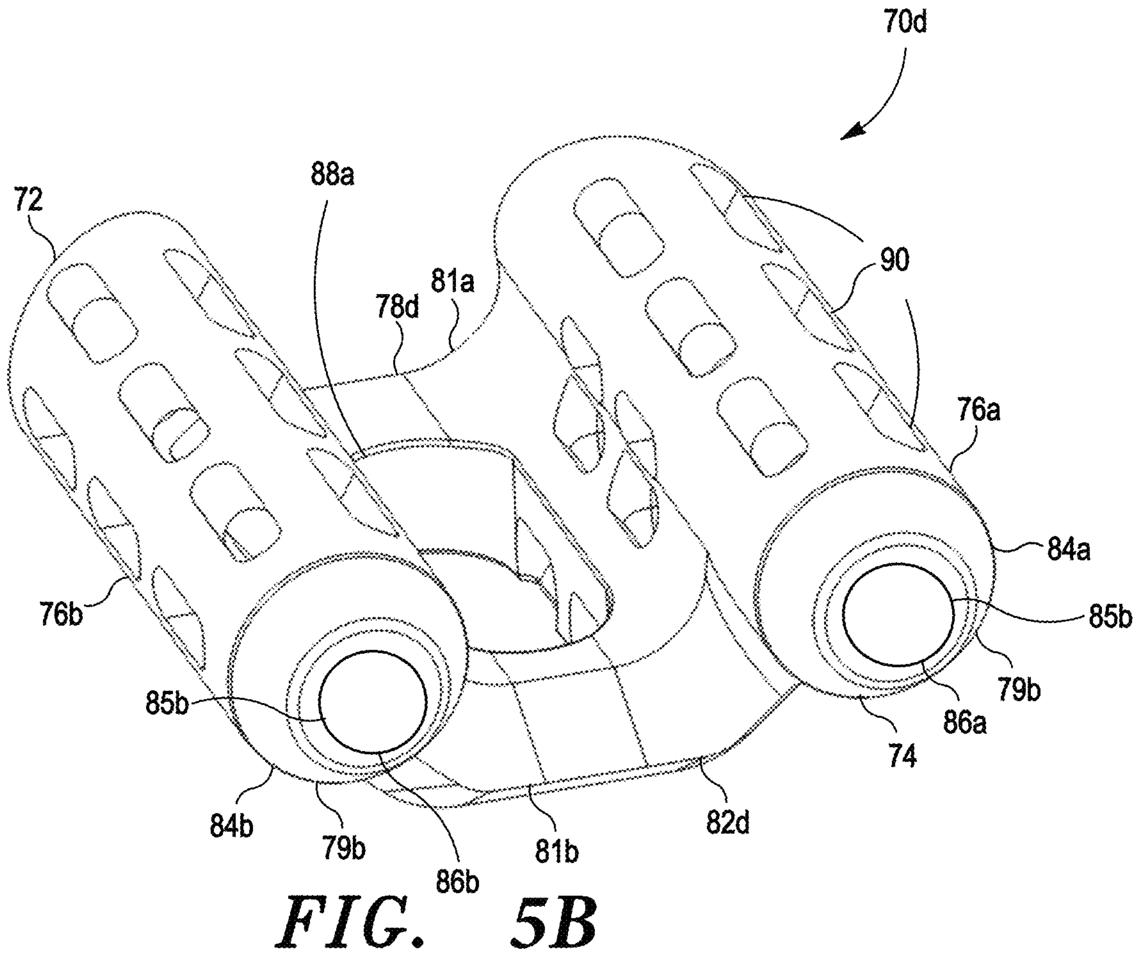
FIG. 5B is a front perspective view of the prosthesis shown in FIG. 5A, in accordance with the invention.
Figure 5C:
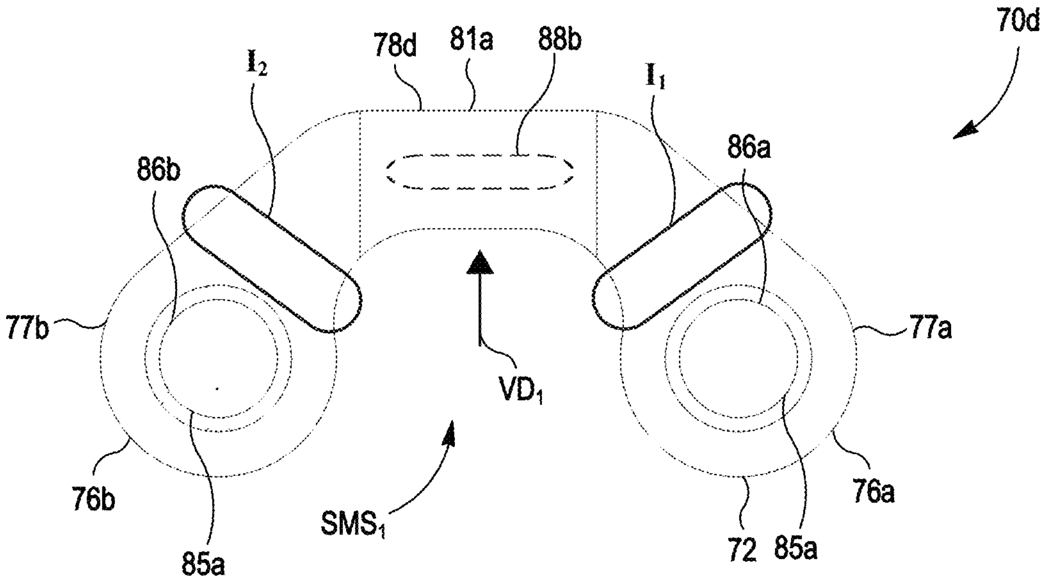
FIG. 5C is an end plan view of the prosthesis shown in FIG. 5A, in accordance with the invention.

Referring now to FIGS. 5A-5C, there is shown another embodiment of a SI joint prosthesis of the invention (denoted "70*d*"), which is similarly adapted to be advanced into a pilot SI joint opening created by a drill guide assembly of the invention and, thereby, into a dysfunctional SI joint in a posterior trajectory.

In a preferred embodiment, when the SI joint prosthesis 70*d* is advanced into a dysfunctional SI joint in a posterior trajectory, the SI joint prosthesis 70*d* similarly transfixes and, thereby, stabilizes the dysfunctional SI joint.

As illustrated in FIGS. 5A and 5B, the SI joint prosthesis 70*d* similarly comprises a monolithic structure comprising first and second elongated sections 76*a*, 76*b*, which similarly comprise the same features of the first and second elongated sections 76*a*, 76*b* of SI joint prosthesis 70*a* described above.

As illustrated in FIGS. 5B and 5C, the SI joint prosthesis 70*d* similarly comprises a bridge section or osteotome (in this embodiment, denoted "78*d*"), which similarly comprises an off-set structure.

As further illustrated in FIGS. 5B and 5C, the offset bridge 78*d* is similarly disposed between the first and second elongated partially cylindrical sections 76*a*, 76*b*, whereby the SI joint prosthesis 70*d* similarly comprises a first interface of the bridge section 78*d* and the first elongated section 76*a* (denoted "I1") and a second interface of the bridge section 78*d* and the second elongated section 76*b* (denoted "I2").

As illustrated in FIG. 5A, in a preferred embodiment, the bridge section 78*d* similarly does not extend beyond the proximal and distal ends 79*a*, 79*b* of the first and second elongated sections 76*a*, 76*b*. However, in some embodiments of the invention, the distal end 81*b* of the bridge section 78*d* extends beyond the distal ends 79*b* of the first and second elongated sections 76*a*, 76*b*.

As further illustrated in FIGS. 5B and 5C, in a preferred embodiment, the bridge section 78*d* comprises a U-shaped structure that is similarly offset in a vertical direction relative to the first and second elongated sections 76*a*, 76*b* (again denoted by arrow "VD1"), whereby the bridge section 78*d* and the first and second elongated sections 76*a*, 76*b* similarly define a prosthesis support member space between the first and second elongated sections 76*a*, 76*b* (denoted "SMS1").

In a preferred embodiment, the prosthesis support member space SMS1 of SI joint prosthesis 70*d* similarly comprises a size that is sufficient to receive and/or position a primary or supplemental joint support member or device, such as a surgical pin or screw, in the prosthesis support member space SMS1 when the SI joint prosthesis 70*d* is advanced into and/or positioned in a dysfunctional SI joint.

In some embodiments, the offset of the bridge section 78*d* is similarly further extended, such as illustrated in FIG. 5C, whereby the bridge section 78*d* similarly extends beyond the first interface I1 of the bridge section 78*d* and the first elongated section 76*a* and a second interface I2 of the bridge section 78*d* and the second elongated section 76*b* to further facilitate the receipt and/or positioning of the primary or supplemental joint support member (or device) in the prosthesis support member space SMS1 when the SI joint prosthesis 70*d* is advanced into and/or positioned in a dysfunctional SI joint.

As illustrated in FIG. 5B, in a preferred embodiment, the distal end 81*b* of the bridge section 78*d*, i.e., U-shaped structure, similarly comprises a taper region 82*d* that is similarly configured to cut into and through at least articular cartilage and cortical bone, and, thereby facilitate advancement of SI joint prosthesis 70*d* into a dysfunctional SI joint.

As illustrated in FIG. 5A, in a preferred embodiment, the bridge section 78*d* similarly comprises central opening 88*a*.

As illustrated in FIG. 5C, according to the invention, the bridge section 78*d* can similarly further comprise the bridge section opening 88*b* on the proximal end 81*a* (shown in phantom), which would similarly extend from the bridge section proximal end 81*a* to the central opening 88*a* and, hence, in communication therewith.

According to the invention, the bridge section 78*d* can similarly comprise a plurality of slots 90, such as slots 90 in the first and second elongated sections 76*a*, 76*b*, with and without the central opening 88*a*.

Figure 6A:
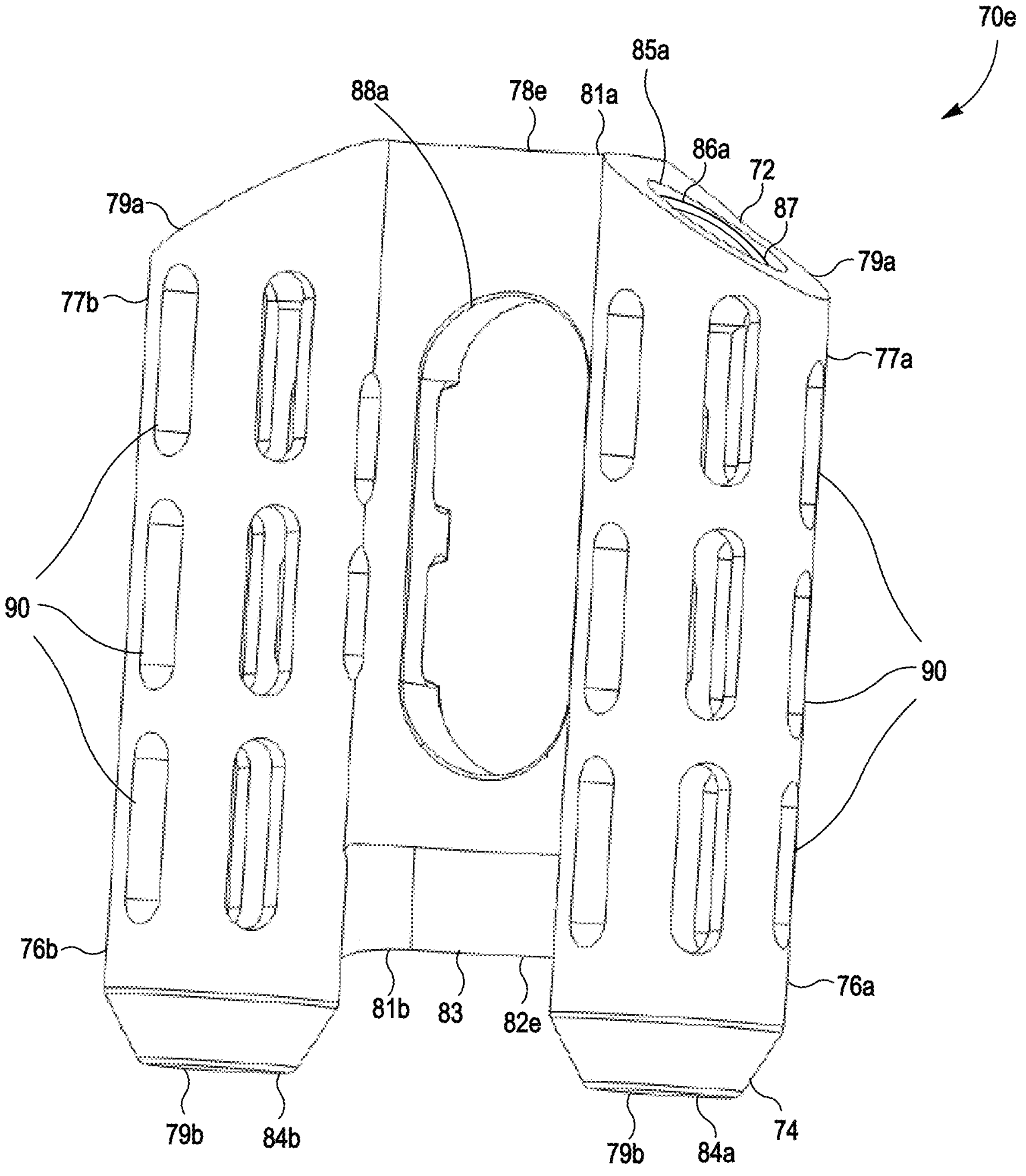
FIG. 6A is a top perspective view of another embodiment of a prosthesis having a planar-shaped bridge section, in accordance with the invention.
Figure 6B:
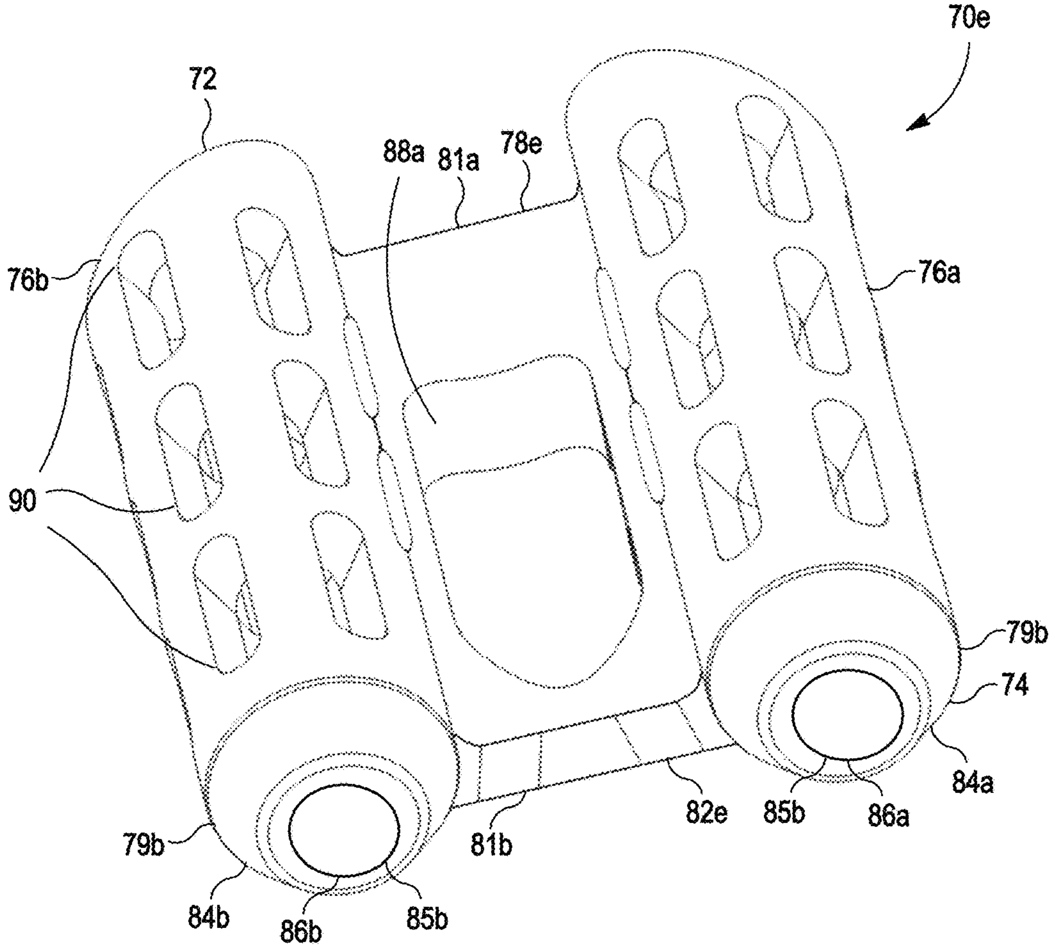
FIG. 6B is a front perspective view of the prosthesis shown in FIG. 6A, in accordance with the invention.
Figure 6C:
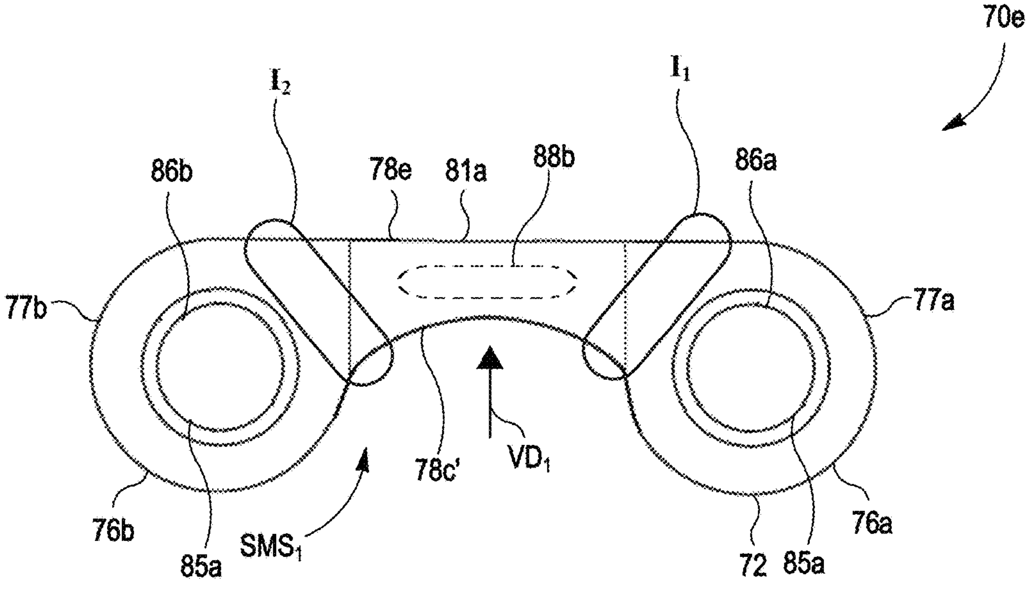
FIG. 6C is an end plan view of the prosthesis shown in FIG. 6A, in accordance with the invention.

Referring now to FIGS. 6A-6C, there is shown another embodiment of a SI joint prosthesis of the invention (denoted "70*e*"), which is similarly adapted to be advanced into a pilot SI joint opening created by a drill guide assembly of the invention and, thereby, into a dysfunctional SI joint in a posterior trajectory.

In a preferred embodiment, when the SI joint prosthesis 70*e* is advanced into a dysfunctional SI joint in a posterior trajectory, the prosthesis 70*e* similarly transfixes and, thereby, stabilizes the dysfunctional SI joint.

As illustrated in FIGS. 6A and 6B, the prosthesis 70*e* similarly comprises a monolithic structure comprising first and second elongated sections 76*a*, 76*b*, which similarly comprise the same features of the first and second elongated sections 76*a*, 76*b* of SI joint prosthesis 70*a* described above.

As further illustrated in FIGS. 6A and 6B, the SI joint prosthesis 70*e* similarly comprises a bridge section or osteotome (in this embodiment, denoted "78*e*"), which, in this embodiment, similarly comprises an off-set structure.

As further illustrated in FIGS. 6B and 6C, the offset bridge 78*e* is similarly disposed between the first and second elongated partially cylindrical sections 76*a*, 76*b*, whereby SI joint prosthesis 70*e* similarly comprises a first interface of the bridge section 78*e* and the first elongated section 76*a* (denoted "I1") and a second interface of the bridge section 78*e* and the second elongated section 76*b* (denoted "I2").

As illustrated in FIG. 6A, in a preferred embodiment, the bridge section 78*e* similarly does not extend beyond the proximal and distal ends 79*a*, 79*b* of the first and second elongated sections 76*a*, 76*b*. However, in some embodiments of the invention, the distal end 81*b* of the bridge section 78*e* similarly extends beyond the distal ends 79*b* of the first and second elongated sections 76*a*, 76*b*.

As further illustrated in FIGS. 6B and 6C, in a preferred embodiment, the bridge section 78*e* comprises a planar-shaped structure that is similarly offset in a vertical direction relative to the first and second elongated sections 76*a*, 76*b* (again denoted by arrow "VD1"), whereby the bridge section 78*e* and the first and second elongated sections 76*a*, 76*b* similarly define a prosthesis support member space between the first and second elongated sections 76*a*, 76*b* (denoted "SMS1").

In a preferred embodiment, the prosthesis support member space SMS1 of SI joint prosthesis 70*e* similarly comprises a size that is sufficient to receive and/or position a primary or supplemental joint support member or device, such as a surgical pin or screw, in the prosthesis support member space SMS1 when the SI joint prosthesis 70*e* is advanced into and/or positioned in a dysfunctional SI joint.

As further illustrated in FIG. 6C, in some embodiments, the inner surface 78*c*' of the bridge section 78*e* comprises a curvilinear shape to further facilitate the receipt and/or positioning of the primary or supplemental joint support member (or device) in the prosthesis support member space SMS1 when the SI joint prosthesis 70*e* is advanced into and/or positioned in a dysfunctional SI joint.

As illustrated in FIG. 6B, in a preferred embodiment, the distal end 81*b* of the bridge section 78*e* similarly comprises a taper region 82*e* that is similarly configured to cut into and through at least articular cartilage and cortical bone, and, thereby facilitate advancement of SI joint prosthesis 70*e* into the dysfunctional SI joint.

As illustrated in FIG. 6A, in a preferred embodiment, the bridge section 78*e* similarly comprises central opening 88*a*.

As illustrated in FIG. 6C, according to the invention, the bridge section 78*e* can similarly further comprise the bridge section opening 88*b* on the proximal end 81*a* (shown in phantom), which would similarly extend from the bridge section proximal end 81*a* to the central opening 88*a* and, hence, in communication therewith.

According to the invention, the bridge section 78*e* can similarly comprise a plurality of slots 90, such as slots 90 in the first and second elongated sections 76*a*, 76*b*, with and without the central opening 88*a*.

Figure 7A:
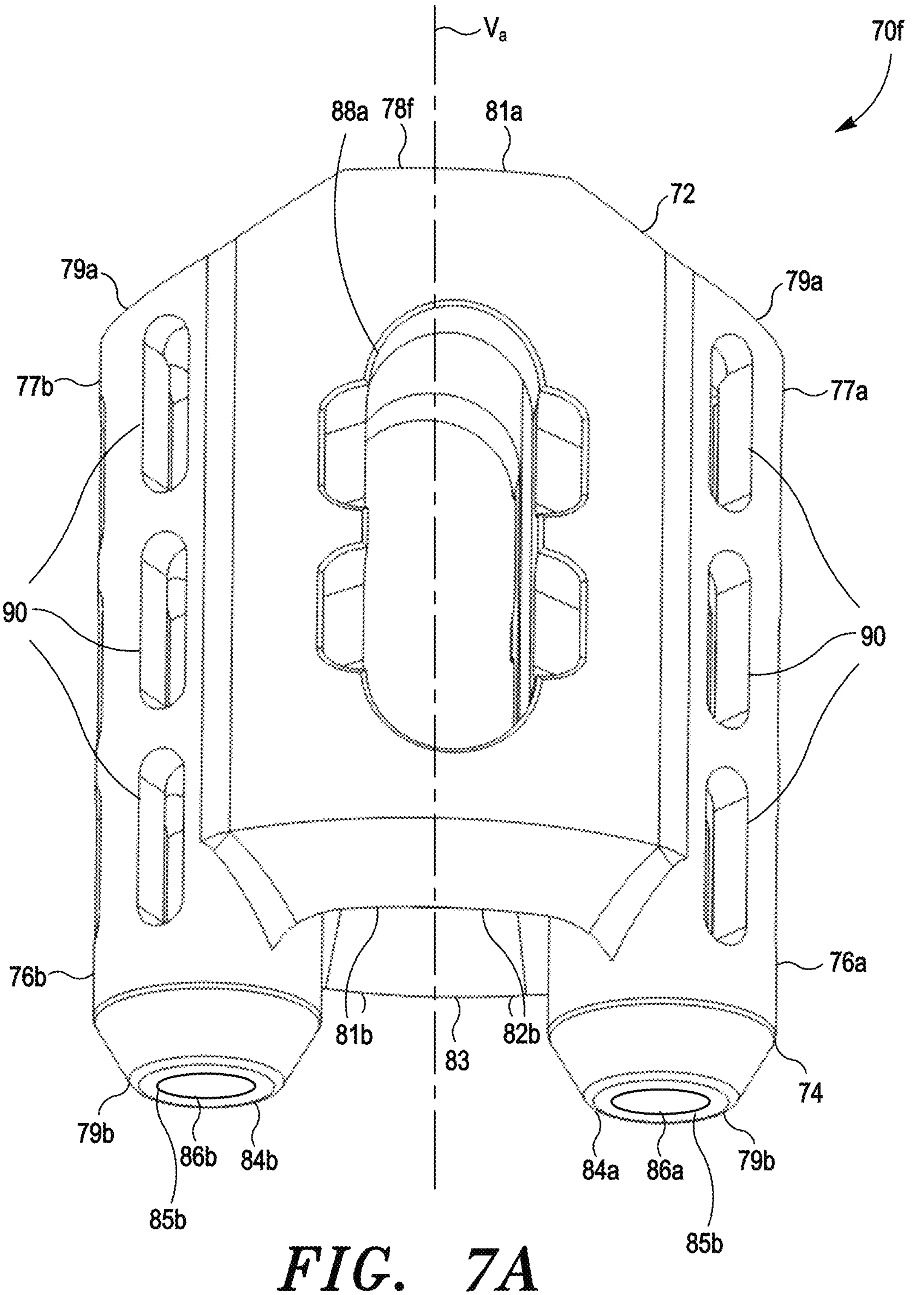
FIG. 7A is a top perspective view of an embodiment of a prosthesis having ovate or arcuate-shaped open bridge section, in accordance with the invention.
Figure 7B:
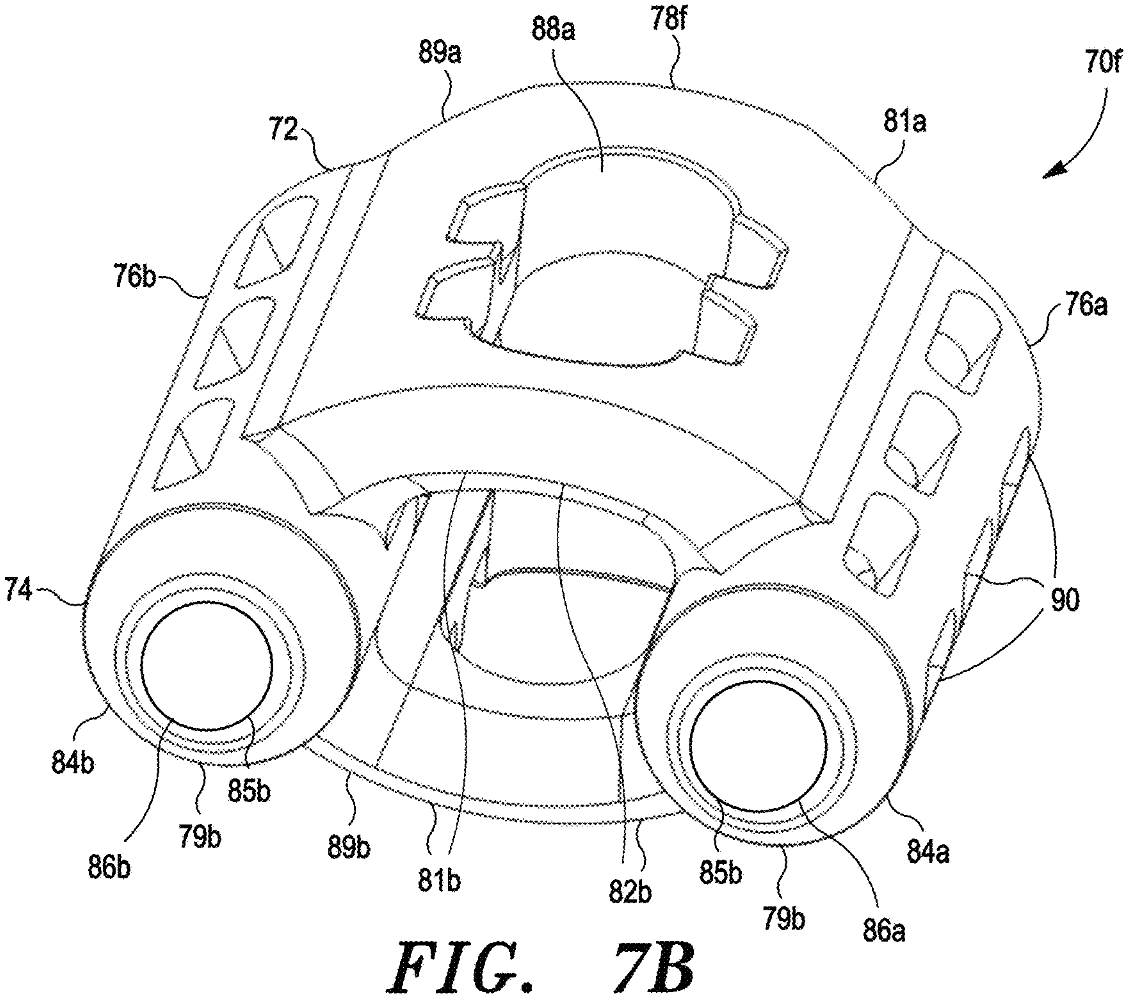
FIG. 7B is a front perspective view of the prosthesis shown in FIG. 7A, in accordance with the invention.
Figure 7C:
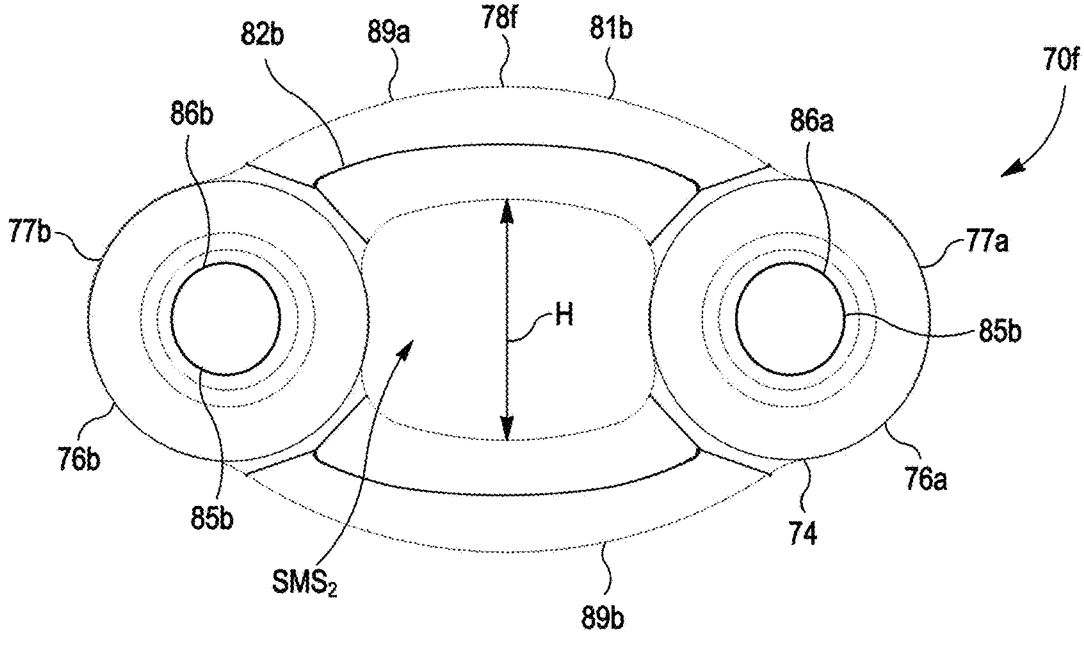
FIG. 7C is an end plan view of the prosthesis shown in FIG. 7A, in accordance with the invention.

Referring now to FIGS. 7A-7C, there is shown another embodiment of a SI joint prosthesis of the invention (denoted "70*f*"), which is similarly adapted to be advanced into a pilot SI joint opening created by a drill guide assembly of the invention and, thereby, into a dysfunctional SI joint in a posterior trajectory.

In a preferred embodiment, when SI joint prosthesis 70*f* is advanced into a dysfunctional SI joint in a posterior trajectory, SI joint prosthesis 70*f* similarly transfixes and, thereby, stabilizes the dysfunctional SI joint.

As illustrated in FIGS. 7A and 7B, the SI joint prosthesis 70*f* similarly comprises a monolithic structure comprising first and second elongated sections 76*a*, 76*b*, which similarly comprise the same features of the first and second elongated sections 76*a*, 76*b* of SI joint prosthesis 70*a* described above.

As further illustrated in FIGS. 7A and 7B, the SI joint prosthesis 70*f* similarly further comprises a bridge section (in this embodiment, denoted "78*f*").

As illustrated in FIGS. 7B and 7C, in a preferred embodiment, the bridge section 78*f* comprises an open "ovate shaped" structure comprising separate top and bottom bridge members 89*a*, 89*b*.

Figure 7D:
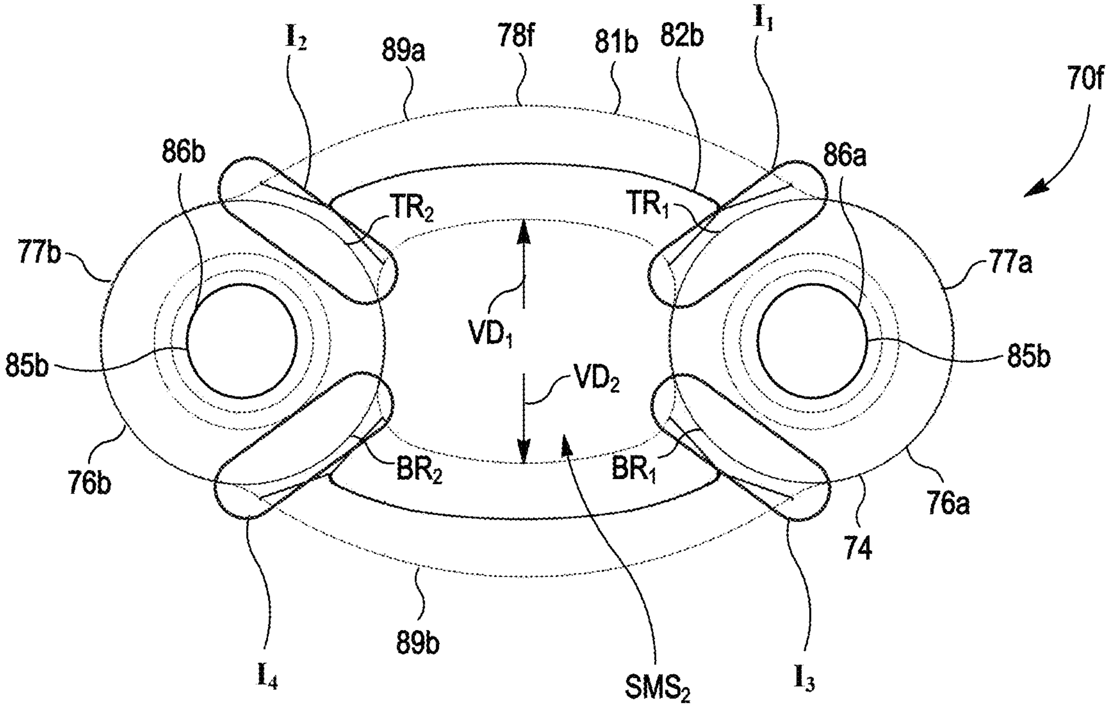
FIG. 7D is a further end plan view of the prosthesis shown in FIG. 7A, in accordance with the invention.

As illustrated in FIGS. 7C and 7D, in a preferred embodiment, the open region of the ovate shaped structure is disposed between the top and bottom bridge members 89*a*, 89*b*, whereby the SI joint prosthesis 70*f* comprises a first interface (denoted "I1") of the top bridge member 89*a* at a first top region (denoted "TR1") of the first elongated section 76*a* and a second interface (denoted "I2") of the top bridge member 89*a* at a second top region (denoted "TR2") of the second elongated section 76*b*, a third interface (denoted "I3") of the bottom bridge member 89*b* and at a first bottom region (denoted "BR1") of the first elongated section 76*a* and a fourth interface (denoted "I4") of the bottom bridge member 89*b* at a second bottom region (denoted "BR2") of the second elongated section 76*b*.

In a preferred embodiment, the first interface I1 of the top bridge member 89*a* and the first elongated section 76*a* and the third interface I3 of the bottom bridge member 89*b* and the first elongated section 76*a* are spaced a first distance apart, and the second interface I2 of the top bridge member 89*a* and the second elongated section 76*b* and the fourth interface 14 of the bottom bridge member 89*b* and the second elongated section 76*b* are spaced a second distance apart.

As indicated above and illustrated in FIG. 7C, in a preferred embodiment, the top and bottom bridge members 89*a*, 89*b* and the first and second elongated sections 76*a*, 76*b* define a prosthesis support member space (i.e., open region of the ovate shaped structure) between the top and bottom bridge members 89*a*, 89*b* and the first and second elongated sections 76*a*, 76*b* (denoted "SMS2").

Figure 13:
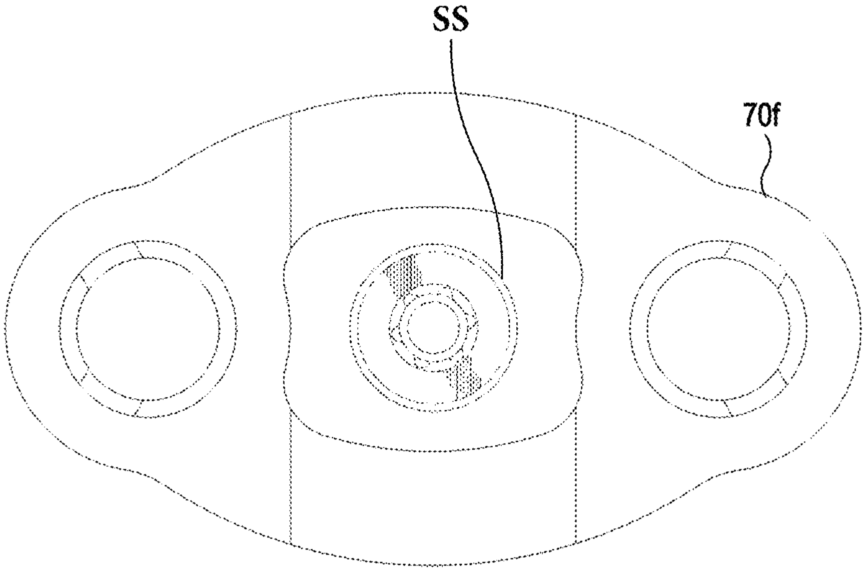
FIG. 13 is an illustration of the prosthesis shown in FIG. 7A with a surgical implant, i.e., surgical dowel, disposed between the elongated sections thereof, in accordance with the invention.

In a preferred embodiment, the prosthesis support member space SMS2 of prosthesis 70*f* is similarly sized and configured to facilitate the receipt and/or positioning of a primary or supplemental joint support member or device, such as a surgical pin or screw, in the prosthesis support member space SMS2 of prosthesis 70*f* when SI joint prosthesis 70*f* is advanced into and/or positioned in a dysfunctional SI joint, such as illustrated in FIG. 13 wherein the supplemental support is denoted "SS."

In a preferred embodiment, the prosthesis support member space SMS2 comprises a minimum height (denoted "H") proximate the vertical axis of SI joint prosthesis 70*f* (denoted "Va") in the range of 25.0 mm to 17.0 mm, more preferably, in the range of 20.0 mm to 17.0 mm.

In some embodiments, the bridge section 78*f* is offset relative to the first and second elongated sections 76*a*, 76*b*, such as illustrated in FIG. 7C, whereby the top bridge member 89*a* of the bridge section 78*f* extends beyond the first interface I1 of the top bridge member 89*a* and the first elongated section 76*a* and the second interface I2 of the top bridge member 89*a* and the second elongated section 76*b* in a first vertical direction (denoted again by arrow "VD1"), and the bottom bridge member 89*b* of the bridge section 78*f* extends beyond the third interface I3 of the bottom bridge member 89*b* and the first elongated section 76*a* and the fourth interface 14 of the bottom bridge member 89*b* and the second elongated section 76*b* in a second vertical direction (denoted by arrow "VD2") to further facilitate the receipt and/or positioning of a primary or supplemental joint support member (or device) in the prosthesis support member space SMS2 when the SI joint prosthesis 70*f* is advanced into and/or positioned in a dysfunctional SI joint.

As illustrated in FIG. 7A, in a preferred embodiment, the top and bottom bridge members 89*a*, 89*b* similarly comprise a central opening 88*a*.

As illustrated in FIG. 7B, in a preferred embodiment, the distal ends 81*b* of the top and bottom bridge members 89*a*, 89*b* similarly comprise taper regions 82*b* that are configured to cut into and through at least articular cartilage and cortical bone of a SI joint, and, thereby, facilitate advancement of SI joint prosthesis 70*f* into a dysfunctional SI joint.

According to the invention, the top and/or bottom bridge members 89*a*, 89*b* can similarly further comprise a plurality of slots 90, such as slots 90 in the first and second elongated sections 76*a*, 76*b*.

Figure 8A:
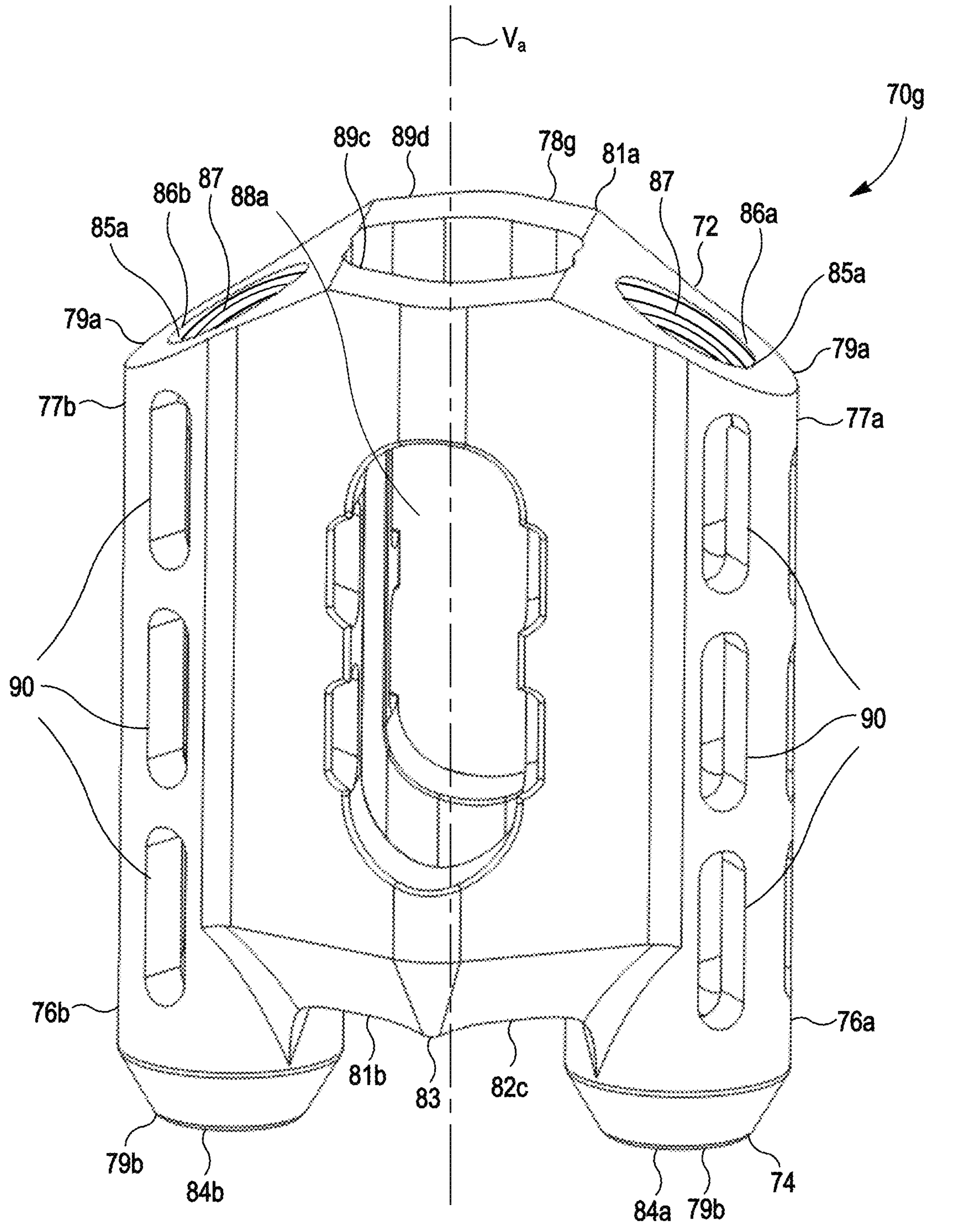
FIG. 8A is a top perspective view of an embodiment of a prosthesis having open bridge section comprising opposing V-shaped top and bottom members, in accordance with the invention.
Figure 8B:
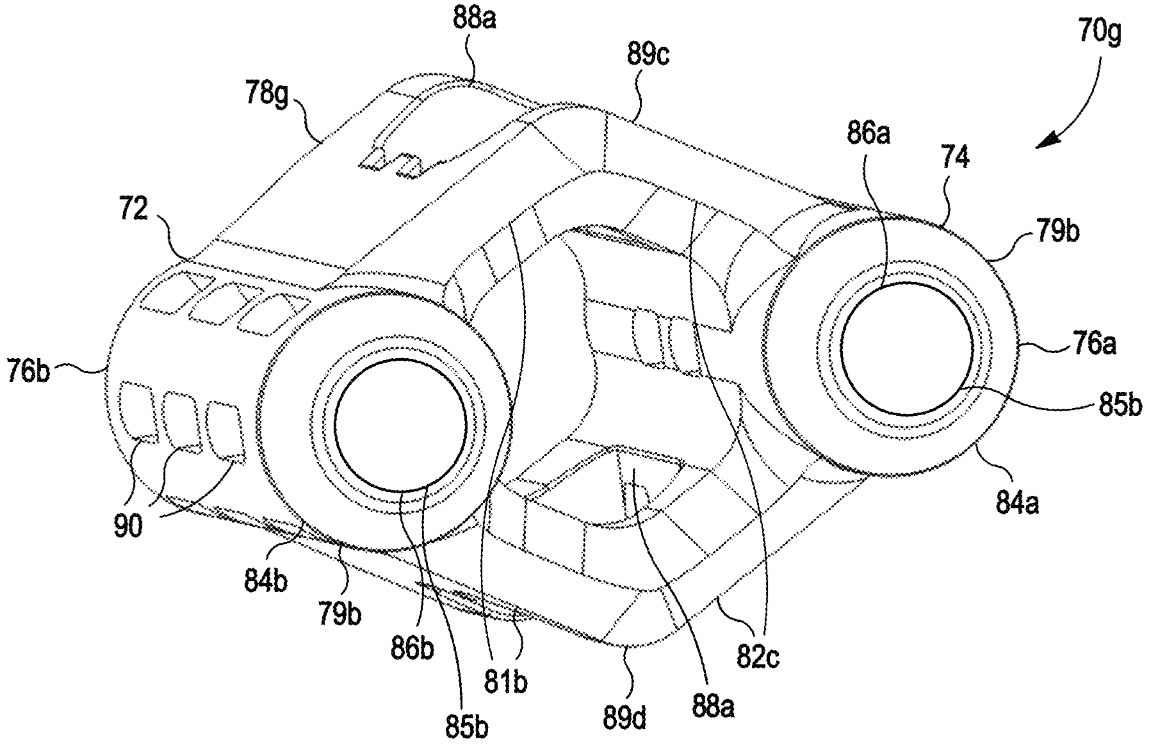
FIG. 8B is a front perspective view of the prosthesis shown in FIG. 8A, in accordance with the invention.
Figure 8C:
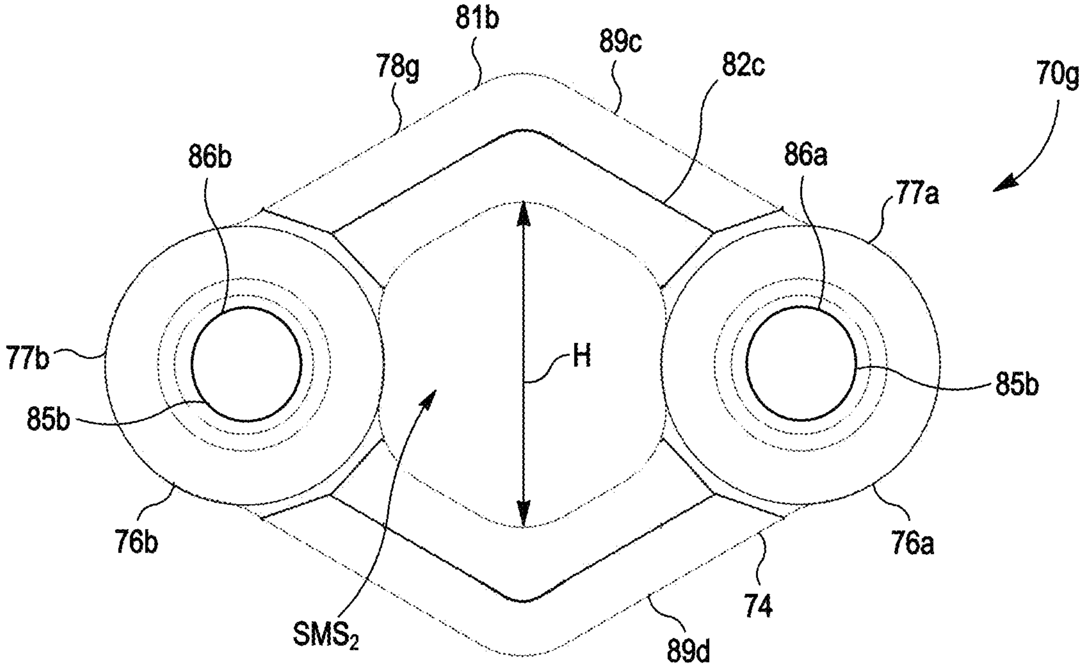
FIG. 8C is an end plan view of the prosthesis shown in FIG. 8A, in accordance with the invention.

Referring now to FIGS. 8A-8C, there is shown another embodiment of a SI joint prosthesis of the invention (denoted "70*g*"), which is similarly adapted to be advanced into a pilot SI joint opening created by a drill guide assembly of the invention and, thereby, into a dysfunctional SI joint in a posterior trajectory.

In a preferred embodiment, when SI joint prosthesis 70*g* is advanced into a dysfunctional SI joint in a posterior trajectory, SI joint prosthesis 70*g* similarly transfixes and, thereby, stabilizes the dysfunctional SI joint.

As illustrated in FIGS. 8A and 8B, the SI joint prosthesis 70*g* similarly comprises a monolithic structure comprising first and second elongated sections 76*a*, 76*b*, which similarly comprise the same features of the first and second elongated sections 76*a*, 76*b* of SI joint prosthesis 70*a* described above.

As further illustrated in FIGS. 8A and 8B, the SI joint prosthesis 70*g* similarly further comprises a bridge section (in this embodiment, denoted "78*g*").

As illustrated in FIGS. 8B and 8C, in a preferred embodiment, the bridge section 78*g* comprises an open structure comprising separate opposing V-shaped top and bottom bridge members 89*c*, 89*d*.

Figure 8D:
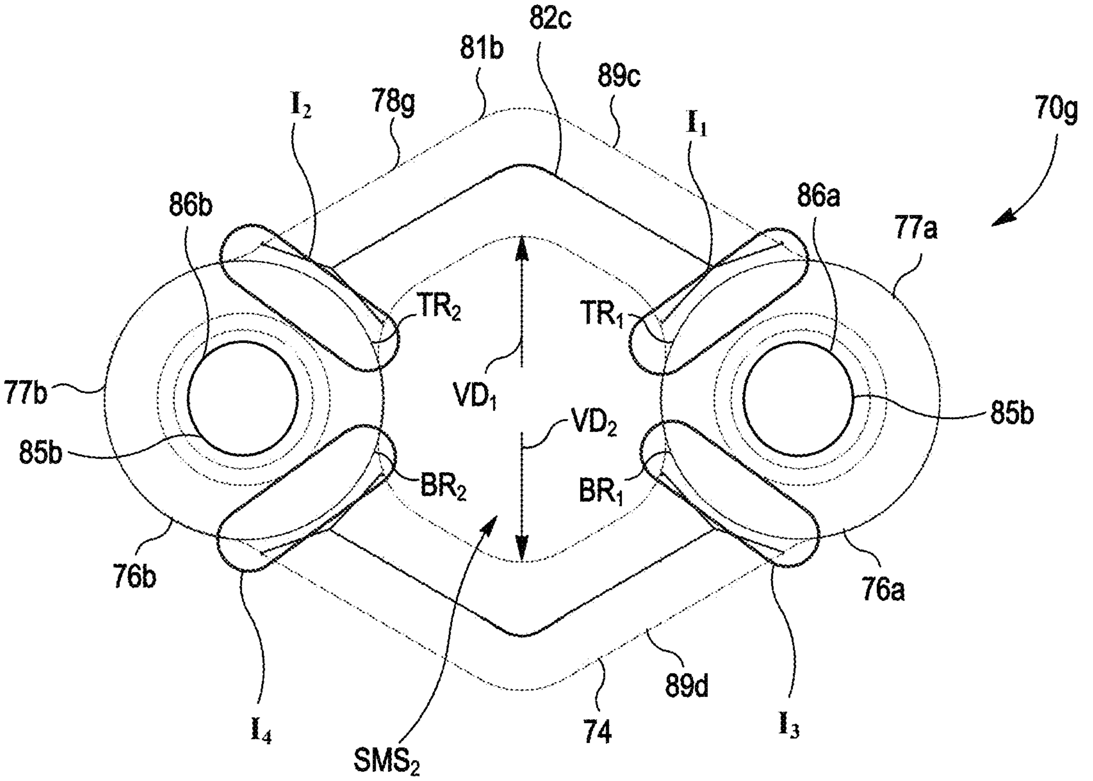
FIG. 8D is a further end plan view of the prosthesis shown in FIG. 8A, in accordance with the invention.

As illustrated in FIG. 8D, the open region of the open bridge structure is similarly disposed between the first and second elongated sections 76*a*, 76*b*, whereby the SI joint prosthesis 70*g* comprises a first interface (denoted "I1") of the top bridge member 89*c* at a first top region (denoted "TR1") of the first elongated section 76*a* and a second interface (denoted "I2") of the top bridge member 89*c* at a second top region (denoted "TR2") of the second elongated section 76*b*, a third interface (denoted "I3") of the bottom bridge member 89*d* and at a first bottom region (denoted "BR1") of the first elongated section 76*a* and a fourth interface (denoted "I4") of the bottom bridge member 89*d* at a second bottom region (denoted "BR2") of the second elongated section 76*b*.

In a preferred embodiment, the first interface I1 of the top bridge member 89*c* and the first elongated section 76*a* and the third interface I3 of the bottom bridge member 89*d* and the first elongated section 76*a* are spaced a first distance apart, and the second interface I2 of the top bridge member 89*c* and the second elongated section 76*b* and the fourth interface 14 of the bottom bridge member 89*d* and the second elongated section 76*b* are spaced a second distance apart.

As indicated above and illustrated in FIG. 8C, in a preferred embodiment, the top and bottom bridge members 89*c*, 89*d* and the first and second elongated sections 76*a*, 76*b* similarly define a prosthesis support member space (i.e., open region of the open bridge structure) between the top and bottom bridge members 89*c*, 89*d* and the first and second elongated sections 76*a*, 76*b* (again denoted “SMS2”).

In a preferred embodiment, the prosthesis support member space SMS2 of SI joint prosthesis 70*g* is similarly sized and configured to facilitate the receipt and/or positioning of a primary or supplemental joint support member or device, such as a surgical pin or screw, in the prosthesis support member space SMS2 of SI joint prosthesis 70*g* when prosthesis 70*g* is advanced into and/or positioned in a dysfunctional SI joint.

In a preferred embodiment, the prosthesis support member space SMS2 of SI joint prosthesis 70*g* similarly comprises a minimum height (denoted “H”) proximate the vertical axis (denoted “Va”) in the range of 25.0 mm to 17.0 mm, more preferably, in the range of 20.0 mm to 17.0 mm.

In some embodiments, the bridge section 78*g* is similarly offset relative to the first and second elongated sections 76*a*, 76*b*, such as illustrated in FIGS. 8C and 8D, whereby the top bridge member 89*c* of the bridge section 78*g* extends beyond the first interface I1 of the top bridge member 89*c* and the first elongated section 76*a* and the second interface I2 of the top bridge member 89*c* and the second elongated section 76*b* in a first vertical direction (denoted again by arrow “VD1”), and the bottom bridge member 89*d* of the bridge section 78*g* extends beyond the third interface I3 of the bottom bridge member 89*d* and the first elongated section 76*a* and the fourth interface I4 of the bottom bridge section 89*d* and the second elongated section 76*b* in a second vertical direction (denoted by arrow “VD2”) to further facilitate receipt and/or positioning of a primary or supplemental joint support member (or device) in the prosthesis support member space SMS2 of SI joint prosthesis 70*g* when prosthesis 70*g* is advanced into and/or positioned in a dysfunctional SI joint.

As illustrated in FIGS. 8A and 8B, in a preferred embodiment, the top and bottom bridge members 89*c*, 89*d* similarly comprise central opening 88*a*.

As illustrated in FIG. 8B, in a preferred embodiment, the distal ends 81*b* of the top and bottom bridge members 89*c*, 89*d* similarly comprise taper regions 82*c* that are configured to cut into and through at least articular cartilage and cortical bone, and, thereby, similarly facilitate advancement of SI joint prosthesis 70*g* into a dysfunctional SI joint.

According to the invention, the top and/or bottom bridge members 89*c*, 89*d* can similarly further comprise a plurality of slots 90, such as slots 90 in the first and second elongated sections 76*a*, 76*b*.

Figure 9A:
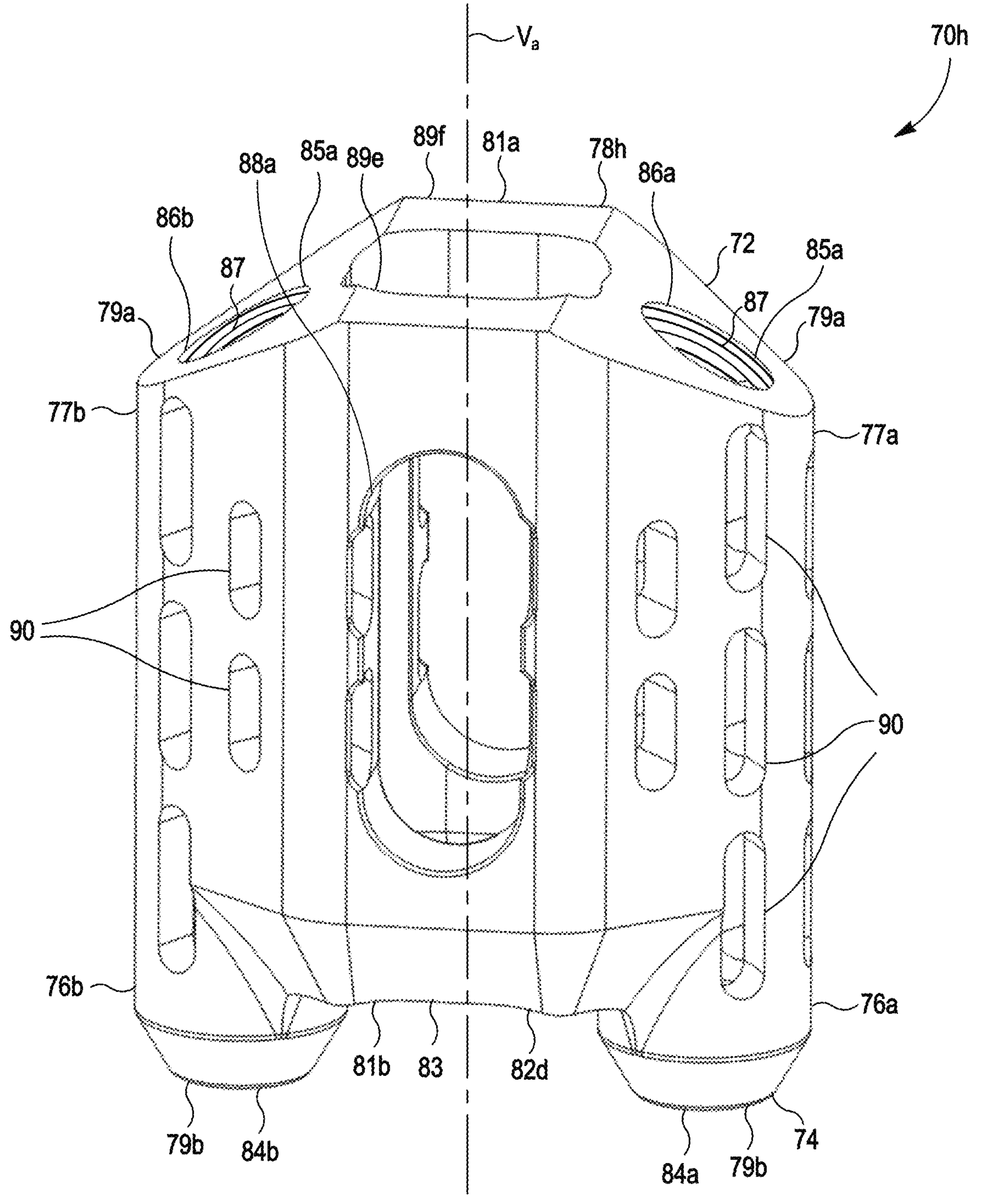
FIG. 9A is a top perspective view of an embodiment of a prosthesis having an open bridge section comprising opposing U-shaped top and bottom members, in accordance with the invention.
Figure 9B:
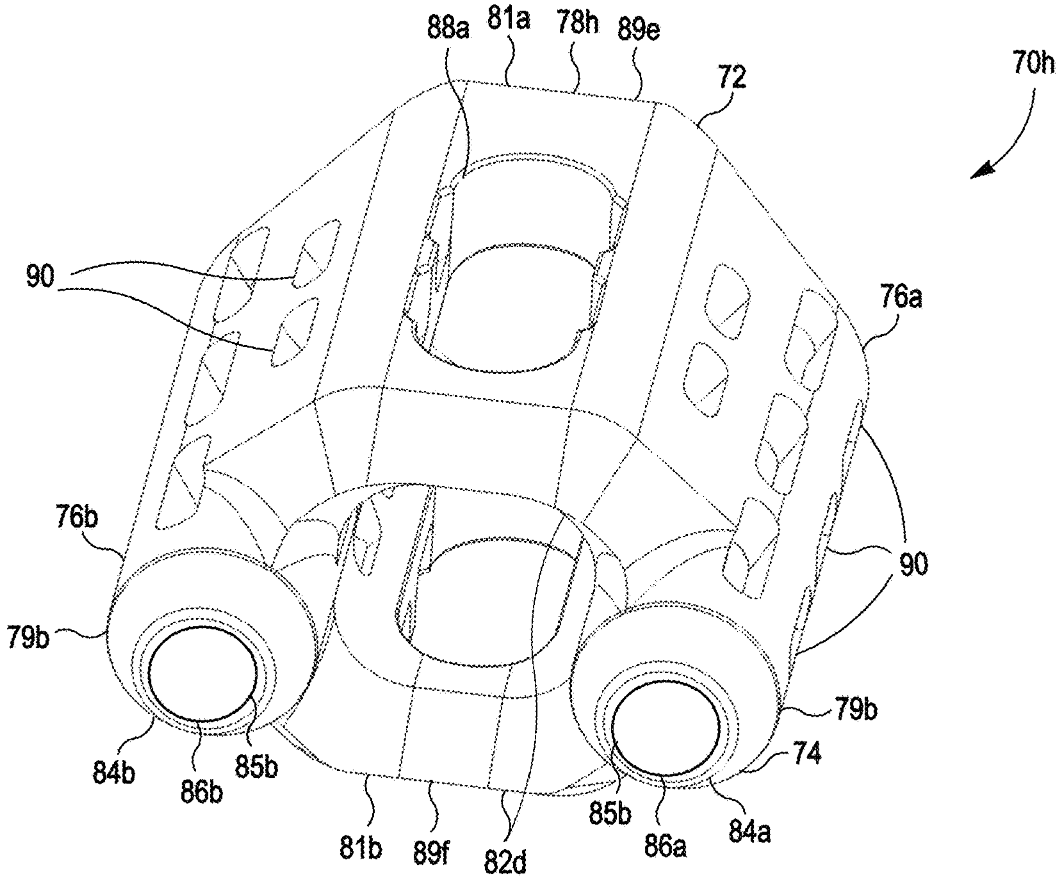
FIG. 9B is a front perspective view of the prosthesis shown in FIG. 9A, in accordance with the invention.
Figure 9C:
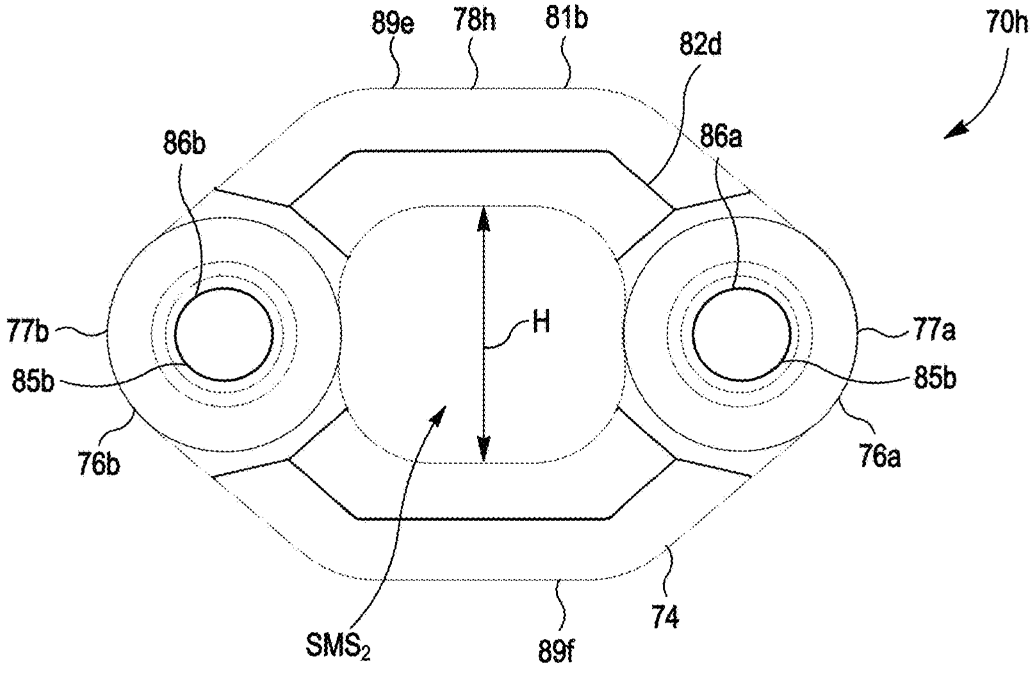
FIG. 9C is an end plan view of the prosthesis shown in FIG. 9A, in accordance with the invention.

Referring now to FIGS. 9A-9C, there is shown another embodiment of a SI joint prosthesis of the invention (denoted “70*h*”), which is similarly adapted to be advanced into a pilot SI joint opening created by a drill guide assembly of the invention and, thereby, into a dysfunctional SI joint in a posterior trajectory.

In a preferred embodiment, when SI joint prosthesis 70*h* is advanced into a dysfunctional SI joint in a posterior trajectory, SI joint prosthesis 70*h* similarly transfixes and, thereby, stabilizes the dysfunctional SI joint.

As illustrated in FIGS. 9A and 9B, SI joint prosthesis 70*h* similarly comprises a monolithic structure comprising first and second elongated sections 76*a*, 76*b*, which similarly comprise the same features of the first and second elongated sections 76*a*, 76*b* of SI joint prosthesis 70*a* described above.

As further illustrated in FIGS. 9A and 9B, SI joint prosthesis 70*h* similarly also comprises a bridge section (in this embodiment, denoted “78*h*”).

As illustrated in FIGS. 9B and 9C, in a preferred embodiment, the bridge section 78*h* comprises an open structure comprising separate opposing U-shaped top and bottom bridge members 89*e*, 89*f*.

Figure 9D:
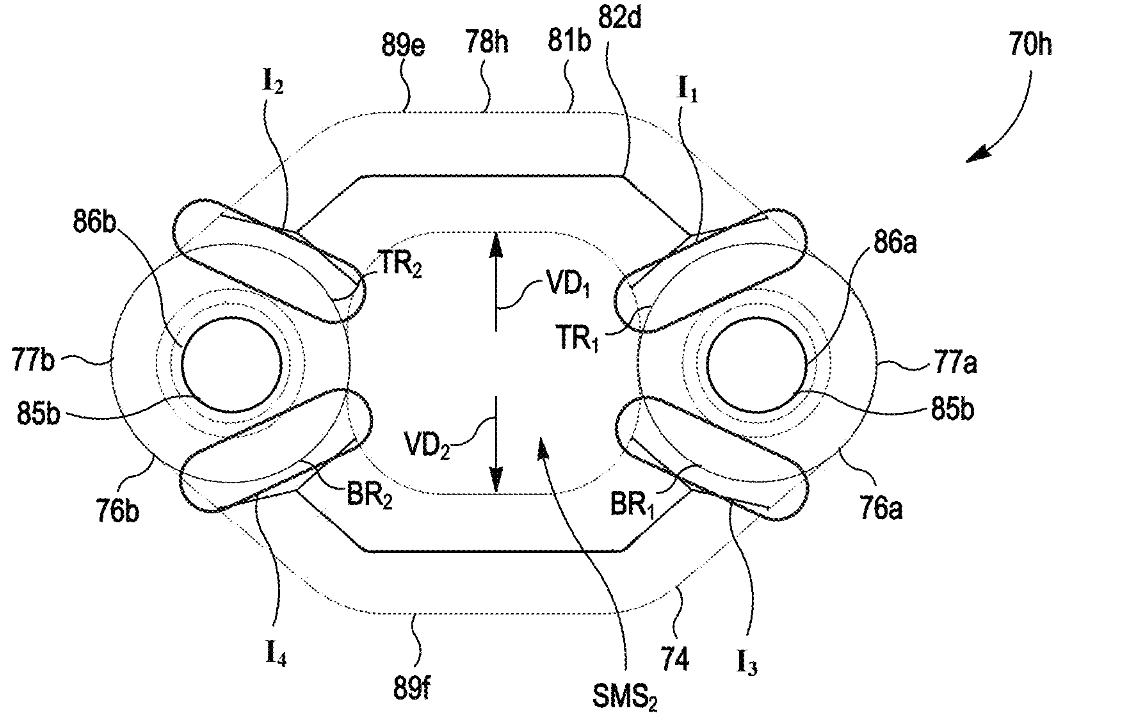
FIG. 9D is a further end plan view of the prosthesis shown in FIG. 9A, in accordance with the invention.

As illustrated in FIG. 9D, the open region of the open bridge structure is similarly disposed between the first and second elongated sections 76*a*, 76*b*, whereby the prosthesis 70*h* comprises a first interface (denoted “I1”) of the top bridge member 89*e* at a first top region (denoted “TR1”) of the first elongated section 76*a* and a second interface (denoted “12”) of the top bridge member 89*e* at a second top region (denoted “TR2”) of the second elongated section 76*b*, a third interface (denoted “I3”) of the bottom bridge member 89*f* and at a first bottom region (denoted “BR1”) of the first elongated section 76*a* and a fourth interface (denoted “14”) of the bottom bridge member 89*f* at a second bottom region (denoted “BR2”) of the second elongated section 76*b*.

In a preferred embodiment, the first interface I1 of the top bridge member 89*e* and the first elongated section 76*a* and the third interface I3 of the bottom bridge member 89*f* and the first elongated section 76*a* are spaced a first distance apart, and the second interface I2 of the top bridge member 89*e* and the second elongated section 76*b* and the fourth interface 14 of the bottom bridge member 89*f* and the second elongated section 76*b* are spaced a second distance apart.

As indicated above and illustrated in FIG. 9C, in a preferred embodiment, the top and bottom bridge members 89*e*, 89*f* and the first and second elongated sections 76*a*, 76*b* similarly define a prosthesis support member space (i.e., open region of the open bridge structure) between the top and bottom bridge members 89*e*, 89*f* and the first and second elongated sections 76*a*, 76*b* (again denoted “SMS2”).

In a preferred embodiment, the prosthesis support member space SMS2 of SI joint prosthesis 70*h* is similarly sized and configured to facilitate the receipt and/or positioning of a primary or supplemental joint support member or device, such as a surgical pin or screw, in the prosthesis support member space SMS2 of SI joint prosthesis 70*h* when prosthesis 70*h* is advanced into and/or positioned in a dysfunctional SI joint.

In a preferred embodiment, the prosthesis support member space SMS2 of SI joint prosthesis 70*h* similarly comprises a minimum height (denoted “H”) proximate the vertical axis (denoted “Va”) in the range of 25.0 mm to 17.0 mm, more preferably, in the range of 20.0 mm to 17.0 mm.

In some embodiments, the bridge section 78*h* is similarly offset relative to the first and second elongated sections 76*a*, 76*b*, such as illustrated in FIGS. 9C and 9D, whereby the top bridge member 89*e* of the bridge section 78*h* extends beyond the first interface I1 of the top bridge member 89*e* and the first elongated section 76*a* and the second interface 12 of the top bridge member 89*e* and the second elongated section 76*b* in a first vertical direction (denoted again by arrow “VD1”), and the bottom bridge member 89*f* of the bridge section 78*h* extends beyond the third interface I3 of the bottom bridge member 89*f* and the first elongated section 76*a* and the fourth interface I4 of the bottom bridge section 89*f* and the second elongated section 76*b* in a second vertical direction (denoted by arrow “VD2”) to further facilitate receipt and/or positioning of a primary or supplemental joint support member (or device) in the prosthesis support member space SMS2 of prosthesis 70*h* when SI joint prosthesis 70*h* is advanced into and/or positioned in a dysfunctional SI joint.

As illustrated in FIGS. 9A and 9B, in a preferred embodiment, the top and bottom bridge members 89*e*, 89*f* similarly comprise central opening 88*a*.

As illustrated in FIG. 9B, in a preferred embodiment, the distal ends 81*b* of the top and bottom bridge members 89*e*, 89*f* similarly comprise taper regions 82*d* that are configured to cut into and through at least articular cartilage and cortical bone of a SI joint, and, thereby, facilitate advancement of SI joint prosthesis 70*h* into a dysfunctional SI joint.

According to the invention, the top and/or bottom bridge members 89*e*, 89*f* can similarly further comprise a plurality of slots 90, such as slots 90 in the first and second elongated sections 76*a*, 76*b*.

Figure 10A:
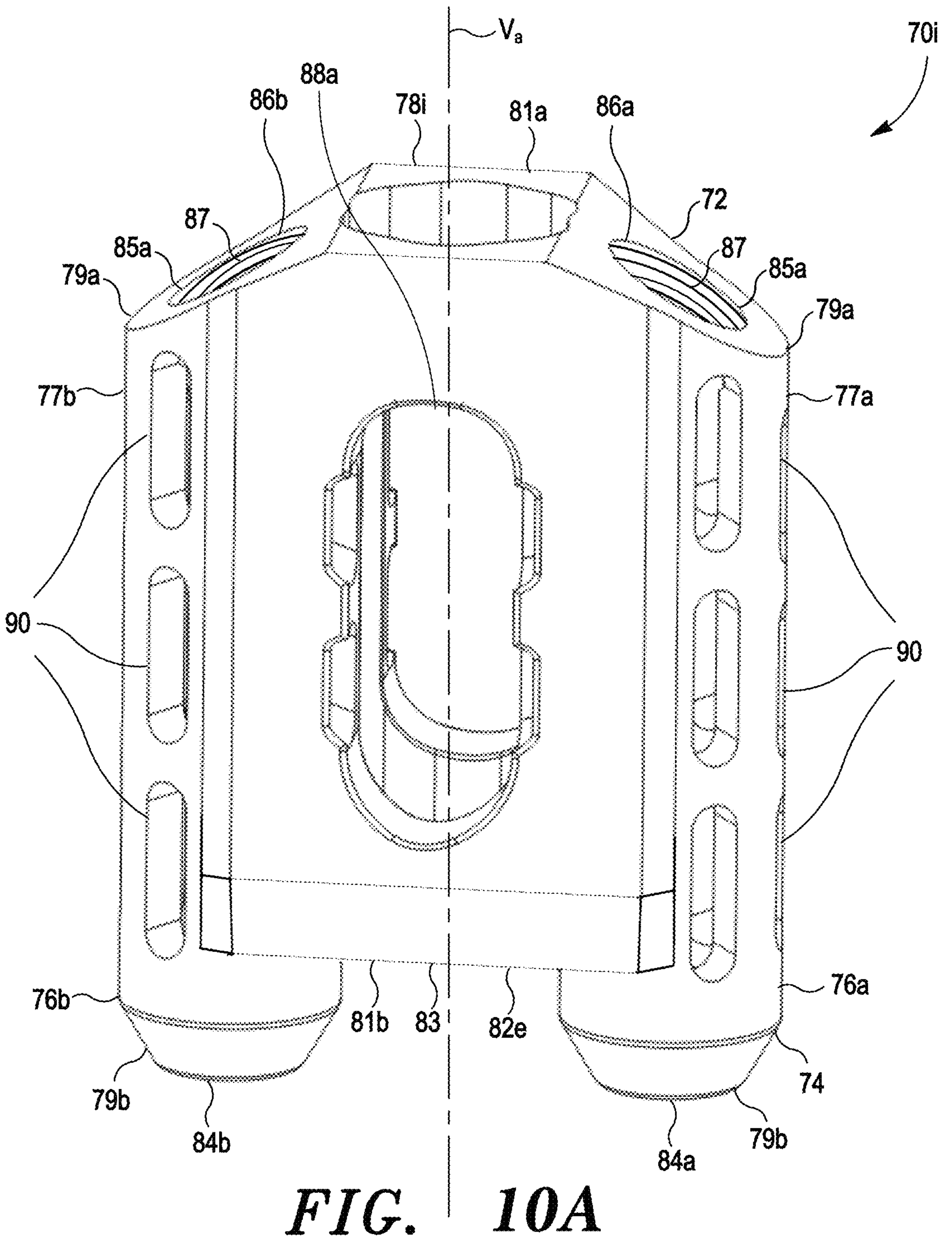
FIG. 10A is a top perspective view of an embodiment of a prosthesis having an open bridge section comprising opposing planar top and bottom members, in accordance with the invention.
Figure 10B:
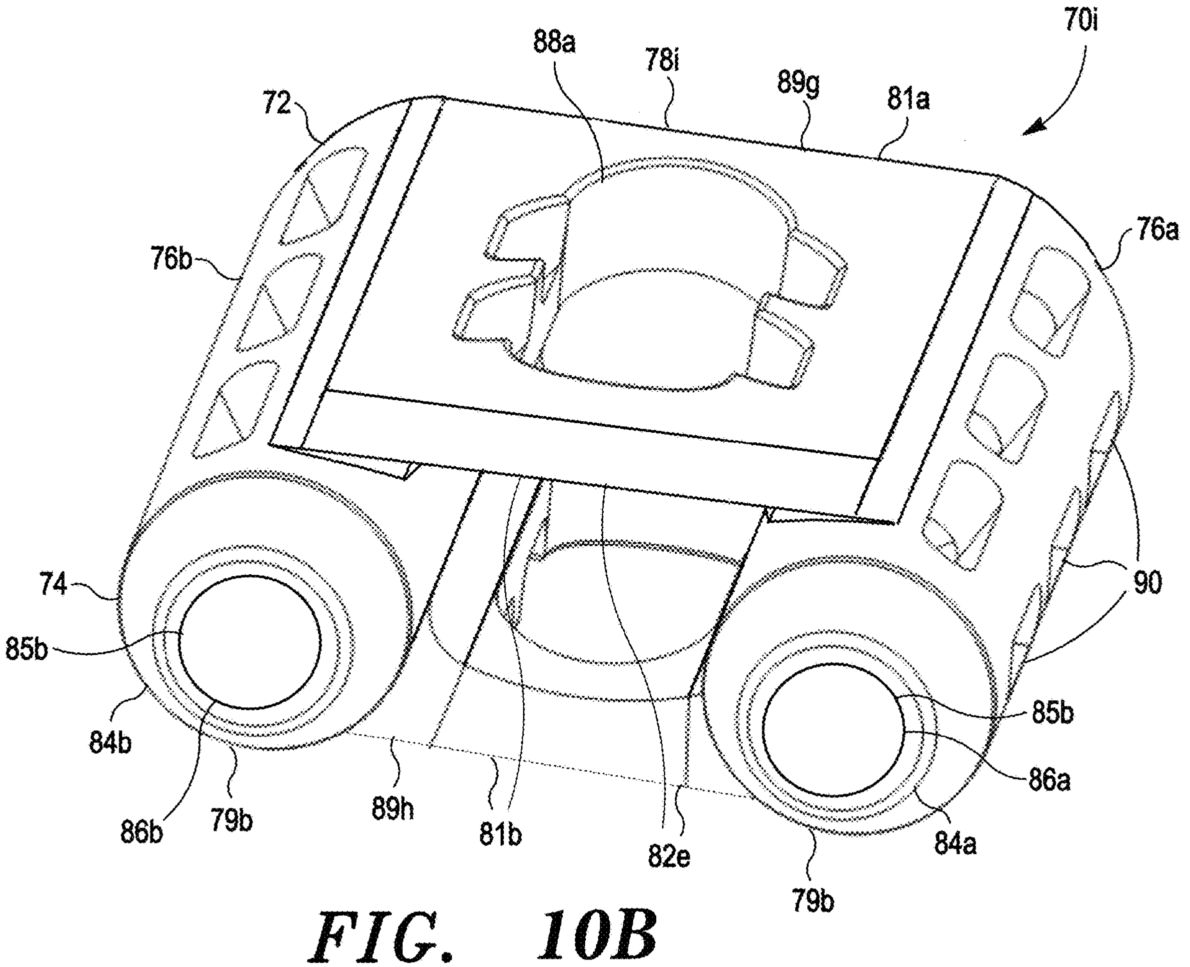
FIG. 10B is a front perspective view of the prosthesis shown in FIG. 10A, in accordance with the invention.
Figure 10C:
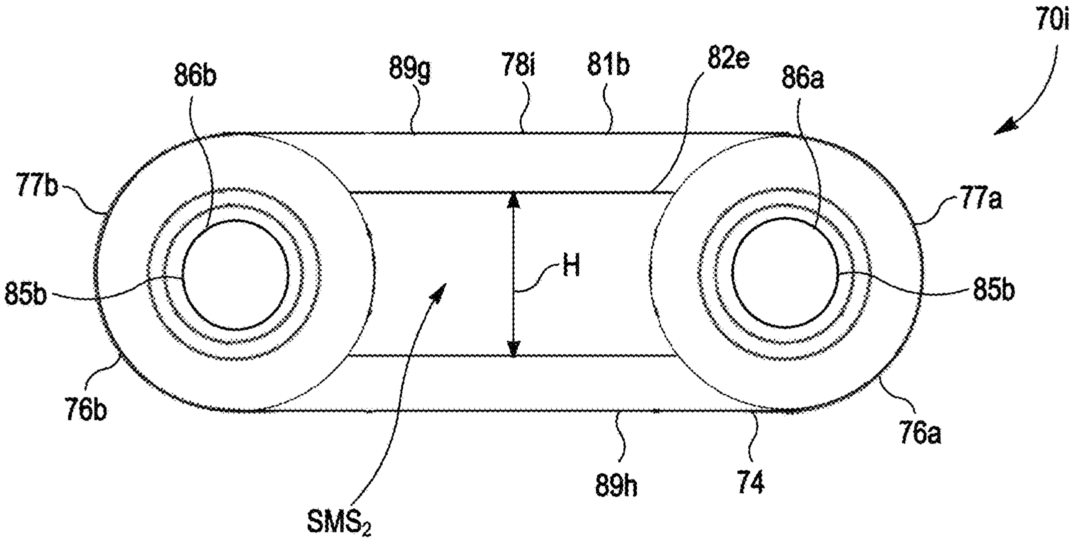
FIG. 10C is an end plan view of the prosthesis shown in FIG. 10A, in accordance with the invention.

Referring now to FIGS. 10A-10C, there is shown another embodiment of a SI joint prosthesis of the invention (denoted "70*i*"), which is similarly adapted to be advanced into a pilot SI joint opening created by a drill guide assembly of the invention and, thereby, into a dysfunctional SI joint in a posterior trajectory.

In a preferred embodiment, when SI joint prosthesis 70*i* is advanced into a dysfunctional SI joint in a posterior trajectory, SI joint prosthesis 70*i* similarly transfixes and, thereby, stabilizes the dysfunctional SI joint.

As illustrated in FIGS. 10A and 10B, SI joint prosthesis 70*i* similarly comprises a monolithic structure comprising first and second elongated sections 76*a*, 76*b*, which similarly comprise the same features of the first and second elongated sections 76*a*, 76*b* of SI joint prosthesis 70*a* described above.

As further illustrated in FIGS. 10A and 10B, SI joint prosthesis 70*i* similarly also comprises a bridge section (in this embodiment, denoted "78*i*").

As illustrated in FIGS. 10B and 10C, in a preferred embodiment, the bridge section 78*i* comprises an open structure comprising separate opposing planar-shaped top and bottom bridge members 89*g*, 89*h*.

Figure 10D:
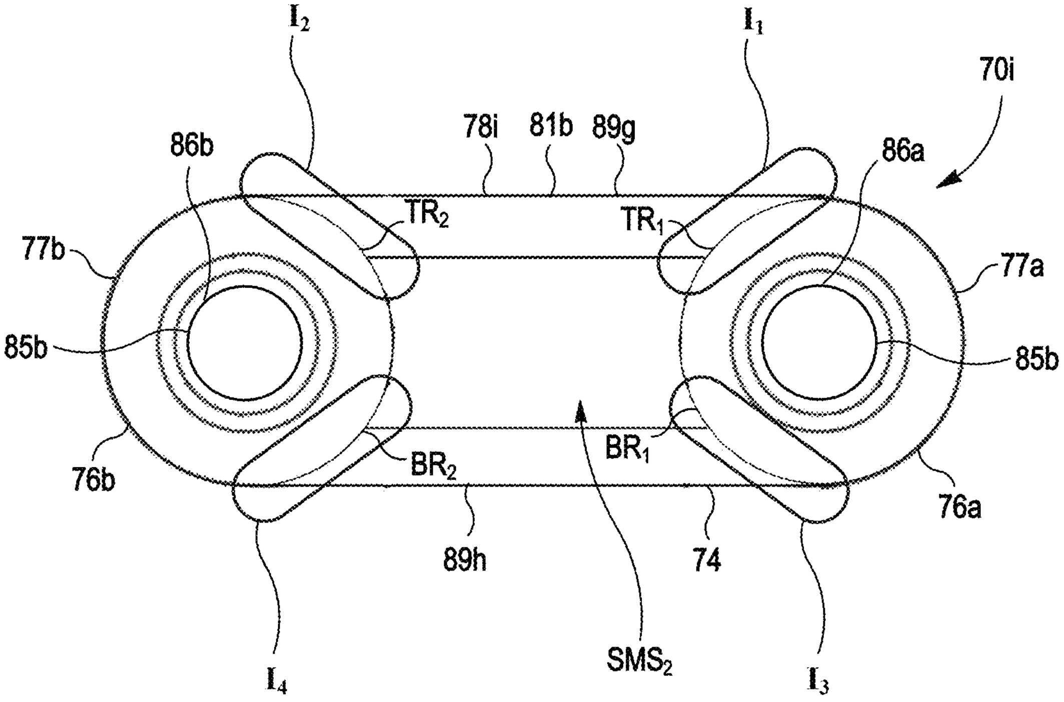
FIG. 10D is a further end plan view of the prosthesis shown in FIG. 10A, in accordance with the invention.

As illustrated in FIG. 10D, the open region of the open bridge structure is similarly disposed between the first and second elongated sections 76*a*, 76*b*, whereby the prosthesis 70*i* comprises a first interface (denoted "I1") of the top bridge member 89*g* at a first top region (denoted "TR1") of the first elongated section 76*a* and a second interface (denoted "I2") of the top bridge member 89*g* at a second top region (denoted "TR2") of the second elongated section 76*b*, a third interface (denoted "I3") of the bottom bridge member 89*h* and at a first bottom region (denoted "BR1") of the first elongated section 76*a* and a fourth interface (denoted "I4") of the bottom bridge member 89*h* at a second bottom region (denoted "BR2") of the second elongated section 76*b*.

In a preferred embodiment, the first interface I1 of the top bridge member 89*g* and the first elongated section 76*a* and the third interface I3 of the bottom bridge member 89*h* and the first elongated section 76*a* are spaced a first distance apart, and the second interface 12 of the top bridge member 89*g* and the second elongated section 76*b* and the fourth interface 14 of the bottom bridge member 89*h* and the second elongated section 76*b* are spaced a second distance apart.

As indicated above and illustrated in FIG. 10C, the top and bottom bridge members 89*g*, 89 *h* and the first and second elongated sections 76*a*, 76*b* similarly define a prosthesis support member space (i.e., open region of the open bridge structure) between the top and bottom bridge members 89*g*, 89 *h* and the first and second elongated sections 76*a*, 76*b* (again denoted "SMS2").

In a preferred embodiment, the prosthesis support member space SMS2 of SI joint prosthesis 70*i* is similarly sized and configured to facilitate the receipt and/or positioning of a primary or supplemental joint support member or device, such as a surgical pin or screw, in the prosthesis support member space SMS2 of SI joint prosthesis 70*i* when prosthesis 70*i* is advanced into and/or positioned in a dysfunctional SI joint.

In a preferred embodiment, the prosthesis support member space SMS2 of SI joint prosthesis 70*i* similarly comprises a minimum height (denoted "H") proximate the vertical axis (denoted "Va") in the range of 25.0 mm to 17.0 mm, more preferably, in the range of 20.0 mm to 17.0 mm.

As illustrated in FIGS. 10A and 10B, in a preferred embodiment, the top and bottom bridge members 89*g*, 89 *h* similarly comprise central opening 88*a*.

As illustrated in FIG. 10B, in a preferred embodiment, the distal ends 81*b* of the top and bottom bridge members 89*g*, 89 *h* similarly comprise taper regions 82*e* that are configured to cut into and through at least articular cartilage and cortical bone, and, thereby, facilitate advancement of SI joint prosthesis 70*i* into a dysfunctional SI joint.

According to the invention, the top and/or bottom bridge members 89*e*, 89*f* can similarly further comprise a plurality of slots 90, such as slots 90 in the first and second elongated sections 76*a*, 76*b*.

As indicated above, SI joint prostheses 70*a*, 70*b*, 70*c*, 70*d*, 70*e*, 70*f*, 70*g*, 70 *h* and 70*i* discussed above, are specifically adapted to be advanced into dysfunctional SI joints in a posterior trajectory, wherein the prostheses transfix and, thereby stabilize the dysfunctional SI joints.

According to the invention, the SI joint prostheses with offset bridge structures, i.e., SI joint prostheses 70*b*, 70*c*, 70*d* and 70*e*, can be advanced into SI joints in different orientations. In a preferred embodiment, the orientations include (i) a first orientation, wherein the offset bridge structure is disposed on a first plane, whereby the offset bridge structure is disposed proximate the bottom of a prior surgical implant (e.g., surgical pin, dowel or screw), such as illustrated in FIG. 12, or a new surgical implant, and (ii) a second orientation, wherein the offset bridge structure is disposed on a second plane, whereby the offset bridge structure is disposed proximate the top of a prior surgical implant or a new surgical implant.

In a preferred embodiment, when SI joint prostheses 70*b*, 70*c*, 70*d* and 70*e* are advanced into dysfunctional SI joints, the prior surgical implant or new surgical implant is spaced a distance in the range of 4.0 mm to 7.0 mm from the offset bridge structures thereof.

According to the invention, the SI joint prostheses of the invention, i.e., SI joint prostheses 70*a*, 70*b*, 70*c*, 70*d*, 70*e*, 70*f*, 70*g*, 70 *h* and 70*i*, can comprise various biocompatible materials, including metals and metal alloys, such as titanium, stainless-steel, cobalt-chromium alloys and nickel-titanium alloys, and various biocompatible polymers, including, without limitation, reinforced polymers, such as carbon fiber reinforced polymers and metal-framed polymers.

According to the invention, SI joint prostheses 70*a*, 70*b*, 70*c*, 70*d*, 70*e*, 70*f*, 70*g*, 70*h* and 70*i* can also comprise porous structures to facilitate (i) adhesion of prostheses to a post-prosthesis insertion SI joint opening and, thereby, to SI joint bone structures, i.e., sacrum and ilium bone structures, and (ii) bone or osseous tissue ingrowth into the SI joint prostheses.

According to the invention, SI joint prostheses 70*a*, 70*b*, 70*c*, 70*d*, 70*e*, 70*f*, 70*g*, 70*h* and 70*i* can also comprise various exterior surface textures and roughness to facilitate or enhance engagement of the SI joint prostheses to a post-prosthesis insertion SI joint opening and, thereby, to SI joint bone structures, i.e., sacrum and ilium bone structures, and/or maintain engagement thereto and positioning therein.

According to the invention, the surface(s) of the SI joint prostheses of the invention can comprise a roughness grade number of N1 (Ra=~0.025 μm), N2 (Ra=~0.05 μm), N3 (Ra=~0.1 μm), N4 (Ra=~0.2 μm), N5 (Ra=~0.4 μm), N6 (Ra=~0.08 μm), N7 (Ra=~1.6 μm), N8 (Ra=~3.2 μm), N9 (Ra=~6.3 μm), N10 (Ra=~12.5 μm), N11 (Ra=~25.0 μm) or N12 (Ra=~50.0 μm) to facilitate or enhance engagement of the SI joint prostheses to SI joint bone structures and/or maintain engagement thereto and positioning therein.

According to the invention, SI joint prostheses 70*a*, 70*b*, 70*c*, 70*d*, 70*e*, 70*f*, 70*g*, 70*h* and 70*i* can also comprise an outer coating.

According to the invention, the outer coating can comprise one of the aforementioned osteogenic compositions; particularly, a demineralized bone matrix, autograft bone material, allograft bone material, xenograft bone material, polymethyl-methacrylate, or calcium-based bone material, such as hydroxyapatite (HA), α-tricalcium phosphate (α-TCP), and tricalcium phosphate (TCP).

According to the invention, the outer coating can also comprise one of the aforementioned biologically active agents; particularly, a basic fibroblast growth factor (bFGF), a transforming growth factor-β (TGF-β), a vascular endothelial growth factor (VEGF), a platelet derived growth factor (PDGF), an insulin-like growth factor (IGF), an epidermal growth factor (EGF), or a growth and differentiation factor-5 (GDF-5).

According to the invention, the outer coating can also comprise one of the aforementioned pharmacological agents.

According to the invention, the outer coating can also comprise a biologically active composition comprising one of the aforementioned biologically active agents and/or a pharmacological composition comprising one of the forementioned pharmacological agents.

According to the invention, the outer coating can also comprise a biocompatible and, preferably, biodegradable adhesive composition. According to the invention, suitable adhesive compositions include, without limitation, poly(L-glutamic acid)-based compositions, poly(γ-glutamic acid)-based compositions, poly(alkyl cyano acrylate)-based compositions, polyacrylic acid-based compositions, including polyacrylic acid crosslinked with pentaerythritol and/or allyl sucrose, polyacrylic acid crosslinked with divinyl glycol and combinations thereof; fibrin-based compositions, collagen-based compositions, including collagen and poly(L-glutamic acid) compositions; albumin-based compositions, including BioGlue® (comprises purified bovine serum albumin (BSA) and glutaraldehyde); cyanoacrylate compositions, including butyl-2-cyanoacrylate adhesives (e.g., Indermil®, Histoacryl®, Histoacryl® Blue, and LiquiBand®) and octyl-2-cyanoacrylate adhesives (e.g., Dermabond®, SurgiSeal™, LiquiBand® Flex, and OctylSeal); poly(ethylene glycol) (PEG) based compositions, including FocalSeal®, Progel™, Duraseal™, DuraSeal™ Xact, Coseal® and ReSure Sealant; polysaccharide-based compositions, polypeptide-based compositions, and radiation curable materials, such as poly(glycerol-co-sebacate) acrylate (PGSA), discussed below.

According to the invention, the outer coating can also comprise one of the aforementioned polymers and/or compositions comprising same.

In some embodiments of the invention, the polymer comprises poly(glycerol sebacate) (PGS) or a derivative thereof, including, without limitation, poly(glycerol-co-sebacate) acrylate (PGSA) and PGS co-polymers, such as poly(glycerol sebacate)-co-poly(ethylene glycol) (PGS-PEG); and/or composites thereof, e.g., PGS-hydroxyapatite (HA) composites and PGS-poly(ε-caprolactone) (PGS-PCL) composites, and compositions comprising same.

As set forth in U.S. application Ser. No. 17/463,779, PGS and derivatives thereof possess a unique property of inducing remodeling of damaged osseous or bone tissue, such as at pilot SI joint openings, and, hence, healing of the associated bone structures when disposed proximate thereto.

A further seminal property of PGS, which is set forth in Table I below, is that its physical state can be modulated during synthesis by controlling the "degree of esterification" via at least one crosslinking agent, e.g., methylene diphenyl diisocyanate (MDI).

TABLE 1

| Degree of Esterification | Physical State |
|---|---|
| ≤46% | Solid (Brittle Wax) |
| ~47%-64% | Semi-Solid (Soft Wax) |
| ~65%-75% | Viscous Liquid |
| ~76%-83% | Sticky Elastomer |
| ≥84% | Elastomer |

According to the invention, any suitable degree of esterification of PGS can be employed for PGS when employed in or for PGS based outer coatings (i.e., polymer compositions comprising PGS) and biologically active agent compositions of the invention.

In some embodiments, the PGS based outer coatings comprise a degree of esterification in the range of ~76%-83%, whereby the PGS exhibits adhesive properties, which will enhance engagement of the SI joint prostheses of the invention; particularly SI joint prostheses 70*a*, 70*b*, 70*c*, 70*d*, 70*e*, 70*f*, 70*g*, 70 *h* and 70*i*, to SI joint bone structures, i.e., sacrum and ilium bone structures.

As is well established, the physical state of poly(glycerol-co-sebacate) acrylate (PGSA) can also be modulated by combining the PGSA with a suitable photo-initiator and subjecting the PGSA to radiation.

Indeed, as set forth in Nijst, et al., *Synthesis and Characterization of Photocurable Elastomers from Poly* (*Glycerol-Co-Sebacate*), Biomacromolecules, vol. 8, no. 10, pp. 3067-3073 (2007), PGSA can be induced to transition from a liquid or flowable state to a solid elastomer state when combined with a photoinitiator, such as 2-hydroxy-1-[4-hydroxyethoxy)phenyl]-2-methyl-1-propanone (D 2959, Ciba Geigy), 2,2-dimethoxy-2-phenylacetophenone, titanocenes, fluorinated diaryltitanocenes, iron arene complexes, manganese decacarbonyl and methylcyclopentadienyl manganese tricarbonyl, and subjected to radiation, such as visible light; particularly, radiation in the range of approximately 380.0 nm-750.0 nm, and ultraviolet (UV) light, particularly, radiation in the range of 10.0 nm-400.0 nm.

Thus, in some embodiments, a composition comprising PGSA (also referred to herein as a "PGSA based composition" and "fixation composition") is employed to enhance the engagement of SI joint prostheses 70*a*, 70*b*, 70*c*, 70*d*, 70*e*, 70*f*, 70*g*, 70 *h* and 70*i* to SI joint openings and, thereby, SI joint bone structures, i.e., sacrum and ilium bone structures.

In some embodiments, a PGSA based composition (in a flowable state) is thus disposed in the internal prosthesis lumens 86*a*, 86*b* of SI joint prostheses 70*a*, 70*b*, 70*c*, 70*d*, 70*e*, 70*f*, 70*g*, 70 *h* and 70*i*, whereby the PGSA based composition is dispersed when the SI joint prostheses are positioned in the dysfunctional SI joint and fills any gaps between the SI joint prostheses and SI joint openings and, thereby, SI joint bone structures, and is thereafter cured via radiation and solidified, whereby the solidified PGSA enhances the engagement of the SI joint prostheses to the sacrum and ilium bone structures.

PGS and its derivatives; particularly, PGSA are also excellent platforms for delivery and, hence, administration of biologically active agents and pharmacological agents to mammalian tissue, including osseous or bone tissue.

Thus, in some embodiments of the invention, the PGS based outer coatings and PGS and PGSA based compositions further comprise one or more of the aforementioned biologically active or pharmacological agents.

SI Joint Prosthesis Assemblies

In a preferred embodiment, the SI joint prosthesis assemblies of the invention comprise one of the aforedescribed SI joint prostheses, i.e., SI joint prostheses 70*a*, 70*b*, 70*c*, 70*d*, 70*e*, 70*f*, 70*g*, 70 *h* and 70*i*, and supplemental bone fixation means.

In some embodiments of the invention, the supplemental bone fixation means comprises a bone stabilizing pin that is also adapted to be advanced into a pilot SI joint opening created by a drill guide assembly of the invention.

It is to be understood that, although the bone stabilizing pins of the invention, discussed below, are described herein in connection with SI joint prostheses assemblies, i.e., employed therewith, the bone stabilizing pins are not limited to use solely with the SI joint prostheses assemblies. According to the invention, the bone stabilizing pins can also be employed alone to stabilize various bone structures and joints, including dysfunctional SI joints and bone structures thereof.

In a preferred embodiment, the bone stabilizing pins of the invention are sized and configured to slidably advance into and through the internal prosthesis lumens 86*a*, 86*b* of SI joint prostheses 70*a*, 70*b*, 70*c*, 70*d*, 70*e*, 70*f*, 70*g*, 70 *h* and 70*i* of the invention, and into bone structures of a dysfunctional SI joint to enhance engagement of the SI joint prostheses to the dysfunctional SI joint and, thereby, further stabilize the dysfunctional SI joint when advanced therein.

Figure 14A:
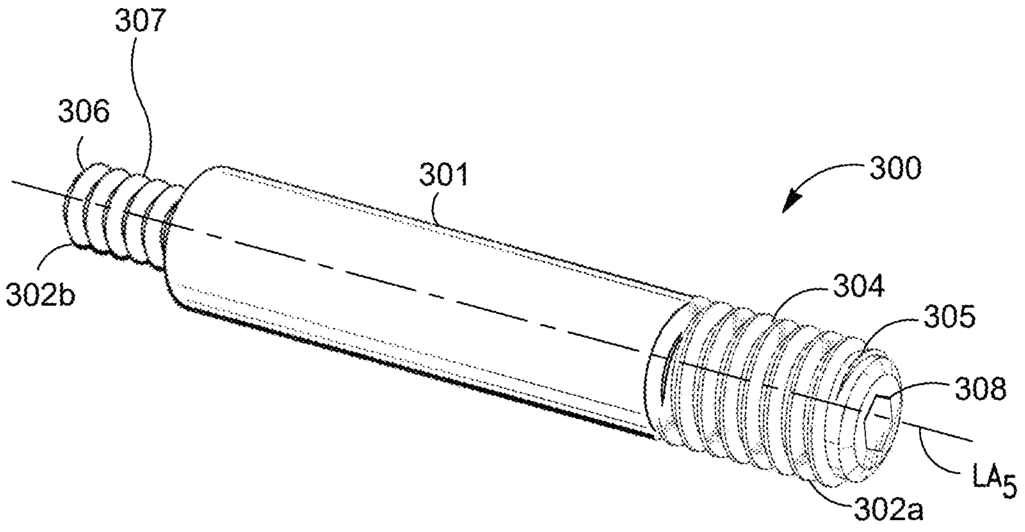
FIG. 14A is a perspective view of one embodiment of a bone stabilizing pin, in accordance with the invention.
Figure 14B:
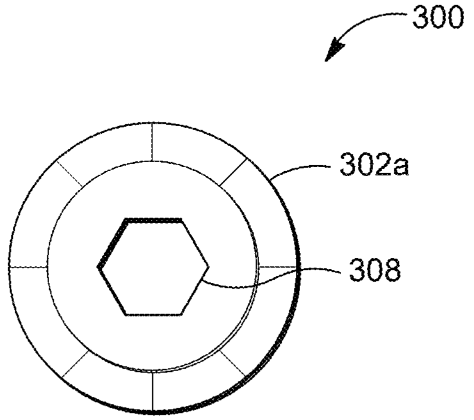
FIG. 14B is an end plan view of the bone stabilizing pin shown in FIG. 14A, in accordance with the invention.

Referring now to FIGS. 14A and 14B, there is shown one embodiment of a bone stabilizing pin of the invention (denoted "300"). As illustrated in FIG. 14A, the bone stabilizing pin 300 comprises an elongated cylindrical-shaped body 301 comprising proximal and distal ends 302*a*, 302*b*, and longitudinal axis LA5.

In a preferred embodiment, the bone stabilizing pin 300 comprises a length that is at least equal to the length from the open proximal end 79*a* to the open distal end 79*b* of the internal prosthesis lumens 86*a*, 86*b* of SI joint prostheses 70*a*, 70*b*, 70*c*, 70*d*, 70*e*, 70*f*, 70*g*, 70*h* and 70*i* of the invention. However, according to the invention, the bone stabilizing pin 300 can comprise various lengths greater than the length from the open proximal end 79*a* to the open distal end 79*b* of the internal prosthesis lumens 86*a*, 86*b* of SI joint prostheses 70*a*, 70*b*, 70*c*, 70*d*, 70*e*, 70*f*, 70*g*, 70 *h* and 70*i* to accommodate advancement of the expandable end members of the invention, discussed below, into desired locations in bone structures; particularly, bone structures of dysfunctional SI joints.

As further illustrated in FIG. 14A, in a preferred embodiment, the proximal end 302*a* of the bone stabilizing pin 300 comprises a threaded region 304 comprising threads 305 that are sized and configured to engage and cooperate with the internal threads 87 of the internal prosthesis lumens 86*a*, 86*b* of SI joint prostheses 70*a*, 70*b*, 70*c*, 70*d*, 70*e*, 70*f*, 70*g*, 70 *h* and 70*i*.

In a preferred embodiment, the threaded region 304 of the bone stabilizing pin 300 comprises sufficient length to facilitate advancement of the distal end 302*b* of the bone stabilizing pin 300 and, thereby, an expandable end member of the invention engaged thereto (discussed below) out of an internal prosthesis lumen, i.e., internal prosthesis lumen 86*a* or 86*b*, of a SI joint prothesis of the invention to a desired predetermined position in a pilot SI joint opening and, hence, SI joint bone structure.

In a preferred embodiment, the distal end 302*b* of the bone stabilizing pin 300 also comprises a threaded region 306 comprising threads 307 that are sized and configured to engage and cooperate with the internal threads of the expandable end members of the invention.

As illustrated in FIG. 14B, in a preferred embodiment, the proximal end 302*a* of the bone stabilizing pin 300 comprises a countersunk or internal hex section 308 that is sized and configured to receive a conventional hex socket head (or driver) to facilitate threadable engagement of the bone stabilizing pin 300 to the internal prosthesis lumens 86*a*, 86*b* of the SI joint protheses of the invention.

According to the invention, the bone stabilizing pin 300 can similarly comprise various biocompatible materials, including metals and metal alloys, such as titanium, stainless-steel, cobalt-chromium alloys and nickel-titanium alloys, and various biocompatible polymers, including, without limitation, reinforced polymers, such as carbon fiber reinforced polymers and metal-framed polymers.

According to the invention, various expandable end members can be employed with the bone stabilizing pin 300.

Figure 15A:
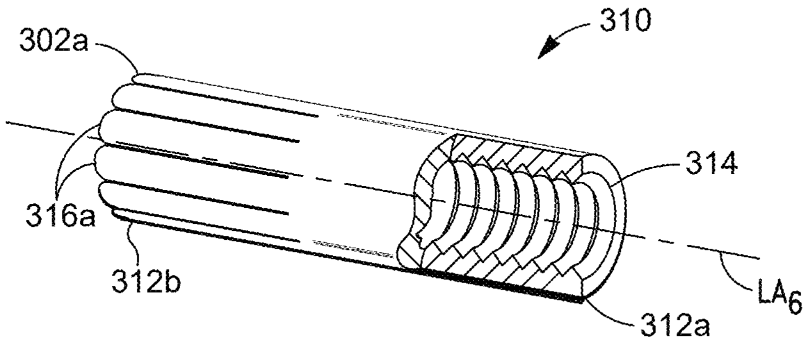
FIG. 15A is a perspective partial sectional view of one embodiment of an expandable end member configured to engage the bone stabilizing pin shown in FIG. 14A, the expandable end member comprising a plurality of expandable bands, which in FIG. 15A, are shown in a compressed configuration, in accordance with the invention.

Referring now to FIG. 15A, there is shown one embodiment of an expandable end member (denoted "310") that is designed and configured to cooperate with the bone stabilizing pin 300.

As illustrated in FIG. 15A, in a preferred embodiment, the expandable end member 310 comprises a cylindrical-shaped body that preferably conforms with the cylindrical-shaped body 301 of the bone stabilizing pin 300. In a preferred embodiment, the outer diameter of the expandable end member 310 is less than the outer diameter of the bone stabilizing pin 300 to facilitate smooth advancement of the expandable end member 310 into a pilot SI joint opening in a SI joint bone structure.

As further illustrated in FIG. 15A, the expandable end member 310 comprises proximal and distal ends 312*a*, 312*b* and a longitudinal axis LA6, the proximal end 312*a* of the expandable end member 310 comprising internal threads 314 that are sized and configured to engage and cooperate with the external threads 307 on the distal end 302*b* of the bone stabilizing pin 300.

As also illustrated in FIG. 15A, the distal end 312*b* of the expandable end member 310 comprises a plurality of expandable branches 316*a*, which are illustrated in FIG. 15A in a compressed configuration.

Figure 15B:
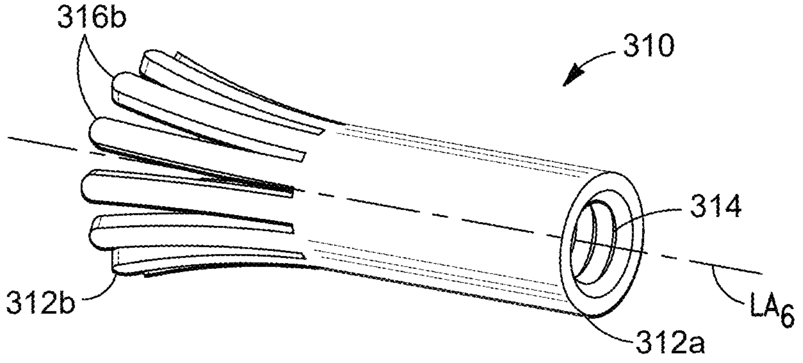
FIG. 15B is a perspective view of the expandable end member shown in FIG. 15A with the expandable bands in a first expanded configuration, in accordance with the invention.
Figure 15C:
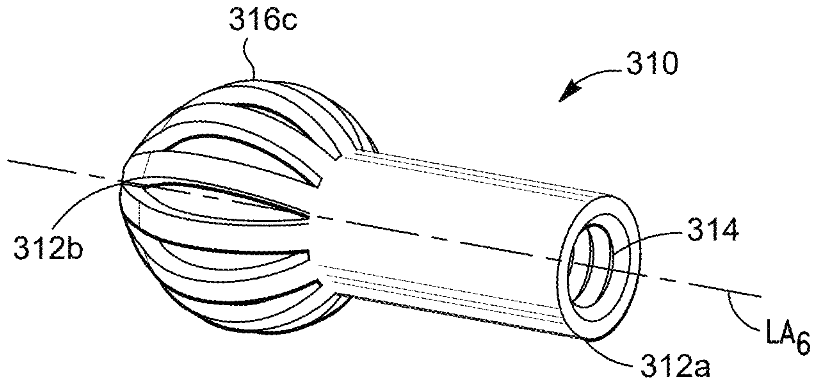
FIG. 15C is a further perspective view of the expandable end member shown in FIG. 15A with the expandable bands in a second expanded configuration, in accordance with the invention.

Referring now to FIGS. 15B and 15C, there are illustrated expandable end member 310 with the expandable branches 316*a* in a first expanded configuration (denoted "316*b*" in FIG. 15B) and a second expanded configuration (denoted "316*c*" in FIG. 15C).

In a preferred embodiment, the expandable end member 310 and, hence, expandable branches 316*a* comprise an elastomeric material, whereby, as discussed in detail below, the expandable branches 316*a* are adapted to expand outwardly and, in some embodiments, circumferentially, as illustrated in FIGS. 15B and 15C, with respect to the longitudinal axis, LA6, from the compressed configuration illustrated in FIG. 15A to expanded "pre-formed" configurations, when the expandable end member 310 is engaged to the bone stabilizing pin 300 and the bone stabilizing pin 300 is advanced into an internal prosthesis lumen, i.e., internal prosthesis lumen 86*a* or 86*b*, of a SI joint prosthesis of the invention, i.e., SI joint prosthesis 70*a*, 70*b*, 70*c*, 70*d*, 70*e*, 70*f*, 70*g*, 70 *h* or 70*i*, after the SI joint prosthesis is advanced into a dysfunctional SI joint of a patient (and, hence, subject to the core temperature of the patient), wherein, when the bone stabilizing pin 300 (and expandable end member 310 engaged thereto) is advanced into the internal prosthesis lumen of the SI joint prosthesis and the expandable end member 310 extends out of the internal prosthesis lumen, the expandable branches 316*a* of the expandable end member 310 transition from the compressed configuration illustrated in FIG. 15A to an expanded "pre-formed" configuration, such as illustrated in FIG. 15B, and fix the bone stabilizing pin 300 to the dysfunctional SI joint and, thereby, enhance fixation of SI joint prosthesis to the dysfunctional SI joint.

As discussed in detail below, according to the invention, the expandable branches 316*a* of expandable end member 310 can be pre-formed in various configurations and, thereby, expand to various expanded configurations corresponding thereto.

Figure 16:
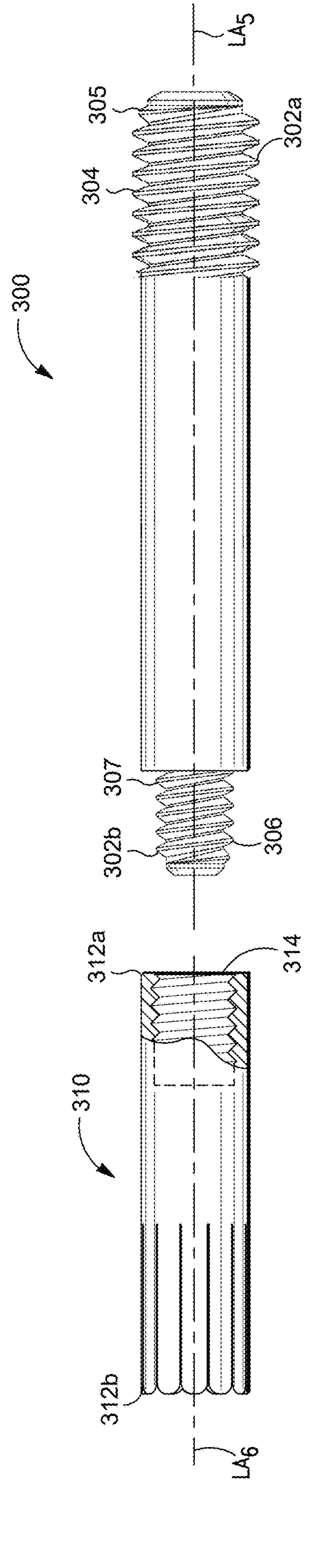
FIG. 16 is a side plan view of bone stabilizing pin shown in FIG. 14A and expandable end member shown in FIG. 15A in aligned pre-assembly positions, in accordance with the invention.

Referring now to FIG. 16, there is illustrated bone stabilizing pin 300 and expandable end member 310 in pre-engagement positions. As illustrated in FIG. 16, in the noted pre-engagement positions of the bone stabilizing pin 300 and expandable end member 310, the expandable end member 310 is aligned with bone stabilizing pin 300, whereby the external threads 307 of bone stabilizing pin 300 are in an aligned position to engage the internal threads 314 of the expandable end member 310.

According to the invention, when the bone stabilizing pin 300 and expandable end member 310 are engaged, the longitudinal axes of the bone stabilizing pin 300 and expandable end member 310, LA5 and LA6, are coincident.

Figure 17A:
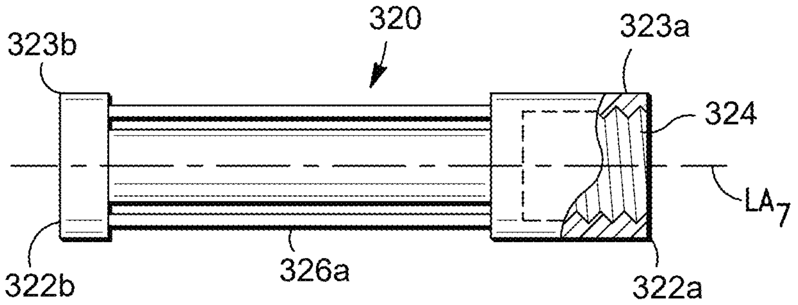
FIG. 17A is a side partial sectional plan view of another embodiment of an expandable end member configured to engage the bone stabilizing pin shown in FIG. 14A, the expandable end member similarly comprising a plurality of expandable bands, which in FIG. 17A, are shown in a compressed configuration, in accordance with the invention.

Referring now to FIG. 17A, there is shown another embodiment of an expandable end member (denoted "320") that is designed and configured to cooperate with the bone stabilizing pin 300.

As illustrated in FIG. 17A, in a preferred embodiment, the expandable end member 320 similarly comprises a cylindrical-shaped body that corresponds to the cylindrical-shaped body 301 of the bone stabilizing pin 300.

As further illustrated in FIG. 17A, the expandable end member 320 comprises proximal and distal ends 322*a*, 322*b*, proximal and distal end caps 323*a*, 323*b*, and a longitudinal axis LA7.

In a preferred embodiment, the proximal and distal end caps 323*a*, 323*b* of expandable end member 320 comprise cylindrical-shaped bodies that also conform with the cylindrical-shaped body 301 of the bone stabilizing pin 300.

In a preferred embodiment, the outer diameter of the proximal and distal end caps 323*a*, 323*b* of expandable end member 320 are similarly less than the outer diameter of the bone stabilizing pin 300 to similarly facilitate smooth advancement of the expandable end member 320 into a pilot SI joint opening in a SI joint bone structure.

As also illustrated in FIG. 17A, the proximal end cap 323*a* of the expandable end member 320 similarly comprises internal threads 324 that are sized and configured to engage and cooperate with the external threads 307 on the distal end 302*b* of the bone stabilizing pin 300.

As further illustrated in FIG. 17A, the distal end 322*b* of the expandable end member 320 similarly comprises a plurality of expandable branches 326*a*, which are shown in FIG. 17A in a compressed configuration.

In the embodiment of the expandable end member 320 illustrated in FIG. 17A, the expandable end member 320 comprises two (2) expandable branches 326*a*. However, according to the invention, the expandable end member 320 can comprise more than two (2) expandable branches 326*a*, e.g., four (4) equally spaced expandable branches 326*a*.

Figure 17B:
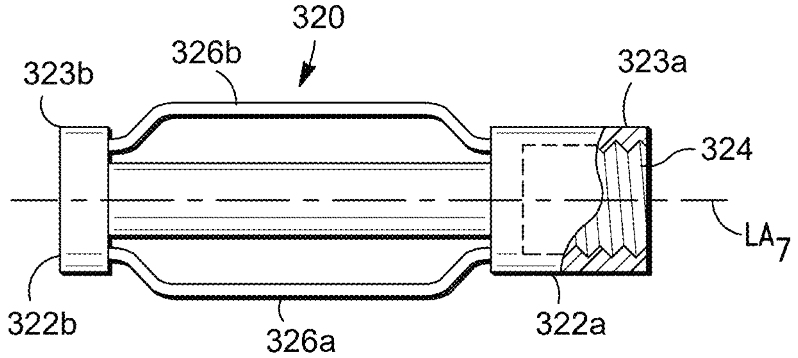
FIG. 17B is a side partial sectional plan view of the expandable end member shown in FIG. 17A with the expandable bands in a first expanded configuration, in accordance with the invention.
Figure 17C:
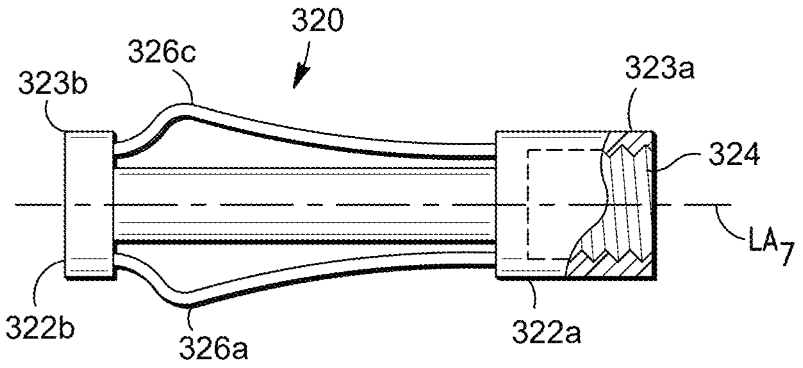
FIG. 17C is a side partial sectional plan view of the expandable end member shown in FIG. 17A with the expandable bands in a second expanded configuration, in accordance with the invention.

Referring now to FIGS. 17B and 17C, there are illustrated expandable end member 320 with the expandable branches 326*a* in a first expanded configuration (denoted "326*b*" in FIG. 17B) and a second expanded configuration (denoted "326*c*" in FIG. 17C).

In a preferred embodiment, the expandable end member 320 and, hence, expandable branches 326*a* similarly comprise an elastomeric material, whereby the expandable branches 326*a* are similarly adapted to expand outwardly with respect to the longitudinal axis, LA7, from the compressed configuration illustrated in FIG. 17A to expanded "pre-formed" configurations, such as illustrated in FIGS. 17B and 17C, when the expandable end member 320 is engaged to the bone stabilizing pin 300 and the bone stabilizing pin 300 is advanced into an internal lumen, i.e., internal lumen 86*a* or 86*b*, of a SI joint prosthesis of the invention i.e., SI joint prosthesis 70*a*, 70*b*, 70*c*, 70*d*, 70*e*, 70*f*, 70*g*, 70 *h* or 70*i*, after the SI joint prosthesis is advanced into a dysfunctional SI joint of a patient (and, hence, subject to the core temperature of the patient), wherein, when the bone stabilizing pin 300 and expandable end member 320 engaged thereto are advanced into the internal prosthesis lumen of the SI joint prosthesis and the expandable end member 320 extends out of the internal prosthesis lumen, the expandable branches 326*a* of the expandable end member 320 transition from the compressed configuration illustrated in FIG. 17A to an expanded "pre-formed" configuration, such as illustrated in FIGS. 17B and 17C, and similarly fix the bone stabilizing pin 300 to the dysfunctional SI joint and, thereby, enhance fixation of SI joint prosthesis to the dysfunctional SI joint.

According to the invention, the expandable branches 326*a* of expandable end member 320 can also similarly be pre-formed in various other configurations and, thereby, expand to other expanded configurations corresponding thereto.

Figure 18:
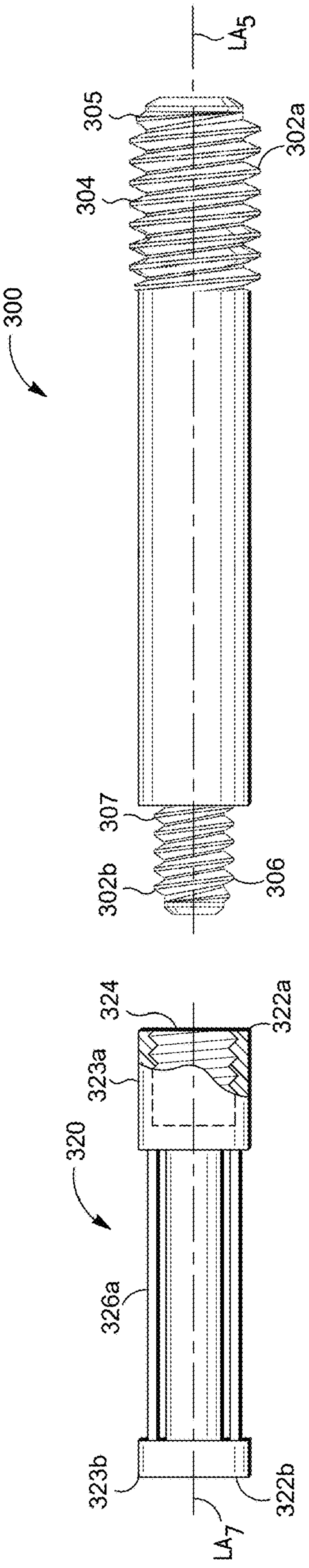
FIG. 18 is a side plan view of bone stabilizing pin shown in FIG. 14A and expandable end member shown in FIG. 17A in aligned pre-assembly positions, in accordance with the invention.

Referring now to FIG. 18, there are illustrated bone stabilizing pin 300 and expandable end member 320 in pre-engagement positions. As illustrated in FIG. 18, in the noted pre-engagement positions of the bone stabilizing pin 300 and expandable end member 320, the expandable end member 320 is similarly aligned with bone stabilizing pin 300, whereby the external threads 307 of bone stabilizing pin 300 are in an aligned position to engage the internal threads 324 of expandable end member 320.

According to the invention, when the bone stabilizing pin 300 and expandable end member 320 are engaged, the longitudinal axes of the bone stabilizing pin 300 and expandable end member 320, LA5 and LA7, are similarly coincident.

Figure 19:
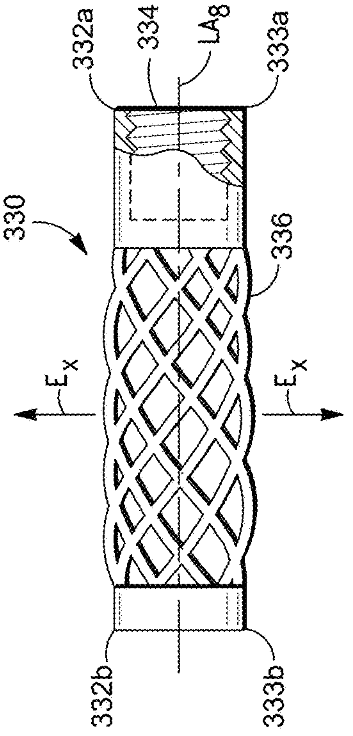
FIG. 19 is a side plan partial sectional view of another embodiment of an expandable end member configured to engage the bone stabilizing pins shown in FIG. 14A, the expandable end member similarly comprising a mesh body, which in FIG. 19, is shown in a compressed state, in accordance with the invention.

Referring now to FIG. 19, there is shown another embodiment of an expandable end member (denoted "330") that is also designed and configured to cooperate with the bone stabilizing pin 300.

As illustrated in FIG. 19, in a preferred embodiment, the expandable end member 330 comprises proximal and distal ends 332*a*, 332*b*, proximal and distal end caps 333*a*, 333*b*, and a longitudinal axis LA8.

In a preferred embodiment, the proximal and distal end caps 333*a*, 333*b* of expandable end member 330 similarly comprise cylindrical-shaped bodies that corresponds to the cylindrical-shaped body 301 of the bone stabilizing pin 300.

In a preferred embodiment, the outer diameter of the proximal and distal end caps 333*a*, 333*b*, and mesh body 336, discussed below, is similarly less than the outer diameter of the bone stabilizing pin 300 to facilitate smooth advancement of the expandable end member 330 into a pilot SI joint opening in a SI joint bone structure.

As also illustrated in FIG. 19, the proximal end cap 333*a* of the expandable end member 330 similarly comprises internal threads 334 that are sized and configured to engage and cooperate with the external threads 307 on the distal end 302*b* of the bone stabilizing pin 300.

As further illustrated in FIG. 19, the expandable end member 330 comprises a mesh body 336 disposed between the proximal and distal end caps 333*a*, 333*b*, which, in FIG. 19, is illustrated in a compressed configuration.

According to the invention, the mesh body 336 similarly comprises a biocompatible elastomeric material, whereby the mesh body 336 is adapted to expand outwardly and circumferentially with respect to the longitudinal axis, LA8, (denoted by arrows "Ex") from the compressed configuration illustrated in FIG. 19 to the expanded pre-formed configuration when the expandable end member 330 is engaged to the bone stabilizing pin 300 and the bone stabilizing pin 300 is advanced into an internal prosthesis lumen, i.e., internal lumen 86*a* or 86*b*, of a SI joint prosthesis of the invention, i.e., SI joint prosthesis 70*a*, 70*b*, 70*c*, 70*d*, 70*e*, 70*f*, 70*g*, 70 *h* or 70*i*, after the SI joint prosthesis is advanced into a dysfunctional SI joint of a patient (and, hence, subject to the core temperature of the patient), wherein, when the bone stabilizing pin 300 (and expandable end member 330 engaged thereto) is advanced into the internal prosthesis lumen of the SI joint prosthesis and the expandable end member 330 extends out of the internal prosthesis lumen, the mesh body 336 of the expandable end member 330 transitions from the compressed configuration illustrated in FIG. 19 to an expanded "pre-formed" configuration and similarly fixes the bone stabilizing pin 300 to the dysfunctional SI joint and, thereby, enhances fixation of SI joint prosthesis to the dysfunctional SI joint.

Figure 20:
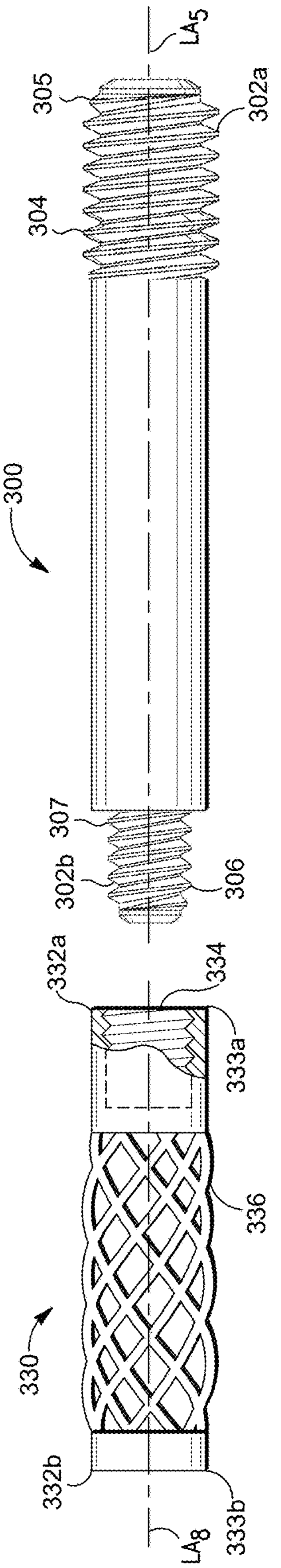
FIG. 20 is a side plan view of bone stabilizing pin shown in FIG. 14A and expandable end member shown in FIG. 19 in aligned pre-assembly positions, in accordance with the invention.

Referring now to FIG. 20, there are illustrated bone stabilizing pin 300 and expandable end member 330 in pre-engagement positions. As illustrated in FIG. 20, in the noted pre-engagement positions of the bone stabilizing pin 300 and expandable end member 330, the expandable end member 330 is similarly aligned with bone stabilizing pin 300, whereby the external threads 307 of bone stabilizing pin 300 are in an aligned position to engage the internal threads 334 of expandable end member 330.

According to the invention, when the bone stabilizing pin 300 and expandable end member 330 are engaged, the longitudinal axes of the bone stabilizing pin 300 and expandable end member 320, LA5 and LA8, are similarly coincident.

In some embodiments of the invention, the expandable members 310, 320, 330 further comprise at least one radiopaque marker to facilitate determining the position of expandable members 310, 320, 330 when being advanced into and when positioned in a SI joint bone structure via a CT scan.

As indicated above, the expandable members 310, 320, 330 preferably comprise elastomeric materials. According to the invention, suitable elastomeric materials, include, without limitation, shape memory alloys (SMAs) (e.g., nickel-titanium (Ni—Ti) alloys, Copper (Cu)-Zinc (Zn)-Aluminum (Al)-Nickel (Ni) alloys and Cu—Al—Ni alloys), superelastic SMAs, nickel-titanium (Ni—Ti) alloys (Nitinol™, including Nitinol 55 and Nitinol 60), MP35, Elgiloy®, spring steels, cobalt-chromium alloys (e.g., cobalt-chromium alloy 1058), cobalt-based 35N alloys, nickel-based 625 alloys, and molybdenum alloys (e.g., a molybdenum alloy including about 0.4% to about 0.8% of lanthanum oxide ($La_2O_3$)), and various elastomeric plastic materials.

In a preferred embodiment, the expandable members 310, 320, 330 preferably comprise a SMA.

As is well established, SMAs are capable of transitioning from a first shape to a predetermined, pre-formed expanded shape via a change of phase or structure by an external stimulus such as temperature change or electrical current.

In a preferred embodiment, the SMA comprises Nitinol™. Nitinol™ has desirable electrical and mechanical properties, a long fatigue life, high corrosion resistance, and has similar properties to residual annular tissue and cartilaginous tissues.

According to the invention, the expandable end members 310, 320, 330 can also comprise a superelastic SMA. Superelastic SMAs can be compressed into a small shape and upon release automatically expand to a predetermined shape. Thus, no external activation, such as temperature or electrical stimulation, is required. One preferred superelastic SMA is superelastic Nitinol™, which has similar properties to the Nitinol™ discussed above, but because it is a superelastic SMA does not require activation.

Expandable end members 310, 320, 330 comprising superelastic Nitinol™, or other suitable superelastic SMAs, can thus be disposed in a compressed state, as shown in FIGS. 15A, 17A and 19, advanced into a pilot SI joint opening or into a surgical deficit, such as an annular or nuclear defect or bone fracture and, upon release, expand to a predetermined shape to engage the pilot SI joint opening or fill the deficit.

Referring now to FIG. 21, there is shown expandable end member 320 engaged to bone stabilizing pin 300, and inserted into and through the internal prosthesis lumen 86*a* of SI joint prosthesis 70*a* shown in FIGS. 2A and 2B.

Figure 22A:
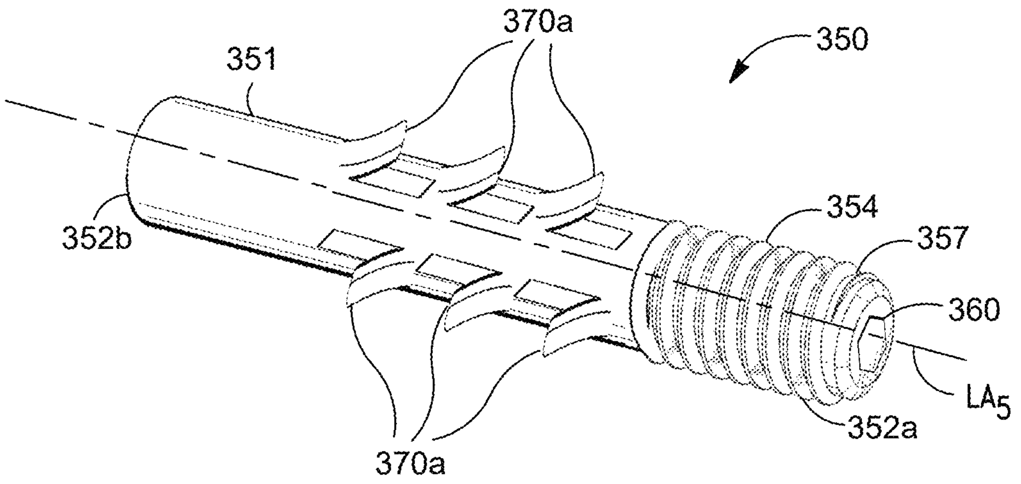
FIG. 22A is a perspective view of another embodiment of a bone stabilizing pin comprising a first plurality of tabs in an outwardly projecting configuration, in accordance with the invention.

Referring now to FIG. 22A, there is shown another embodiment of a bone stabilizing pin of the invention (denoted "350"). As illustrated in FIG. 22A, the bone stabilizing pin 350 similarly comprises an elongated cylindrical-shaped body 351 comprising proximal and distal ends 352*a*, 352*b*.

In a preferred embodiment, the bone stabilizing pin 350 similarly comprises a length that is at least equal to the length from the open proximal end 79*a* to the open distal end 79*b* of the internal prosthesis lumens 86*a*, 86*b* of SI joint prostheses 70*a*, 70*b*, 70*c*, 70*d*, 70*e*, 70*f*, 70*g*, 70 *h* and 70*i* of the invention. However, according to the invention, the bone stabilizing pin 350 can similarly comprise various lengths greater than the length from the open proximal end 79*a* to the open distal end 79*b* of the internal prosthesis lumens 86*a*, 86*b* of SI joint prostheses 70*a*, 70*b*, 70*c*, 70*d*, 70*e*, 70*f*, 70*g*, 70 *h* and 70*i* to accommodate advancement of the distal end 352*b* of the bone stabilizing pin 350 to desired locations in bone structures; particularly, bone structures of dysfunctional SI joints.

As further illustrated in FIG. 22A, in a preferred embodiment, the proximal end 352*a* of the bone stabilizing pin 350 similarly comprises a threaded region 354 comprising threads 357 that are sized and configured to engage and cooperate with the internal threads 87 of the internal prosthesis lumens 86*a*, 86*b* of SI joint prostheses 70*a*, 70*b*, 70*c*, 70*d*, 70*e*, 70*f*, 70*g*, 70 *h* and 70*i*.

In a preferred embodiment, the threaded region 354 of the bone stabilizing pin 350 comprises sufficient length to facilitate advancement of the distal end 352*b* of the bone stabilizing pin 350 (and, hence, tabs 370*b*, discussed below) out of an internal prosthesis lumen, i.e., internal prosthesis lumen 86*a* or 86*b*, of SI joint prostheses 70*a*, 70*b*, 70*c*, 70*d*, 70*e*, 70*f*, 70*g*, 70 *h* and 70*i* to a desired predetermined position in a pilot SI joint opening and, hence, SI joint bone structure.

Figure 23:
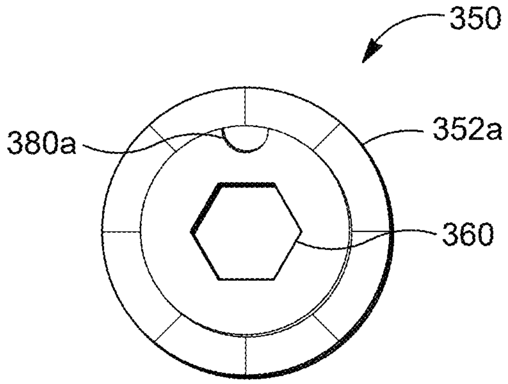
FIG. 23 is an end plan view of the bone stabilizing pins shown in FIGS. 22A and 22B, in accordance with the invention.

As illustrated in FIG. 23, in a preferred embodiment, the proximal end 352*a* of the bone stabilizing pin 350 similarly comprises a countersunk or internal hex section 360 that is sized and configured to receive a conventional hex socket head (or driver) to facilitate threadable engagement of the bone stabilizing pin 350 to the internal prosthesis lumens 86*a*, 86*b* of SI joint prostheses 70*a*, 70*b*, 70*c*, 70*d*, 70*e*, 70*f*, 70*g*, 70 *h* and 70*i*.

Referring back to FIG. 22A, in a preferred embodiment, the bone stabilizing pin 350 further comprises a first plurality of tabs 370*a* disposed on a mid-region of the cylindrical-shaped body 351, which are illustrated in FIG. 22A in outwardly projected configurations. As illustrated in FIG. 22A, the tabs 370*a* are preferably equally spaced longitudinally and circumferentially in four (4) rows.

In a preferred embodiment, the bone stabilizing pin 350 and, hence, first plurality of tabs 370*a* (and second plurality of tabs 370*b*, discussed below) similarly comprise a biocompatible elastomeric material, whereby, as discussed in detail below, the first plurality of tabs 370*a* (and second plurality of tabs 370*b*) are adapted to transition from a compressed configuration to outwardly projecting configurations, such as illustrated in FIG. 22A, when the bone stabilizing pin 350 is advanced into an internal prosthesis lumen, i.e., internal prosthesis lumen 86*a* or 86*b*, of a SI joint prosthesis of the invention, i.e., SI joint prosthesis 70*a*, 70*b*, 70*c*, 70*d*, 70*e*, 70*f*, 70*g*, 70 *h* or 70*i*, after the SI joint prosthesis is advanced into a dysfunctional SI joint of a patient (and, hence, subject to the core temperature of the patient).

As illustrated in FIG. 22A, when the tabs 370*a* are in outwardly projecting configurations, the tabs 370*a* are preferably projecting outwardly in a proximal direction in two (2) rows and outwardly in a distal direction in two (2) rows.

Figure 24:
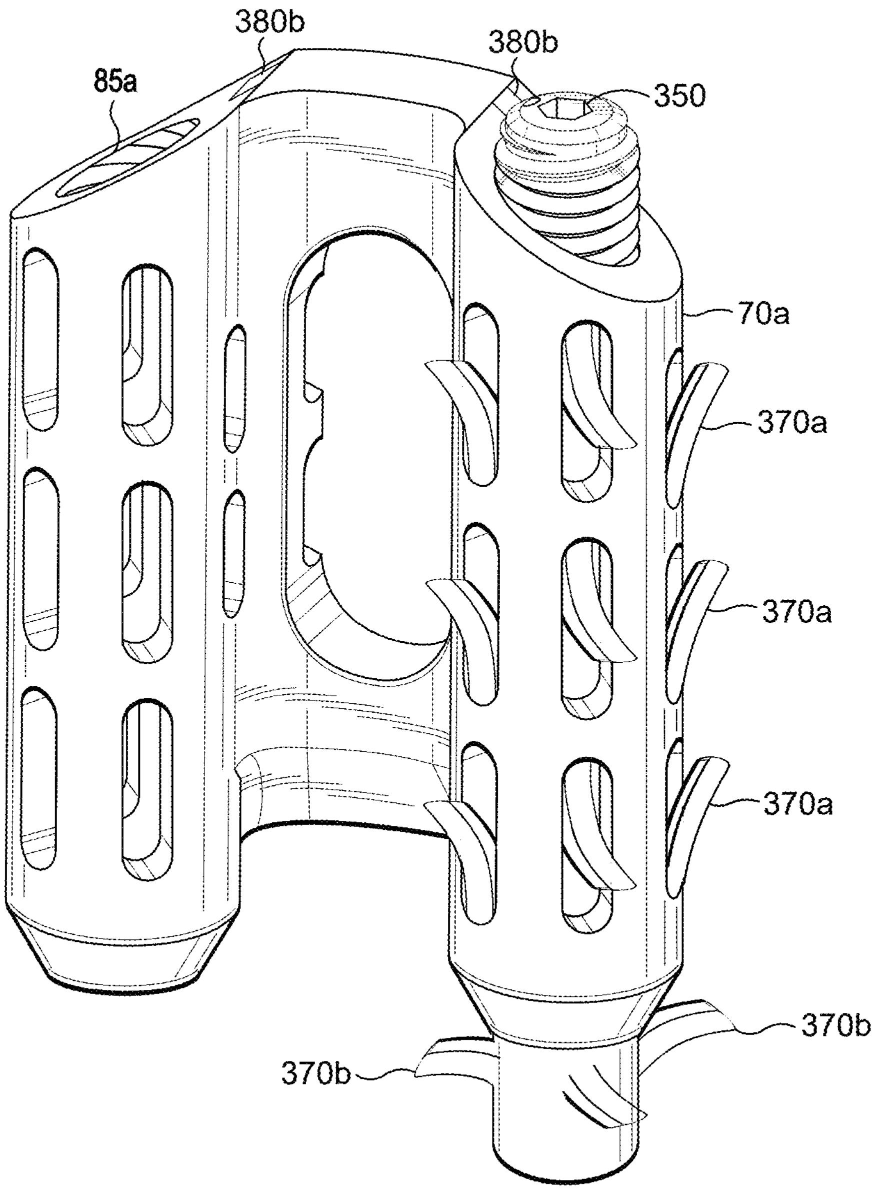
FIG. 24 is a perspective view of the bone stabilizing pin shown in FIG. 22B, which is operatively inserted in and through an internal lumen of the SI joint prosthesis shown in FIGS. 2A and 2B; in accordance with the invention.

In a preferred embodiment, the tabs 370*a* are in alignment with the fenestrations (or slots) 90 of SI joint prosthesis 70*a* and, hence, SI joint prostheses 70*b*, 70*c*, 70*d*, 70*e*, 70*f*, 70*g*, 70 *h* and 70*i*, whereby, as illustrated in FIG. 24, when the tabs 370*a* transition from the compressed configuration to the outwardly projecting configurations, at least one tab 370*a*, more preferably, each tab 370*a* projects outwardly through the slots 90 of SI joint prosthesis 70*a* and, hence, SI joint prostheses 70*b*, 70*c*, 70*d*, 70*e*, 70*f*, 70*g*, 70 *h* and 70*i*, and fixes the bone stabilizing pin 350 to a first plurality of regions in the dysfunctional joint and, thereby, similarly enhance fixation of SI joint prosthesis 70*a* and, hence, SI joint prostheses 70*b*, 70*c*, 70*d*, 70*e*, 70*f*, 70*g*, 70 *h* and 70*i*, to the dysfunctional SI joint.

Figure 22B:
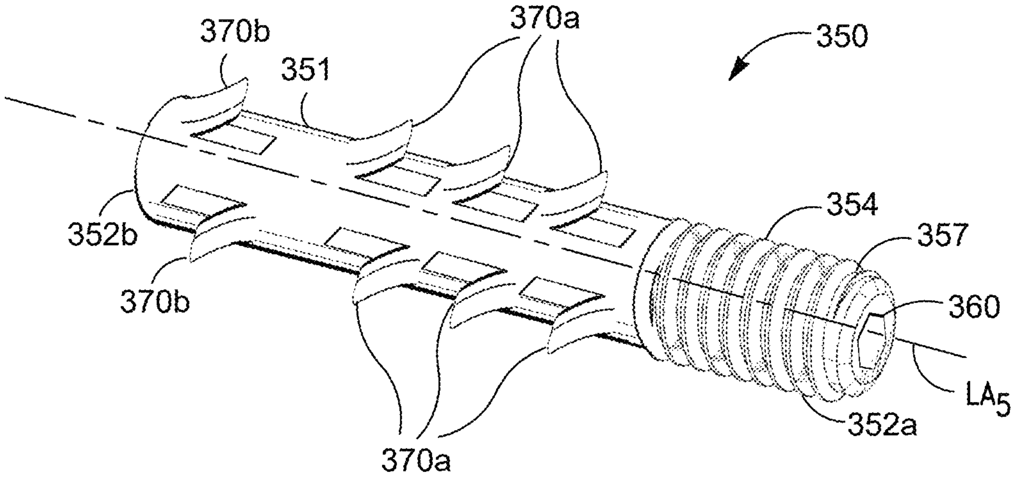
FIG. 22B is a perspective view of another embodiment of the bone stabilizing pin shown in FIG. 22A comprising a second plurality of tabs disposed on the distal end of the bone stabilizing pin and in outwardly projecting configurations, in accordance with the invention.

Referring now to FIG. 22B, there is illustrated a further embodiment of bone stabilizing pin 350. As illustrated in FIG. 22B, the bone stabilizing pin 350 further comprises a second plurality of tabs 370*b* disposed proximate the distal end 352*b* of bone stabilizing pin 350, which, as indicated above, are similarly adapted to transition from a compressed configuration to outwardly projecting configurations, such as illustrated in FIG. 22A, when the bone stabilizing pin 350 is advanced into an internal prosthesis lumen, i.e., internal prosthesis lumen 86*a* or 86*b*, of a SI joint prosthesis of the invention, i.e., SI joint prosthesis 70*a*, 70*b*, 70*c*, 70*d*, 70*e*, 70*f*, 70*g*, 70 *h* or 70*i*, after the SI joint prosthesis is advanced into a dysfunctional SI joint of a patient.

In a preferred embodiment, when the bone stabilizing pin 350 is advanced into an internal prosthesis lumen, i.e., internal prosthesis lumen 86*a* or 86*b*, of a SI joint prosthesis of the invention, i.e., SI joint prosthesis 70*a*, 70*b*, 70*c*, 70*d*, 70*e*, 70*f*, 70*g*, 70 *h* or 70*i*, such as illustrated in FIG. 24, after the SI joint prosthesis is advanced into a dysfunctional SI joint, tabs 370*b* additionally fix the bone stabilizing pin 350 to a second plurality of regions in the dysfunctional joint and, thereby, similarly enhance fixation of SI joint prosthesis 70*a* and, hence, SI joint prostheses 70*b*, 70*c*, 70*d*, 70*e*, 70*f*, 70*g*, 70 *h* and 70*i*, to the dysfunctional SI joint.

According to the invention, various outward projections of the tabs 370*a*, 370*b* can be employed within the scope of the invention, e.g., all of tabs 370*a* projecting outwardly in a proximal direction, each of tabs 370*b* projecting outwardly in a proximal direction, etc.

According to the invention, tabs 370*a*, 370*b* can also comprise various other shapes.

Referring now to FIGS. 23 and 24, in a preferred embodiment, the proximal end 352*a* of the bone stabilizing pin 350 and proximal end 79*a* of SI joint prosthesis 70*a* (and SI joint prostheses 70*b*, 70*c*, 70*d*, 70*e*, 70*f*, 70*g*, 70 *h* and 70*i*) comprise radiopaque markers 380*a*, 380*b*, respectively, to facilitate proper alignment of the bone stabilizing pin 350 in the internal prosthesis lumens 86*a*, 86*b* of SI joint prosthesis 70*a* and, hence, SI joint prostheses 70*b*, 70*c*, 70*d*, 70*e*, 70*f*, 70*g*, 70 *h* and 70*i*. According to the invention, when radiopaque markers 380*a*, 380*b* are aligned, the bone stabilizing pin 350 is properly positioned in an internal prosthesis lumen, i.e., internal prosthesis lumen 86*a* or 86*b* of SI joint prosthesis 70*a* (and, hence, SI joint prostheses 70*b*, 70*c*, 70*d*, 70*e*, 70*f*, 70*g*, 70 *h* and 70*i*), whereby, as illustrated in FIG. 24, tabs 370*a* are properly positioned to project outwardly through the slots 90 of SI joint prosthesis 70*a* and, hence, SI joint prostheses 70*b*, 70*c*, 70*d*, 70*e*, 70*f*, 70*g*, 70 *h* and 70*i*.

In a preferred embodiment, the bone stabilizing pin 350 similarly preferably comprises Nitinol™, whereby the tabs 370*a*, 370*b* can similarly be formed in the outwardly projecting configurations illustrated in FIGS. 22A and 22B (or other desired configurations) and transition from collapsed configurations, which allows the bone stabilizing pin 350 to be advanced into the internal prosthesis lumens 86*a*, 86*b* of SI joint prostheses 70*a*, 70*b*, 70*c*, 70*d*, 70*e*, 70*f*, 70*g*, 70 *h* and 70*i*, to the pre-formed outwardly projecting configurations.

Referring again to FIG. 24, there is illustrated bone stabilizing pin 350 positioned in the internal prosthesis lumen 86*a* of SI joint prosthesis 70*a* shown in FIGS. 2A and 2B with tabs 370*a* in outwardly projecting configurations and tabs 370*b* positioned outside internal prosthesis lumen 86*a* and also in outwardly projecting configurations.

As will readily be appreciated by one having ordinary skill in the art, the bone stabilizing pins 300, 350 of the invention, when properly positioned in internal prosthesis lumens 86*a*, 86*b* of SI joint prostheses 70*a*, 70*b*, 70*c*, 70*d*, 70*e*, 70*f*, 70*g*, 70 *h* and 70*i*, will significantly enhance fixation of the SI joint prostheses to a dysfunctional SI joint and, thereby, further stabilize the dysfunctional SI joint when the SI joint prostheses are advanced therein.

In some embodiments of the invention, the supplemental bone fixation means comprises a phase change osteogenic composition that is adapted to be disposed in the first and second internal lumens 86*a*, 86*b* of SI joint prosthesis 70*a* (and, hence, SI joint prostheses 70*b*, 70*c*, 70*d*, 70*e*, 70*f*, 70*g*, 70 *h* and 70*i*), in the fluidized state and transition to a solid state when SI joint prosthesis 70*a* (and, hence, SI joint prostheses 70*b*, 70*c*, 70*d*, 70*e*, 70*f*, 70*g*, 70 *h* and 70*i*) is/are advanced into the dysfunctional SI joint, wherein, when the phase change osteogenic composition is disposed in the first internal lumen of the SI joint prostheses of the invention, i.e. SI joint prostheses 70*a*, 70*b*, 70*c*, 70*d*, 70*e*, 70*f*, 70*g*, 70 *h* and 70*i*, the phase change osteogenic composition flows through and out of at least a first fenestration of the first plurality of fenestrations of the SI joint prostheses, transitions to a solid state and enhances fixation of the SI joint prostheses to the dysfunctional SI joint, and, when the phase change osteogenic composition is disposed in the second internal lumen of the SI joint prostheses, the phase change osteogenic composition flows through and out of at least a second fenestration of the second plurality of fenestrations of the SI joint prostheses, transitions to a solid state and similarly enhances fixation of the SI joint prostheses to the dysfunctional SI joint.

In a preferred embodiment, the phase change osteogenic composition, and, hence, fixation composition, comprises α-tricalcium phosphate (α-TCP) and one of the aforementioned biologically active agents and/or pharmacological agents.

In some embodiments of the invention, the supplemental bone fixation means comprises a poly(glycerol sebacate) (PGS)-based composition that is similarly adapted to be disposed in the first and second internal lumens 86*a*, 86*b* of SI joint prosthesis 70*a* (and, hence, SI joint prostheses 70*b*, 70*c*, 70*d*, 70*e*, 70*f*, 70*g*, 70 *h* and 70*i*), in the fluidized state and transition to a solid state when the SI joint prostheses are advanced into a dysfunctional SI joint.

According to the invention, when the PGS-based composition is disposed in the first internal lumen of the SI joint prostheses of the invention, i.e., SI joint prostheses 70*a*, 70*b*, 70*c*, 70*d*, 70*e*, 70*f*, 70*g*, 70 *h* and 70*i*, the PGS-based composition flows through and out of at least a first fenestration of the first plurality of fenestrations of the SI joint prostheses, transitions to a solid state and enhances fixation of the SI joint prostheses to the dysfunctional SI joint and osseous tissue ingrowth into the SI joint prostheses, and, when the PGS-based composition is disposed in the second internal lumen of the SI joint prostheses, the PGS-based composition flows through and out of at least a second fenestration of the second plurality of fenestrations of the SI joint prostheses, transitions to a solid state and similarly enhances fixation of the SI joint prostheses to the dysfunctional SI joint and osseous tissue ingrowth into the SI joint prostheses.

Drill Guide Assemblies

As indicated above, in a preferred embodiment, the SI joint stabilization systems of the invention further comprise a drill guide assembly configured and adapted to access a dysfunctional SI joint via a posterior approach and create at least one pilot SI joint opening therein that is sized and configured to receive a SJ joint prosthesis of the invention; particularly, SI joint protheses 70*a*, 70*b*, 70*c*, 70*d*, 70*e*, 70*f*, 70*g*, 70 *h* and 70*i* described above, therein.

In a preferred embodiment of the invention, the drill guide assembly comprises an elongated guide pin and a drill guide assembly.

Figure 25B:
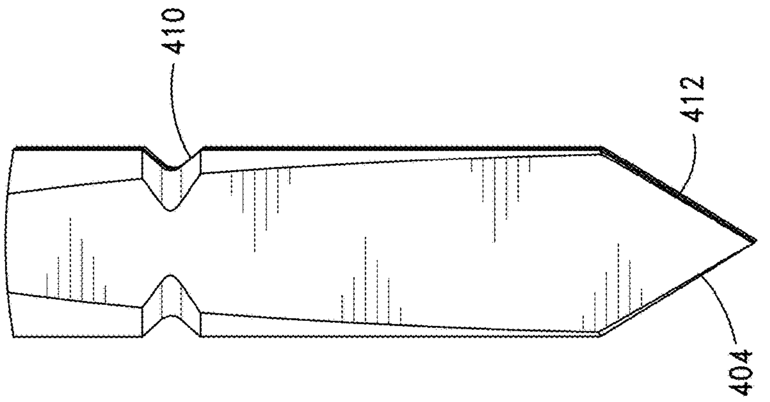
FIG. 25B is a partial side plan view of the guide pin shown in FIG. 25A showing a guide pin marking, in accordance with the invention.
Figure 25A:
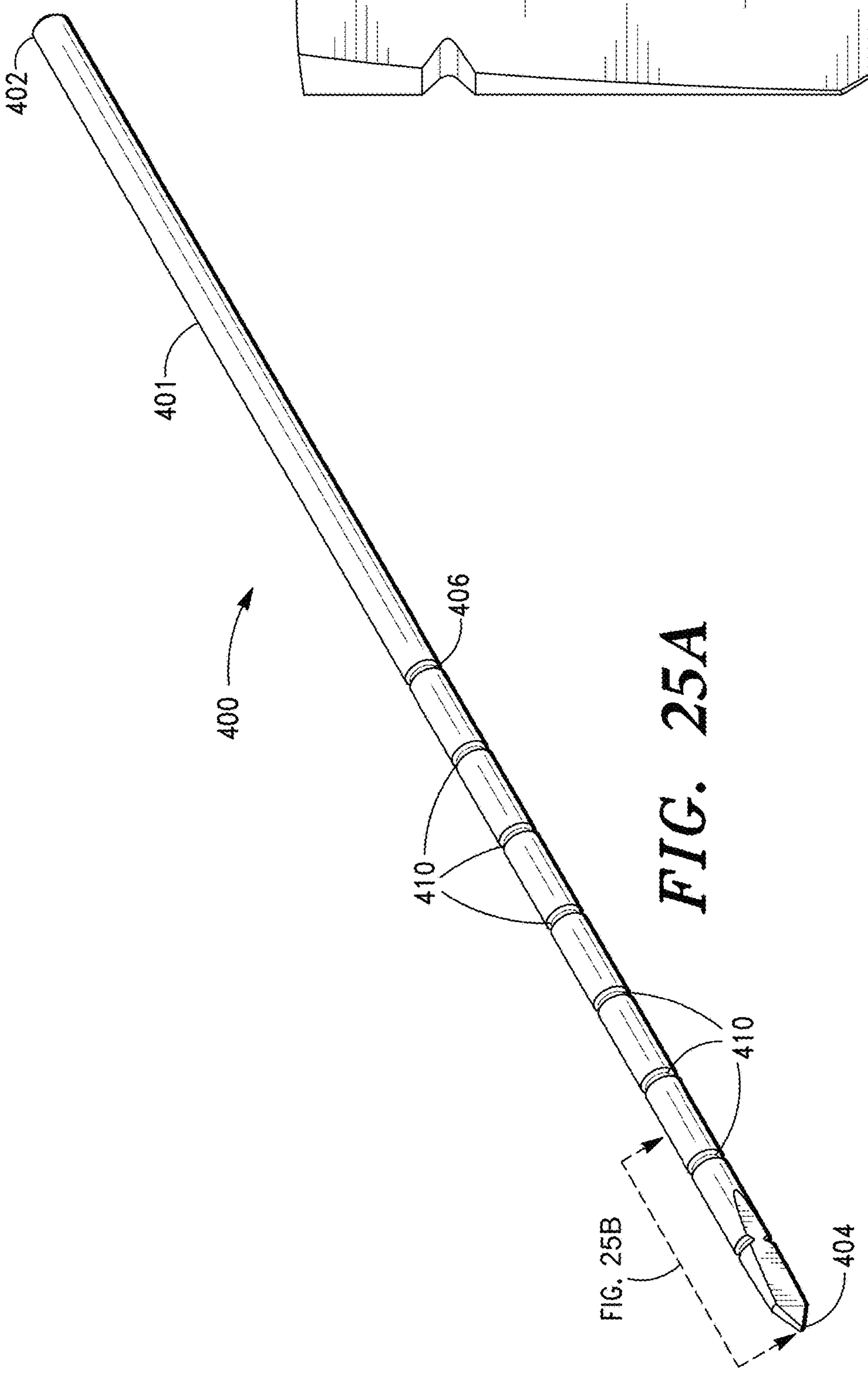
FIG. 25A is a perspective view of one embodiment of a guide pin, in accordance with the invention.

Referring now to FIG. 25A, there is shown a preferred embodiment of an elongated guide pin of the invention (denoted "400").

As discussed in detail below, the guide pin 400 is sized and configured to be positioned in a dysfunctional SI joint and, when positioned therein, function as (i) a guide for the drill guide assemblies, i.e. drill guides thereof, and, thereby, positioning of the pilot SI joint opening(s) created by the drill guide assemblies, (ii) a landmark for the SI joint prosthesis to be disposed in the dysfunctional SI joint, and (iii) in some embodiments, a guide for the prosthesis deployment assembly and, hence, SI joint prosthesis engaged thereto into the pilot SI joint opening created by the drill guide assemblies and, thereby, positioning of the SI joint prosthesis in the dysfunctional SI joint.

As illustrated in FIG. 25A, the guide pin 400 comprises an elongated graduated wire or rod structure 401 comprising proximal and distal ends 402, 404 and a plurality of spaced guide pin markings 410 that extend from the distal end 404 of the guide pin 400 to preferably at least the mid-region 406 of the guide pin 401.

According to the invention, the guide pin markings 410 can comprise various distinguishable surface markings, symbols, lines and/or structural patterns and arrangements, which preferably are readily detectable and, hence, readable via a conventional image capture apparatus, such as a fluoroscope and radiography system.

As illustrated in FIG. 25B, in a preferred embodiment of the invention, the guide pin markings 410 comprise a plurality of graduated or spaced grooves or depressions in the wire structure 401. According to the invention, any number of spaced grooves, i.e., markings 410, can be employed on the wire structure 401 and, hence, guide pin 400 and can be spaced apart at any desired dimension.

As illustrated in FIG. 25A, in a preferred embodiment of the invention, the guide pin 400 includes eight (8) grooves, i.e., markings 410, which are uniformly spaced approximately 10.0 mm apart.

As further illustrated in FIGS. 25A and 25B, in a preferred embodiment, the distal end 404 of the guide pin 400 comprises a pointed configuration 412 to facilitate entry of the distal end 404 of the guide pin 400 into and through tissue, articular cartilage, and SI joint bone structures.

Figure 26A:
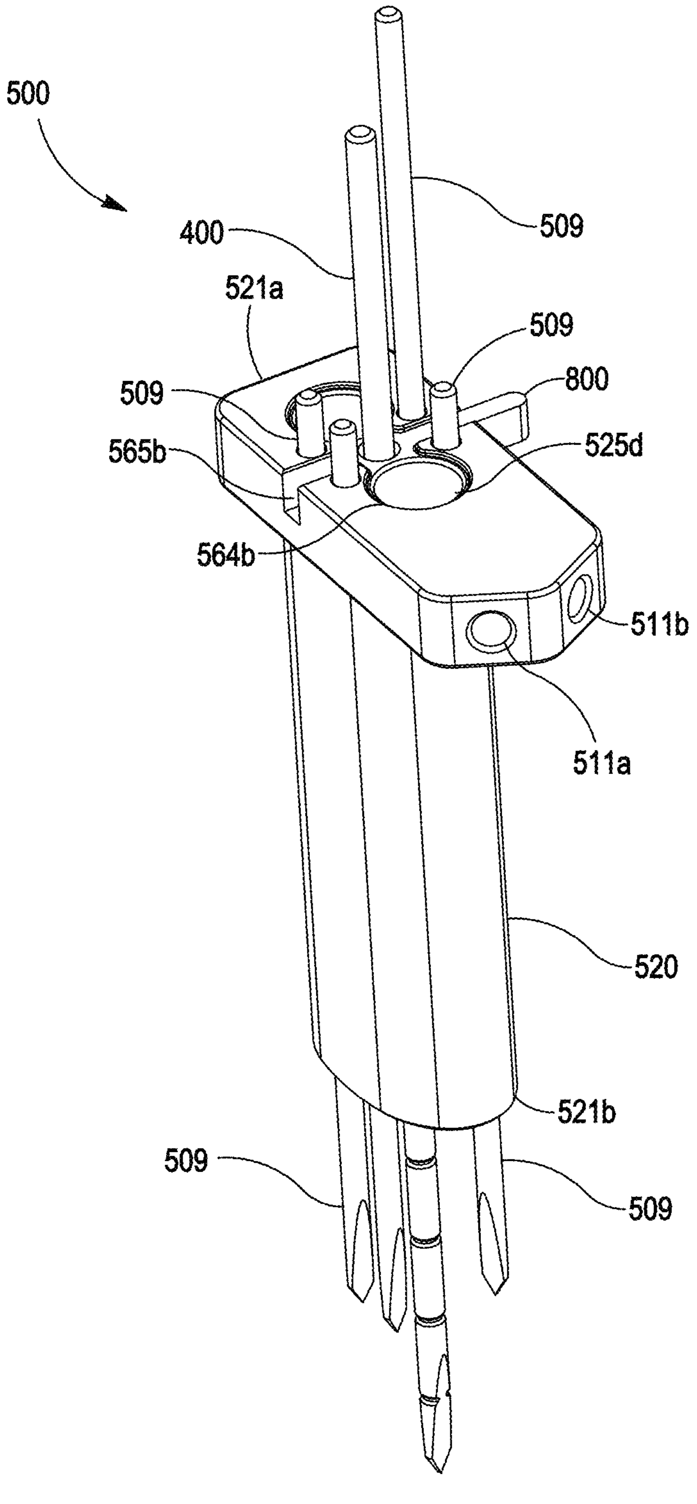
FIG. 26A is a perspective view of one embodiment of a drill guide assembly, in accordance with the invention.
Figure 26B:
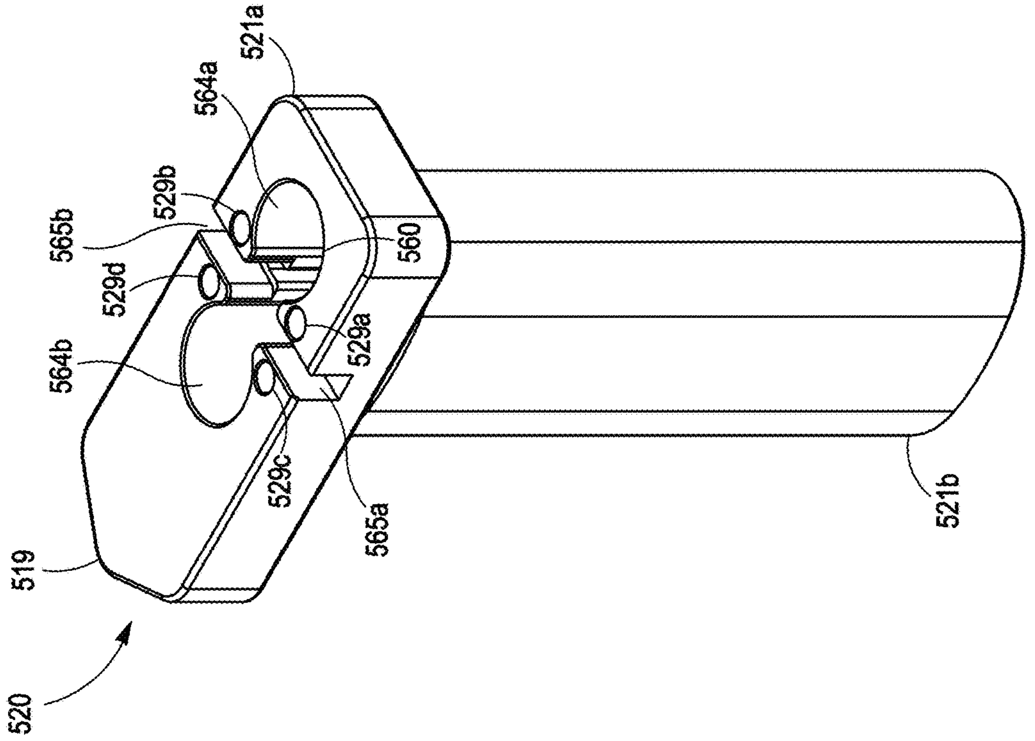
FIG. 26B is a rear perspective view of an embodiment of the drill guide of the drill guide assembly shown in FIG. 26A, in accordance with the invention.
Figure 26C:
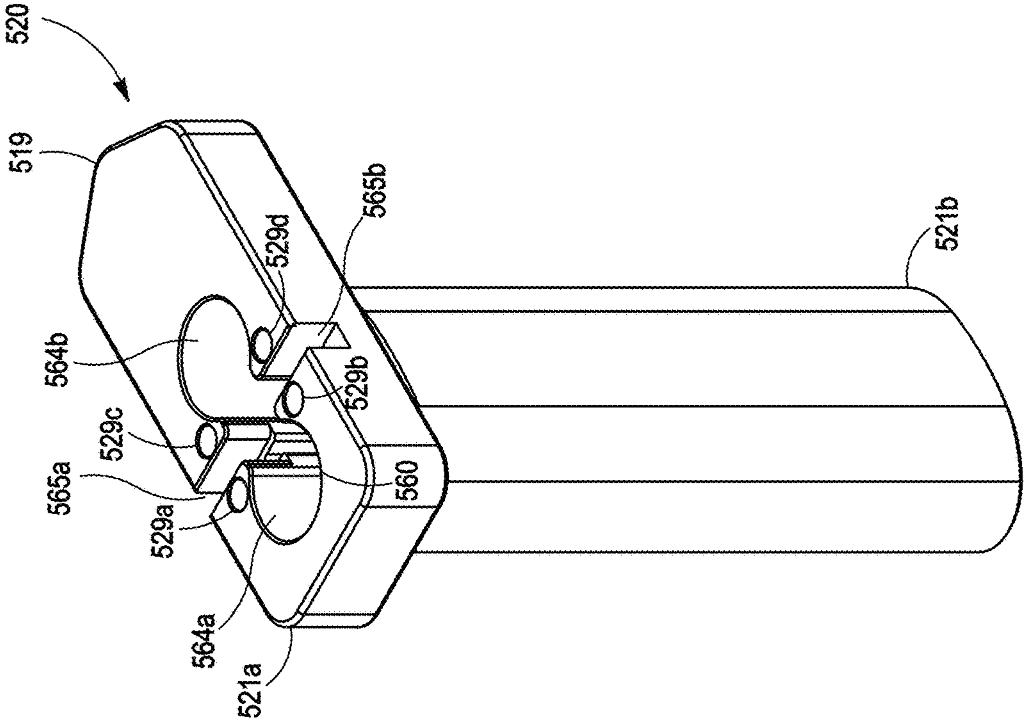
FIG. 26C is another rear perspective view of the drill guide shown in FIG. 26B, in accordance with the invention.
Figure 26E:
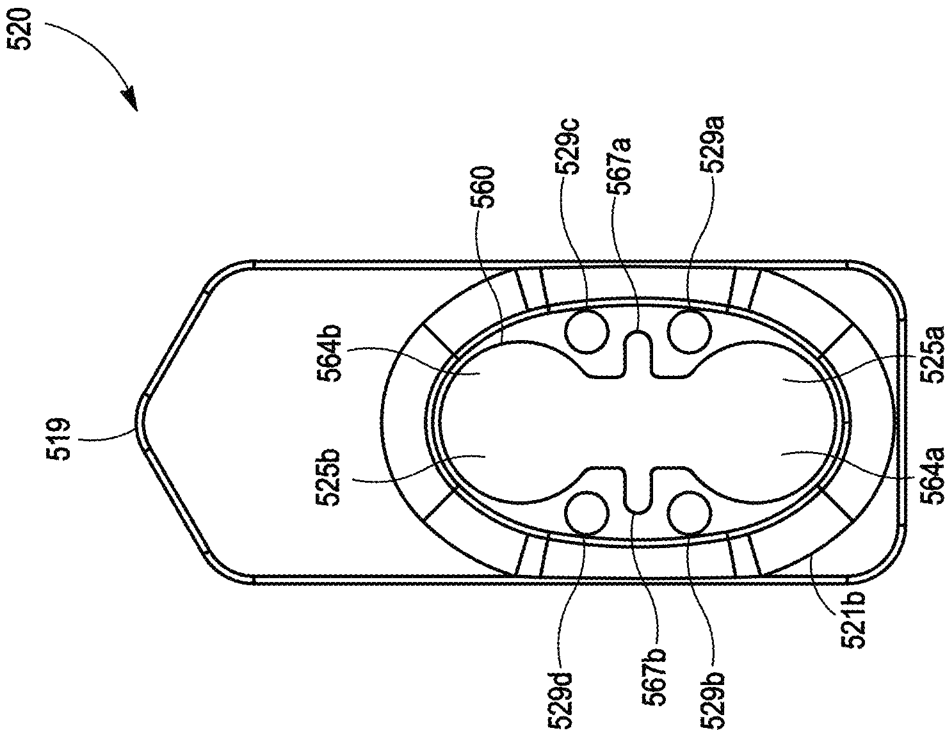
FIG. 26E is a bottom plan view of the drill guide shown in FIG. 26B, in accordance with the invention.
Figure 26D:
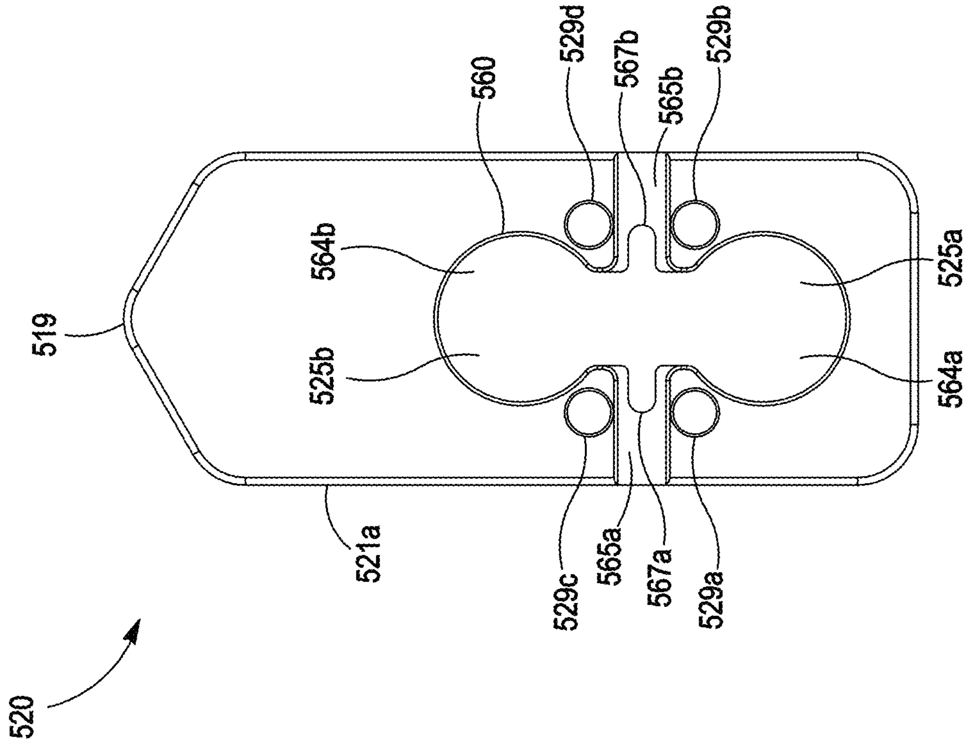
FIG. 26D is a top plan view of the drill guide shown in FIG. 26B, in accordance with the invention.

Referring now to FIG. 26A, there is shown one embodiment of a drill guide assembly 500 of the invention.

According to the invention, the drill guide assembly 500 is configured and adapted to create pre-determined pilot SI joint openings in a SI joint; particularly, a dysfunctional SI joint, to accommodate placement of a SI joint prosthesis of the invention therein.

As illustrated in FIG. 26A, the drill guide assembly 500 generally comprises a drill guide 520, drill guide or insert 800, K-wires 509 and a K-wire driver 820.

As discussed in detail below, in a preferred embodiment, the drill guide assembly 500 further comprises a bone dislodging member; preferably, drill bit 501 discussed below, a K-wire pin member 550, and a drill alignment pin 530.

As illustrated in FIGS. 26B-26E, the drill guide 520 comprises proximal and distal ends 521*a*, 521*b*, the two (2) drill guide receiving slots 565*a*, 565*b*, which are disposed on the proximal end 521*a* of the drill guide 520, and the four (4) K-wire lumens 529*a*, 529*b*, 529*c*, 529*d*, which similarly extend from the proximal end 521*a* to the distal end 521*b* of the drill guide 520, and two (2) drill guide insert channels 567*a*, 567*b*.

In some embodiments, the distal end 521*b* of the drill guide 520 comprises anchor members that project from the distal end 521*b* of the drill guide 520, which are designed and configured to pierce and, preferably, engage biological tissue to maintain a fixed position of the drill guide 520 proximate thereto.

In a preferred embodiment, as additionally shown in FIG. 26A, the proximal end 521*a* of the drill guide 520, i.e., extended region 519 of drill guide 520, further comprises two (2) threaded holes 511*a*, 511*b*, which are preferably disposed on opposing edge regions of the extended region 519.

According to the invention, the threaded holes 511*a*, 511*b* are sized and configured to receive the threaded end 514 of the drill guide handle 510, discussed below.

Referring now to FIGS. 3Q and 3R, there is shown a preferred embodiment of the drill guide handle 510.

As illustrated in FIGS. 3Q and 3R, the handle 510 preferably comprises an elongated cylindrical shaped member comprising proximal and distal ends 512*a*, 512*b*.

As further illustrated in FIG. 3Q, in a preferred embodiment, the distal end 512*b* of the handle 510*a* comprises a threaded extension 514 that is sized and configured to cooperate with the threaded holes threaded holes 511*a*, 511*b* of the drill guide 520, whereby the drill guide handle 510 can be threadably engaged to the drill guide 520.

Referring back to FIGS. 26B-26E, the drill guide 520 similarly comprises a prosthesis internal access opening 560, which, as discussed in detail below, is sized and configured to receive the drill guide insert 800 therein.

As further illustrated in FIGS. 26B-26E, the prosthesis internal access opening 560 similarly comprises first and second lobe portions 564*a*, 564*b*.

As also illustrated in FIGS. 26B-26E, in this instance, K-wire lumens 529*a* and 529*b* are disposed proximate the first lobe portion 564*a* and guide member receiving slots 565*a*, 565*b* on a plane that is perpendicular to the longitudinal axis of the proximal end 521*a* of the drill guide 520, and K-wire lumens 529*c* and 529*d* disposed proximate the second lobe portion 564*b* and guide member receiving slots 565*a*, 565*b* on a plane that is parallel to the plane of K-wire lumens 529*a* and 529*b* and, hence, also perpendicular to the longitudinal axis of the proximal end 521*a* of the drill guide 520.

As indicated above and illustrated in FIG. 26A, the K-wire lumens 529*a*, 529*b*, 529*c*, 529*d* are sized and configured to receive K-wires 509 therein.

Figure 26G:
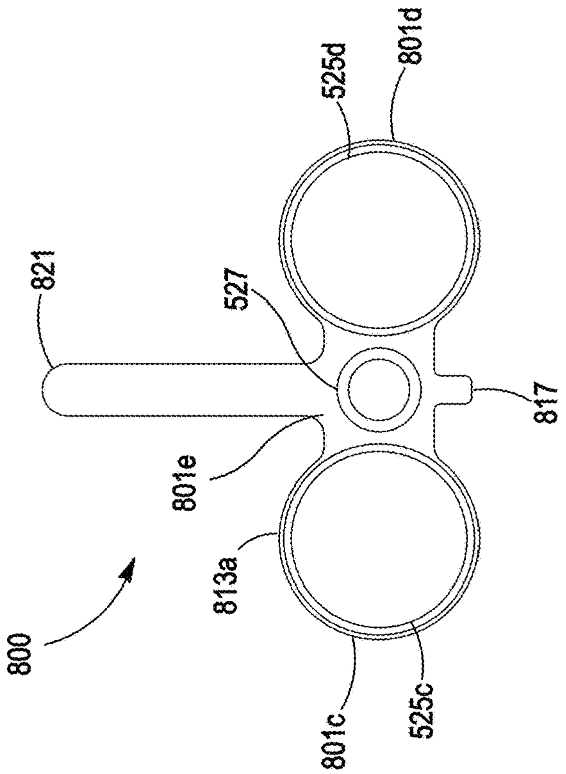
FIG. 26G is an end plan view of the drill guide insert shown in FIG. 26F, in accordance with the invention.
Figure 26F:
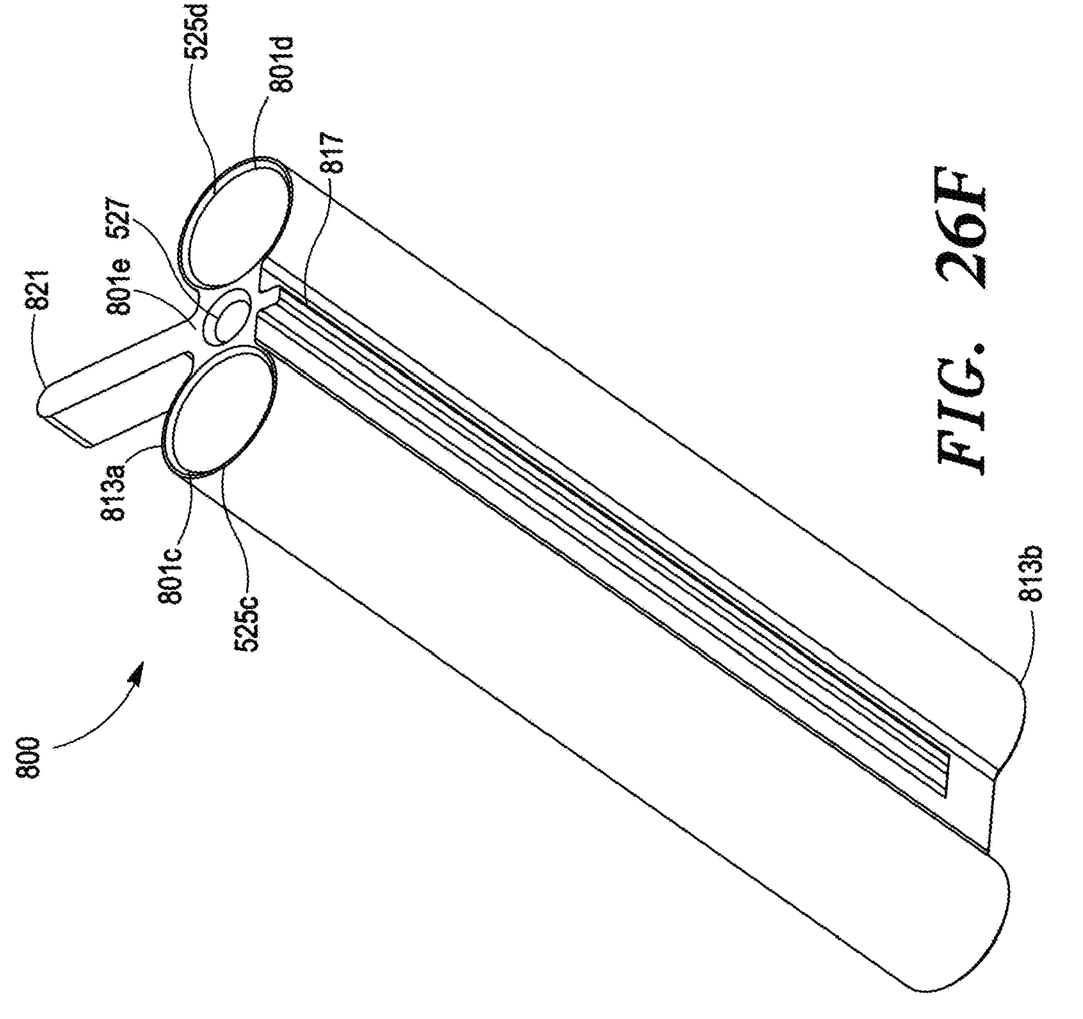
FIG. 26F is a perspective view of a drill guide insert of the drill guide assembly shown in FIG. 26A, in accordance with the invention.
Figure 26H:
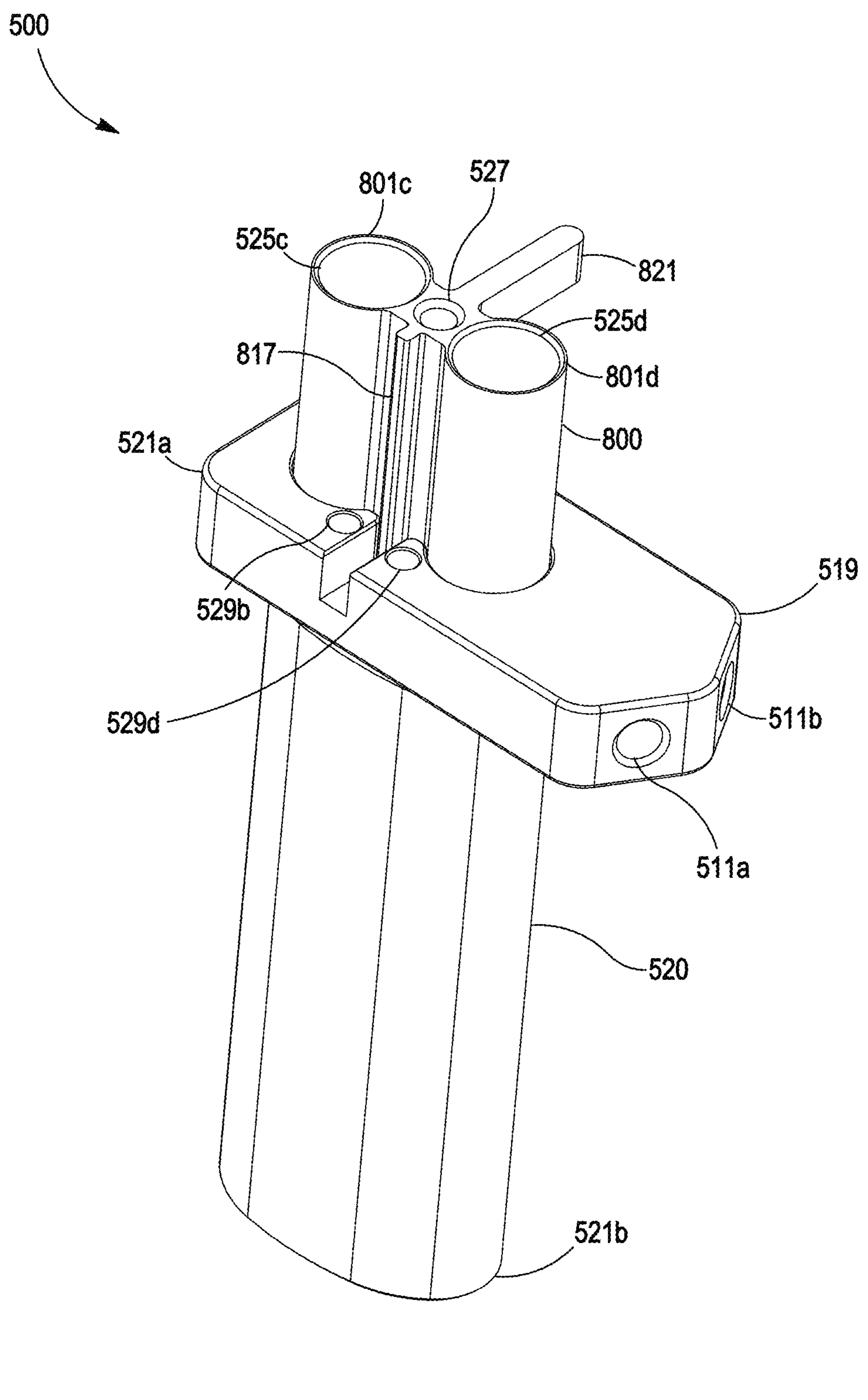
FIG. 26H is a perspective view of a drill guide assembly having the drill guide shown in FIG. 26B with the drill guide insert shown in FIGS. 26F and 26G positioned therein, in accordance with the invention.
Figure 26J:
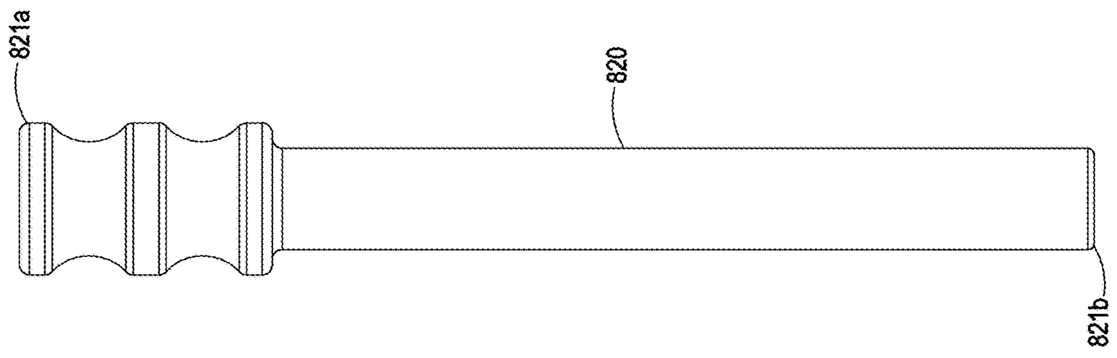
FIG. 26J is a side plan view of the K-wire driver shown in FIG. 26I, in accordance with the invention.

Referring now to FIGS. 261 and 26J, to facilitate advancement of the K-wires into bone structures; particularly, bone structures of a SI joint (as discussed in detail below), in a preferred embodiment of the invention, the drill guide 520 further comprises a K-wire driver 820.

As illustrated in FIGS. 261 and 26J, the K-wire driver 820 comprises an elongated member comprising proximal and distal ends 821*a*, 821*b*.

Figure 26I:
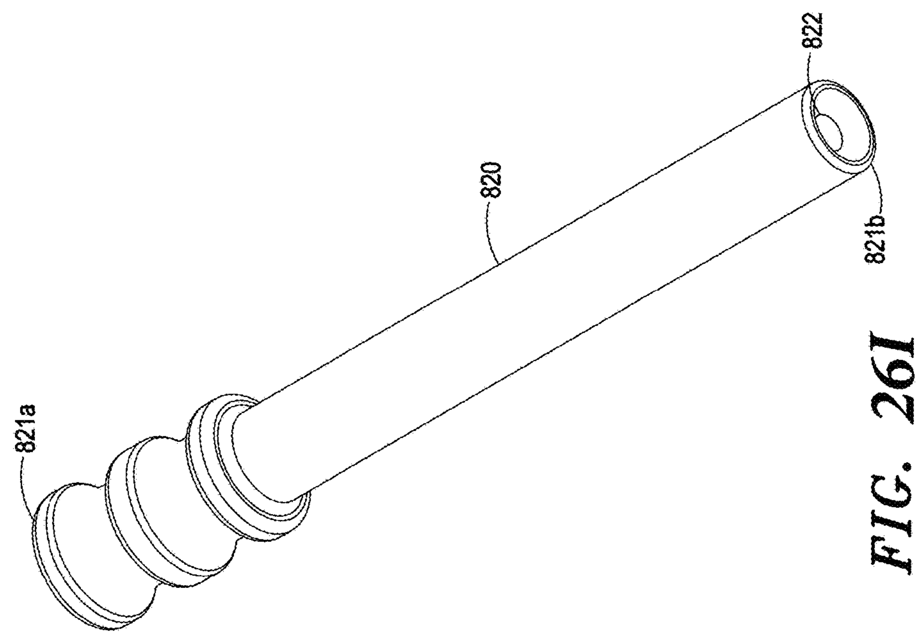
FIG. 26I is a perspective view of a K-wire driver of the drill guide assembly shown in FIG. 26A, in accordance with the invention.
Figure 26K:
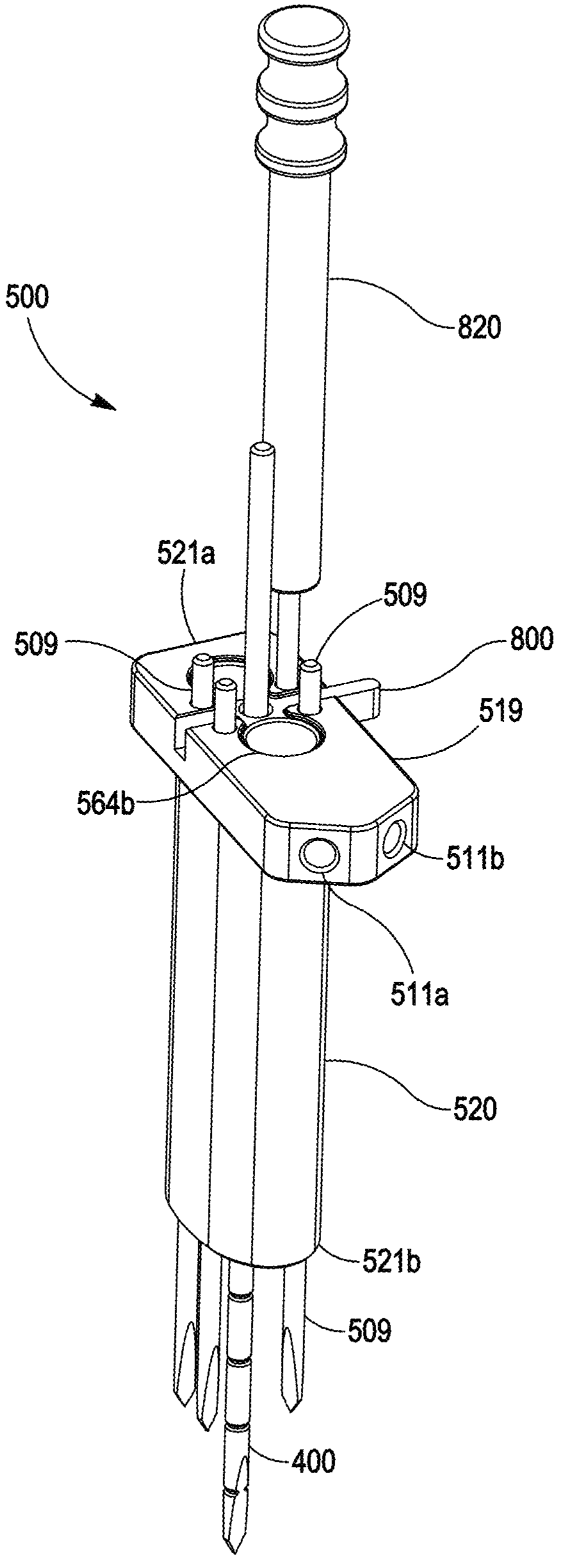
FIGS. 26K and 26L are further perspective views of the drill guide shown in FIG. 26B, showing K-wires positioned therein and the K-wire driver shown in FIGS. 261 and 26J positioned on one of the K-wires, in accordance with the invention.
Figure 26L:
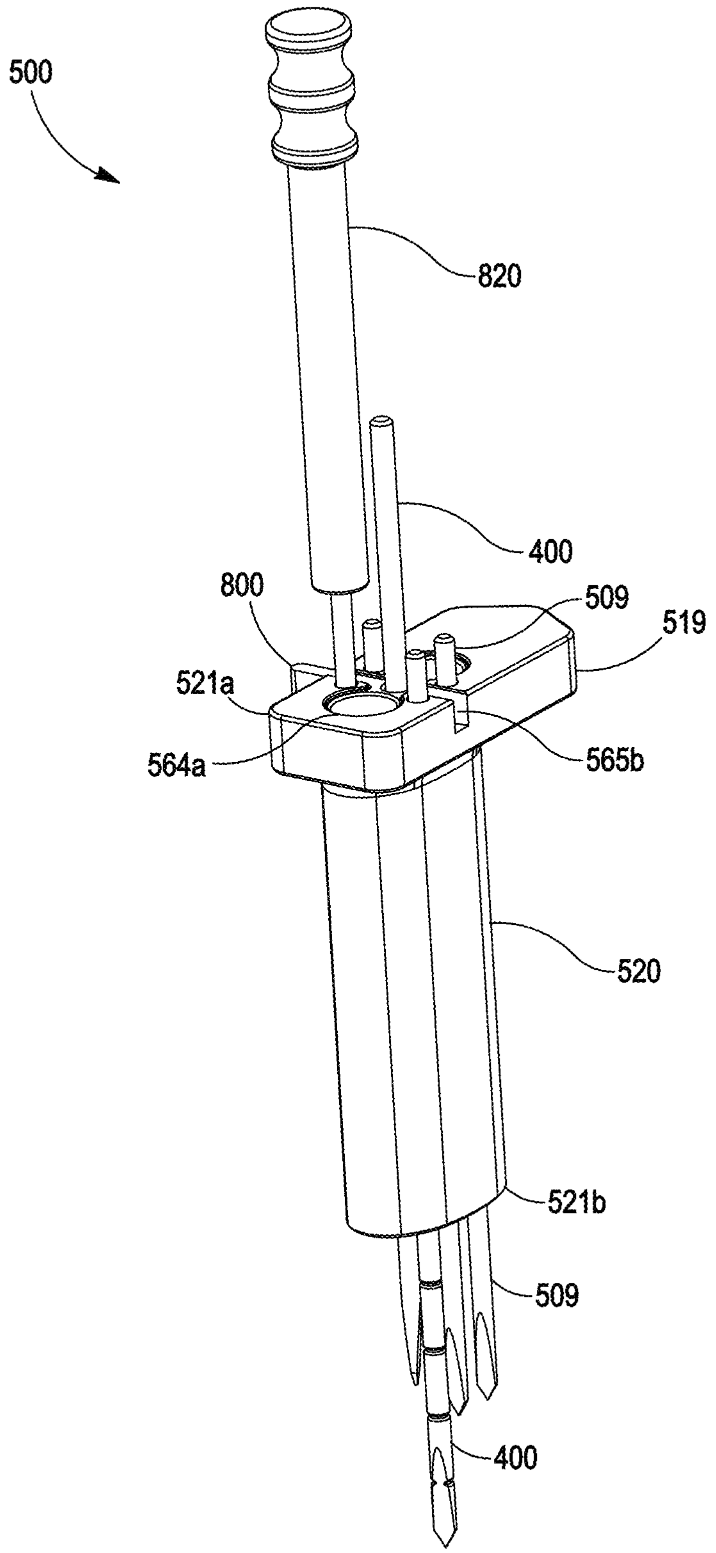

As illustrated in FIG. 26I, the distal end 821*b* of the K-wire driver 820 comprises an internal K-wire seat 822 that is sized and configured to receive a proximal end of a K-wire 509 therein, as illustrated in FIGS. 26K and 26L.

In a preferred embodiment, the K-wire seat 822 has a predetermined depth (into the K-wire driver 820) to facilitate a desired advancement of the K-wires 509 into bone structures.

Referring again to FIGS. 26F and 26G, there is shown a preferred embodiment of the drill guide insert 800.

As illustrated in FIGS. 26F and 26G, the drill guide insert 800 comprises an elongated member comprising proximal and distal ends 813*a*, 813*b*, first and second elongated cylindrical regions 801*c*, 801*d*, and a mid-region 801*e* disposed therebetween.

As further illustrated in FIGS. 26F and 26G, the first cylindrical region 801*c* comprises a first drill guide lumen 525*c* and the second cylindrical region 801*d* comprises a second drill guide lumen 525*d*, each of the drill guide lumens extending from the proximal end 813*a* to the distal end 813*b* of the drill guide insert 800.

As also illustrated in FIGS. 26F and 26G, the mid-region 801*e* of the drill guide insert 800 also comprises a drill medial lumen (similarly denoted "527"), which is sized and configured to receive and guide the guide pin 400 of the invention.

According to the invention, the first and second drill guide lumens 525*c*, 525*d* and drill guide medial lumen 527 can be sized and configured to receive various other suitable instruments, such as surgical scopes, center punches, location pins, drill probes, and drill stop assemblies, to facilitate the creation of a pilot SI joint opening.

As further illustrated in FIGS. 26F and 26G, the drill guide insert 800 further comprises an extended, substantially perpendicular end region 821 that is disposed on the proximal end 813*a* of the drill guide insert 800, which is sized and configured to seat in the two (2) guide member receiving slots 565*a*, 565*b* of the drill guide 520, and a raised elongated region 817 disposed opposite the end region 821, which is sized and configured to be received in the drill guide insert channels 567*a*, 567*b* of the drill guide 520, as illustrated in FIG. 26H, and guide the drill guide insert 800 into the drill guide 520.

In a preferred embodiment, the drill guide lumens 525*c*, 525*d* are sized and configured to receive a bone dislodging member of the invention; preferably, drill bit 501, drill alignment pin 530, and, if employed, K-wire pin member 550.

Figure 26M:
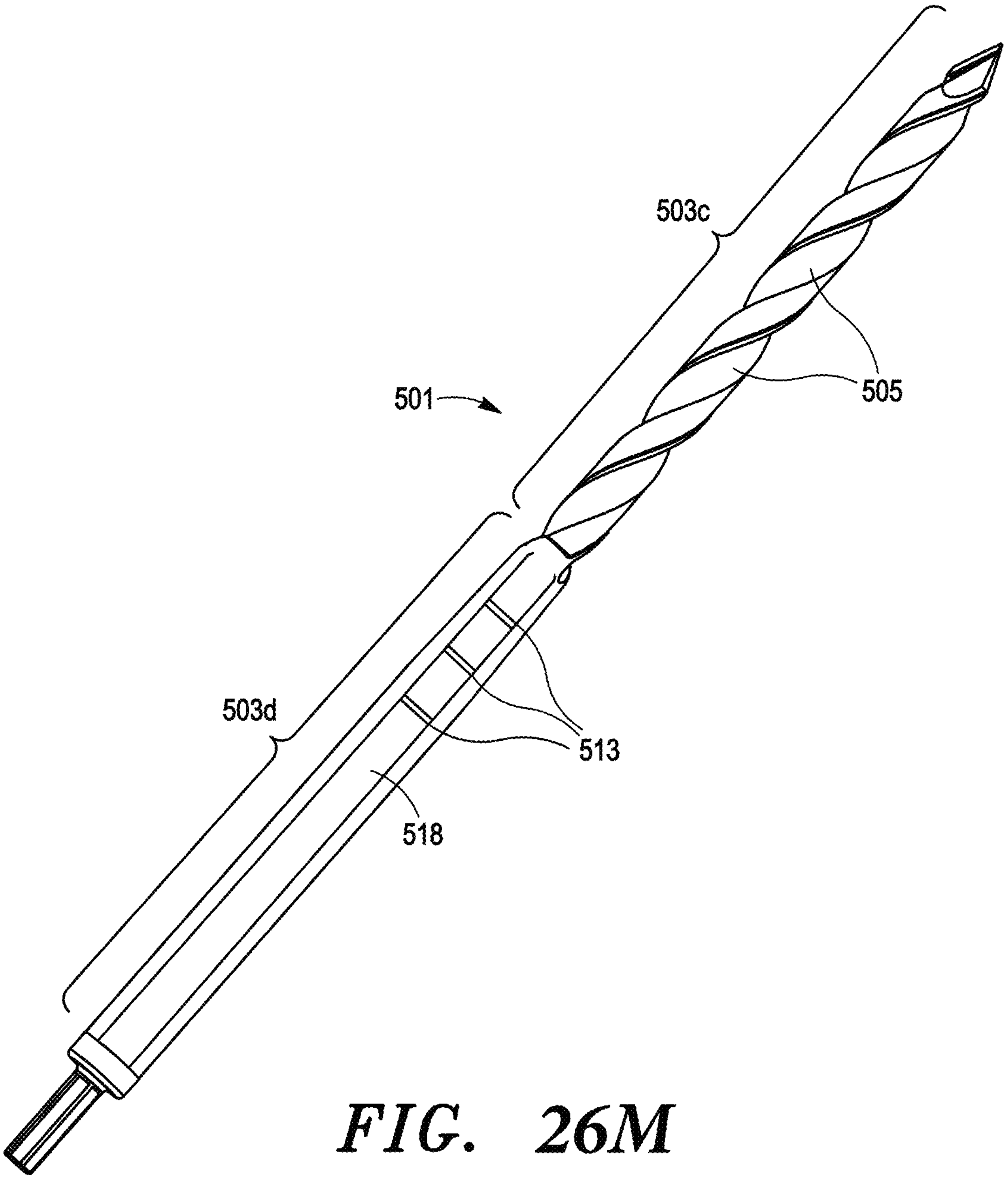
FIG. 26M is a perspective view of an embodiment of a bone dislodging member of the drill guide assembly shown in FIG. 26A, in accordance with the invention.

Referring now to FIG. 26M, there is shown one embodiment of drill bit 501.

As illustrated in FIG. 26M, the drill bit 501 similarly comprises an elongated rod structure having a proximal end region 503*d* and a bone dislodging end region 503*c*. However, as further illustrated in FIG. 26M, the proximal end region 503*d* comprises a plurality of graduated markings 513 to facilitate visual indications of the depth of the drill bit 501 into bone structures, i.e., SI joint bone structures, when, as discussed in detail below, the drill bit 501 is employed to create a SI joint pilot opening.

As further illustrated in FIG. 26M, the graduated markings 513 are thus preferably disposed on the proximal end region 503*d* of the drill bit 501 proximate the bone dislodging end region 503*c*.

In a preferred embodiment, the graduated markings 513 are spaced approximately 10 mm apart and, by virtue of unique configuration of the drill guide 520 and the location of the graduated markings 513, can be directly visualized and, hence, read during creation of pilot SI joint openings with the drill bit 501.

The graduated markings 513 are also readily detectable and, hence, readable via a conventional image capture apparatus, such as a fluoroscopy and radiography system.

Figure 26N:
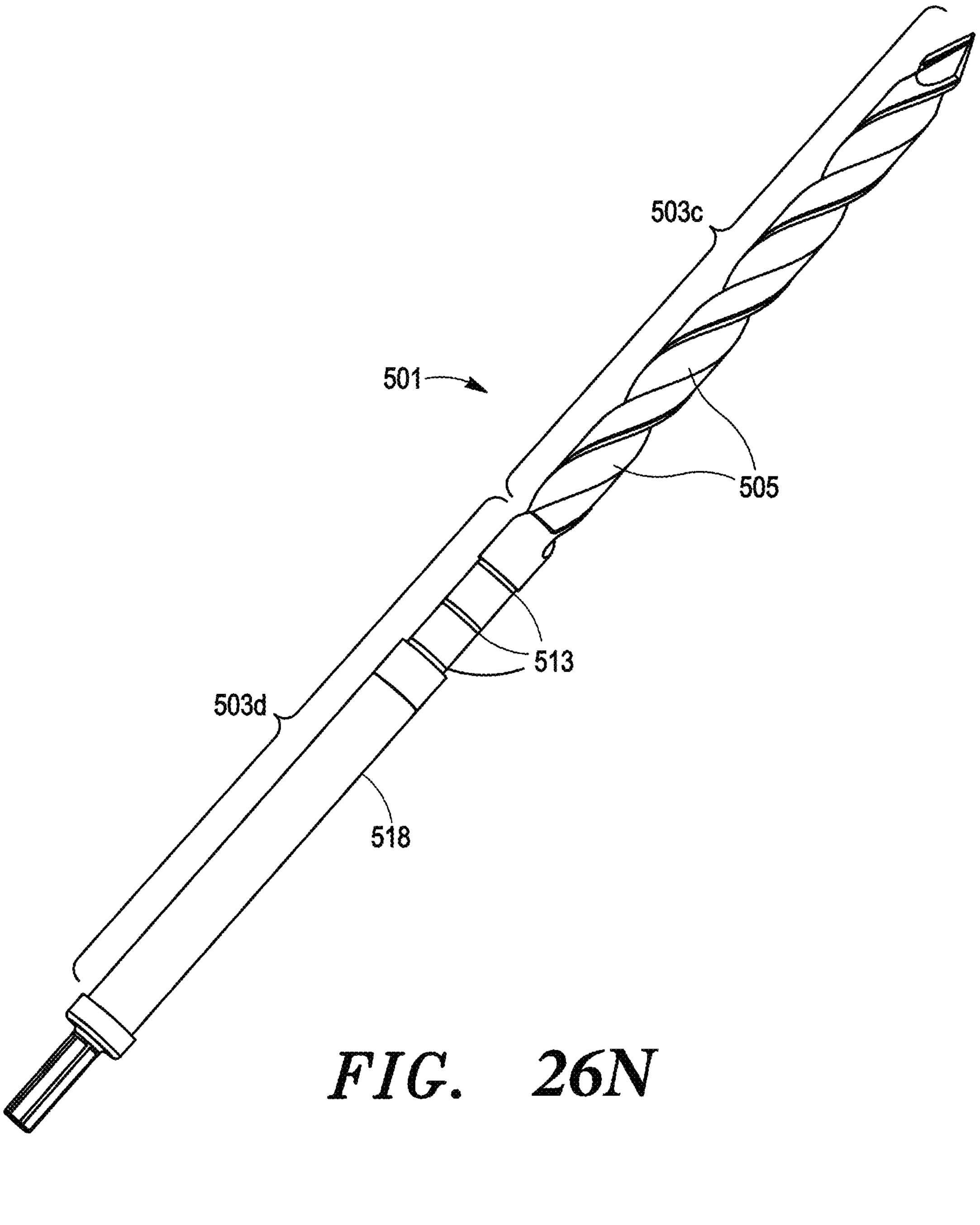
FIG. 26N is a perspective view of another embodiment of the bone dislodging member shown in FIG. 26M, in accordance with the invention.

Referring now to FIG. 26N, there is shown a further embodiment of drill bit 501. As illustrated in FIG. 26N, the drill bit 501 similarly comprises an elongated rod structure having the proximal end region 503*d*, bone dislodging end region 503*c* and graduated markings 513.

As further illustrated in FIG. 26N, in this embodiment, the proximal end region 503*d* of the drill bit 501 comprises a larger circumference than the bone dislodging end region 503*c* to enhance alignment of the drill bit 501 in the larger lobe portions 564*a*, 564*b* of the prosthesis internal access opening 560 in the drill guide.

To abate premature wear of the graduated markings 513 and, hence, compromised detection and readability of the markings 513 when the drill bit 501 is repeatedly advanced into and through bone structures, the graduated markings 513 are preferably positioned on a flat region 518 on the proximal end region 503*d* of the drill bit 501, whereby the graduated markings 513 are inset relative to the outer periphery of the proximal end region 503*d* of the drill bit 501.

As set forth in U.S. application Ser. No. 17/463,779, according to the invention, the drill bit 501 can operate with various conventional manual, pneumatic, and/or electromechanical tools, such as a conventional surgical drill.

Figure 26O:
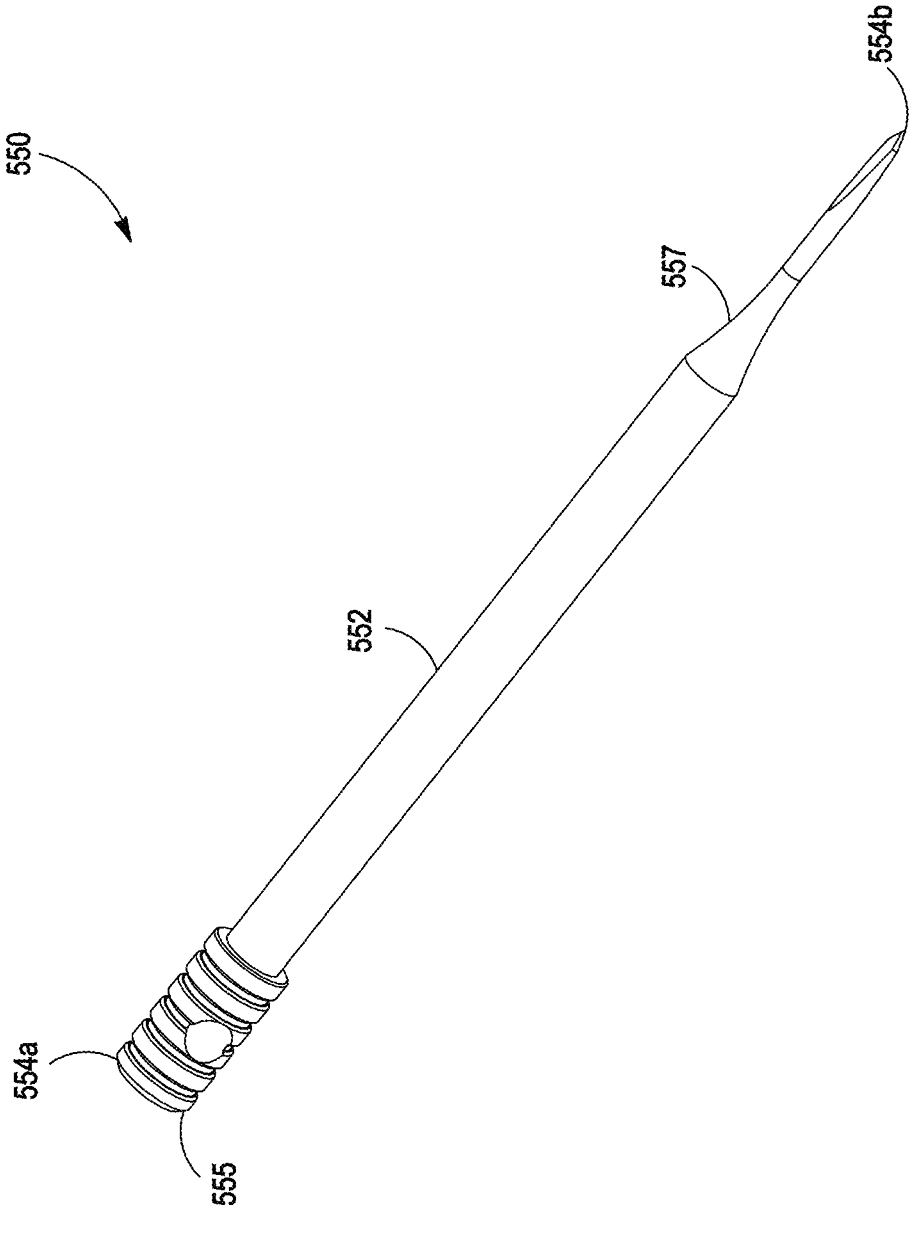
FIG. 26O is a perspective view of a K-wire member of the drill guide assembly shown in FIG. 26A, in accordance with the invention.

Referring now to FIG. 26O, there is shown one embodiment of a K-wire pin member 550.

As illustrated in FIG. 26O, the K-wire pin member 550 comprises an elongated cylindrical shaped member 552 comprising proximal and distal ends 554*a*, 554*b*, a head region 555 disposed on the proximal end 554*a*, and a K-wire tip 557.

As further illustrated in FIG. 26O, in some embodiments of the invention, the head region 555 of the elongated member 552 comprises a textured configuration to facilitate insertion of the K-wire pin member 550 into SI joint structures.

Figure 26P:
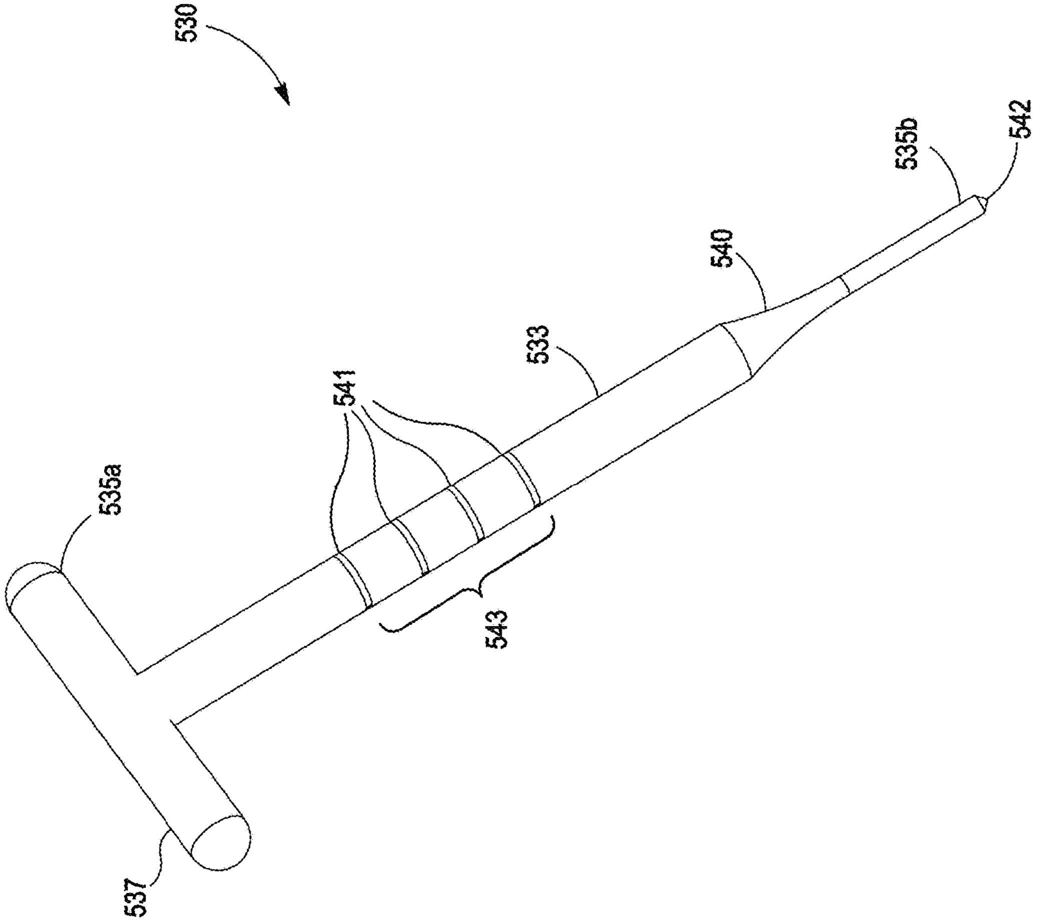
FIG. 26P is a perspective view of a temporary fixation pin of the drill guide assembly shown in FIG. 26A, in accordance with the invention.

Referring now to FIG. 26P, there is shown an embodiment of a drill alignment pin 530 that is adapted to be employed with drill guide 520.

As illustrated in FIG. 26P, the drill alignment pin 530 preferably comprises an elongated guide member 533 comprising proximal and distal ends 535*a*, 535*b*, and a handle 537 that is disposed on the proximal end 535*a* of the guide member 533.

As further illustrated in FIG. 26P, the elongated guide member 533 of the drill alignment pin 530 comprises a center region 543 similarly comprising a plurality of graduated markings 541, which preferably are readily detectable and, hence, readable via a conventional image capture apparatus, and a distal tapered end 540 that tapers to a point 542, which is adapted and configured to pierce bone structures and, as discussed below, when employed during creation of SI joint pilot openings, further supports and stabilizes the drill guide 520.

According to the invention, the drill guide assembly 500 provides a plurality of seminal advantages, including the following:

- only a minimal incision, i.e., an incision length in the range of 2.0 cm to 3.0 cm, is required to create the pilot openings in the SI joint structures and implant a SI joint prosthesis therein;
- direct visualization of the drill bit 501 and, hence, markings (i.e., drill bit depth markings) 513 thereon is provided during creation of pilot SI joint openings;
- direct (and optimal) visualization of the SI joint structures is provided after creation of the pilot openings in the SI joint structures; and
- consistent, optimal arthrodesis of the dysfunctional SI joint is achieved after placement of a SI joint prosthesis therein.

The drill guide assembly 500 also provides consistent, optimal guidance of (i) the bone dislodging member of the invention; particularly, drill bit 501, during creation of the SI joint openings in bone structures; particularly, SI joint bone structures, therewith, and (ii) the SI joint prostheses of the invention into the pilot SI joint openings.

Further features and related functions of drill guide assembly 500 are set forth in Applicant's Co-Pending U.S. application Ser. No. 18/240,197, which is incorporated by reference herein in its entirety.

As indicated above, in a preferred embodiment, the drill guide assembly 500 is configured and adapted to create pilot SI joint openings in SI joint bone structures of a SI joint to accommodate placement of a SI joint prosthesis of the invention; particularly, SI joint protheses 70*a*, 70*b*, 70*c*, 70*d*, 70*e*, 70*f*, 70*g*, 70 *h* and 70*i* described above, in the SI joint.

According to the invention, other suitable drill guide assemblies, which can be employed to create pilot SI joint openings in SI joint bone structures of a SI joint to accommodate placement of a SI joint prosthesis of the invention therein, are also disclosed in Applicant's Co-Pending U.S. application Ser. No. 18/240,197.

Referring now to FIG. 27A, there is shown pilot SI joint opening 100 referenced above, which is one embodiment of a pilot SI joint opening that can be created with drill guide assembly 500 (and the other drill guide assemblies disclosed in Applicant's Co-Pending U.S. application Ser. No. 18/240,197).

As illustrated in FIG. 27A and indicated above, the pilot SI joint opening 100 comprises ilium and sacrum guide portions (or openings) 104, 103.

According to the invention, the ilium and sacrum guide portions 104, 103 can comprise various configurations, e.g., cross-sectional shapes, and sizes to, as discussed in detail below, accommodate insertion of defined regions of a prosthesis of the invention therein and transition of the ilium and sacrum guide portions 104, 103 from pilot or first configurations and sizes to expanded second configurations and sizes when a SI joint prosthesis is inserted therein.

According to the invention, the ilium and sacrum guide portions 104, 103 can also be disposed at various locations in the ilium and sacrum, such as shown in FIGS. 27A and 27B, to accommodate desired placement of a SI joint prosthesis in the dysfunctional SI joint.

In some embodiments, there are thus provided systems for stabilizing dysfunctional SI joints.

In one embodiment, a system for stabilizing a dysfunctional SI joint comprises a drill guide assembly of the invention and a prosthesis assembly of the invention, the prosthesis assembly comprising a prosthesis and supplemental bone fixation means,

- the drill guide assembly adapted to advance toward the dysfunctional SI joint in a posterior trajectory and create a pilot SI joint opening in the dysfunctional SI joint in the posterior trajectory,
- the prosthesis configured and adapted to be advanced into the pilot SI joint opening in the dysfunctional SI joint in the posterior trajectory, whereby the prosthesis transfixes and, thereby, stabilizes the dysfunctional SI joint,
- the prosthesis comprising a first elongated section, a second elongated section, and a bridge section disposed between and connected to the first and second elongated sections,
- the first elongated section comprising a first open proximal end, a first open distal end, a first plurality of fenestrations, and a first internal lumen that extends from the first open proximal end to the first open distal end of the first elongated section,
- the second elongated section comprising a second open proximal end, a second open distal end, a second plurality of fenestrations, and a second internal lumen that extends from the second open proximal end to the second open distal end of the second elongated section,
- the supplemental bone fixation means comprising an expandable member or composition that is configured and adapted to be advanced into the first and second internal lumens of the prosthesis, expand and, thereby, enhance fixation of the prosthesis to the dysfunctional SI joint when the prosthesis is advanced into the dysfunctional SI joint.

In some embodiments, the supplemental bone fixation means comprises a bone stabilization pin configured and adapted to be advanced into and through the first and second internal lumens of the prosthesis, and into the dysfunctional SI joint.

In some embodiments, the bone stabilization pin comprises a plurality of tabs that are adapted to transition from a collapsed configuration to at least a first outwardly projecting configuration when the prosthesis is advanced into the dysfunctional SI joint and the bone stabilizing pin is advanced into the first and second internal lumens of the prosthesis, wherein, when the bone stabilizing pin is advanced into the first internal lumen of the prosthesis, at least a first tab of the plurality of tabs extends through and out of a first fenestration of the first plurality of fenestrations of the prosthesis and fixes the bone stabilizing pin to a first SI joint region in the dysfunctional SI joint and, thereby, enhances fixation of the prosthesis to the dysfunctional SI joint, and when the bone stabilizing pin is advanced into the second internal lumen of the prosthesis, at least a second tab of the plurality of tabs extends through and out of a second fenestration of the second plurality of fenestrations of the prosthesis and fixes the bone stabilizing pin to a second SI joint region in the dysfunctional SI joint and, thereby, enhances fixation of the prosthesis to the dysfunctional SI joint.

In some embodiments, the bone stabilization pin comprises an elongated pin member and an expandable end member adapted to engage the elongated pin member on a distal end, the expandable end member further adapted to transition from a collapsed configuration to an expanded configuration when the prosthesis is advanced into the dysfunctional SI joint, wherein, when the expandable end member is engaged to the bone stabilizing pin and the bone stabilizing pin is advanced into the first or second internal lumen of the prosthesis, wherein the expandable end member extends from the first or second internal lumen of the prosthesis, the expandable end member fixes the bone stabilizing pin to a third SI joint region in the dysfunctional SI joint and, thereby, enhances fixation of the prosthesis to the dysfunctional SI joint.

In some embodiments, the supplemental bone fixation means comprises a phase change osteogenic composition that is adapted to be disposed in the first and second internal lumens of the prosthesis in a fluidized state and transition to a solid state when the prosthesis is advanced into the dysfunctional SI joint, wherein, when the phase change osteogenic composition is disposed in the first internal lumen of the prosthesis, the phase change osteogenic composition flows through and out of at least a first fenestration of the first plurality of fenestrations of the prosthesis, transitions to a solid state and enhances fixation of the prosthesis to the dysfunctional SI joint, and, when the phase change osteogenic composition is disposed in the second internal lumen of the prosthesis, the phase change osteogenic composition flows through and out of at least a second fenestration of the second plurality of fenestrations of the prosthesis, transitions to a solid state and similarly enhances fixation of the prosthesis to the dysfunctional SI joint.

In a preferred embodiment, the drill guide assembly comprises a guide pin, drill guide, drill guide insert and bone dislodging member, the guide pin configured and adapted to be advanced into a desired target position in the dysfunctional SI joint to guide the drill guide thereto, the drill guide comprising first and second drill guide fixation sub-systems, the first drill guide fixation sub-system comprising a plurality of first drill guide lumens configured and adapted to receive a plurality of K-wires therein, the plurality of K-wires configured and adapted to pierce and engage first and second bone structures of the dysfunctional SI joint, the second drill guide fixation sub-system comprising a K-wire pin member and a temporary fixation pin, the K-wire pin member and the temporary fixation pin adapted to pierce and engage the first and second bone structures of the dysfunctional SI joint, the drill guide further comprising a prosthesis internal access opening sized and configured to receive the drill guide insert and monolithic member therein, the drill guide insert comprising a second and third drill guide lumens, the second and third drill guide lumens adapted to receive the K-wire pin member, the temporary fixation pin, and the bone dislodging member therein, the bone dislodging member adapted to dislodge portions of bone in the dysfunctional SI joint to create the pilot SI joint opening in the dysfunctional SI joint.

Bone Harvester Assemblies

In a preferred embodiment of the invention, the drill guide assemblies of the invention further comprise a bone harvester assembly adapted to dislodge, and extract and contain the dislodged bone from the bone dislodging member, i.e., drill bit, after creating the SI joint opening or a portion thereof.

Referring now to FIGS. 28A-28E, there is shown one embodiment of a bone harvester assembly of the invention (denoted "900").

Figure 28A:
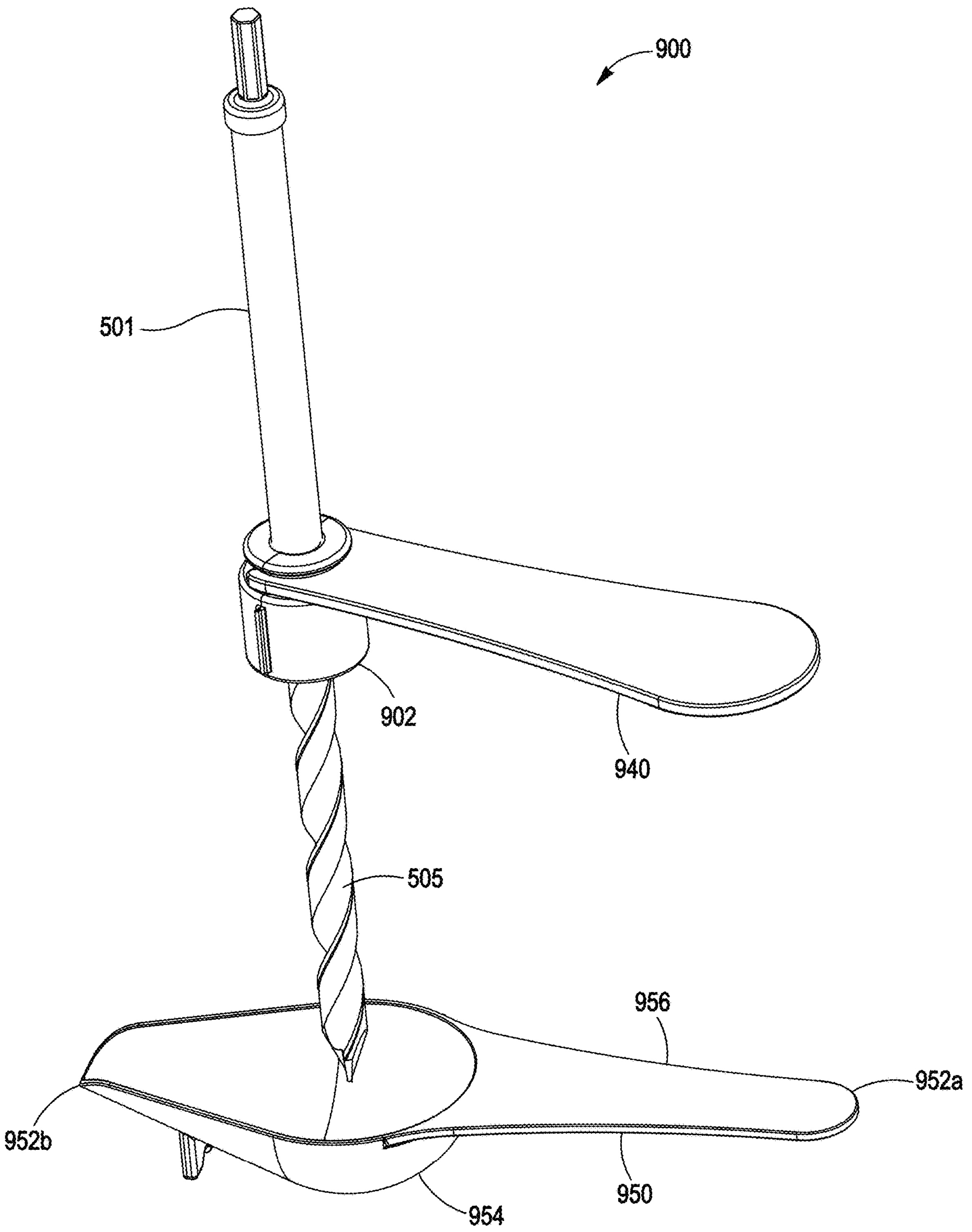
FIG. 28A is a perspective view of one embodiment of a bone harvester assembly, in accordance with the invention.
Figure 28B:
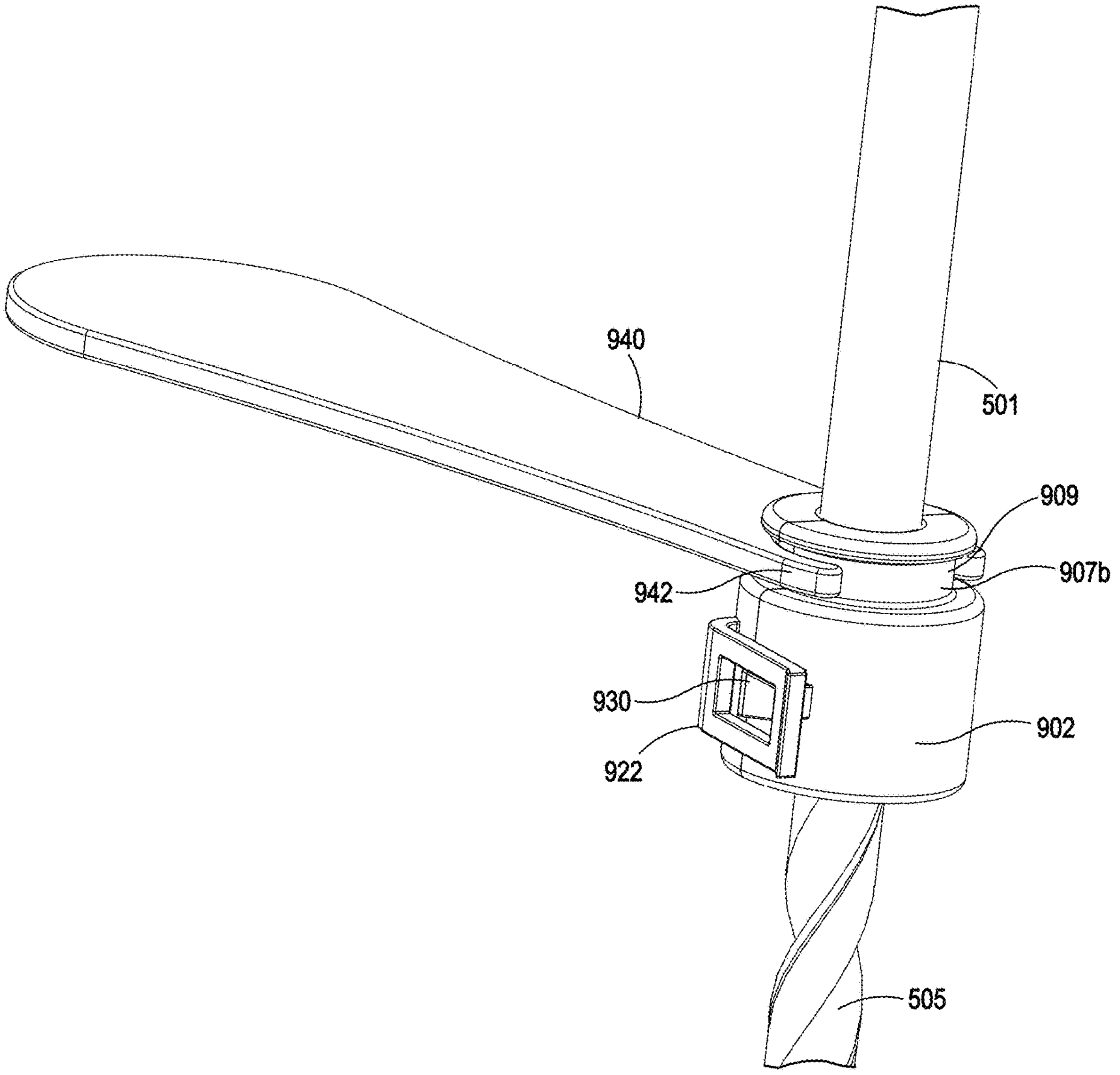
FIG. 28B is a partial further perspective view of the bone harvester assembly shown in FIG. 28A, in accordance with the invention.

As illustrated in FIGS. 28A and 28B, the bone harvester assembly 900 generally comprises a bone retraction sleeve 902, which, as discussed below, is adapted to directly remove (or extract) dislodged bone from the drill bit; particularly, drill bit 501 of the invention, and a handle 940.

Figure 28C:
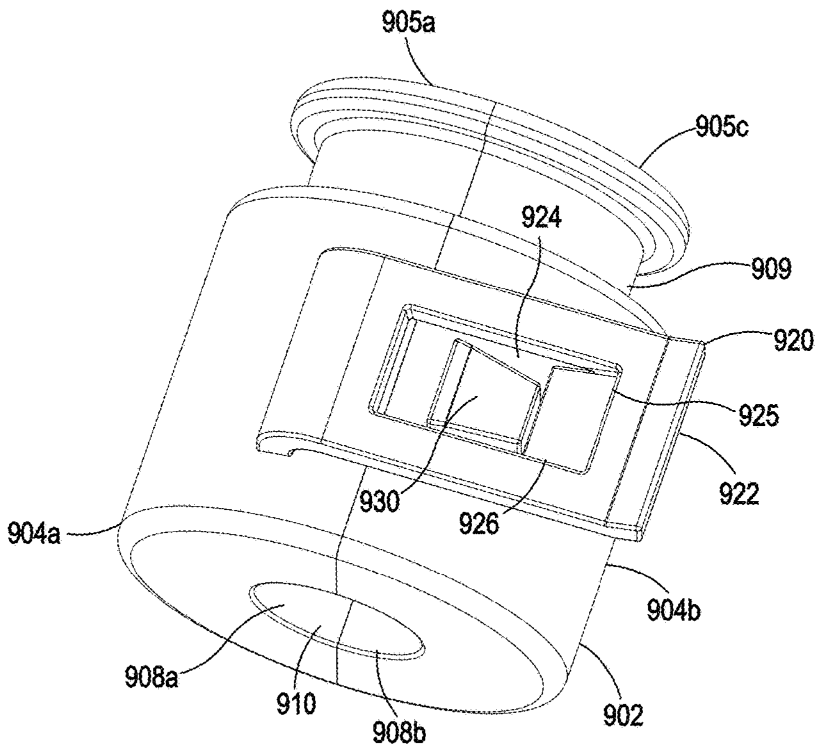
FIG. 28C is a perspective view of the bone retraction sleeve of the bone harvester assembly shown in FIG. 28A, in accordance with the invention.
Figure 28D:
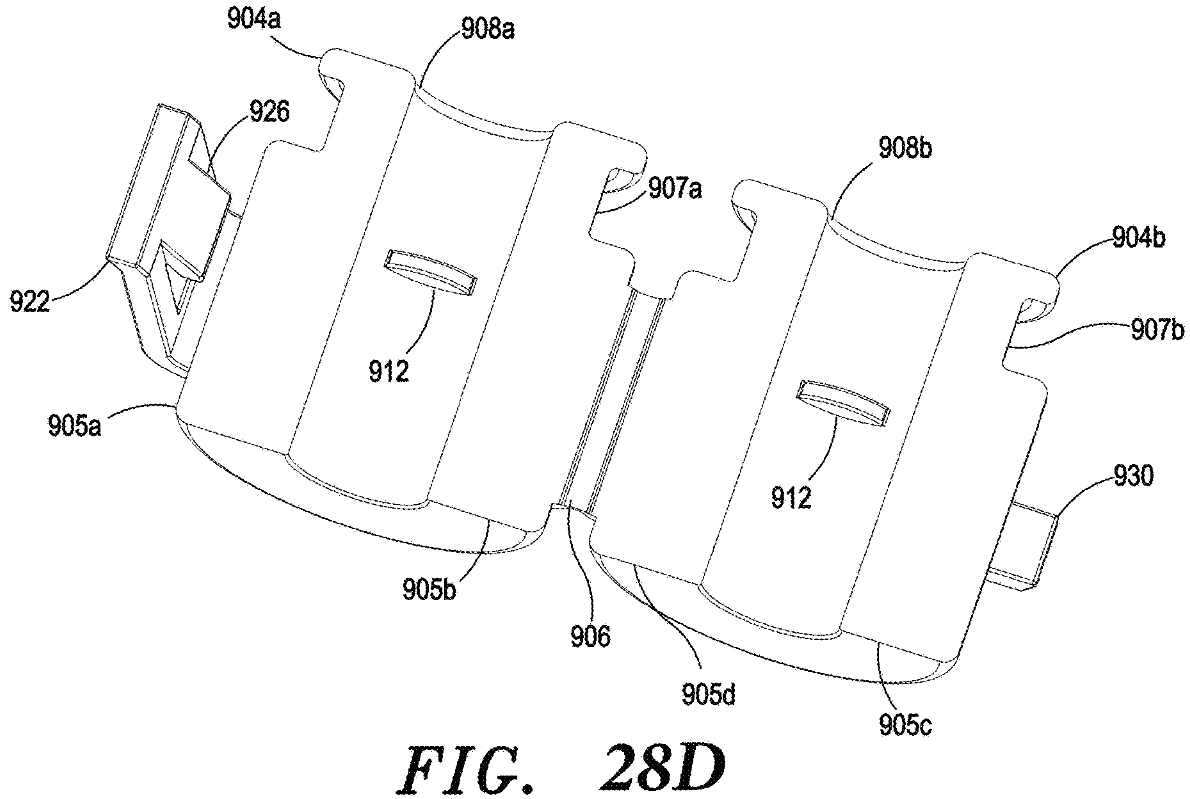
FIG. 28D is a perspective view of the bone retraction sleeve shown in FIG. 28C in an open configuration, in accordance with the invention.

As illustrated in FIG. 28D, in a preferred embodiment of the invention, the bone retraction sleeve 902 comprises two (2) corresponding shaped bone harvester members **904*a*, 904*b*; bone harvester member 904*a* comprising first and second edge regions 905*a*, 905*b* and bone harvester member 904*b* comprising first and second edge regions 905*c*, 905*d***.

As further illustrated in FIG. 28D, the bone harvester assembly 900 further comprises a hinge assembly 906, which is adapted to engage the second edge region **905*b* of bone harvester member 904*a* and the second edge region 905*d* of bone harvester member 904*b* to allow translation of the bone harvester assembly 900 from an open configuration, as illustrated in FIG. 28D, to a closed configuration, as illustrated in FIG. 28C, whereby the bone harvester assembly 900** comprises a substantially uniform cylindrical shape, and vice versa, i.e., from the closed configuration to the open configuration.

As further illustrated in FIG. 28D, each bone harvester member **904*a*, 904*b* further comprises a correspondingly shaped and sized drill bit seat 908*a*, 908*b*. In a preferred embodiment, the drill bit seats 908*a*, 908*b* are aligned and positioned in the bone harvester members 904*a*, 904*b*, whereby, when the bone harvester assembly 900 is in the closed configuration illustrated in FIG. 28C, the drill bit seats 908*a*, 908*b* form a uniform drill bit guide lumen 910 that is sized and configured to receive a drill bit; preferably, drill bit 501 of the invention, therein, as illustrated in FIGS. 28A and 28**B.

As additionally illustrated in FIG. 28D, each bone harvester member 904*a*, 904*b* further comprises a correspondingly shaped handle seat 907*a*, 907*b*.

As illustrated in FIGS. 28B and 28C, when the bone harvester assembly 900 is in the closed configuration, handle seats 907*a*, 907*b* of the bone harvester members 904*a*, 904*b* form a bone harvester assembly seat 909 that is sized and configured to receive and seat the bone harvester assembly handle 940 thereon.

To secure the bone harvester members 904*a*, 904*b* in the closed configuration illustrated in FIG. 28C and, hence, secure the drill bit in the drill bit guide lumen 910, the bone harvester assembly 900 further comprises bone harvester assembly securing means 920.

As illustrated in FIGS. 28C and 28D, in a preferred embodiment, the bone harvester assembly securing means 920 comprises a securing arm 922 and engagement member 930.

In a preferred embodiment, the securing arm 922 is connected proximate to the first edge region 905*a* of bone harvester member 904*a* and the engagement member 930 is connected proximate the first edge region 905*c* of bone harvester member 904*b*.

As further illustrated in FIGS. 28C and 28D, in a preferred embodiment, the securing arm 922 is rotatably connected proximate to the first edge region 905*a* of bone harvester member 904*a* to allow translation of the securing arm 922 from a closed or engaged configuration, i.e., engaged to the engagement member 930, as discussed below, to an open configuration, i.e., disengaged from the engagement member 930, as illustrated in FIG. 28D.

According to the invention, the securing arm 922 can also be adapted to flex from the closed configuration to the noted open configuration and vice versa when engaged to the bone harvester member 904*a*. Such arm flexure can be provided and/or achieved via the securing arm composition, i.e., comprising a flexible material, or securing arm configuration.

As illustrated in FIG. 28C, in a preferred embodiment, the securing arm 922 comprises an engagement member receiving slot 924 that is adapted to receive the engagement member 930 therein when the securing arm 922 is in the closed configuration illustrated in FIGS. 28B and 28C.

In a preferred embodiment, the securing arm 922 further comprises a retainer flap 926 disposed on the distal end 925 of the engagement member receiving slot 924 that is sized and configured to releasably engage the engagement member 930 when the engagement member 930 is positioned in the receiving slot 924 and the securing arm 922 is in the closed configuration.

Referring now to FIG. 28D, in a preferred embodiment, each bone harvester member 904*a*, 904*b* further comprises at least one bone extracting tab (or projection) 912 disposed on and extending from each drill bit seat 908*a*, 908*b*. In a preferred embodiment, the bone extracting tabs 912 are sized, positioned and configured to seat in a flute (or flutes) of a drill bit of the invention; particularly, flutes 505 of drill bit 501, when the drill bit is seated in drill bit guide lumen 910 and the bone harvester assembly 900 is in the closed configuration illustrated in FIGS. 28A and 28B.

In a preferred embodiment, the bone extracting tabs 912 are sized, positioned and configured to extract bone material from the drill bit flute (or flutes) when the bone harvester assembly 900 is in the closed configuration and the bone retraction sleeve 902 is translated linearly over the drill bit.

According to the invention, the bone extracting tabs 912 can be disposed at any position on the drill bit seats 908*a*, 908*b*, e.g., mid-regions, proximal end regions, distal end regions, combinations thereof, etc.

As indicated above, one or both of the drill bit seats 908*a*, 908*b* can also comprise a plurality of bone extracting tabs 912.

In an alternative embodiment, one or both of the drill bit seats 908*a*, 908*b* comprises a brush apparatus that is similarly sized and adapted to seat in the drill bit flute(s) and extract dislodged bone from the drill bit flute(s) when the bone retraction sleeve 902 is translated linearly over the drill bit.

As indicated above and illustrated in FIGS. 28A and 28B, in a preferred embodiment, the bone harvester assembly 900 further comprises a handle 940.

Figure 28E:
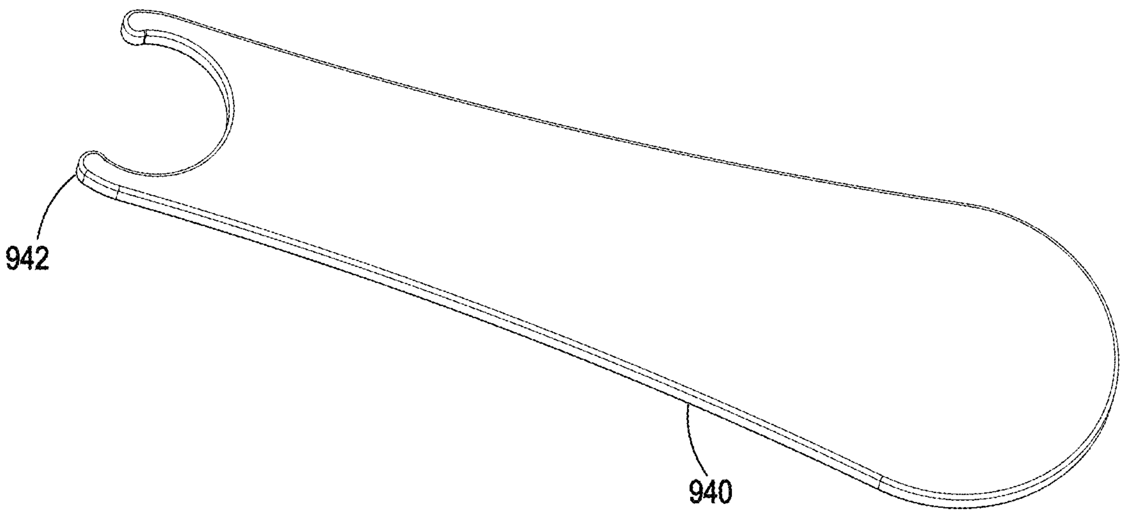
FIG. 28E is a perspective view of the handle of the bone harvester assembly shown in FIG. 28A, in accordance with the invention.

As illustrated in FIG. 28E, in a preferred embodiment, the handle 940 comprises a sleeve engagement end 942 sized and configured to releasably engage the bone harvester assembly seat 909 of the bone retraction sleeve 902, and allow the bone retraction sleeve 902 to rotate during linear translation of the bone retraction sleeve 902 over the drill bit.

According to the invention, the handle 940 facilitates manual linear translation of the bone retraction sleeve 902 over a drill bit and rotation thereof during the linear translation, and, hence, extraction of dislodged bone from the drill bit.

In some envisioned embodiments, powered translation means are employed to induce linear translation of the bone retraction sleeve 902 over the drill bit to extract dislodged bone therefrom.

According to the invention, various means and apparatus can be employed to harvest or capture the dislodged bone that is extracted from the drill bit by the bone retraction sleeve 902.

Referring again to FIG. 28A, in one embodiment, the bone harvester assembly 900 further comprises a bone receiving member 950, comprising proximal and distal ends 952*a*, 952*b*, a recessed region 954 disposed on the distal end 952*b*, which is sized and configured to capture and retain dislodged bone therein, and a handle 956.

Figure 28F:
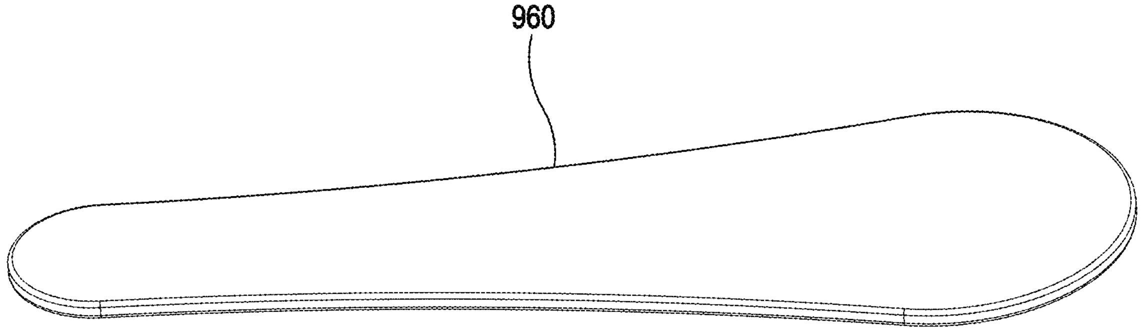
FIG. 28F is a perspective view of one embodiment of a bone material extractor, in accordance with the invention.

As illustrated in FIG. 28F, in some embodiments, the bone harvester assembly 900 further comprises a bone extractor 960 that is adapted to facilitate transfer the dislodged bone from the receiving member 950 to a storage container, e.g., vial, or an agent delivery system that is adapted to deliver the dislodged bone (and/or an osteogenic composition thereof) directly to SI joint prostheses of the invention, i.e., SI joint prostheses 70*a*, 70*b*, 70*c*, 70*d*, 70*e*, 70*f*, 70*g*, 70*h* and 70*i*.

Referring now to FIGS. 29A-29K, there is shown a further embodiment of a bone harvester assembly of the invention that is adapted to extract and contain dislodged bone from a bone dislodging member of the invention, i.e., drill bit, after creating a SI joint opening or a portion thereof.

As illustrated in FIGS. 29A-29H, in a preferred embodiment, the bone harvester assembly comprises a bone extractor member 1002, a prosthesis holder 1020, and a bone tamp or compactor 1040.

Figure 29A:
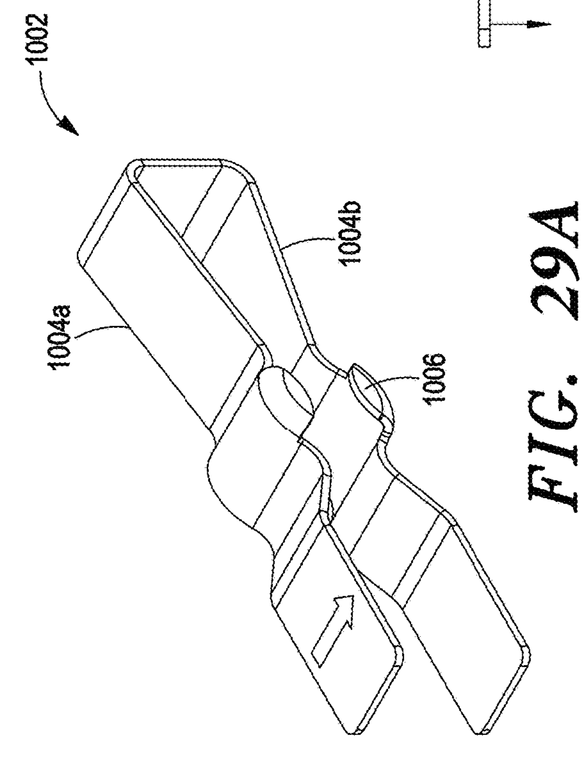
FIG. 29A is a perspective view of a tong member of a further bone harvesting assembly, in accordance with the invention.
Figure 29B:
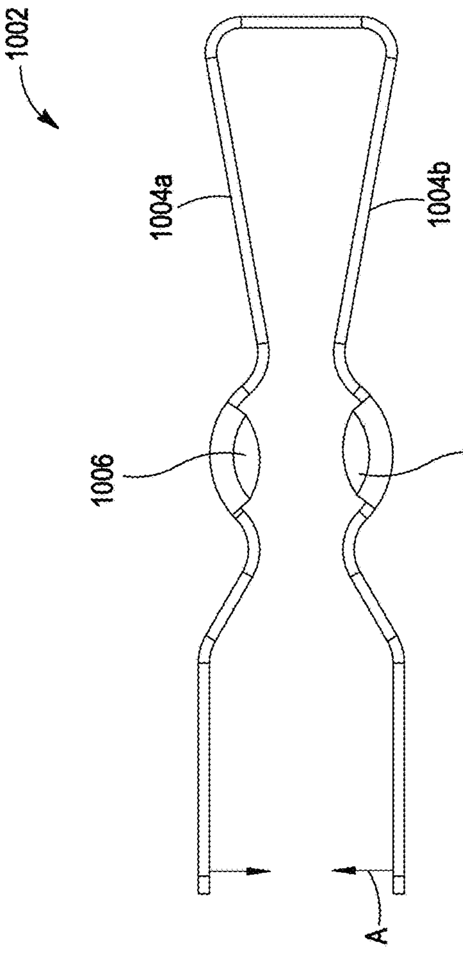
FIG. 29B is a bottom plan view of the tong member shown in FIG. 29A, in accordance with the invention.
Figure 29C:
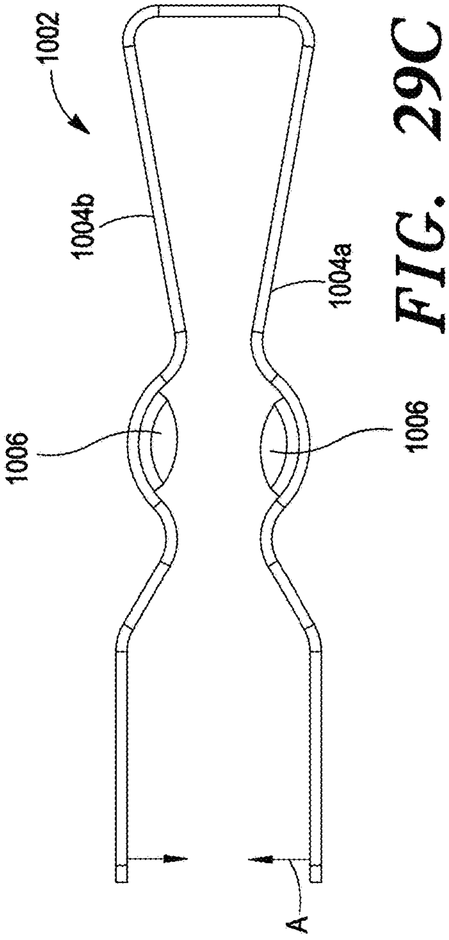
FIG. 29C is a top plan view of the tong member shown in FIG. 29A, in accordance with the invention.

As illustrated in FIGS. 29A-29C, the bone extractor member 1002 preferably comprises a tong member 1002 comprising two (2) interconnected arms 1004*a*, 1004*b*.

As further illustrated in FIGS. 29A-29C, each of the tong member arms 1004*a*, 1004*b* comprises at least one bone extracting tab (or projection) 1006, which, according to the invention, is sized, positioned, and configured to seat in a flute (or flutes) of a drill bit of the invention; particularly, flutes 505 of drill bit 501.

According to the invention, the bone extracting tabs 1006 are also sized and configured to extract dislodged bone from the drill bit, i.e., flute (or flutes) thereof, when the tong member 1002 is contracted in a direction denoted by Arrow "A", whereby the tong member 1002 is in a closed configuration, and the drill bit, i.e., drill bit 501 is rotated, whereby the tong member 1002 and, hence, bone extracting tabs 1006 translate linearly down the drill bit in a helical fashion.

Figure 29D:
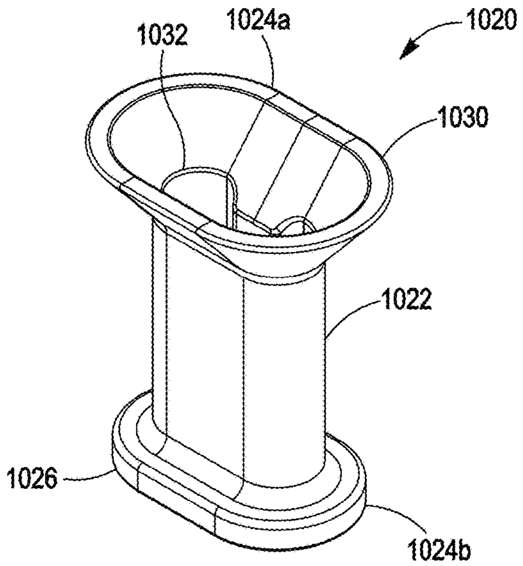
FIG. 29D is a perspective view of a prosthesis holder, in accordance with the invention.
Figure 29E:
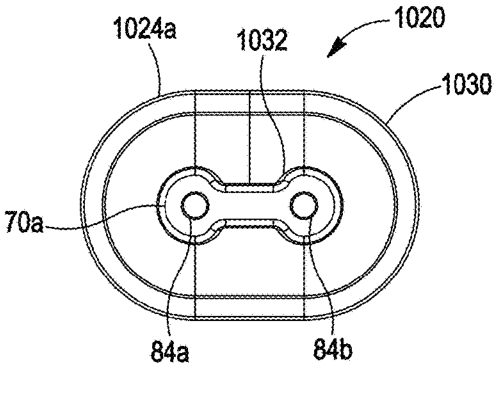
FIG. 29E is a top plan view of the prosthesis holder shown in FIG. 29D, showing a SI joint prosthesis seated therein, in accordance with the invention.
Figure 29F:
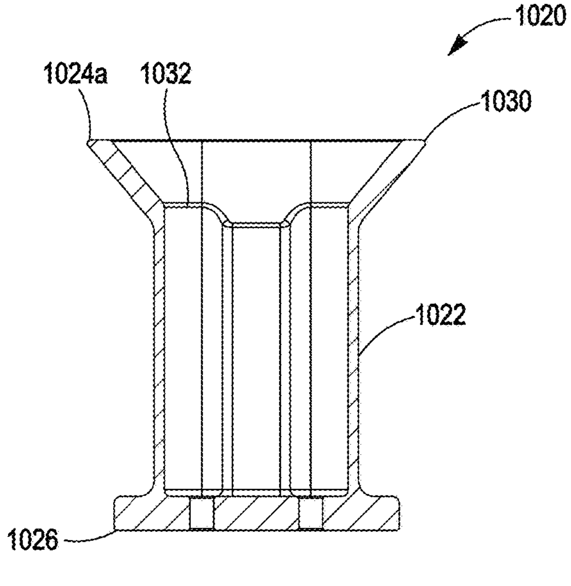
FIG. 29F is a front sectional plan view of the prosthesis holder shown in FIG. 29D, in accordance with the invention.

Referring now to FIGS. 29D-29F, there is shown one embodiment of a prosthesis holder 1020.

As illustrated in FIGS. 29D and 29F, in a preferred embodiment, the prosthesis holder 1020 comprises an elongated body 1022 comprising proximal and distal ends 1024*a*, 1024*b*, a flanged seat 1026 disposed on the distal end 1024*b*, and a bone receiving region 1030 disposed on the proximal end 1024*a* of the prosthesis holder 1020.

As further illustrated in FIGS. 29D and 29F, in a preferred embodiment, the bone receiving region 1030 comprises a concave cup-shaped region that is thus configured to receive and contain extracted dislodged bone therein.

As further illustrated in FIGS. 29D and 29F, in a preferred embodiment, the bone receiving region 1030 comprises a prosthesis internal access opening 1032, i.e., prosthesis seat, which, as illustrated in FIG. 29E, is sized and configured to receive and position a SI joint prosthesis of the invention therein.

According to the invention, when dislodged bone is extracted from a bone dislodging member, i.e., drill bit, and deposited into the bone receiving region 1030 of the prosthesis holder 1020, the extracted dislodged bone is delivered into the internal lumens of the SI joint prostheses, e.g., internal lumens 86*a*, 86*b* of SI joint prostheses 70*a*, 70*b*, 70*c*, 70*d*, 70*e*, 70*f*, 70*g*, 70 *h* and 70*i*, when seated in the prosthesis seat 1032.

To facilitate compaction of the dislodged bone into the SI joint prostheses, the harvesting assembly further comprises a bone tamp or compactor 1040.

Figure 29G:
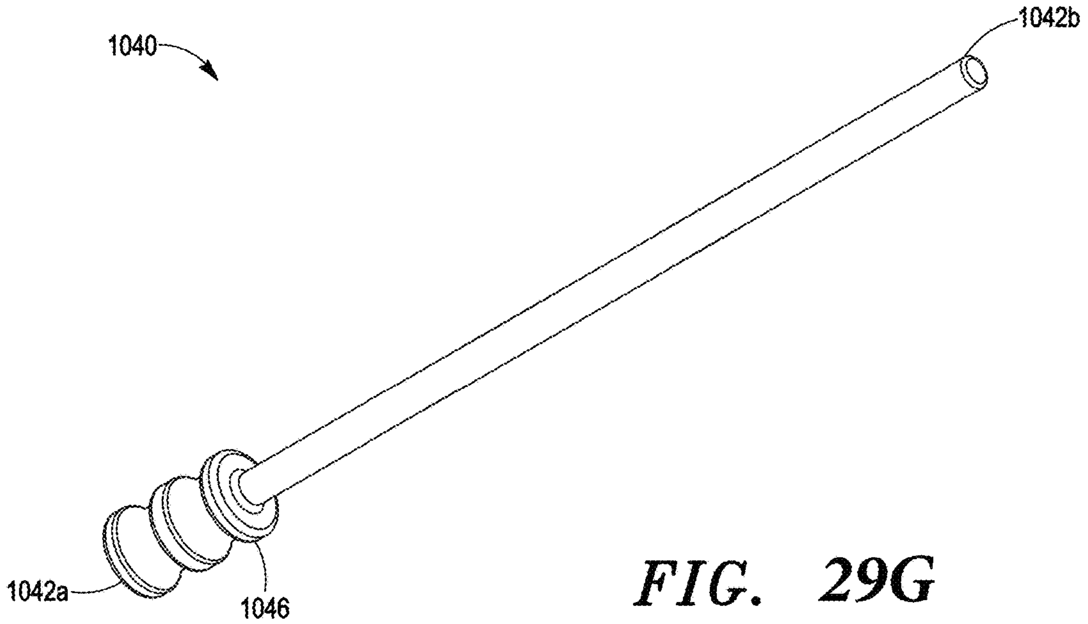
FIG. 29G is a perspective view of a bone material compactor, in accordance with the invention.
Figure 29H:
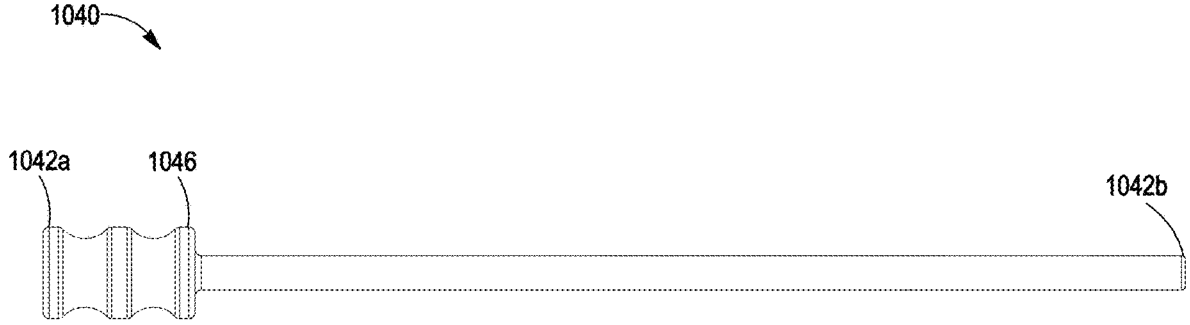
FIG. 29H is a side plan view of the bone material compactor shown in FIG. 29G, in accordance with the invention.

Referring now to FIGS. 29G and 29H, in a preferred embodiment, the bone tamp (or compactor) 1040 comprises an elongated rod member comprising proximal and distal ends 1042*a*, 1042*b*, and a handle region 1046 disposed on the proximal end 1042*b*.

In a preferred embodiment, the distal end 1042*b* of the bone tamp 1040 is sized and configured to be received in the internal lumens 86*a*, 86*b* of the SI joint prostheses 70*a*, 70*b*, 70*c*, 70*d*, 70*e*, 70*f*, 70*g*, 70 *h* and 70*i* to, as indicated above, compact the dislodged bone delivered thereto.

In some embodiments of the invention, the bone harvester assembly further comprises a bone delivery apparatus, which, as discussed in detail below, is configured and adapted to deliver dislodged bone extracted from the bone dislodging member directly into the internal lumens 86*a*, 86*b* of SI joint prostheses 70*a*, 70*b*, 70*c*, 70*d*, 70*e*, 70*f*, 70*g*, 70 *h* and 70*i*.

Figure 29I:
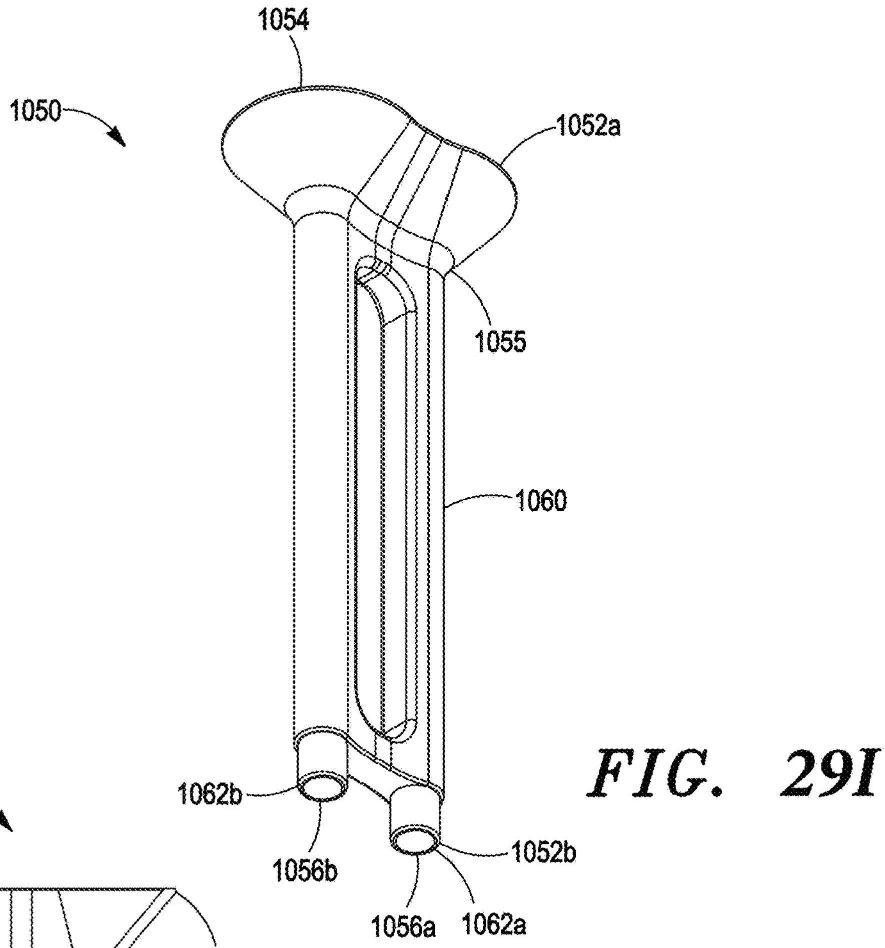
FIG. 29I is a perspective view of a bone material delivery apparatus, in accordance with the invention.
Figure 29J:
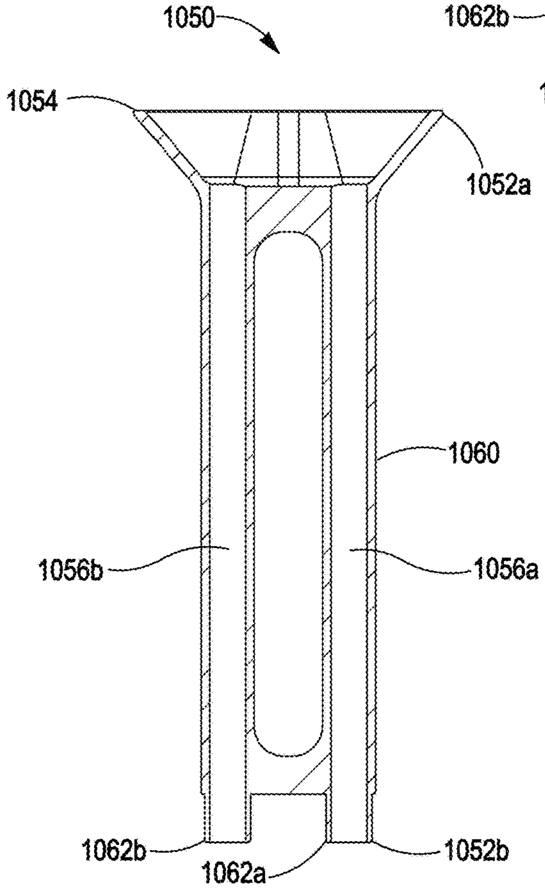
FIG. 29J is a front sectional plan view of the bone material delivery apparatus shown in FIG. 291, in accordance with the invention.
Figure 29K:
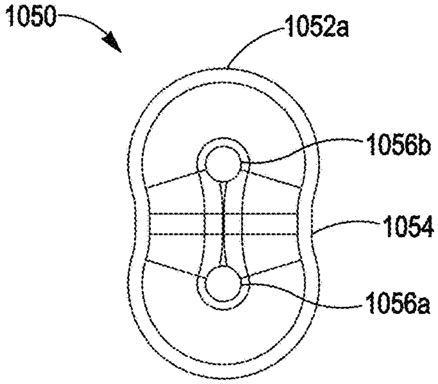
FIG. 29K is a top plan view of the bone material delivery apparatus shown in FIG. 291, in accordance with the invention.

Referring now to FIGS. 29I-29K, there is illustrated one embodiment of a bone delivery apparatus of the invention.

As illustrated in FIGS. 291 and 29J, the bone delivery apparatus 1050 comprises proximal and distal ends 1052*a*, 1052*b* and a similar bone receiving region 1054 disposed on the proximal end 1052*a*.

As illustrated in FIGS. 29J and 29K, in a preferred embodiment, the bone receiving region 1054 similarly comprises a concave cup-shaped region that is thus configured to receive and contain extracted bone material therein.

As further illustrated in FIGS. 29J and 29K, in a preferred embodiment, the bone material receiving region 1054 comprises two (2) bone delivery lumens 1056*a*, 1056*b*, which extend through the bone delivery apparatus 1050.

As further illustrated in FIGS. 291 and 29J, the bone delivery apparatus 1050 further comprises an elongated body region 1060 that is in communication with the base 1055 of the bone receiving region 1054; the body region 1060 also comprising the two (2) bone delivery lumens 1056*a*, 1056*b*.

In a preferred embodiment, the length of the elongated body region (and, hence, bone delivery lumens 1056*a*, 1056*b*) is sufficient to receive and, hence, deliver a sufficient amount of dislodged bone to SI joint prostheses 70*a*, 70*b*, 70*c*, 70*d*, 70*e*, 70*f*, 70*g*, 70 *h* and 70*i* to substantially fill the internal lumens 86*a*, 86*b* of SI joint prostheses 70*a*, 70*b*, 70*c*, 70*d*, 70*e*, 70*f*, 70*g*, 70 *h* and 70*i*.

As further illustrated in FIGS. 291 and 29J, the distal end 1052*b* of the bone delivery apparatus 1050 (and, hence, body region 1060) comprises first and second prosthesis engagement regions 1062*a*, 1062*b* that extend from the distal end 1052*b* of the bone delivery apparatus 1050 (and, hence, body region 1060).

In a preferred embodiment, the first and second prosthesis engagement regions 1062*a*, 1062*b* are sized and configured to be received into the internal lumens of the SI joint prostheses, e.g., internal lumens 86*a*, 86*b* of SI joint prostheses 70*a*, 70*b*, 70*c*, 70*d*, 70*e*, 70*f*, 70*g*, 70 *h* and 70*i*, and, hence, deliver extracted dislodged bone from the bone dislodging member directly into the internal lumens 86*a*, 86*b* of SI joint prostheses 70*a*, 70*b*, 70*c*, 70*d*, 70*e*, 70*f*, 70*g*, 70 *h* and 70*i*.

Prosthesis Deployment Assembly

As indicated above, in some embodiments, the SI joint stabilization systems of the invention further comprise a prosthesis deployment assembly configured and adapted to engage a SJ joint prosthesis of the invention; particularly, SI joint protheses 70*a*, 70*b*, 70*c*, 70*d*, 70*e*, 70*f*, 70*g*, 70 *h* and 70*i* described above, and guide the prostheses 70*a*, 70*b*, 70*c*, 70*d*, 70*e*, 70*f*, 70*g*, 70 *h* and 70*i* into pilot SI joint openings created by the drill guide assemblies of the invention.

Referring now to FIGS. 30A-30G, there is shown one embodiment of a prosthesis deployment assembly of the invention (denoted "600*a*").

As illustrated in FIGS. 30A-30C, the prosthesis deployment assembly 600*a* comprises an elongated guide member 601*a* comprising proximal and distal ends 602, 604.

As further illustrated in FIGS. 30B and 30E, the elongated guide member 601*a* further comprises a prosthesis guide pin 606 that extends from the guide member distal end 604. As indicated above and shown in FIG. 30G, the prosthesis guide pin 606 is sized and configured to seat in internal prosthesis engagement member lumens 86*a*, 86*b* of SI joint prostheses 70*a*, 70*b*, 70*c*, 70*d*, 70*e*, 70*f*, 70*g*, 70 *h* and 70*i*.

As illustrated in FIGS. 30A, 30D, and 30E, the elongated guide member 601*a* further comprises an internal lumen 608 that extends from the proximal end 602 of the elongated guide member 601*a* to the distal end 604 of the elongated guide member 601*a*.

As illustrated in FIG. 30G, in a preferred embodiment of the invention, the internal lumen 608 is sized and configured to receive the prosthesis engagement rod 700 (i.e., prosthesis engagement means) of the prosthesis deployment assembly 600*a* (and prosthesis deployment assembly 600*b*, discussed below).

Referring now to FIG. 30F, there is shown a preferred embodiment of a prosthesis engagement rod 700 of the invention. As illustrated in FIG. 30F, the prosthesis engagement rod 700 comprises a proximal end 702 and a threaded distal end 704, which is sized and configured to threadably engage an internal prosthesis lumen, i.e. 86*a* or 86*b*, of SI joint prostheses 70*a*, 70*b*, 70*c*, 70*d*, 70*e*, 70*f*, 70*g*, 70 *h* and 70*i*.

As further illustrated in FIG. 30F, in a preferred embodiment, the proximal end 702 of the prosthesis engagement rod 700 comprises a knurled configuration to facilitate threading the prosthesis engagement rod 700 into an internal prosthesis engagement member lumen, i.e. 86*a* or 86*b*, of SI joint prostheses 70*a*, 70*b*, 70*c*, 70*d*, 70*e*, 70*f*, 70*g*, 70 *h* and 70*i*.

Referring back to FIGS. 30A and 30B, to further facilitate threading the prosthesis engagement rod 700 into an internal prosthesis engagement member lumen of SI joint prostheses 70*a*, 70*b*, 70*c*, 70*d*, 70*e*, 70*f*, 70*g*, 70 *h* and 70*i*. In a preferred embodiment, prosthesis deployment assembly 600*a* (and prosthesis deployment assembly 600*b*) further comprises an access port 607 that provides access to the knurled proximal end 602 of the prosthesis engagement rod 700 when positioned in the internal lumen 608 of the elongated guide member 601*a*, as shown in FIG. 30G, and elongated guide member 601*b*, as shown in FIG. 31B.

Figure 31A:
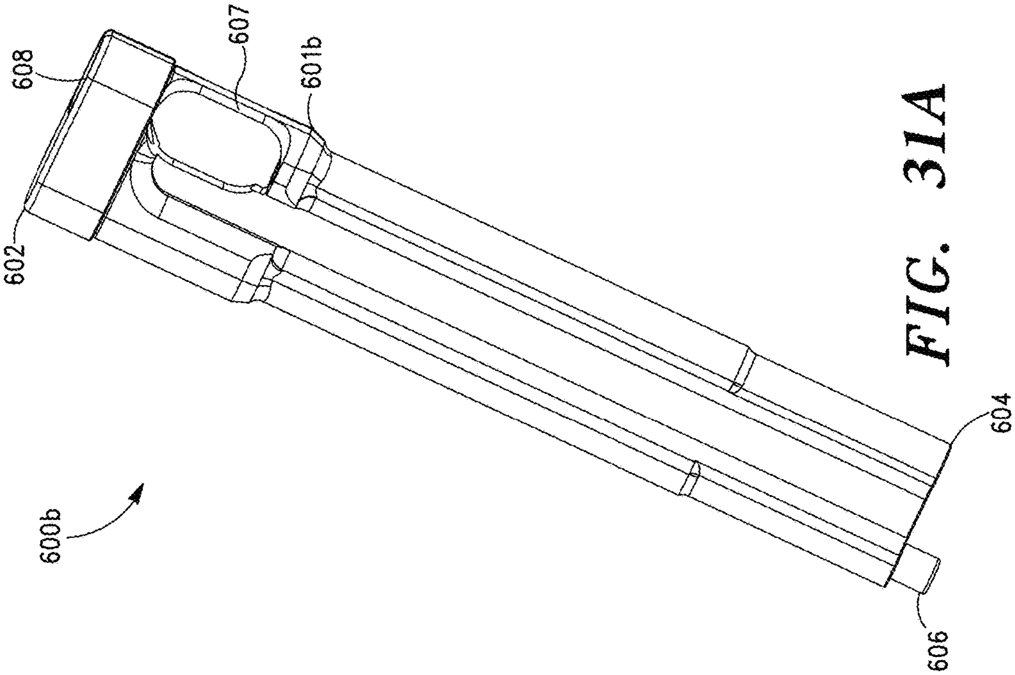
FIG. 31A is a perspective view of another embodiment of a prosthesis deployment assembly, in accordance with the invention.

Referring now to FIGS. 31A and 31B, there is shown another embodiment of a prosthesis deployment assembly of the invention (denoted "600*b*").

As illustrated in FIG. 31A, in a preferred embodiment, the prosthesis deployment assembly 600*b* is similarly configured and adapted to connect to SI joint prostheses 70*a*, 70*b*, 70*c*, 70*d*, 70*e*, 70*f*, 70*g*, 70 *h* and 70*i*, and guide the prostheses into pilot SI joint openings created by the drill guide assemblies of the invention.

As illustrated in FIGS. 31A and 31B, the prosthesis deployment assembly 600*b* similarly comprises an elongated guide member (denoted 601*b* in this embodiment) comprising proximal and distal ends 602, 604, prosthesis guide pin 606, internal lumen 608, access port 607, and prosthesis engagement rod 700.

As illustrated in FIGS. 31A and 31B, in some embodiments, the elongated guide member 601*b* has a narrower body that preferably comprises a cross-sectional shape that corresponds to the prosthesis internal access opening 560 in the drill guide assembly 500, whereby the elongated guide member 601*b* (and, hence, prosthesis 70*a* engaged thereto) can be readily received and positioned in the prosthesis internal access opening 560 in the drill guide assemblies of the invention.

Image Capture Apparatus

In some embodiments of the invention, the system for stabilizing dysfunctional SI joints further comprises an image capture apparatus configured and adapted to capture images reflecting positions and/or orientations of the elongated guide probe and/or drill guide assembly, i.e., a component thereof, e.g., drill bit, and, most importantly, SI joint prostheses when disposed in the body; particularly, during advancement of the elongated guide probe, component of a drill guide assembly and SI joint prostheses toward and into the dysfunctional SI joint.

According to the invention, suitable image capture apparatus can comprise a fluoroscope, a CT system, an ultrasound system, a radiography system, or a magnetic resonance imaging system.

In at least one embodiment, there is thus provided a system for stabilizing a dysfunctional SI joint of a patient comprising (i) a drill guide assembly of the invention, (ii) a prosthesis assembly of the invention, (iii) a prosthesis deployment assembly and (iv) a CT scan system, the drill guide assembly adapted to advance toward the dysfunctional SI joint in a posterior trajectory and create a pilot SI joint opening in the dysfunctional SI joint in the posterior trajectory, the prosthesis configured and adapted to be advanced into the pilot SI joint opening in the dysfunctional SI joint in the posterior trajectory, whereby the prosthesis transfixes and, thereby, stabilizes the dysfunctional SI joint, the prosthesis comprising a first elongated section, a second elongated section, and a bridge section disposed between and connected to the first and second elongated sections, the supplemental bone fixation means comprising an expandable member or composition that is configured and adapted to be advanced into the first and second internal lumens of the prosthesis, expand and, thereby, enhance fixation of the prosthesis to the dysfunctional SI joint when the prosthesis is advanced into the pilot SI joint opening in the dysfunctional SI joint, the prosthesis deployment assembly adapted to engage the prosthesis and guide the prosthesis into the pilot SI joint opening in the dysfunctional SI joint, the CT scan system configured and adapted to capture images reflecting positions and orientations of the drill guide assembly, prosthesis deployment assembly and SI joint 70*a* in the patient's body.

Figure 26R:
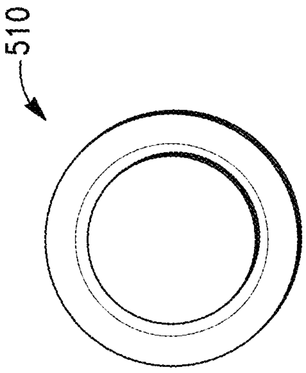
FIG. 26R is an end plan view of the drill guide handle shown in FIG. 26Q, in accordance with the invention.
Figure 26Q:
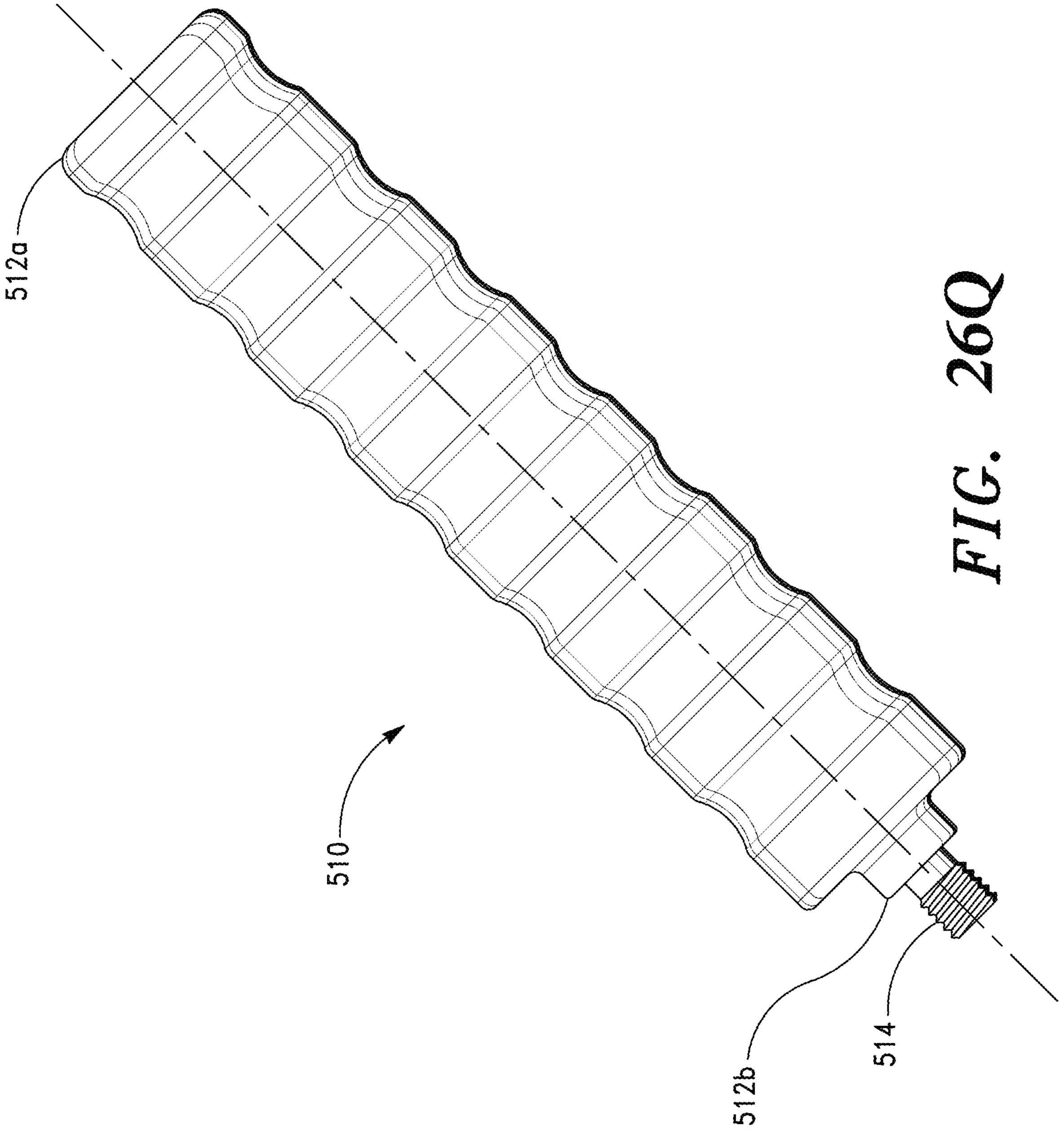
FIG. 26Q is a perspective view of one embodiment of a drill guide handle that is configured to engage the drill guide shown in FIG. 26B, in accordance with the invention.
Figure 32A:
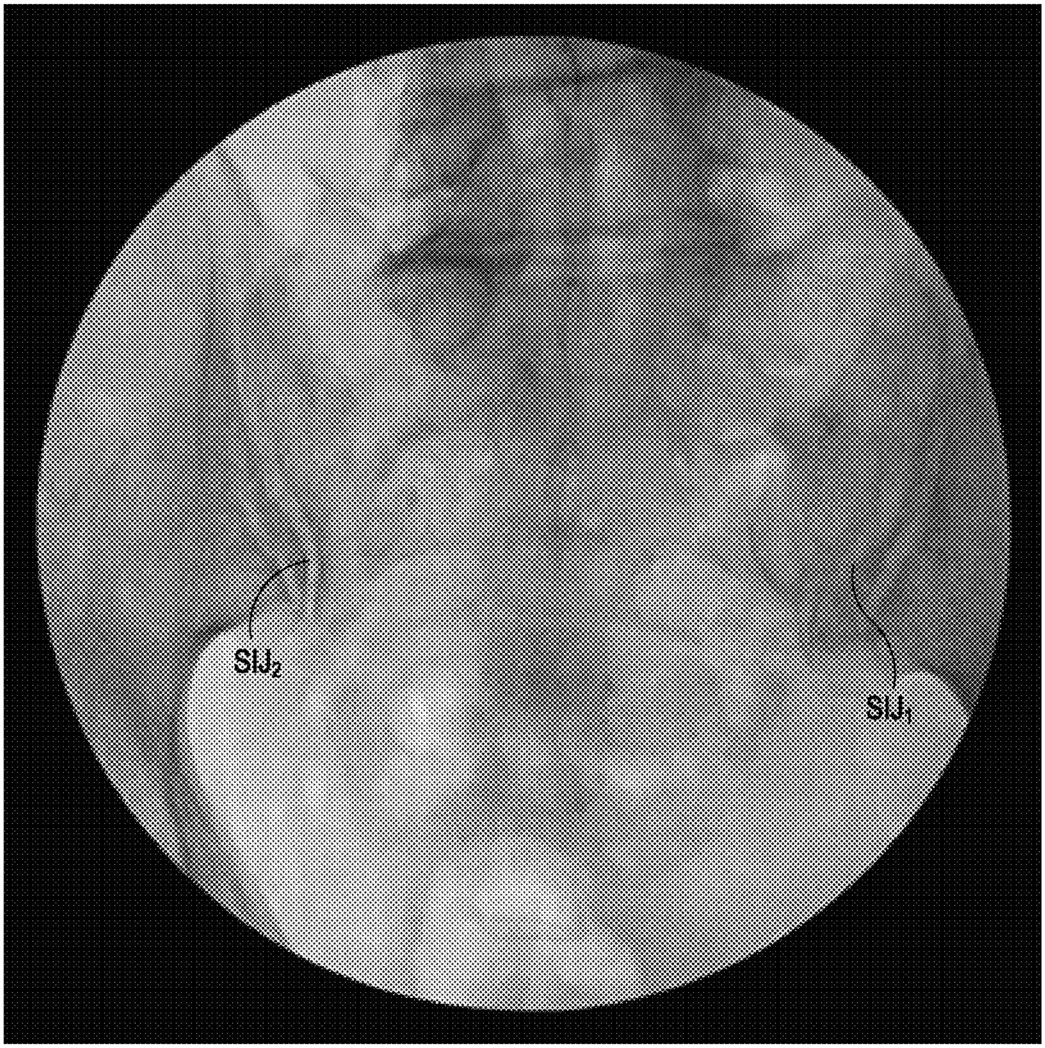
FIG. 32A is a conventional computed tomography (CT) scan image showing an anteroposterior (AP) view of a pelvic structure and SI joints associated therewith.
Figure 32B:
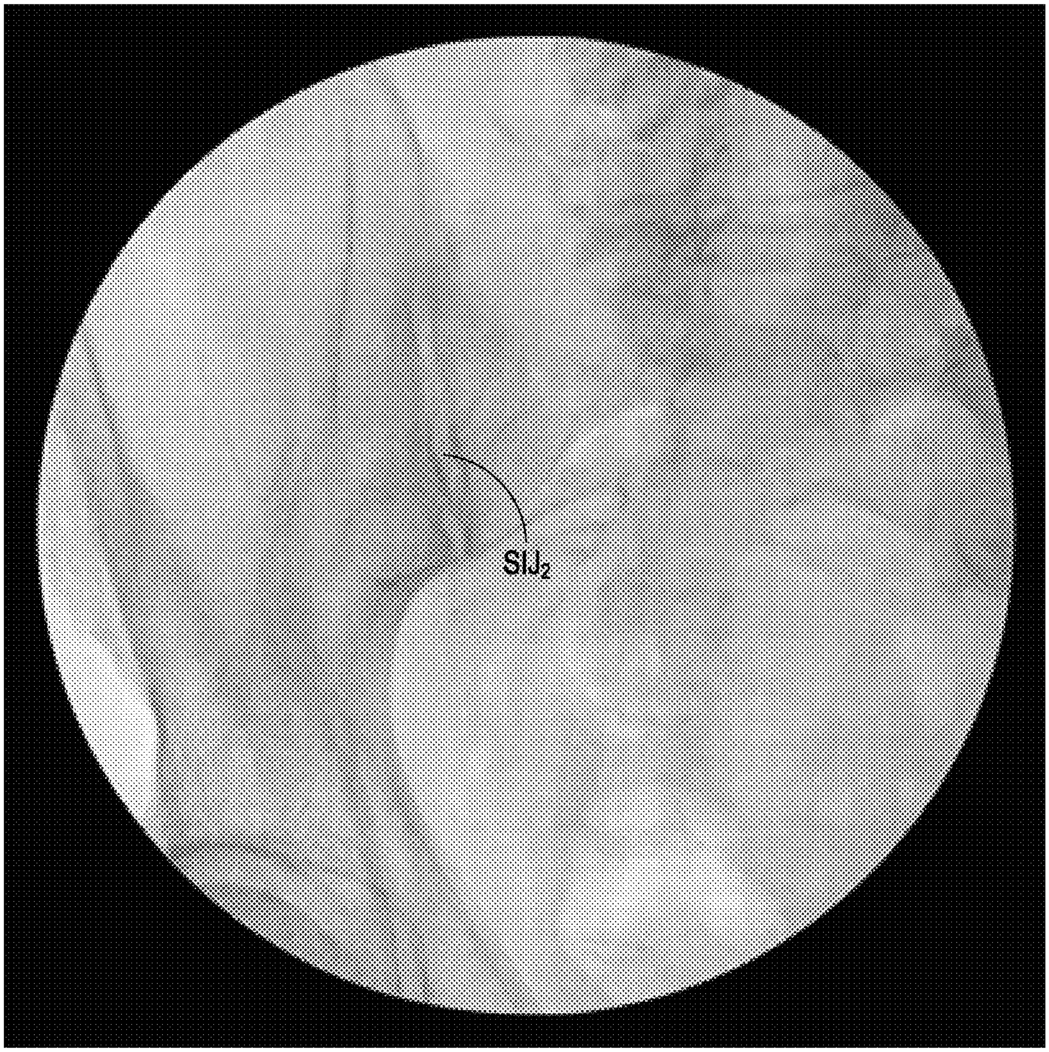
FIG. 32B is a CT scan image showing a modified AP view of a dysfunctional SI joint, in accordance with the invention.
Figure 32C:
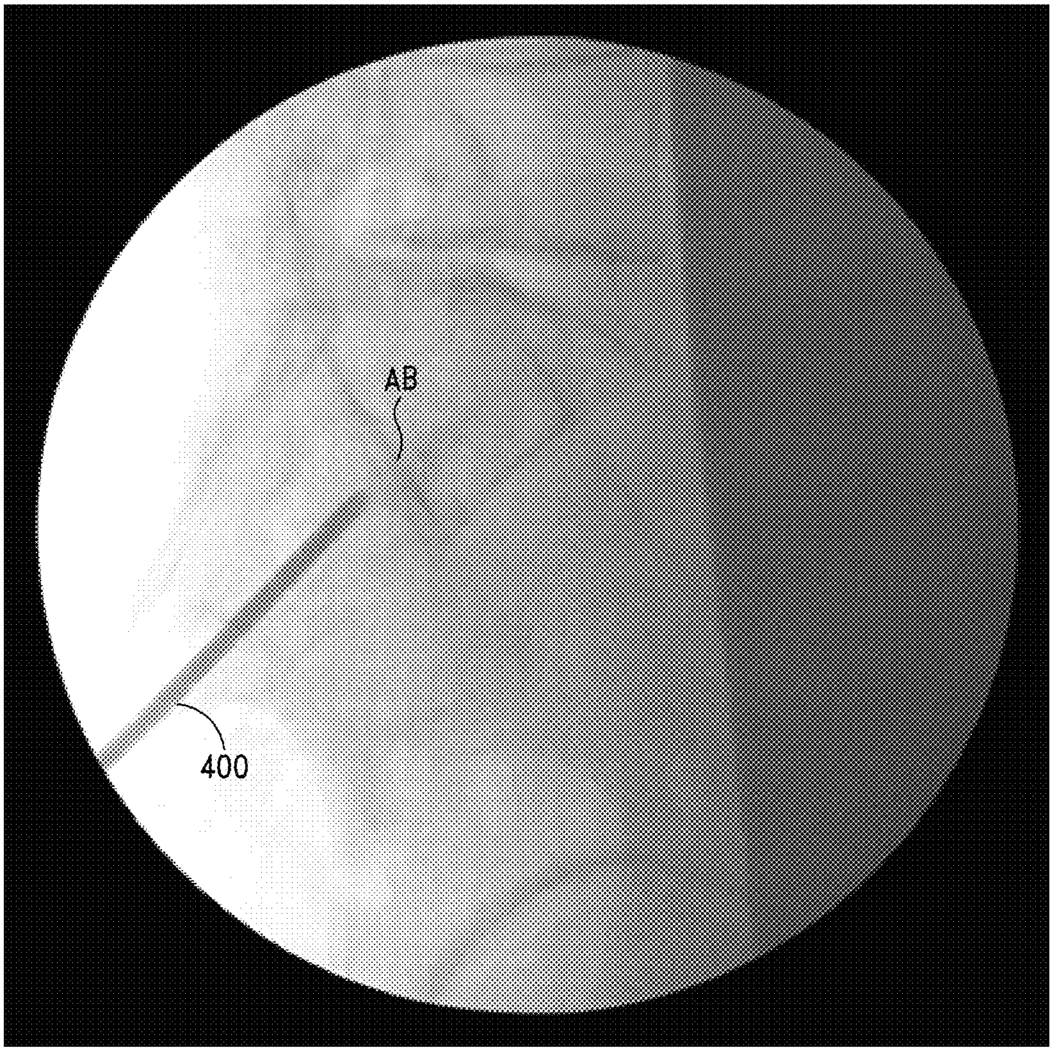
FIG. 32C is a CT scan image showing a tangent lateral view of the dysfunctional SI joint shown in FIG. 32B, showing a guide pin properly positioned therein, in accordance with the invention.
Figure 32D:
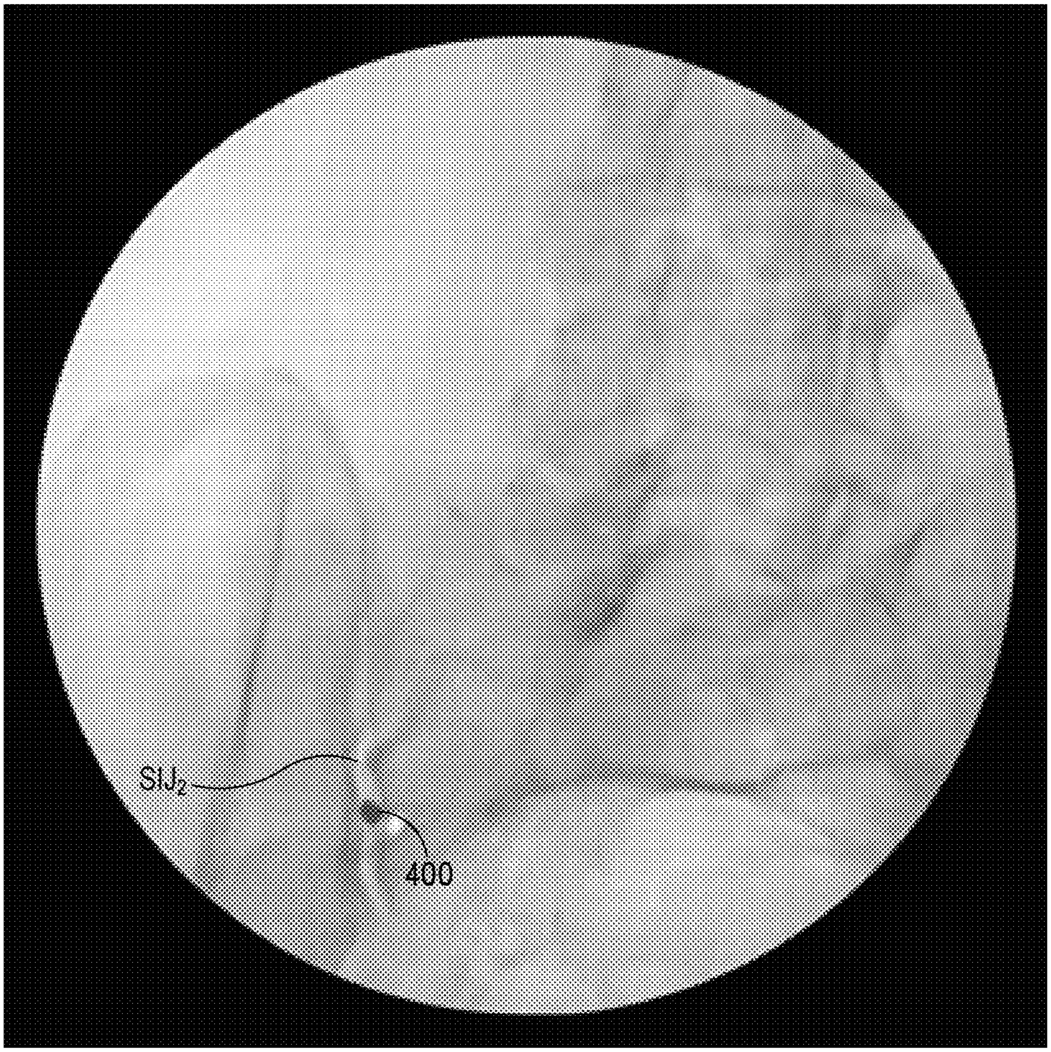
FIG. 32D is a CT scan image showing a trajectory inlet view of the dysfunctional SI joint shown in FIG. 32B, showing a guide pin properly positioned therein, in accordance with the invention.
Figure 32E:
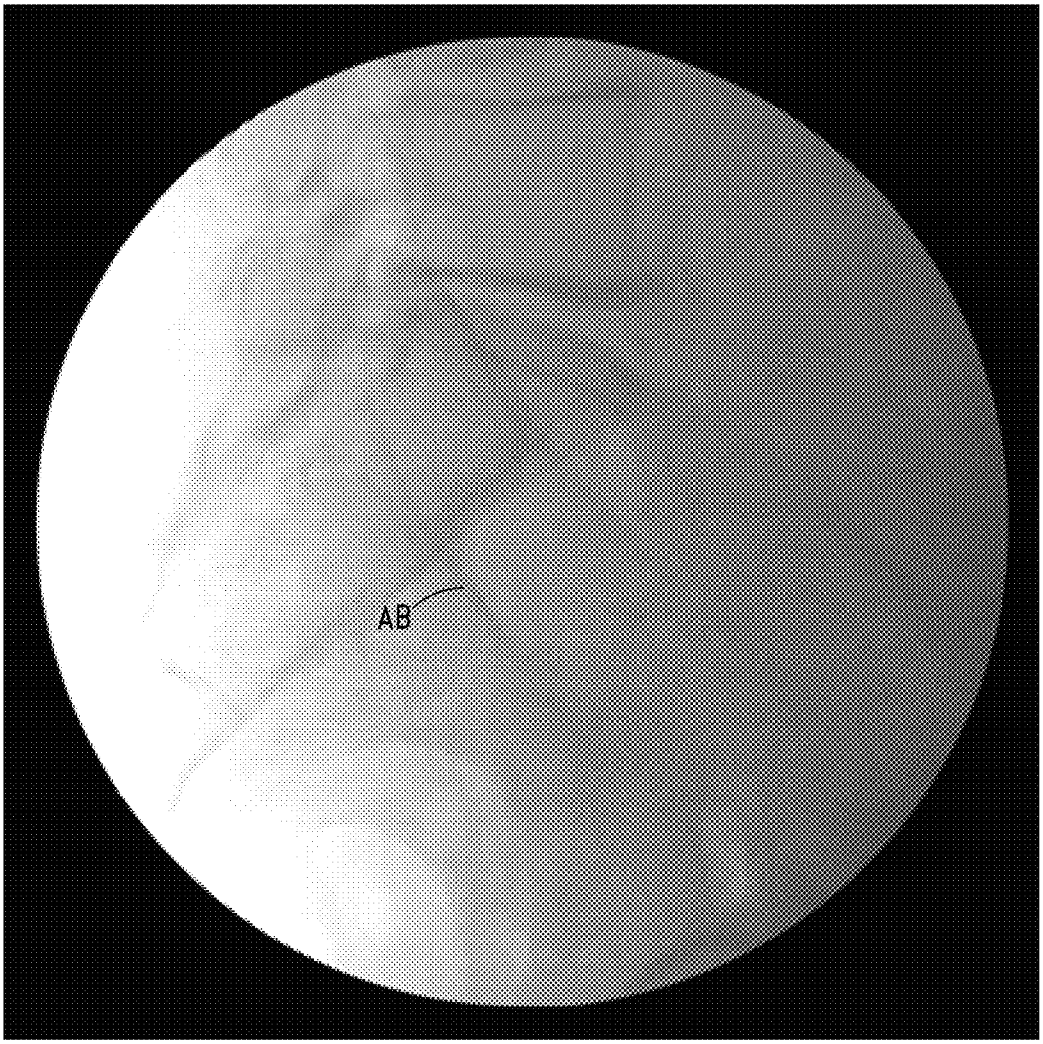
FIG. 32E is a CT scan image showing a lateral view of the dysfunctional SI joint shown in FIG. 32B, showing the alar boundary thereof, in accordance with the invention.
Figure 32F:
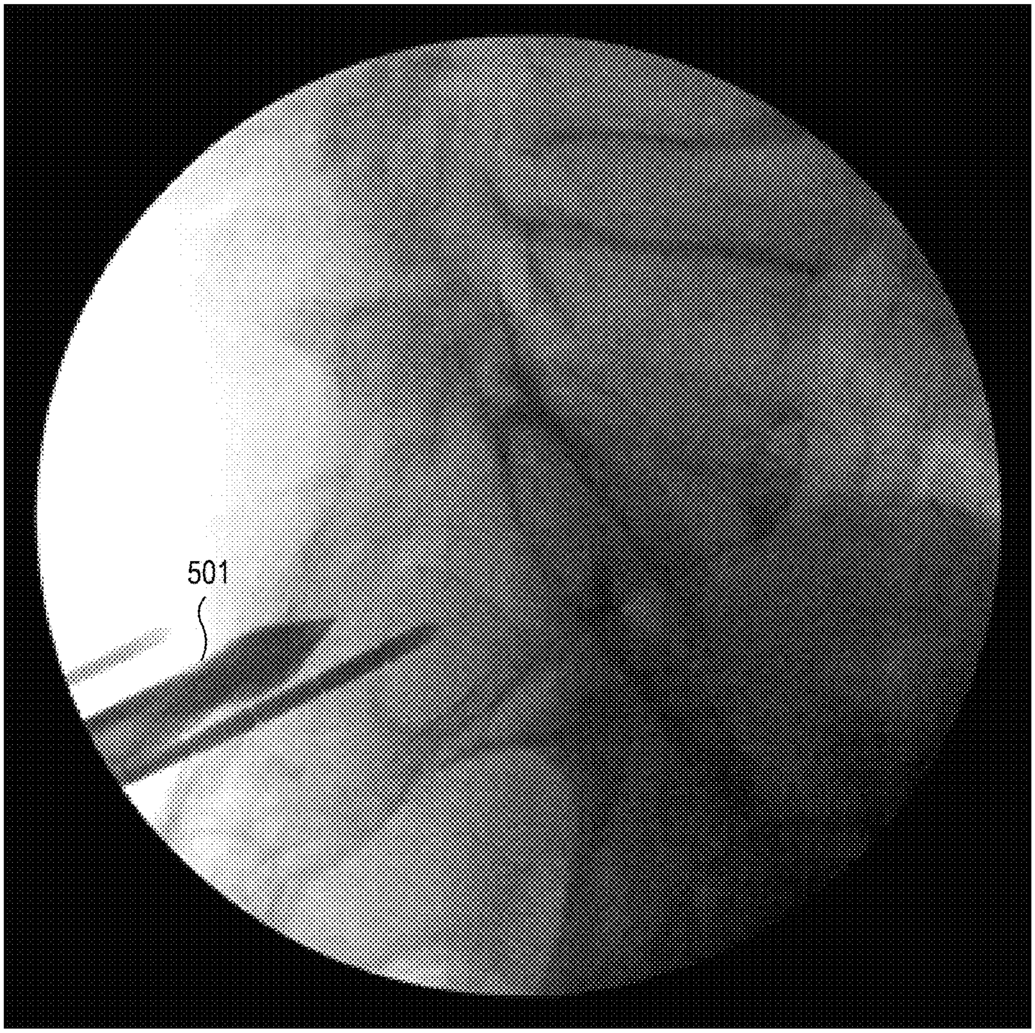
FIG. 32F is a CT scan image showing a further lateral view of the drill guide assembly disposed proximate a dysfunctional SI joint, in accordance with the invention.
Figure 32G:
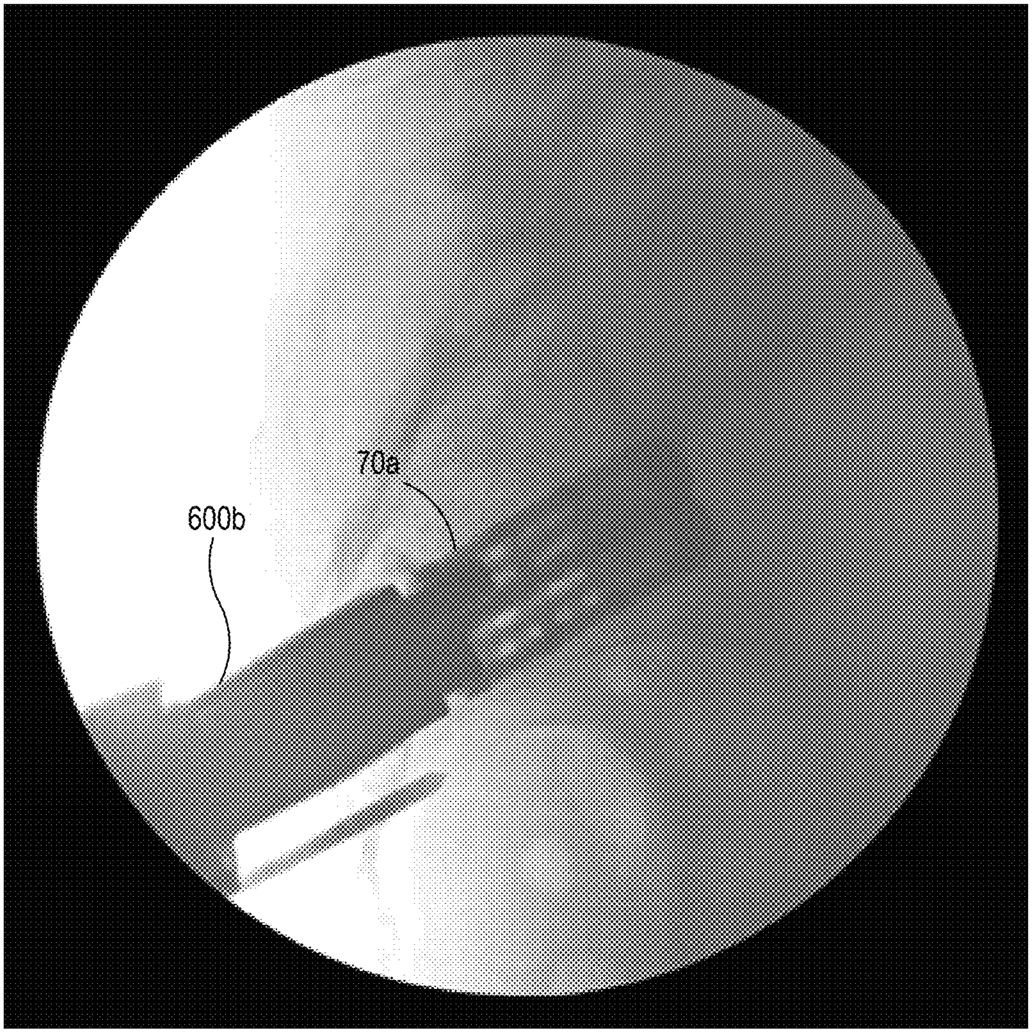
FIG. 32G is a CT scan image showing a lateral view of the prosthesis deployment assembly with a SI joint prosthesis engaged thereto disposed proximate a dysfunctional SI joint, in accordance with the invention.
Figure 32H:
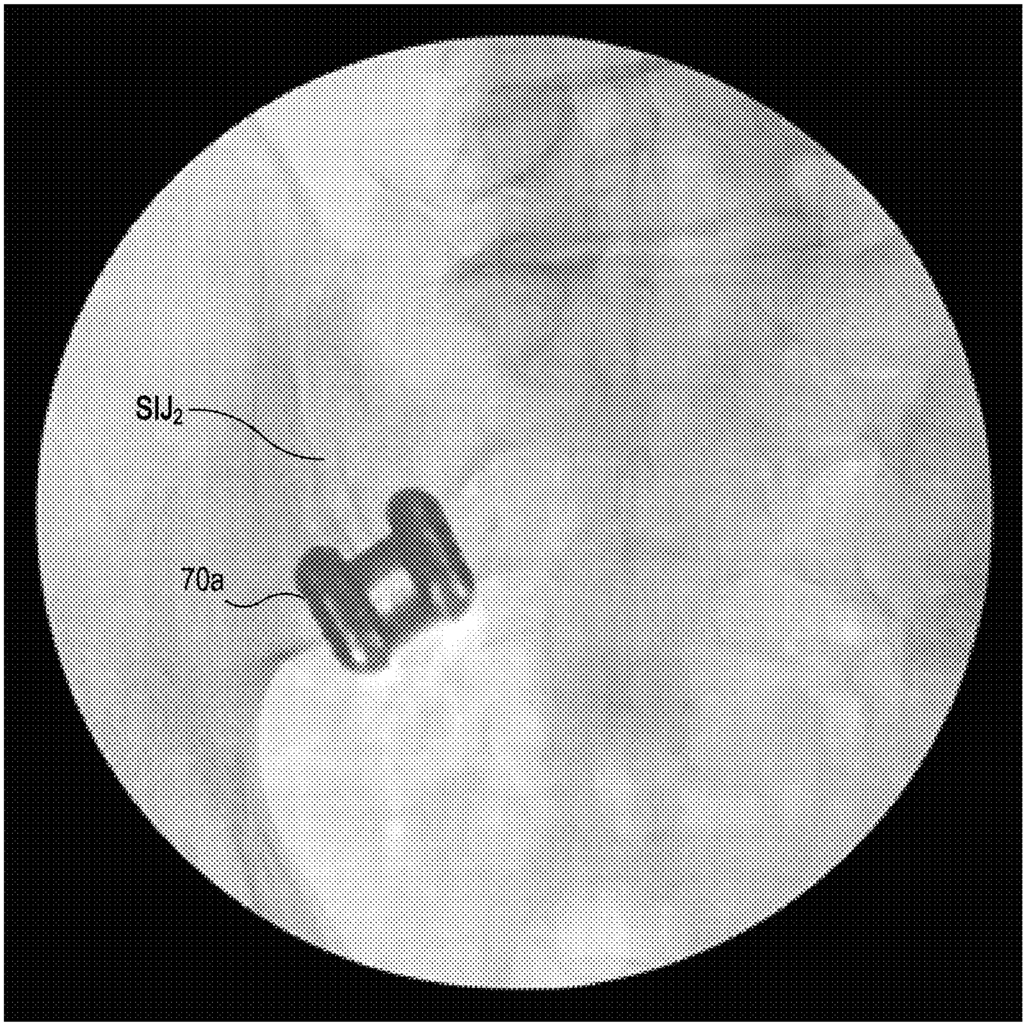
FIG. 32H is a CT scan image showing a modified AP view of the dysfunctional SI joint shown in FIG. 32B, showing a SI joint prosthesis properly positioned therein, in accordance with the invention.
Figure 32I:
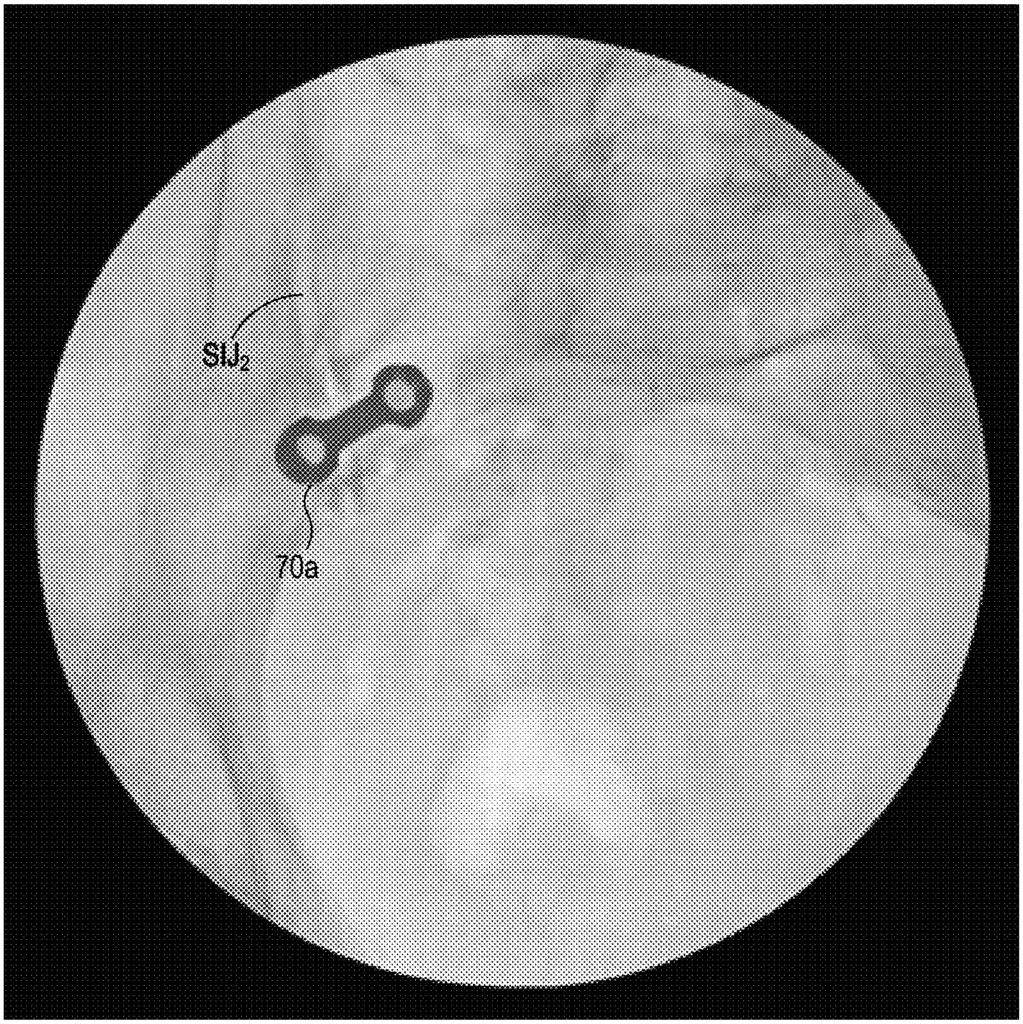
Figure 33A:
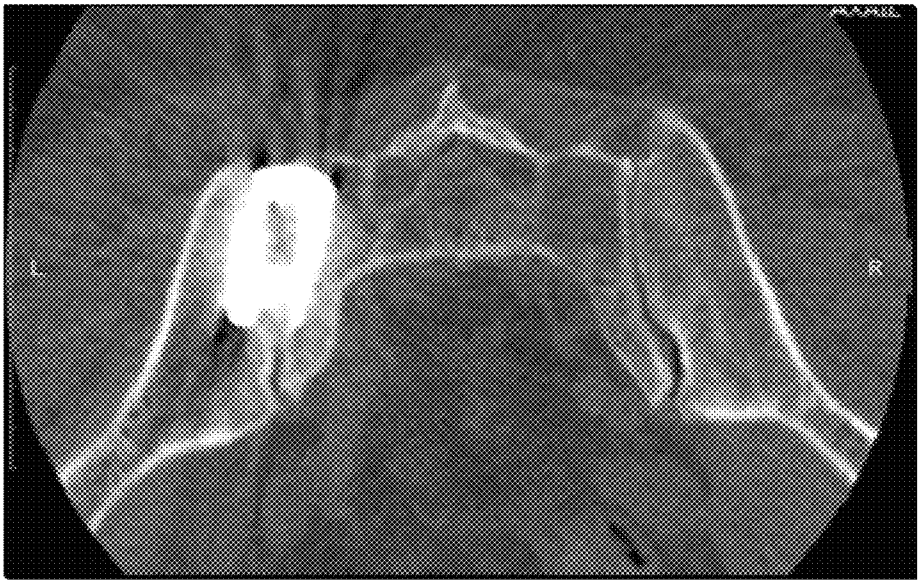
FIGS. 33A and 33B are further CT scan images of the SI joint prosthesis shown in FIGS. 2A and 2B properly positioned in a dysfunctional SI joint, in accordance with the invention.
Figure 33B:
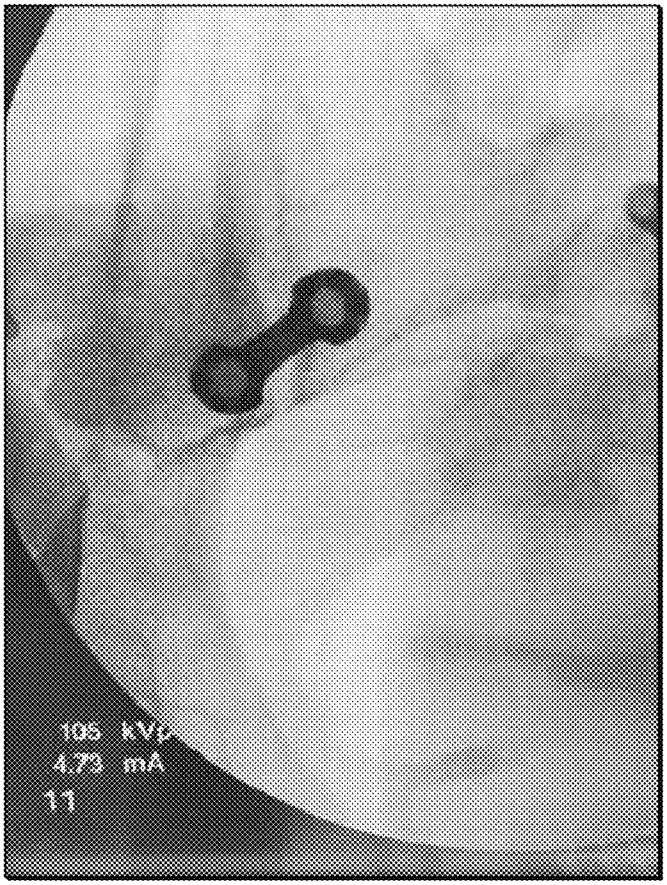

In one preferred embodiment of the invention, there is also provided a method of stabilizing a dysfunctional SI joint of a patient comprising the following steps:

providing a drill guide assembly 500;

providing a SI joint prostheses assembly of the invention, comprising SI joint prosthesis 70*a* and bone stabilizing pin 350;

providing a prosthesis deployment assembly of the invention, in this instance prosthesis deployment assembly 600*b;* making an incision in and through tissue of the patient to provide posterior access to the patient's dysfunctional SI joint; preferably, a 2.0 cm to 3.0 cm incision;

creating a pilot SI joint opening in the dysfunctional SI joint with drill guide assembly, as described above, i.e., (i) attaching a drill guide handle, i.e., handle 510 shown in FIGS. 26Q and 26R, to the drill guide 520, (ii) positioning the drill guide insert 800 in the drill guide 520, (iii) inserting the guide pin 400 into and through the drill guide medial lumen 527 of the drill guide insert 800, (iv) advancing the drill guide assembly 500 with a posterior trajectory in and through the incision site and, thereby positioning the drill guide assembly 500 proximate the dysfunctional SI joint, (v) inserting K-wires 509 into and through K-wire lumens 529*a*, 529*b*, 529*c*, 529*d* of the drill guide 520 and into dysfunctional SI joint structures, e.g., soft and hard skeletal tissue, to position and stabilize the drill guide assembly 500 proximate the dysfunctional SI joint, (vi) advancing the bone dislodging member, in this instance, drill bit 501, through drill guide internal lumen 525*d* of the drill guide insert 800 and to the first bone structure, i.e., ilium or sacrum, of the dysfunctional SI joint, (vii) creating a first portion of a pilot SI joint opening in the first bone structure with the drill bit 501, (viii) retracting the drill bit 501 out of the first bone structure and the drill guide internal lumen 525*d* of the drill guide insert 800, (ix) inserting the drill alignment pin 530 into and through the drill guide internal lumen 525*d* of the drill guide insert 800 and into the first portion of the pilot SI joint opening to further stabilize the drill guide assembly 500 proximate the dysfunctional SI joint, (x) advancing the drill bit 501 through drill guide internal lumen 525*c* of the drill guide insert 800 to the second (or opposing) bone structure of the dysfunctional SI joint, (xi) creating a second portion of the pilot SI joint opening in the second bone structure with the drill bit 501, (xii) retracting the drill bit 501 out of the second bone structure and drill guide internal lumen 525*c* of the drill guide insert 800, (xiii) retracting the drill alignment pin 530 out of the first portion of the pilot SI joint opening and drill guide internal lumen 525*d* of the drill guide insert 800, (xiv) removing the drill guide insert 800 from the drill guide 520, and (xv) retracting the guide pin 400 out of the dysfunctional SI joint;

connecting the prosthesis deployment assembly 600*b* to the SI joint prosthesis (in this instance SI joint prosthesis 70*a*);

advancing the SI joint prosthesis, i.e., SI joint prosthesis 70*a*, into the pilot SI joint opening with the prosthesis deployment assembly 600*b*, wherein the SI joint prosthesis, i.e., SI joint prosthesis 70*a*, is spaced a predetermined distance away from the SI joint dorsal recess (such as shown in FIG. 32G);

retracting the prosthesis deployment assembly 600*b* out of the dysfunctional SI joint;

inserting bone stabilizing pin 350 into SI joint prosthesis 70*a;* retracting the K-wires 509 out of the dysfunctional SI joint structures; and retracting the drill guide 520 out of the subject's body.

In some embodiments, the method further comprises the steps of (i) providing a bone harvester assembly of the invention; preferably, the bone harvester assembly illustrated in FIGS. 29A-29K and described above, (ii) extracting dislodged bone from drill bit 501 with the harvester assembly after the first portion of the pilot SI joint opening is created in the first bone structure with the drill bit 501, and (iii) extracting dislodged bone from drill bit 501 with the bone harvester assembly after the second portion of the pilot SI joint opening is created in the second bone structure with the drill bit 501.

As indicated above, in a preferred embodiment, when SI joint prosthesis 70*a* (and SI joint prostheses 70*b*, 70*c*, 70*d*, 70*e*, 70*f*, 70*g*, 70 *h* and 70*i* when employed), is advanced into the pilot SI joint opening with the prosthesis deployment assembly 600*b*, SI joint prosthesis 70*a* (and SI joint prostheses 70*b*, 70*c*, 70*d*, 70*e*, 70*f*, 70*g*, 70 *h* and 70*i* when employed) is preferably disposed at a distance in the range of at least 2.0 mm to 6.0 mm away from the SI joint dorsal recess, more preferably, a distance of at least 3.0 mm away from the SI joint dorsal recess.

In a preferred embodiment, a further initial step in the minimally-invasive SI joint stabilization methods of the invention comprises the step of providing an image capture apparatus configured and adapted to capture images of at least the subject's anatomical structure, including the dysfunctional SI joint and the anatomic structure proximate thereto, the guide pin 400, and SI joint prosthesis 70*a* (and SI joint prostheses 70*b*, 70*c*, 70*d*, 70*e*, 70*f*, 70*g*, 70 *h* and 70*i* when employed) during advancement toward and when disposed proximate to the dysfunctional SI joint.

In a preferred embodiment, the image capture apparatus comprises a CT system.

In a preferred embodiment, before the step of making an incision in and through tissue of the subject, a further step in the minimally-invasive SI joint stabilization methods comprises capturing images of the subject's anatomical structure with the image capture apparatus to properly align the patient on the surgical table. According to the invention, standard or classic lateral images via CT scans can be employed to ensure proper alignment, i.e., a true prone position, of the patient.

After the step of ensuring proper alignment of the patient, a further initial step in the minimally-invasive SI joint stabilization methods of the invention comprises determining key SI joint landmarks, e.g., dogleg, dorsal recess, etc. with the CT scan system to establish at least a sagittal line, incision (or skin entry) site, and guide pin trajectory and, thereby, prosthesis trajectory into the dysfunctional SI joint.

Since the SI joint comprises a unique shape and does not align with the axis of the spine (i.e., the plane of the SI joint defined by the region between the sacrum and the ilium is not aligned with (or parallel with) the sagittal plane or anteroposterior axis of the spine), as discussed in detail below, in a preferred embodiment, modified anteroposterior (AP) views or images of at least the subject's dysfunctional SI joint, and the guide pin 400 and SI joint prostheses when deployed in the subject's body are acquired via CT scans.

As discussed above, advancement of the guide pin 400 into the dysfunctional SI joint is a critical step in the methods for stabilizing a dysfunctional SI joint. The guide pin 400 ensures (i) proper trajectory of the drill guide assemblies of the invention and creation of the pilot SI joint openings, e.g., pilot SI joint opening 100, (ii) proper trajectory of the prosthesis deployment assemblies 600*a*, 600*b* and, hence, SI joint prostheses 70*a*, 70*b*, 70*c*, 70*d*, 70*e*, 70*f*, 70*g*, 70 *h* and 70*i* engaged thereto to and into the pilot SI joint openings and, thereby, accurate and optimal placement of the SI joint prostheses 70*a*, 70*b*, 70*c*, 70*d*, 70*e*, 70*f*, 70*g*, 70 *h* and 70*i* in the dysfunctional SI joint.

In a preferred embodiment, during the step of advancing the guide pin 400 into the dysfunctional SI joint, a further step in the minimally-invasive SI joint stabilization methods thus comprises capturing images of the guide pin 400 with an image capture apparatus of the invention; preferably, a CT scan system, to ensure proper trajectory and placement of the guide pin 400 proximate the dysfunctional SI joint.

As indicated above, since the SI joint comprises a unique shape and does not align with the axis of the spine, in a preferred embodiment, a series modified (or angled) anteroposterior (AP) images of the guide pin 400 and dysfunctional SI joint (and, if necessary, surrounding structures) during advancement of the guide pin 400 toward and, particularly, when disposed proximate to and in the dysfunctional SI joint are preferably acquired with the CT scan system to ensure proper trajectory and placement of the guide pin 400 proximate the dysfunctional SI joint.

Referring now to FIG. 32A there is shown a conventional AP view image of a dysfunctional SI joint. As illustrated in FIG. 32A, the SI joints (denoted "SIJ1" and "SIJ2"), including the dysfunctional SI joint on the left side ("SIJ2"), are represented by multiple non-linear lines, which reflect misalignment of the imaged SI joints ("SIJ1" and "SIJ2"). The mis-alignment of the imaged SI joints ("SIJ1" and "SIJ2") in the conventional AP view image makes properly aligning the guide pin 400 in a SI joint, i.e., "SIJ1" or "SIJ2", very difficult. Indeed, one must guess the advancement trajectory of the guide pin 400.

Referring to FIG. 32B, there is shown a CT scan image showing a modified AP view of the left, i.e., dysfunctional, SI joint ("SIJ2"). As illustrated in FIG. 32B, the dysfunctional SI joint ("SIJ2") is now shown and, hence, represented by a substantially straight line indicating substantial alignment of the imaged dysfunctional SI joint ("SIJ2").

The modified AP view of the dysfunctional SI joint ("SIJ2") shown in FIG. 32B facilitates accurate advancement, trajectory, and positioning of the guide pin 400 in the dysfunctional SI joint ("SIJ2"), as shown in the tangent lateral and trajectory inlet views shown in FIGS. 32C and 32D, respectively.

As indicated above, in a preferred embodiment, the guide pin 400 is advanced into the dysfunctional SI joint to, but no further than, the alar boundary (denoted "AB" in FIGS. 1A, 32C and 32E).

A CT scan image showing a tangent lateral view of the dysfunctional SI joint ("SIJ2") also facilitates accurate advancement and, hence, depth of the guide pin 400 in the dysfunctional SI joint ("SIJ2"), as shown in FIG. 32C.

In a preferred embodiment, during the step of advancing SI joint prosthesis 70*a* (and SI joint prostheses 70*b*, 70*c*, 70*d*, 70*e*, 70*f*, 70*g*, 70 *h* and 70*i* when employed) into the pilot SI joint opening with the prosthesis deployment assemblies 600*a*, 600*b*, a further step in the minimally-invasive SI joint stabilization methods comprises capturing images of the SI joint prosthesis 70*a* (and SI joint prostheses 70*b*, 70*c*, 70*d*, 70*e*, 70*f*, 70*g*, 70 *h* and 70*i* when employed) with the image capture apparatus of the invention; preferably, a CT scan system, to ensure proper trajectory and placement of SI joint prosthesis 70*a* (and SI joint prostheses 70*b*, 70*c*, 70*d*, 70*e*, 70*f*, 70*g*, 70 *h* and 70*i* when employed) in the dysfunctional SI joint, such as shown in FIGS. 32H, 32I, 33A and 33B.

Preferably, the CT scan images depict modified AP and/or trajectory inlet views of the SI joint prosthesis and dysfunctional SI joint (and, if necessary, surrounding structures).

In some embodiments, after the step of creating the pilot SI joint opening with a drill guide assembly of the invention, the methods for stabilizing a dysfunctional SI joint further comprise the step of harvesting the dislodged bone material, e.g., cortical bone, trabecular bone, and bone marrow, with one of the aforediscussed bone harvester assemblies for subsequent use in a biologically active composition of the invention and thereafter delivery to the SI joint prosthesis 70*a* (and SI joint prostheses 70*b*, 70*c*, 70*d*, 70*e*, 70*f*, 70*g*, 70 *h* and 70*i* when employed).

As will readily be appreciated by one having ordinary skill in the art, the present invention provides numerous advantages compared to prior art systems and methods for stabilizing dysfunctional SI joints. Among the advantages are the following:

- the provision of improved minimally-invasive SI joint stabilization systems and apparatus, and methods of using same, which facilitate posterior trajectory placement of SI joint prostheses in dysfunctional SI joints and, thereby, effective stabilization of the dysfunctional SI joints;
- the provision of improved minimally-invasive SI joint stabilization systems, which, when employed to stabilize dysfunctional SI joints, disrupt less tissue and muscles, and avoid nerves and large blood vessels;
- the provision of improved minimally-invasive SI joint stabilization systems and apparatus, including prostheses, which, when employed to stabilize dysfunctional SI joints, effectively ameliorate pain associated with SI joint dysfunction;
- the provision of improved minimally-invasive SI joint stabilization systems comprising drill guide assemblies adapted to create pilot openings in dysfunctional SI joints for placement of SI joint prostheses therein via a minimal incision, i.e., an incision length no greater than 3.0 cm;
- the provision of improved minimally-invasive SI joint stabilization systems comprising drill guide assemblies adapted to create pilot openings in dysfunctional SI joints for placement of SI joint prostheses therein, which provide optimal direct visualization of the bone dislodging member thereof and the pilot opening during and after creation of the pilot openings;
- the provision of improved minimally-invasive SI joint stabilization systems comprising drill guide assemblies adapted to receive and guide and, thereby, provide consistent, optimal placement of SI joint prostheses into dysfunctional SI joints;
- the provision of improved minimally-invasive SI joint stabilization systems comprising drill guide assemblies adapted to create pilot openings in dysfunctional SI joints for placement of SI joint prostheses therein, which provide consistent, optimal arthrodesis of the dysfunctional SI joint after placement of a SI joint prosthesis in the pilot openings;
- the provision of improved minimally-invasive SI joint stabilization systems comprising a bone harvesting assembly adapted to harvest, i.e., retract and collect, bone material, i.e., autograft bone material, directly from a drill bit after creation of SI joint pilot openings (and portions thereof) for subsequent formation of an osteogenic composition and/or direct delivery to SI joint prostheses; and
- the provision of improved SI joint prostheses that can readily be employed in minimally-invasive SI joint stabilization systems, which facilitate remodeling of damaged osseous tissue and regeneration of new osseous tissue and osseous tissue structures.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. An implant for stabilizing a dysfunctional sacroiliac (SI) joint, comprising:

a monolithic member and a bone stabilizing pin, said monolithic member configured and adapted to be advanced into said dysfunctional SI joint in said posterior trajectory, said monolithic member comprising a first elongated section, a second elongated section, and a bridge section, said bridge section disposed between and not extending beyond said first elongated section and said second elongated section of said monolithic member in any direction, said bridge section comprising a bridge proximal end and a bridge distal end, said first elongated section comprising a first open proximal end, a first open distal end, and a first internal lumen that extends from said first open proximal end to said first open distal end of said first elongated section, said first internal lumen comprising a first length from said first open proximal end to said first open distal end of said first elongated section, said first internal lumen sized and configured to receive said bone stabilizing pin therein, said first elongated section further comprising first internal threads, said first internal threads disposed in said first internal lumen and extending from said first open proximal end of said first elongated section, said first elongated section further comprising a first tapered region disposed on said first open distal end, said second elongated section comprising a second open proximal end, a second open distal end, and a second internal lumen that extends from said second open proximal end to said second open distal end of said second elongated section, said second internal lumen comprising a second length from said second open proximal end to said second open distal end of said second elongated section, said second internal lumen sized and configured to receive said bone stabilizing pin therein, said second elongated section further comprising second internal threads, said second internal threads disposed in said second internal lumen and extending from said second open proximal end of said second elongated section, said second elongated section further comprising a second tapered region disposed on said second open distal end, said first elongated section of said monolithic member further comprising a first plurality of fenestrations and said second elongated section of said monolithic member further comprising a second plurality of fenestrations, said bone stabilizing pin comprising a pin proximal end and a pin distal end, said bone stabilizing pin comprising a third length from said pin proximal end to said pin distal end, said third length of said bone stabilizing pin being greater than said first length of said first internal lumen of said first elongated section and said second length of said second internal lumen of said second elongated section, said pin proximal end comprising a threaded region adapted to engage and cooperate with said first internal threads of said first elongated section and said second internal threads of said second elongated section, said bone stabilizing pin configured and adapted to be advanced into said dysfunctional SI joint when said monolithic member is said advanced into said dysfunctional SI joint, said bone stabilizing pin is received in said first internal lumen of said first elongated section, and said bone stabilizing pin is advanced through said first internal lumen of said first elongated section, said bone stabilizing pin comprising a plurality of tabs, each of said plurality of tabs adapted to transition from a second collapsed configuration to a second outwardly projecting configuration when said bone stabilizing pin is advanced into said first internal lumen of said first elongated section.

* * * * *